US011897880B2

(12) United States Patent
Xu et al.

(10) Patent No.: US 11,897,880 B2
(45) Date of Patent: Feb. 13, 2024

(54) 7,8-DIHYDROBENZO[E]PYRIDO[3,4-C] AZOCINE-2,5(3H,6H)-DIONE DERIVATIVES USEFUL AS A FACTOR XIA INHIBITORS

(71) Applicant: Janssen Pharmaceutica NV, Beerse (BE)

(72) Inventors: Guozhang Xu, Chesterbrook, PA (US); Tianbao Lu, Churchville, PA (US); Zhijie Liu, Wilmington, DE (US); Micheal D. Gaul, Apex, NC (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/732,724

(22) Filed: Apr. 29, 2022

(65) Prior Publication Data
US 2022/0389005 A1 Dec. 8, 2022

Related U.S. Application Data
(60) Provisional application No. 63/182,019, filed on Apr. 30, 2021.

(51) Int. Cl.
C07D 471/04 (2006.01)
(52) U.S. Cl.
CPC ................... C07D 471/04 (2013.01)
(58) Field of Classification Search
None
See application file for complete search history.

(56) References Cited

U.S. PATENT DOCUMENTS

| | | | |
|---|---|---|---|
| 4,845,079 A | 7/1989 | Luly et al. | |
| 4,885,292 A | 12/1989 | Ryono et al. | |
| 4,894,437 A | 1/1990 | TenBrink | |
| 4,980,283 A | 12/1990 | Huang et al. | |
| 5,034,512 A | 7/1991 | Hudspeth et al. | |
| 5,036,053 A | 7/1991 | Himmelsbach et al. | |
| 5,036,054 A | 7/1991 | Kaltenbronn et al. | |
| 5,055,466 A | 10/1991 | Weller, III et al. | |
| 5,063,207 A | 11/1991 | Doherty et al. | |
| 5,063,208 A | 11/1991 | Rosenberg et al. | |
| 5,064,965 A | 11/1991 | Ocain et al. | |
| 5,066,643 A | 11/1991 | Abeles et al. | |
| 5,071,837 A | 12/1991 | Doherty et al. | |
| 5,075,451 A | 12/1991 | Ocain et al. | |
| 5,089,471 A | 2/1992 | Hanson et al. | |
| 5,095,119 A | 3/1992 | Ocain et al. | |
| 5,098,924 A | 3/1992 | Poss | |
| 5,104,869 A | 4/1992 | Albright et al. | |
| 5,106,835 A | 4/1992 | Albright et al. | |
| 5,114,937 A | 5/1992 | Hamby et al. | |
| 5,116,835 A | 5/1992 | Rüger et al. | |
| 6,063,847 A | 5/2000 | Chackalamannil et al. | |
| 6,326,380 B1 | 12/2001 | Chackalamannil et al. | |
| 6,645,987 B2 | 11/2003 | Chackalamannil et al. | |
| 7,037,920 B2 | 5/2006 | Chackalamannil et al. | |
| 7,235,567 B2 | 6/2007 | Wu | |
| 7,304,078 B2 | 12/2007 | Chackalamannil et al. | |
| 10,093,683 B2 * | 10/2018 | Lim | ............... C07D 471/10 |
| 10,138,236 B2 * | 11/2018 | Röhrig | ............... C07D 471/04 |
| 2003/0022890 A1 | 1/2003 | Atwal et al. | |

FOREIGN PATENT DOCUMENTS

| | | |
|---|---|---|
| EP | 1495018 B1 | 3/2011 |
| WO | WO 1994/03479 A1 | 2/1994 |
| WO | WO 2001/96330 A2 | 12/2001 |

OTHER PUBLICATIONS

Bhatwadekar et al., Investigational plasma kallikrein inhibitors for the treatment of diabetic macular edema: an expert assessment. Expert Opinion on Investigational Drugs, 2020, 29, 237-244.*
Harrington et al., Clinical Evaluation of Factor XIa Inhibitor Drugs: JACC Review Topic of the Week. Journal of the American College of Cardiology, 2023, 81, 771-779.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Bernatowicz et al., "Development of Potent Thrombin Receptor Antagonist Peptides.", Med. Chem., 1996, pp. 4879-4887, vol. 39.
Chou, T., "Theoretical Basis, Experimental Design, and Computerized Simulation of Synergism and Antagonism in Drug Combination Studies.", Pharmacol. Rev., 2006, pp. 621-681, vol. 58(3).
Gailani et al., "Intrinsic Pathway of Coagulation and Arterial Thrombosis.", Arterioscler. Thromb. Vasc. Biol., 2007, pp. 2507-2513, vol. 27.

(Continued)

*Primary Examiner* — Po-Chih Chen
(74) *Attorney, Agent, or Firm* — BakerHostetler

(57) ABSTRACT

The present invention is directed to 7,8-dihydrobenzo[e]pyrido[3,4-c]azocine-2,5(3H,6H)-dione derivatives, stereoisomers, isotopologues, isotopomers and pharmaceutically acceptable salts thereof, pharmaceutical compositions containing said compounds and the use of said compounds in the treatment and/or prophylaxis of thromboembolic disorders, inflammatory disorders and diseases or conditions in which plasma kallikrein activity is implicated.

11 Claims, No Drawings

(56) References Cited

OTHER PUBLICATIONS

Hoffman, M., "A cell-based model of coagulation and the role of Factor VIIa.", Blood Reviews, 2003, S1-S5, vol. 17.
Howard et al., "Factor IXa Inhibitors as Novel Anticoagulants.", Arterioscler Thromb. Vasc. Biol. 2007. pp. 722-727, vol. 27.
Quan et al., "Factor XIa Inhibitors as New Anticoagulants.", J. Med. Chem. 2018, pp. 7425-7447, vol. 61.

\* cited by examiner

7,8-DIHYDROBENZO[E]PYRIDO[3,4-C] AZOCINE-2,5(3H,6H)-DIONE DERIVATIVES USEFUL AS A FACTOR XIA INHIBITORS

CROSS REFERENCE TO RELATED APPLICATIONS

This application claims the benefit of U.S. Provisional Application No. 63/182,019, filed on Apr. 30, 2021, which is incorporated by reference herein in its entirety.

FIELD OF THE INVENTION

The present invention is directed to 7,8-dihydrobenzo[e]pyrido[3,4-c]azocine-2,5(3H,6H)-dione derivatives, stereoisomers, isotopologues, isotopomers and pharmaceutically acceptable salts thereof, pharmaceutical compositions containing said compounds, and the use of said compounds in the treatment and/or prophylaxis of thromboembolic disorders, inflammatory disorders and diseases or conditions in which plasma kallikrein activity is implicated.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin inhibits the post-translational maturation of coagulation factors VII, IX, X and prothrombin, and has proven effective in both venous and arterial thrombosis. However, its usage is limited due to its narrow therapeutic index with respect to bleeding safety, slow onset of therapeutic effect, numerous dietary and drug-drug interactions, and a need for monitoring and dose adjustment. Novel oral anticoagulants directly targeting either thrombin or factor Xa, e.g., dabigatran, apixaban, betrixaban, edoxaban, rivaroxaban, have been approved for both venous and arterial indications. However, the risk of bleeding is not completely eliminated, and can be as high as 2-3% per year in patients with atrial fibrillation (Quan et al., J. Med. Chem. 2018, pp 7425-7447, Vol. 61). Thus, discovering and developing safe and efficacious oral anticoagulants with minimal impacts on hemostasis for the prevention and treatment of a wide range of thromboembolic disorders has become increasingly important.

SUMMARY OF THE INVENTION

The present invention is directed to compounds of formula (I)

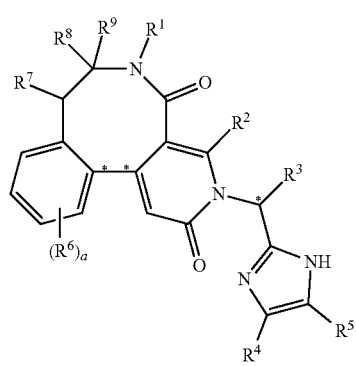

(I)

wherein $R^1$ is selected from the group consisting of hydrogen, $C_{1-2}$ alkyl, —($C_{1-2}$ alkylene)-OH and —($C_{1-2}$ alkylene)-O—($C_{1-2}$ alkyl);

$R^2$ is hydrogen and $R^3$ is cyclopropyl-methyl-;

alternatively, $R^2$ and $R^3$ are taken together with the carbon atoms to which they are bound to form

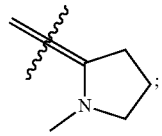 [SMILES: *=C1CCCN1C]

$R^4$ is selected from the group consisting of hydrogen and halogen;

$R^5$ is selected from the group consisting of phenyl, heteroaryl and pyridin-4-yl-1-oxide; wherein the phenyl or heteroaryl is optionally substituted with one or more substituents independently selected from the group consisting of halogen, hydroxy, oxo, $C_{1-4}$ alkyl, hydroxy substituted $C_{1-4}$ alkyl, $NR^A R^B$ and —NH—C(O)—($C_{1-4}$ alkyl); and wherein $R^A$ and $R^B$ are each independently selected from the group consisting of hydrogen and $C_{1-2}$ alkyl;

a is an integer from 0 to 3;

each $R^6$ is independently selected from the group consisting of chloro, fluoro and methyl;

$R^7$ is hydrogen, and $R^8$ and $R^9$ are each independently selected from the group consisting of hydrogen, $C_{1-4}$ alkyl, and $C_{1-4}$ alkoxy;

alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl, cyclopent-1,1-diyl, and cyclohex-1,1-diyl;

alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;

and stereoisomers, isotopologues, isotopomers and pharmaceutically acceptable salts thereof.

In some embodiments, the present invention is directed to compounds of formula (I) wherein the starred "*" bond is present in a stereoisomeric excess of the corresponding R-stereoisomer. In some embodiments, the present invention is directed to compounds of formula (I) wherein the starred "*" bond is present in a stereoisomeric excess of the corresponding S-stereoisomer.

The present invention is further directed to processes for the preparation of the compounds of formula (I). The present invention is further directed to a compound of formula (I) prepared according to any of the process(es) described herein.

Illustrative of the invention are pharmaceutical compositions comprising a pharmaceutically acceptable carrier and a compound of formula (I) as described herein. An illustration of the invention is a pharmaceutical composition made by mixing a compound of formula (I) as described herein and a pharmaceutically acceptable carrier. Illustrating the invention is a process for making a pharmaceutical composition comprising mixing a compound of formula (I) as described herein and a pharmaceutically acceptable carrier.

Exemplifying the invention are methods for the treatment and/or prophylaxis of thromboembolic disorders, inflammatory disorders or diseases or conditions in which plasma kallikrein activity is implicated, as described herein, comprising administering to a subject in need thereof a therapeutically effective amount of any of the compounds or pharmaceutical compositions described above.

Exemplifying the invention are methods or the treatment and/or prophylaxis of thromboembolic disorders, such as arterial cardiovascular thromboembolic disorders, venous cardiovascular thromboembolic disorders, arterial cerebrovascular thromboembolic disorders, and venous cerebrovascular thromboembolic disorders, comprising administering to a subject in need thereof a therapeutically effective amount of any of the compounds or pharmaceutical compositions described herein. Examples of thromboembolic disorders include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In an embodiment, the present invention is directed to a compound of formula (I) for use as a medicament. In another embodiment, the present invention is directed to a compound of formula (I) for use in the treatment and/or prophylaxis of thromboembolic disorders, inflammatory disorders or diseases or conditions in which plasma kallikrein activity is implicated.

In another embodiment, the present invention is directed to a compound of formula (I) for use in the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders. In another embodiment, the present invention is directed to a compound of formula (I) for use in the treatment and/or prophylaxis of a thromboembolic disorder selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention is directed to a compound of formula (I) for use in the treatment and/or prophylaxis of a thromboembolic disorder selected from the group consisting of hereditary angioedema (HAE) and diabetic macular edema (DME).

In another embodiment, the present invention is directed to a composition comprising a compound of formula (I) for use in the treatment and/or prophylaxis of a disorder, disease or condition as described herein. In another embodiment, the present invention is directed to a composition comprising a compound of formula (I) for use in the treatment and/or prophylaxis of a thromboembolic disorder, and inflammatory disorder or a disease or condition in which plasma kallikrein activity is implicated.

In another embodiment, the present invention is directed to a composition comprising a compound of formula (I) for use in the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders. In another embodiment, the present invention is directed to a composition comprising a compound of formula (I) for use in the treatment and/or prophylaxis of a thromboembolic disorder selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or to procedures in which blood is exposed to an artificial surface that promotes thrombosis. In another embodiment, the present invention is directed to a composition comprising a compound of formula (I) for use in the treatment and/or prophylaxis of a thromboembolic disorder such as hereditary angioedema (HAE) or diabetic macular edema (DME).

Another example of the invention is the use of any of the compounds described herein in the preparation of a medicament for the treatment and/or prophylaxis of a disorder, disease or condition as described herein. Another example of the invention is the use of any of the compounds described herein in the preparation of a medicament for the treatment and/or prophylaxis of a thromboembolic disorder, an inflammatory disorder or a disease or condition in which plasma kallikrein activity is implicated.

Another example of the invention is the use of any of the compounds described herein in the preparation of a medicament for the treatment and/or prophylaxis of a thromboembolic disorder selected from the group consisting of (a) arterial cardiovascular thromboembolic disorders, (b) venous cardiovascular thromboembolic disorders, (c) arterial cerebrovascular thromboembolic disorders, and (d) venous cerebrovascular thromboembolic disorders. Another example of the invention is the use of any of the compounds described herein in the preparation of a medicament for the treatment and/or prophylaxis of (a) unstable angina, (b) an acute coronary syndrome, (c) atrial fibrillation, (d) first myocardial infarction, (e) recurrent myocardial infarction, (f) ischemic sudden death, (g) transient ischemic attack, (h) stroke, (i) atherosclerosis, (j) peripheral occlusive arterial disease, (k) venous thrombosis, (l) deep vein thrombosis, (m) thrombophlebitis, (n) arterial embolism, (o) coronary arterial thrombosis, (p) cerebral arterial thrombosis, (q) cerebral embolism, (r) kidney embolism, (s) pulmonary embolism, or (t) thrombosis resulting from medical implants, devices, or procedures in which blood is exposed to an artificial surface that promotes thrombosis. Another example of the invention is the use of any of the compounds described herein in the preparation of a medicament for the treatment and/or prophylaxis of: (a) hereditary angioedema (HAE) or (b) diabetic macular edema (DME).

Another example of the invention is the use of any of the compounds described herein for use in a method for treating a thromboembolic, inflammatory or a disease or condition in which plasma kallikrein activity is implicated as described herein, in a subject in need thereof.

Another example of the invention is the use of any of the compounds described herein for use in a method for the treatment and/or prophylaxis of (a) arterial cardiovascular thromboembolic disorders, (b) venous cardiovascular thromboembolic disorders, (c) arterial cerebrovascular thromboembolic disorders, or (d) venous cerebrovascular thromboembolic disorders, in a subject in need thereof. Another example of the invention is the use of any of the compounds described herein for use in a method for the treatment and/or prophylaxis of (a) unstable angina, (b) an acute coronary syndrome, (c) atrial fibrillation, (d) first myocardial infarction, (e) recurrent myocardial infarction, (f) ischemic sudden death, (g) transient ischemic attack, (h) stroke, (i) atherosclerosis, (j) peripheral occlusive arterial disease, (k) venous thrombosis, (l) deep vein thrombosis, (m) thrombophlebitis, (n) arterial embolism, (o) coronary arterial thrombosis, (p) cerebral arterial thrombosis, (q) cerebral embolism, (r) kidney embolism, (s) pulmonary embolism, or (t) thrombosis resulting from medical implants, devices, or procedures in which blood is exposed to an artificial surface that promotes thrombosis, in a subject in need thereof. Another example of the invention is the use of any of the compounds described herein for use in a method for the treatment and/or prophylaxis of (a) hereditary angioedema (HAE) or (b) diabetic macular edema (DME), in a subject in need thereof.

In another example, the present invention is directed to a compound as described herein, for use in a method for the treatment and/or prophylaxis of disorders, diseases or conditions as described herein, in a subject in need thereof. In another example, the present invention is directed to a compound as described herein, for use in a method for the treatment and/or prophylaxis of a thromboembolic, inflammatory disorder, or a disease or condition in which plasma kallikrein activity is implicated, as described herein, in a subject in need thereof.

In another example, the present invention is directed to a compound as described herein, for use in methods for the treatment and/or prophylaxis of thromboembolic disorder, such as arterial cardiovascular thromboembolic disorders, venous cardiovascular thromboembolic disorders, arterial cerebrovascular thromboembolic disorders, and venous cerebrovascular thromboembolic disorders, in a subject in need thereof. In another example, the present invention is directed to a compound as described herein, for use in methods for the treatment and/or prophylaxis of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis, in a subject in need thereof. In another example, the present invention is directed to a compound as described herein, for use in a method for the treatment and/or prophylaxis of hereditary angioedema (HAE) or diabetic macular edema (DME), in a subject in need thereof.

DETAILED DESCRIPTION OF THE INVENTION 1. 7,8-Dihydrobenzo[e]pyrido[3,4-c]azocine-2,5(3H, 6H)-diones Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and causing a heart attack or stroke. Thromboembolic disorders are the leading cause of mortality and disability in the industrialized world.

Blood clotting is a process of control of the bloodstream essential for the survival of mammals. The process of clotting, and the subsequent dissolution of the clot after wound healing has taken place, commences after vascular injury, and can be divided into four phases. The first phase, vasoconstriction or vasocontraction, can cause a decrease in blood loss in the injured area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting Factor X is activated. The activated Factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue injury or an injury is the result of the extrinsic pathway. Both pathways comprise a relatively large number of proteins, which are known as clotting factors. The intrinsic pathway requires the clotting Factors V, VIII, IX, X, XI and XII and also prekallikrein, high molecular weight kininogen, calcium ions and phospholipids from platelets.

Factor XIa, a plasma serine protease involved in the regulation of blood coagulation, is initiated in vivo by the binding of tissue Factor (TF) to factor VII (FVII) to generate Factor VIIa (FVIIa). The resulting TF:FVIIa complex activates Factor IX (FIX) and Factor X (FX) that leads to the production of Factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007)). The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Factor XIa plays a key role in propagating this amplification loop. Epidemiological studies showed that increased circulating FXI levels in humans have been associated with increased risk for venous and arterial thrombosis, including stroke (se Quan et al. supra). In contrast, patients with congenital FXI deficiency (hemophilia C) are protected from ischemic stroke and venous thromboembolism. Therefore, Factor XIa is an attractive target for antithrombotic therapy.

In addition to stimulation via tissue factor, the coagulation system can be activated particularly on negatively charged surfaces, which include not only surface structures of foreign cells (e.g. bacteria) but also artificial surfaces such as vascular prostheses, stents and extracorporeal circulation. On the surface, initially Factor XII (FXII) is activated to Factor XIIa which subsequently activates Factor XI, attached to cell surfaces, to Factor XIa. This leads to further activation of the coagulation cascade as described above. In addition, Factor XIIa also activates bound plasma prokallikrein to plasma kallikrein (PK) which, in a potentiation loop, leads to further Factor XII activation, overall resulting in amplification of the initiation of the coagulation cascade. In addition, PK is an important bradykinin-releasing protease which leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

The present invention is directed to compounds of formula (I)

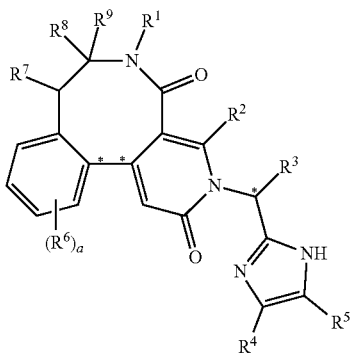

wherein a, $R^1$, $R^2$, $R^3$, $R^4$, $R^5$, $R^6$, $R^8$, $R^9$, etc. are as described herein; and stereoisomers, isotopologues, isotopomers, and pharmaceutically acceptable salts thereof. The compounds of the present invention are useful for the treatment and/or prophylaxis of thromboembolic disorders, inflammatory disorders and diseases or conditions in which plasma kallikrein activity is implicated.

In an embodiment, the present invention is directed to a compound of formula (I) which is a compound of formula (I-A)

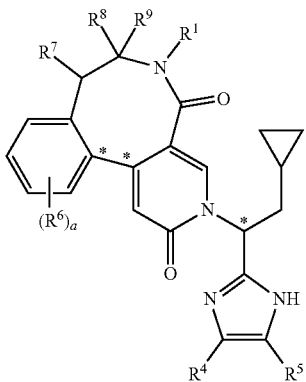

$R^1$ is selected from the group consisting of hydrogen, $C_{1-2}$ alkyl, —($C_{1-2}$ alkylene)-OH and —($C_{1-2}$ alkylene)-O—($C_{1-2}$ alkyl);
$R^2$ is hydrogen and $R^3$ is cyclopropyl-methyl-;
$R^4$ is selected from the group consisting of hydrogen and halogen;
$R^5$ is selected from the group consisting of phenyl, heteroaryl and pyridin-4-yl-1-oxide; wherein the phenyl or heteroaryl is optionally substituted with one or more substituents independently selected from the group consisting of halogen, hydroxy, oxo, $C_{1-4}$ alkyl, hydroxy substituted $C_{1-4}$ alkyl, $NR^AR^B$ and —NH—C(O)—($C_{1-4}$alkyl); and wherein $R^A$ and $R^B$ are each independently selected from the group consisting of hydrogen and $C_{1-2}$ alkyl;
a is an integer from 0 to 3;
each $R^6$ is independently selected from the group consisting of chloro, fluoro and methyl;
$R^7$ is hydrogen, and $R^8$ and $R^9$ are each independently selected from the group consisting of hydrogen, $C_{1-4}$ alkyl, and $C_{1-4}$ alkoxy;
alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl, cyclopent-1,1-diyl, and cyclohex-1,1-yl;
alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;
and stereoisomers, isotopologues, isotopomers, and pharmaceutically acceptable salts thereof. In some embodiments, the present invention is directed to a compound of formula (I) which is a compound of formula (I-B)

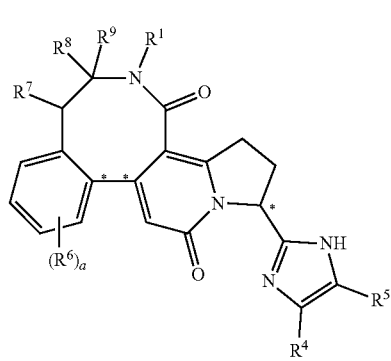

$R^1$ is selected from the group consisting of hydrogen, $C_{1-2}$ alkyl, —($C_{1-2}$ alkylene)-OH and —($C_{1-2}$ alkylene)-O—($C_{1-2}$ alkyl);
$R^2$ and $R^3$ are taken together with the carbon atoms to which they are bound to form

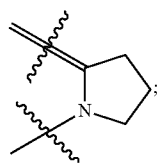 [SMILES: *N1CCCC1=*]

$R^4$ is selected from the group consisting of hydrogen and halogen;

$R^5$ is selected from the group consisting of phenyl, heteroaryl and pyridin-4-yl-1-oxide; wherein the phenyl or heteroaryl is optionally substituted with one or more substituents independently selected from the group consisting of halogen, hydroxy, oxo, $C_{1-4}$ alkyl, hydroxy substituted $C_{1-4}$alkyl, $NR^A R^B$ and —NH—C(O)—($C_{1-4}$alkyl); and wherein $R^A$ and $R^B$ are each independently selected from the group consisting of hydrogen and $C_{1-2}$ alkyl;

a is an integer from 0 to 3;

each $R^6$ is independently selected from the group consisting of chloro, fluoro and methyl;

$R^7$ is hydrogen, and $R^B$ and $R^9$ are each independently selected from the group consisting of hydrogen, $C_{1-4}$ alkyl, and $C_{1-4}$ alkoxy;

alternatively, $R^7$ is hydrogen, and $R^B$ and $R^9$ are taken together with the carbon atom to which they are bound to form a ring structure selected from the group consisting of cycloprop-1,1-diyl, cyclobut-1,1-diyl, cyclopent-1,1-diyl, and cyclohex-1,1-yl;

alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;

and stereoisomers, isotopologues, isotopomers, and pharmaceutically acceptable salts thereof.

In some embodiments, the present invention is directed to compounds of formula (I) wherein $R^1$ is selected from the group consisting of hydrogen, $C_{1-2}$ alkyl, —($C_{1-2}$ alkylene)-OH and —($C_{1-2}$ alkylene)-O—($C_{1-2}$ alkyl); $R^2$ is hydrogen and $R^3$ is cyclopropyl-methyl-;

alternatively, $R^2$ and $R^3$ are taken together with the carbon atoms to which they are bound to form

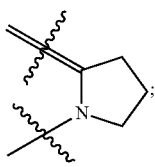

$R^4$ is selected from the group consisting of hydrogen, fluoro and chloro;

$R^5$ is selected from the group consisting of phenyl, nitrogen containing heteroaryl and pyridin-4-yl-1-oxide; wherein the phenyl or heteroaryl is optionally substituted with one to two substituents independently selected from the group consisting of halogen, oxo, $C_{1-2}$ alkyl, hydroxy substituted $C_{1-2}$alkyl, $NR^A R^B$ and —NH—C(O)—($C_{1-2}$alkyl); wherein $R^A$ and $R^B$ are each independently selected from the group consisting of hydrogen and $C_{1-2}$ alkyl;

a is an integer from 1 to 2;

each $R^6$ is independently selected from the group consisting of chloro and fluoro;

$R^7$ is hydrogen, and $R^B$ and $R^9$ are the same and selected from the group consisting of hydrogen, $C_{1-2}$alkyl, and $C_{1-2}$alkoxy;

alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl, and cyclopent-1,1-diyl;

alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;

and stereoisomers, isotopologues, isotopomers, and pharmaceutically acceptable salts thereof.

In some embodiments, the present invention is directed to compounds of formula (I) wherein $R^1$ is selected from the group consisting of hydrogen, methyl, 2-hydroxy-ethyl- and 2-methoxy-ethyl-;

$R^2$ is hydrogen and $R^3$ is cyclopropyl-methyl-;

alternatively, $R^2$ and $R^3$ are taken together with the carbon atoms to which they are bound to form

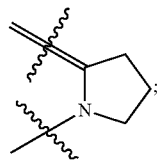 [SMILES: *N1CCCC1=*]

$R^4$ is selected from the group consisting of hydrogen and fluoro;

$R^5$ is selected from the group consisting of 4-fluoro-phenyl, 4-(methoxy-carbonyl-amino)-phenyl, 1-methyl-imidazol-5-yl, 1-methyl-1,2,3-triazol-5-yl, 1-methyl-pyrimidin-4-yl-6-one, 2-fluoro-6-amino-pyridin-3-yl, 2-chloro-6-amino-pyridin-3-yl, 1-methyl-pyridin-3-yl-6-one, pyridin-4-yl, 2-chloro-6-amino-pyridin-4-yl, 2-(hydroxy-methyl)-3-fluoro-pyridin-4-yl, 2-fluoro-6-amino-pyridin-4-yl, 1-methyl-pyridin-4-yl-6-one, pyridin-4-yl-1-oxide, 2-chloro-6-amino-pyridin-5-yl, indol-5-yl, indazol-5-yl, benzimidazol-5-yl, benzothiazol-5-yl, 2-methyl-benzothiazol-5-yl, benzo[1,2,3]thiadiazol-5-yl, imidazo[1,2-a]pyridin-7-yl, 3-bromo-imidazo[1,2-a]pyridin-7-yl and [1,2,4]triazolo[4,3-a]pyridin-7-yl;

a is an integer from 1 to 2;

each $R^6$ is independently selected from the group consisting of 11-chloro and 12-fluoro;

$R^7$ is hydrogen, and $R^8$ and $R^9$ are the same and selected from the group consisting of hydrogen, and methyl;

alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl and cyclopent-1,1-diyl;

alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;

and stereoisomers an pharmaceutically acceptable salts thereof.

In some embodiments, the present invention is directed to compounds of formula (I) wherein $R^1$ is selected from the group consisting of hydrogen, methyl, and 2-hydroxy-ethyl-;

$R^2$ is hydrogen and $R^3$ is cyclopropyl-methyl-;

alternatively, $R^2$ and $R^3$ are taken together with the carbon atoms to which they are bound to form

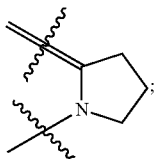

$R^4$ is selected from the group consisting of hydrogen and fluoro;
$R^5$ is selected from the group consisting of 4-fluoro-phenyl, 4-(methoxy-carbonyl-amino)-phenyl, 2-fluoro-6-amino-pyridin-3-yl, 2-chloro-6-amino-pyridin-3-yl, pyridin-4-yl, 2-chloro-6-amino-pyridin-4-yl, 2-(hydroxy-methyl)-3-fluoro-pyridin-4-yl, 2-fluoro-6-amino-pyridin-4-yl, 1-methyl-pyridin-4-yl-6-one, indol-5-yl, indazol-5-yl, benzimidazol-5-yl, benzothiazol-5-yl, 2-methyl-benzothiazol-5-yl, benzo[1,2,3]thiadiazol-5-yl, imidazo[1,2-a]pyridin-7-yl, 3-bromo-imidazo[1,2-a]pyridin-7-yl and [1,2,4]triazolo[4,3-a]pyridin-7-yl;
a is an integer from 1 to 2;
each $R^6$ is independently selected from the group consisting of 11-chloro and 12-fluoro;
$R^7$ is hydrogen, and $R^8$ and $R^9$ are the same and selected from the group consisting of hydrogen, and methyl;
alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl and cyclopent-1,1-diyl;
alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;
and pharmaceutically acceptable salts thereof.

In some embodiments, the present invention is directed to compounds of formula (I) wherein
$R^1$ is selected from the group consisting of hydrogen, and methyl;
$R^2$ is hydrogen and $R^3$ is cyclopropyl-methyl-;
alternatively, $R^2$ and $R^3$ are taken together with the carbon atoms to which they are bound to form

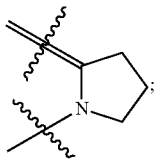

$R^4$ is selected from the group consisting of hydrogen and fluoro;
$R^5$ is selected from the group consisting of 4-(methoxy-carbonyl-amino)-phenyl, 2-fluoro-6-amino-pyridin-3-yl, 2-chloro-6-amino-pyridin-3-yl, 2-chloro-6-amino-pyridin-4-yl, 2-fluoro-6-amino-pyridin-4-yl, indol-5-yl, indazol-5-yl, benzimidazol-5-yl, benzothiazol-5-yl, 2-methyl-benzothiazol-5-yl, benzo[1,2,3]thiadiazol-5-yl, and imidazo[1,2-a]pyridin-7-yl;
a is an integer from 1 to 2;
each $R^6$ is independently selected from the group consisting of 11-chloro and 12-fluoro;
$R^7$ is hydrogen, and $R^8$ and $R^9$ are the same and selected from the group consisting of hydrogen, and methyl;
alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl and cyclopent-1,1-diyl;
and pharmaceutically acceptable salts thereof.

In some embodiments, the present invention is directed to compounds of formula (I) wherein
$R^1$ is hydrogen;
$R^2$ is hydrogen and $R^3$ is cyclopropyl-methyl-;
alternatively, $R^2$ and $R^3$ are taken together with the carbon atoms to which they are bound to form

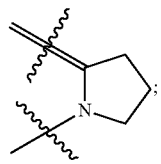 [SMILES: *N1CCCC1=*]

$R^4$ is hydrogen;
$R^5$ is selected from the group consisting of 4-(methoxy-carbonyl-amino)-phenyl, 2-fluoro-6-amino-pyridin-3-yl, 2-chloro-6-amino-pyridin-3-yl, 2-fluoro-6-amino-pyridin-4-yl, indazol-5-yl, benzimidazol-5-yl, and benzothiazol-5-yl;
a is 2;
one $R^6$ is 11-chloro and the other $R^6$ is 12-fluoro;
$R^7$ is hydrogen, and $R^8$ and $R^9$ are each methyl;
alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl and cyclopent-1,1-diyl;
and pharmaceutically acceptable salts thereof.

In some embodiments, the present invention is directed to compounds of formula (I) wherein $R^1$ is selected from the group consisting of hydrogen, $C_{1-2}$ alkyl, —($C_{1-2}$ alkylene)-OH and —($C_{1-2}$ alkylene)-O—($C_{1-2}$ alkyl).

In some embodiments, the present invention is directed to compounds of formula (I) wherein $R^1$ is selected from the group consisting of hydrogen, methyl, 2-hydroxy-ethyl- and 2-methoxy-ethyl-. In some embodiments, the present invention is directed to compounds of formula (I) wherein $R^1$ is selected from the group consisting of hydrogen, methyl, and 2-hydroxy-ethyl-. In some embodiments, the present invention is directed to compounds of formula (I) wherein $R^1$ is selected from the group consisting of hydrogen, and methyl. In some embodiments, the present invention is directed to compounds of formula (I) wherein $R^1$ is hydrogen.

In some embodiments, the present invention is directed to compounds of formula (I) wherein $R^4$ is hydrogen. In some embodiments, the present invention is directed to compounds of formula (I) wherein $R^4$ is halogen. In some embodiments, the present invention is directed to compounds of formula (I) wherein $R^4$ is selected from the group consisting of hydrogen, fluoro and chloro. In some embodiments, the present invention is directed to compounds of formula (I) wherein $R^4$ is selected from the group consisting of hydrogen and fluoro. In some embodiments, the present invention is directed to compounds of formula (I) wherein $R^4$ is fluoro.

In some embodiments, the present invention is directed to compounds of formula (I) wherein $R^5$ is selected from the group consisting of phenyl, nitrogen containing heteroaryl and pyridin-4-yl-1-oxide; wherein the phenyl or heteroaryl is optionally substituted with one to two substituents independently selected from the group consisting of halogen, oxo, $C_{1-2}$ alkyl, hydroxy substituted $C_{1-2}$ alkyl, $NR^A R^B$ and —NH—C(O)—($C_{1-2}$alkyl); wherein $R^A$ and $R^B$ are each independently selected from the group consisting of hydrogen and $C_{1-2}$ alkyl.

In some embodiments, the present invention is directed to compounds of formula (I) wherein $R^5$ is selected from the group consisting of 4-fluoro-phenyl, 4-(methoxy-carbonyl-amino)-phenyl, 1-methyl-imidazol-5-yl, 1-methyl-1,2,3-triazol-5-yl, 1-methyl-pyrimidin-4-yl-6-one, 2-fluoro-6-amino-pyridin-3-yl, 2-chloro-6-amino-pyridin-3-yl, 1-methyl-pyridin-3-yl-6-one, pyridin-4-yl, 2-chloro-6-amino-pyridin-4-yl, 2-(hydroxy-methyl)-3-fluoro-pyridin-4-yl, 2-fluoro-6-amino-pyridin-4-yl, 1-methyl-pyridin-4-yl-6-one, pyridin-4-yl-1-oxide, 2-chloro-6-amino-pyridin-5-yl, indol-5-yl, indazol-5-yl, benzimidazol-5-yl, benzothiazol-5-yl, 2-methyl-benzothiazol-5-yl, benzo[1,2,3]thiadiazol-5-yl, imidazo[1,2-a]pyridin-7-yl, 3-bromo-imidazo[1,2-a]pyridin-7-yl and [1,2,4]triazolo[4,3-a]pyridin-7-yl.

In some embodiments, the present invention is directed to compounds of formula (I) wherein $R^5$ is selected from the group consisting of 4-fluoro-phenyl, 4-(methoxy-carbonyl-amino)-phenyl, 2-fluoro-6-amino-pyridin-3-yl, 2-chloro-6-amino-pyridin-3-yl, pyridin-4-yl, 2-chloro-6-amino-pyridin-4-yl, 2-(hydroxy-methyl)-3-fluoro-pyridin-4-yl, 2-fluoro-6-amino-pyridin-4-yl, 1-methyl-pyridin-4-yl-6-one, indol-5-yl, indazol-5-yl, benzimidazol-5-yl, benzothiazol-5-yl, 2-methyl-benzothiazol-5-yl, benzo[1,2,3]thiadiazol-5-yl, imidazo[1,2-a]pyridin-7-yl, 3-bromo-imidazo[1,2-a]pyridin-7-yl and [1,2,4]triazolo[4,3-a]pyridin-7-yl.

In some embodiments, the present invention is directed to compounds of formula (I) wherein $R^5$ is selected from the group consisting of 4-(methoxy-carbonyl-amino)-phenyl, 2-fluoro-6-amino-pyridin-3-yl, 2-chloro-6-amino-pyridin-3-yl, 2-chloro-6-amino-pyridin-4-yl, 2-fluoro-6-amino-pyridin-4-yl, indol-5-yl, indazol-5-yl, benzimidazol-5-yl, benzothiazol-5-yl, 2-methyl-benzothiazol-5-yl, benzo[1,2,3]thiadiazol-5-yl, and imidazo[1,2-a]pyridin-7-yl.

In some embodiments, the present invention is directed to compounds of formula (I) wherein $R^5$ is selected from the group consisting of 4-(methoxy-carbonyl-amino)-phenyl, 2-fluoro-6-amino-pyridin-3-yl, 2-chloro-6-amino-pyridin-3-yl, 2-fluoro-6-amino-pyridin-4-yl, indazol-5-yl, benzimidazol-5-yl, and benzothiazol-5-yl.

In some embodiments, the present invention is directed to compounds of formula (I) wherein a is an integer from 0 to 2. In some embodiments, the present invention is directed to compounds of formula (I) wherein a is an integer from 1 to 2. In some embodiments, the present invention is directed to compounds of formula (I) wherein a is 0. In some embodiments, the present invention is directed to compounds of formula (I) wherein a is 1. In some embodiments, the present invention is directed to compounds of formula (I) wherein a is 2.

In some embodiments, the present invention is directed to compounds of formula (I) wherein each $R^6$ is independently selected from the group consisting of chloro and fluoro. In some embodiments, the present invention is directed to compounds of formula (I) wherein $R^6$ is 11-chloro. In some embodiments, the present invention is directed to compounds of formula (I) wherein $R^6$ is 12-fluoro. In some embodiments, the present invention is directed to compounds of formula (I) wherein a is 2, one $R^6$ is 11-chloro and the other $R^6$ is 12-fluoro.

In some embodiments, the present invention is directed to compounds of formula (I) wherein $R^7$ is hydrogen. In some embodiments, the present invention is directed to compounds of formula (I) wherein $R^7$, $R^8$ and $R^9$ are each hydrogen.

In some embodiments, the present invention is directed to compounds of formula (I) wherein $R^7$ is hydrogen, and $R^8$ and $R^9$ are selected from the group consisting of hydrogen, $C_{1-2}$alkyl, and $C_{1-2}$ alkoxy. In some embodiments, the present invention is directed to compounds of formula (I) wherein $R^7$ is hydrogen, and $R^8$ and $R^9$ are the same and selected from the group consisting of hydrogen, $C_{1-2}$ alkyl, and $C_{1-2}$ alkoxy. In some embodiments, the present invention is directed to compounds of formula (I) wherein $R^7$ is hydrogen, and $R^8$ and $R^9$ are the same and selected from the group consisting of hydrogen, and $C_{1-2}$ alkyl. In some embodiments, the present invention is directed to compounds of formula (I) wherein $R^7$ is hydrogen, and wherein $R^8$ and $R^9$ are each methyl.

In some embodiments, the present invention is directed to compounds of formula (I) wherein $R^8$ and $R^9$ are taken together with the carbon atoms to which they are bound to form cycloprop-1,1-diyl, cyclobut-1,1-diyl and cyclopent-1,1-diyl. In some embodiments, the present invention is directed to compounds of formula (I) wherein $R^7$ is hydrogen and wherein $R^8$ and $R^9$ are taken together with the carbon atoms to which they are bound to form a ring structure selected from the group consisting of cycloprop-1,1-diyl, cyclobut-1,1-diyl and cyclopent-1,1-diyl.

In some embodiments, the present invention is directed to compounds of formula (I) wherein, $R^7$ is hydrogen, and $R^8$ and $R^9$ are taken together with the carbon atom to which they are bound to form cycloprop-1,1-diyl. In some embodiments, the present invention is directed to compounds of formula (I) wherein, $R^7$ is hydrogen, and $R^8$ and $R^9$ are taken together with the carbon atom to which they are bound to form cyclobut-1,1-diyl. In some embodiments, the present invention is directed to compounds of formula (I) wherein, $R^7$ is hydrogen, and $R^8$ and $R^9$ are taken together with the carbon atom to which they are bound to form cyclopent-1,1-diyl.

In some embodiments, the present invention is directed to compounds of formula (I) wherein $R^9$ is hydrogen and wherein $R^7$ and $R^8$ are taken together with the carbon atoms to which they are bound to form a ring structure selected from the group consisting of phen-1,2-diyl and pyridin-3,4-diyl. In some embodiments, the present invention is directed to compounds of formula (I) wherein $R^7$ and $R^8$ are taken together with the carbon atoms to which they are bound to form phen-1,2-diyl. In some embodiments, the present invention is directed to compounds of formula (I) wherein $R^7$ and $R^8$ are taken together with the carbon atoms to which they are bound to form pyridin-3,4-diyl.

In an embodiment, the present invention is directed to a compound of formula (I) selected from the group consisting of (R*)-12-(5-(1H-benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S*)-12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(R*)-12-(5-(6-amino-2-chloropyridin-3-yl)-1H-imidazol-2-yl)-7-chloro-8-fluoro-3,4,13,14-tetrahydrobenzo[5,6]azocino[4,3-g]indolizine-1,10(2H,12H)-dione;

(S*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione;

(S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclobutane]-1,10(4H,12H)-dione;

(S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopentane]-1,10(4H,12H)-dione;

(S*)-12-(5-(6-amino-2-fluoropyridin-3-yl)-1H-imidazol-2-yl)-7-chloro-8-fluoro-2-methyl-13,14-dihydro-2H-spiro[benzo[5,6]azocino[4,3-g]indolizine-3,1'-cyclopropane]-1,10(4H,12H)-dione;

methyl (S)-(4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)phenyl)carbamate;

and pharmaceutically acceptable salts thereof.

In an embodiment, the present invention is directed to a compound of formula (I) selected from the group consisting of (R*)-12-(5-(1H-benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S*)-12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(R*)-12-(5-(6-amino-2-chloropyridin-3-yl)-1H-imidazol-2-yl)-7-chloro-8-fluoro-3,4,13,14-tetrahydrobenzo[5,6]azocino[4,3-g]indolizine-1,10(2H,12H)-dione;

and pharmaceutically acceptable salts thereof.

In some embodiments, the present invention is directed to compounds of formula (I) wherein the stereocenter denoted with the "*" (more particularly the stereocenter at the carbon atom bound to the $R^3$ group, denoted as "$R^3$ Stereo" in the Tables below) is present as a racemic mixture. In some embodiments, the present invention is directed to compounds of formula (I) wherein the stereocenter denoted with the "*" (more particularly the stereocenter at the carbon atom bound to the $R^3$ group, denoted as "$R^3$ Stereo" in the Tables below) is present in an enantiomeric excess of the R-enantiomer. In some embodiments, the present invention is directed to compounds of formula (I) wherein the stereocenter denoted with the "*" (more particularly the stereocenter at the carbon atom bound to the $R^3$ group, denoted as "$R^3$ Stereo" in the Tables below) is present in an enantiomeric excess of the S-enantiomer.

In some embodiments, the present invention is directed to compounds of formula (I) is present in an enantiomeric excess of one of the R- or S-enantiomers (at the stereocenter denoted with the "*", more particularly the stereocenter at the carbon atom bound to the $R^3$ group, denoted as "$R^3$ Stereo" in the Tables below). In some embodiments of the present invention, the compound of formula (I) is present in an enantiomeric excess of one of the R- or S-enantiomers (at the stereocenter denoted with the "*", more particularly the stereocenter at the carbon atom bound to the $R^3$ group, denoted as "$R^3$ Stereo" in the Tables below) of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably the compound of formula (I) is present in an enantiomeric excess of one of the R- or S-enantiomers (at the stereocenter denoted with the "*", more particularly the stereocenter at the carbon atom bound to the $R^3$ group, denoted as "$R^3$ Stereo" in the Tables below) of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) wherein the carbon atoms denoted with the "*" in the tricyclic ring core structure (denoted as "Ring Stereo" in the Tables below) are present as as a racemic mixture of atropisomers. In some embodiments, the present invention is directed to compounds of formula (I) wherein the carbon atoms denoted with the "*" in the tricyclic ring core structure (denoted as "Ring Stereo" in the Tables below) are present in an excess of the R,R- or R*,R*-atropisomer. In some embodiments, the present invention is directed to compounds of formula (I) wherein the carbon atoms denoted with the "*" in the tricyclic ring core structure (denoted as "Ring Stereo" in the Tables below) are present in an excess of the S,S- or S*,S*-atropisomer.

In some embodiments of the present invention, the compound of formula (I) is present in an excess of the R,R-, R*,R*-, S,S- or S*,S*-atropisomers (at the carbon atoms of the tricyclic ring core denoted with the "*", denoted as "Ring Stereo" in the Tables below). In some embodiments of the present invention, the compound of formula (I) is present in an excess of one of the R,R-, R*,R*-, S,S- or S*,S*-atropisomers (at the carbon atoms of the tricyclic ring core denoted with the "*", denoted as "Ring Stereo" in the Tables below) of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably the compound of formula (I) is present in an excess of one of the R,R-, R*,R*-, S,S- or S*,S*-atropisomer (at the carbon atoms of the tricyclic ring core denoted with the "*", denoted as "Ring Stereo" in the Tables below) of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

Additional embodiments of the present invention include those wherein the substituents selected for one or more of the variables defined herein (i.e. a, $R^1$, $R^2$, $R^3$, $R^4$, $R^5$, $R^6$, $R^8$, $R^9$, etc.) are independently selected to be any individual substituent or any subset of substituents selected from the complete list as defined herein. Additional embodiments of the present invention include those wherein the substituents selected for one or more of the variables defined herein (a, $R^1$, $R^2$, $R^3$, $R^4$, $R^5$, $R^6$, $R^8$, $R^9$, etc.) are independently selected to correspond to any of the embodiments as defined herein.

In additional embodiments, the present invention is directed to any single compound or subset of compounds independently selected from the list of representative compounds in Tables 1 and 2, below.

Representative compounds of the present invention are as listed in Tables 1 and 2, below. Unless otherwise noted, wherein one or more $R^6$ group(s) are listed separately from the complete name of a compound of formula (I) (for example, as in Table 1-2 below), the binding position of said $R^6$ group(s) shall use the following numbering scheme:

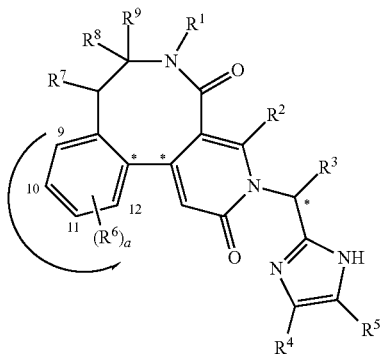

such that the $R^6$ substituents are bound at the 9-, 10-, 11- and/or 12-positions of the tricyclic core structure. One skilled in the art will recognize that IUPAC or other name(s) for the compounds of formula (I) (for example, as listed in the Examples) may number the binding position of the $R^6$ substituents differently, as the numbering used in creating the name will depend on the identity and priorities of all the substituent group(s) present in the named compound of formula (I).

The column headed "$R^3$ Stereo" lists the stereo-orientation at the starred "*" carbon atom bound to the $R^3$ substituent group. Compounds prepared as racemates at this position are denoted as "RAC". The S*- and R*-designations are intended to indicate that although the compound was prepared in an enantiomeric excess of one of the stereo-isomers, the exact stereo-configuration of the stereo-center was not determined; whereas the designations S- and R- are intended to indicate that the compound was prepared in an enantiomeric excess of the corresponding S- or R-stereo-configuration.

The column headed "Ring Stereo" lists the stereo-orientation at the starred "*" carbon atoms of the tricyclic core structure. Compounds prepared as racemic mixtures of the atropisomers are denoted as "RAC". The S*,S* and R*, R* designations are intended to indicate that although the compound was prepared in an excess of one of the corresponding atropisomers, the exact stereo-configuration was not determined.

TABLE 1

Representative Compounds of Formula (I)

| ID No. | Ring Stereo | $R^1$ | $R^3$ Stereo* | $R^5$ | $(R^6)_a$ | $R^8 + R^9$ taken together |
|---|---|---|---|---|---|---|
| 1 | RAC | H | RAC | 2-fluoro-6-amino-pyridin-3-yl | 11-chloro | cycloprop-1,1-diyl |

TABLE 1-continued

Representative Compounds of Formula (I)

| ID No. | Ring Stereo | R¹ | R³ Stereo* | R⁵ | (R⁶)ₐ | R⁸ + R⁹ taken together |
|---|---|---|---|---|---|---|
| 2 | RAC | H | RAC | 2-fluoro-6-amino-pyridin-3-yl | 11-chloro | cycloprop-1,1-diyl |
| 3 | RAC | H | RAC | 2-(hydroxy-methyl)-3-fluoro-pyridin-4-yl | 11-chloro, 12-fluoro | cycloprop-1,1-diyl |
| 4 | RAC | H | S* | 2-methyl-benzothiazol-5-yl | 11-chloro, 12-fluoro | cycloprop-1,1-diyl |
| 5 | RAC | H | R* | 2-methyl-benzothiazol-5-yl | 11-chloro, 12-fluoro | cycloprop-1,1-diyl |
| 6 | RAC | H | R* | benzimidazol-5-yl | 11-chloro, 12-fluoro | cycloprop-1,1-diyl |
| 7 | RAC | H | S* | imidazo[1,2-a]pyridin-7-yl | 11-chloro, 12-fluoro | cycloprop-1,1-diyl |
| 8 | RAC | H | R* | imidazo[1,2-a]pyridin-7-yl | 11-chloro, 12-fluoro | cycloprop-1,1-diyl |
| 9 | R*, R* | 2-hydroxy-ethyl | S* | 2-fluoro-6-amino-pyridin-3-yl | 11-chloro, 12-fluoro | cycloprop-1,1-diyl |
| 10 | R*, R* | 2-hydroxy-ethyl | R* | 2-fluoro-6-amino-pyridin-3-yl | 11-chloro, 12-fluoro | cycloprop-1,1-diyl |
| 11 | S*, S* | 2-hydroxy-ethyl | S* | 2-fluoro-6-amino-pyridin-3-yl | 11-chloro, 12-fluoro | cycloprop-1,1-diyl |
| 12 | S*, S* | 2-hydroxy-ethyl | R* | 2-fluoro-6-amino-pyridin-3-yl | 11-chloro, 12-fluoro | cycloprop-1,1-diyl |
| 13 | R*, R* | H | S* | indol-5-yl | 11-chloro, 12-fluoro | cycloprop-1,1-diyl |
| 14 | R*, R* | H | R* | indol-5-yl | 11-chloro, 12-fluoro | cycloprop-1,1-diyl |
| 15 | RAC | H | S* | [1,2,4]triazolo[4,3-a]pyridin-7-yl | 11-chloro, 12-fluoro | cycloprop-1,1-diyl |
| 16 | S*, S* | H | S* | indol-5-yl | 11-chloro, 12-fluoro | cycloprop-1,1-diyl |
| 17 | S*, S* | H | R* | indol-5-yl | 11-chloro, 12-fluoro | cycloprop-1,1-diyl |
| 18 | RAC | H | R* | [1,2,4]triazolo[4,3-a]pyridin-7-yl | 11-chloro, 12-fluoro | cycloprop-1,1-diyl |
| 19 | RAC | H | R* | indazol-5-yl | 11-chloro, 12-fluoro | cycloprop-1,1-diyl |
| 22 | RAC | H | R* | imidazo[1,2-a]pyridin-7-yl | 11-chloro, 12-fluoro | cycloprop-1,1-diyl |
| 23 | RAC | H | S* | imidazo[1,2-a]pyridin-7-yl | 11-chloro, 12-fluoro | cycloprop-1,1-diyl |
| 24 | RAC | 2-methoxy-ethyl | R* | 2-fluoro-6-amino-pyridin-3-yl | 11-chloro, 12-fluoro | cycloprop-1,1-diyl |
| 25 | RAC | 2-methoxy-ethyl | S* | 2-fluoro-6-amino-pyridin-3-yl | 11-chloro, 12-fluoro | cycloprop-1,1-diyl |
| 26 | RAC | H | R* | benzothiazol-5-yl | 11-chloro, 12-fluoro | cycloprop-1,1-diyl |
| 27 | RAC | H | S* | benzothiazol-5-yl | 11-chloro, 12-fluoro | cycloprop-1,1-diyl |
| 30 | RAC | H | R* | benzo[1,2,3]thiadiazol-5-yl | 11-chloro, 12-fluoro | cycloprop-1,1-diyl |

TABLE 1-continued

Representative Compounds of Formula (I)

| ID No. | Ring Stereo | R¹ | R³ Stereo* | R⁵ | (R⁶)ₐ | R⁸ + R⁹ taken together |
|---|---|---|---|---|---|---|
| 31 | RAC | H | S* | benzo[1,2,3]thiadiazol-5-yl | 11-chloro, 12-fluoro | cycloprop-1,1-diyl |
| 32 | RAC | H | S* | 2-fluoro-6-amino-pyridin-3-yl | 11-chloro, 12-fluoro | cyclobut-1,1-diyl |
| 33 | RAC | H | R* | 2-fluoro-6-amino-pyridin-3-yl | 11-chloro, 12-fluoro | cyclobut-1,1-diyl |
| 34 | RAC | H | R* | 2-fluoro-6-amino-pyridin-3-yl | 11-chloro, 12-fluoro | cyclopent-1,1-diyl |
| 35 | RAC | H | S* | 2-fluoro-6-amino-pyridin-3-yl | 11-chloro, 12-fluoro | cyclopent-1,1-diyl |
| 40 | RAC | methyl | R* | 2-fluoro-6-amino-pyridin-4-yl | 11-chloro, 12-fluoro | cycloprop-1,1-diyl |
| 41 | RAC | methyl | S* | 2-fluoro-6-amino-pyridin-4-yl | 11-chloro, 12-fluoro | cycloprop-1,1-diyl |
| 42 | RAC | H | S* | 1-methyl-1,2,3-triazol-5-yl | 11-chloro, 12-fluoro | cycloprop-1,1-diyl |
| 43 | RAC | H | R* | 1-methy-1,2,3-triazol-5-yl | 11-chloro, 12-fluoro | cycloprop-1,1-diyl |
| 50 | RAC | H | S* | 1-methyl-imidazol-5-yl | 11-chloro, 12-fluoro | cycloprop-1,1-diyl |
| 51 | RAC | H | R* | 1-methyl-imidazol-5-yl | 11-chloro, 12-fluoro | cycloprop-1,1-diyl |
| 52 | RAC | H | S | 2-chloro-6-amino-pyridin-3-yl | 11-chloro, 12-fluoro | cycloprop-1,1-diyl |
| 53 | RAC | H | R* | 2-chloro-6-amino-pyridin-3-yl | 11-chloro, 12-fluoro | cycloprop-1,1-diyl |
| 54 | RAC | H | R* | 2-fluoro-6-amino-pyridin-4-yl | 11-chloro, 12-fluoro | cycloprop-1,1-diyl |
| 55 | RAC | H | S | 2-fluoro-6-amino-pyridin-4-yl | 11-chloro, 12-fluoro | cycloprop-1,1-diyl |
| 70 | RAC | H | S* | benzimidazol-5-yl | 11-chloro, 12-fluoro | cycloprop-1,1-diyl |
| 71 | RAC | H | S* | 3-bromo-imidazo[1,2-a]pyridin-7-yl | 11-chloro, 12-fluoro | cycloprop-1,1-diyl |
| 72 | RAC | H | R* | 3-bromo-imidazo[1,2-a]pyridin-7-yl | 11-chloro, 12-fluoro | cycloprop-1,1-diyl |

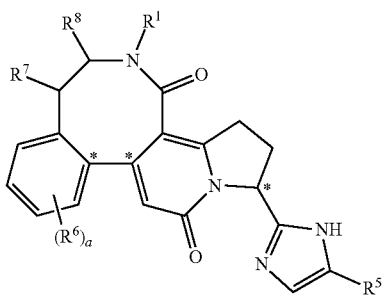

| ID No. | Ring Stereo | R¹ | R³ Stereo* | R⁵ | (R⁶)ₐ | R⁸ + R⁹ taken together |
|---|---|---|---|---|---|---|
| 36 | RAC | H | S* | 2-fluoro-6-amino-pyridin-3-yl | 11-chloro, 12-fluoro | pyridin-3,4-diyl |
| 37 | RAC | H | R* | 2-fluoro-6-amino-pyridin-3-yl | 11-chloro, 12-fluoro | pyridin-3,4-diyl |
| 38 | RAC | H | R* | 2-fluoro-6-amino-pyridin-3-yl | 11-chloro, 12-fluoro | phen-1,2-diyl |
| 39 | RAC | H | S* | 2-fluoro-6-amino-pyridin-4-yl | 11-chloro, 12-fluoro | phen-1,2-diyl |

TABLE 1-continued

Representative Compounds of Formula (I)

| ID No. | Ring Stereo | R¹ | R³ Stereo* | R⁵ | (R⁶)ₐ | R⁸ | R⁹ |
|---|---|---|---|---|---|---|---|
| 20 | R*, R* | H | S* | 2-fluoro-6-amino-pyridin-3-yl | 11-chloro, 12-fluoro | methyl | methyl |
| 21 | R*, R* | H | R* | 2-fluoro-6-amino-pyridin-3-yl | 11-chloro, 12-fluoro | methyl | methyl |
| 28 | S*, S* | H | R* | 2-fluoro-6-amino-pyridin-3-yl | 11-chloro, 12-fluoro | methyl | methyl |
| 29 | S*, S* | H | S* | 2-fluoro-6-amino-pyridin-3-yl | 11-chloro, 12-fluoro | methyl | methyl |
| 44 | RAC | H | S* | 1-methyl-1,2,3-triazol-5-yl | 11-chloro, 12-fluoro | H | H |
| 45 | RAC | H | R* | 1-methyl-1,2,3-triazol-5-yl | 11-chloro, 12-fluoro | H | H |
| 46 | RAC | H | S* | 2-fluoro-6-amino-pyridin-4-yl | 11-chloro, 12-fluoro | H | H |
| 47 | RAC | H | R* | 2-fluoro-6-amino-pyridin-4-yl | 11-chloro, 12-fluoro | H | H |
| 48 | RAC | H | R* | 2-chloro-6-amino-pyridin-4-yl | 11-chloro, 12-fluoro | H | H |
| 49 | RAC | H | S* | 2-chloro-6-amino-pyridin-5-yl | 11-chloro, 12-fluoro | H | H |

TABLE 2

Representative Compounds of Formula (I)

| ID No. | Ring Stereo | R¹ | R³ Stereo* | R⁵ | (R⁶)ₐ | R⁸ + R⁹ taken together |
|---|---|---|---|---|---|---|
| 56 | RAC | H | S* | pyridin-4-yl-1-oxide | 11-chloro, 12-fluoro | cycloprop-1,1-diyl |
| 57 | RAC | H | R* | pyridin-4-yl-1-oxide | 11-chloro, 12-fluoro | cycloprop-1,1-diyl |
| 58 | RAC | H | R* | 1-methyl-pyrimidin-4-yl-6-one | 11-chloro, 12-fluoro | cycloprop-1,1-diyl |
| 59 | RAC | H | S* | 1-methyl-pyrimidin-4-yl-6-one | 11-chloro, 12-fluoro | cycloprop-1,1-diyl |
| 60 | RAC | H | R* | 1-methyl-pyridin-3-yl-6-one | 11-chloro, 12-fluoro | cycloprop-1,1-diyl |
| 61 | RAC | H | S | 4-(methoxy-carbonyl-amino)-phenyl | 11-chloro, 12-fluoro | cycloprop-1,1-diyl |
| 62 | RAC | H | R* | 4-(methoxy-carbonyl-amino)-phenyl | 11-chloro, 12-fluoro | cycloprop-1,1-diyl |
| 63 | RAC | H | S* | 1-methyl-pyridin-3-yl-6-one | 11-chloro, 12-fluoro | cycloprop-1,1-diyl |
| 64 | RAC | H | R* | 4-fluoro-phenyl | 11-chloro, 12-fluoro | cycloprop-1,1-diyl |
| 65 | RAC | H | S* | 4-fluoro-phenyl | 11-chloro, 12-fluoro | cycloprop-1,1-diyl |
| 66 | RAC | H | R* | pyridin-4-yl | 11-chloro, 12-fluoro | cycloprop-1,1-diyl |

TABLE 2-continued

Representative Compounds of Formula (I)

| 67 | RAC | H | S  | pyridin-4-yl                  | 11-chloro, 12-fluoro | cycloprop-1,1-diyl |
| -- | --- | - | -- | ----------------------------- | -------------------- | ------------------ |
| 68 | RAC | H | R* | 1-methyl-pyridin-4-yl-6-one   | 11-chloro, 12-fluoro | cycloprop-1,1-diyl |
| 69 | RAC | H | S  | 1-methyl-pyridin-4-yl-6-one   | 11-chloro, 12-fluoro | cycloprop-1,1-diyl |

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. It is further understood that atropisomers (a specific type of stereoisomer resulting from steric or other hinderances to rotation) are also encompassed within the scope of the present invention.

Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer or stereoisomer, the diastereomer or stereoisomer is present at a diastereomeric or stereoisomeric excess of greater than or equal to about 80%, more preferably, at a diastereomeric or stereoisomeric excess of greater than or equal to about 90%, more preferably still, at a diastereomeric or stereoisomeric excess of greater than or equal to about 95%, more preferably still, at a diastereomeric or stereoisomeric excess of greater than or equal to about 98%, most preferably, at a diastereomeric or stereoisomeric excess of greater than or equal to about 99%.

In some embodiments, the present invention is directed to compounds of formula (I) in an enantiomeric excess of one of the R- or S-enantiomers (at the $R^3$ stereocenter denoted with the "*"). In some embodiments of the present invention, the compound of formula (I) is present in an enantiomeric excess of one of the R- or S-enantiomers (at the $R^3$ stereocenter denoted with the "*") of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably the compound of formula (I) is present in an enantiomeric excess of one of the R- or S-enantiomers (at the $R^3$ stereocenter denoted with the "*") of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) in a diastereomeric or stereoisomeric excess of one of the possible diastereomers or stereoisomers. In some embodiments of the present invention, the compound of formula (I) is present in a diastereomeric or stereoisomeric excess of one of the possible diastereomers or stereoisomers, of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a diastereomeric or stereoisomeric excess of one of the possible diastereomers or stereoisomers of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isotopologues" shall mean molecules that differ only in their isotopic composition. More particularly, an isotopologue of a molecule differs from the parent molecule in that it contains at least one atom which is an isotope (i.e. has a different number of neutrons from its parent atom).

For example, isotopologues of water include, but are not limited to, "light water" (HOH or $H_2O$), "semi-heavy water" with the deuterium isotope in equal proportion to protium (HDO or $^1H_2HO$), "heavy water" with two deuterium isotopes of hydrogen per molecule ($d_2O$ or $^2H_2O$), "super-heavy water" or tritiated water ($T_2O$ or $^3H_2O$), where the hydrogen atoms are replaced with tritium ($^3H$) isotopes, two heavy-oxygen water isotopologues ($H_2^{18}O$ and $H_2^{17}O$) and isotopologues where the hydrogen and oxygen atoms may each independently be replaced by isotopes, for example the doubly labeled water isotopologue $d_2^{18}O$.

It is intended that within the scope of the present invention, any one or more element(s), in particular when mentioned in relation to a compound of formula (I), shall comprise all isotopes and isotopic mixtures of said element(s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise one or more radioactive isotope(s) selected from the group of $^3H$, $^{11}C$, $^{18}F$, $^{122}I$, $^{123}I$, $^{125}I$, $^{131}I$, $^{76}Br$, $^{76}Br$, $^{77}Br$ and $^{82}Br$. Preferably, the radioactive isotope is selected from the group of $^3H$, $^{11}C$ and $^{18}F$.

As used herein, unless otherwise noted, the term "isotopomer" shall mean isomers with isotopic atoms, having the same number of each isotope of each element but differing in their position. Isotopomers include both constitutional isomers and stereoisomers solely based on isotopic location. For example, $CH_3CHDCH_3$ and $CH_3CH_2CH_2D$ are a pair of constitutional isotopomers of n-propane; whereas (R)—$CH_3CHDOH$ and (S)—$CH_3CHDOH$ or (Z)—$CH_3CH=CHD$ and (E)-$CH_3CH=CHD$ are examples of isotopic stereoisomers of ethanol and n-propene, respectively.

It is further intended that the present invention includes the compounds described herein, including all isomers thereof (including, but not limited to stereoisomers, enantiomers, diastereomers, tautomers, isotopologues, isotopomers, and the like).

Under standard nomenclature used throughout this disclosure, the terminal portion of the designated side chain is described first, followed by the adjacent functionality toward the point of attachment. Thus, for example, a "phenyl-($C_1$-$C_6$alkylene)-amino-carbonyl-($C_1$-$C_6$alkylene)-" substituent refers to a group of the formula

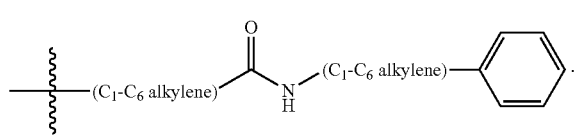

As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

2. General Synthesis Schemes

Compounds of formula (I) of the present invention may be prepared as described in the general synthesis schemes and Examples which follow hereinafter, selecting and substituting suitable reagents and conditions, as would be well within the skill of persons versed in the art. Additionally, the preparation of any starting materials used in the schemes and synthesis examples which follow hereinafter is well within the skill of persons versed in the art.

Compounds of formula (I) wherein $R^1$ is selected from the group consisting of hydrogen and $C_{1-2}$ alkyl, may be prepared as described in Scheme 1, below.

Scheme 1

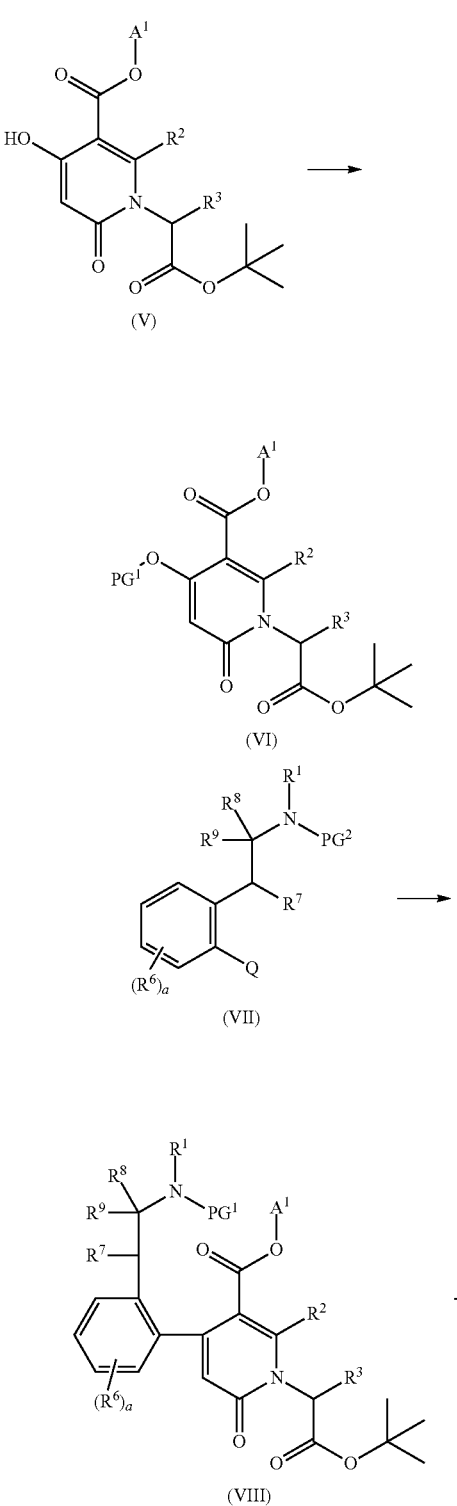

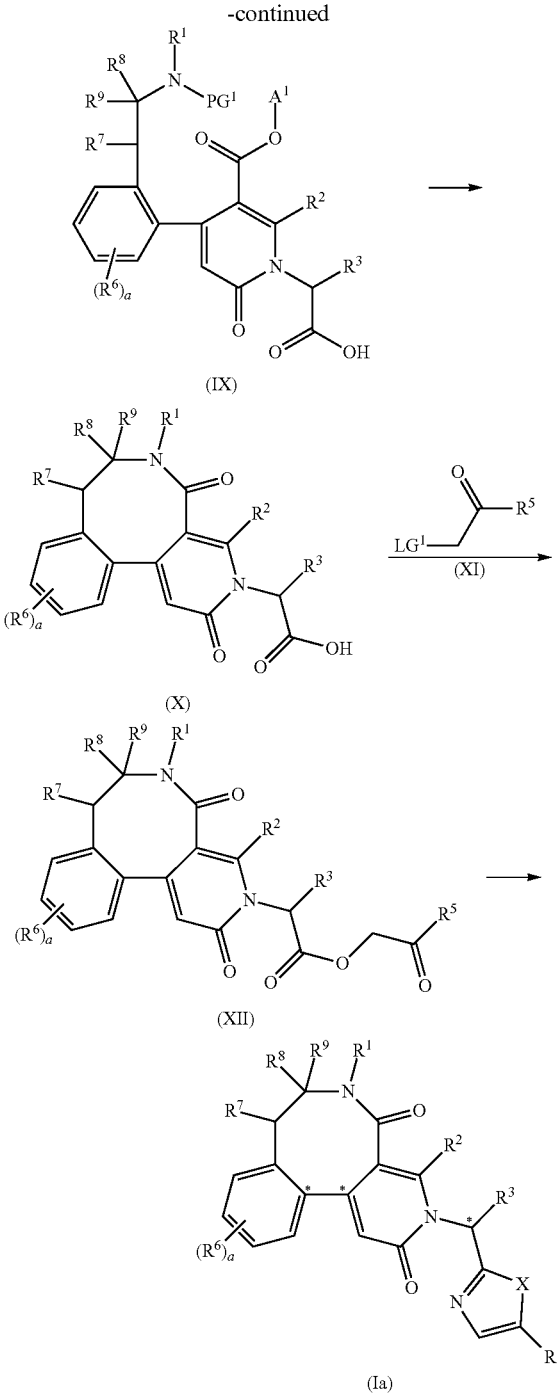

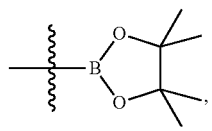 [SMILES: *B1OC(C)(C)C(C)(C)O1]

such as about room temperature; to yield the corresponding compound of formula (VI) wherein $PG^1$ is triflyl (—$SO_2$—$CF_3$).

The compound of formula (VI) is reacted with a suitably substituted compound of formula (VII), wherein Q is selected from the group consisting of $B(OH)_2$, $BF_4$ and and wherein $PG^2$ is a suitably selected nitrogen protecting group such as Boc, and the like, a known compound or compound prepared for example, as described in Schemes 5-9, below; in the presence of a suitably selected coupling agent such as $Pd(PPh_3)_4$, $PdCl_2dppf$, $PdCl_2(PPh_3)_2$, and the like; in the presence of a suitably selected base such as CsF, $K_3PO_4$, $K_2CO_3$, and the like; in a suitably selected solvent or mixture of solvents such as a mixture of 1,4-dioxane/water, PhMe/water, DMF/water, and the like; to yield the corresponding compound of formula (VIII).

The compound of formula (VIII) is reacted with a suitably selected acid such as TFA, HCl, and the like; in a suitably selected solvent such as DCM, MeCN, THF, and the like; at a suitable temperature such as about room temperature; to yield the corresponding compound of formula (IX).

The compound of formula (IX) is subjected to ring closure conditions, to yield the corresponding compound of formula (X). For example, the compound of formula (IX) may be reacted with a suitably selected base such as NaOEt, KOt-Bu, and the like; in the presence of a suitably selected corresponding alcohol, such a EtOH, MeOH, and the like; in the presence of molecular sieves; in a suitably selected solvent such as THF, 1,4-dioxane, and the like; at a suitable temperature such as about room temperature; to yield the corresponding compound of formula (X).

The compound of formula (X) is reacted with a suitably substituted compound of formula (XI), a known compound or compound prepared for example as described in Scheme 10, below; in the presence of a suitably selected base such as $Cs_2CO_3$, $K_2CO_3$, $Na_2CO_3$, and the like; in a suitably selected solvent such as DMF, MeCN, DMSO, and the like; to yield the corresponding compound of formula (XII).

The compound of formula (XII) is reacted with a suitable agent such as $NH_4OAc$, and the like; in the presence of a suitably selected acid such as acetic acid, and the like; in a suitably selected solvent such as toluene, and the like; to yield the corresponding compound of formula (Ia).

Accordingly, a suitably substituted compound of formula (V), a known compound or compound which may be prepared as for example, as described in Schemes 3-4, below, is protected according to known methods, to yield the corresponding compound of formula (VI), wherein $PG^1$ is the corresponding oxygen protecting group. For example, the compound of formula (V) may be reacted with 1,1,1-trifluoro-N-phenyl-N-((trifluoromethyl)sulfonyl) methanesulfonamide, a known compound, in the presence of a suitably selected organic amine such as TEA; in a suitably selected solvent such as DCM; at a suitable temperature Compounds of formula (I) wherein $R^1$ is —($C_{1-2}$ alkylene)-OH or —($C_{1-2}$ alkylene)-O—($C_{1-2}$alkyl) may be prepared from the corresponding compound of formula (X) wherein $R^1$ is —($C_{1-2}$alkylene)-OH or —($C_{1-2}$ alkylene)-O—($C_{1-2}$ alkyl). Compound of formula (X) wherein $R^1$ is hydrogen, as described in Scheme 2, below.

Scheme 2

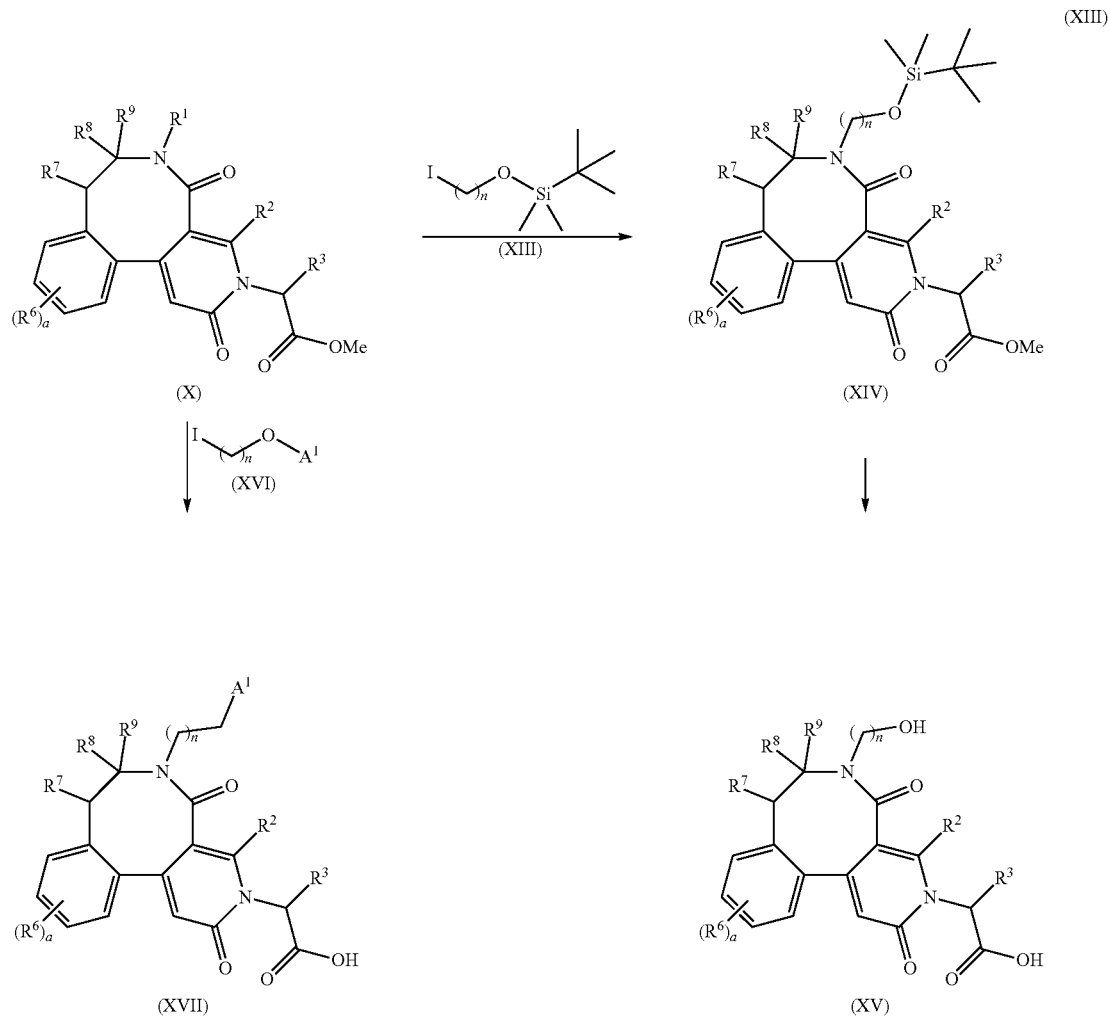

Accordingly, a suitably substituted compound of formula (X) with a suitably substituted compound of formula (XIII), wherein n is 1 or 2, a known compound or compound prepared by known methods; in the presence of a suitably selected base such as t-BuOK, NaH, LiHMDS, and the like; in a suitably selected solvent such as DMF, THF, Et$_2$O, and the like; to yield the corresponding compound of formula (XIV).

The compound of formula (XIV) is reacted with remove the t-butyldimethylsilyl group according to known methods, for example by reacting with a suitably reagent such as Bu$_4$NF, BiCl$_3$/NaI, KHSO$_4$, and the like; in a suitably selected solvent or mixture of solvents such as a mixture of THF, MeOH and water, MeCN, and the like; to yield the corresponding compound of formula (XV).

Alternatively, the compound of formula (X) is reacted with a suitably substituted compound of formula (XVI) wherein A$^1$ is selected from the group consisting of methyl and ethyl, a known compound or compound prepared by known methods; in the presence of a suitably selected base such as t-BuOK, NaH, LiHMDS, and the like; in a suitably selected solvent such as DMF, THF, and the like; to yield the corresponding compound of formula (XVII).

The compound of formula (XV) or formula (XVII) is then substituted for the compound of formula (X) in Scheme 1, and reacted as described therein, to yield the corresponding compound of formula (I), wherein R$^1$ is selected from the group consisting of —(C$_{1-2}$ alkylene)-OH and —(C$_{1-2}$alkylene)-O—(C$_{1-2}$ alkyl).

Compounds of formula (I) wherein R$^4$ is fluoro may be prepared by reacting a the corresponding compound of formula (I) wherein R$^4$ is hydrogen, and wherein any reactive groups are suitably protected (as would be recognized by those skilled in the art) with a suitably selected fluorinating agent such as NFSI, SelectFluor™, XeF$_2$, and the like; in a suitably selected solvent or mixture of solvents such as a mixture of DCM/acetone, DMF, MeCN, and the like. (See for example, Example 1 which follows hereinafter).

One skilled in the art will recognize, that wherein the compound of formula (I) is prepared as a racemate or mixture of stereoisomers, said racemate or mixture may be further purified and/or separated into its corresponding stereoisomers according to known methods, for example by chiral SFC purification.

Compounds of formula (V) wherein R$^2$ is hydrogen and R$^3$ is cyclopropyl-methyl- may be prepared for example, as described in Scheme 3, below.

Scheme 3

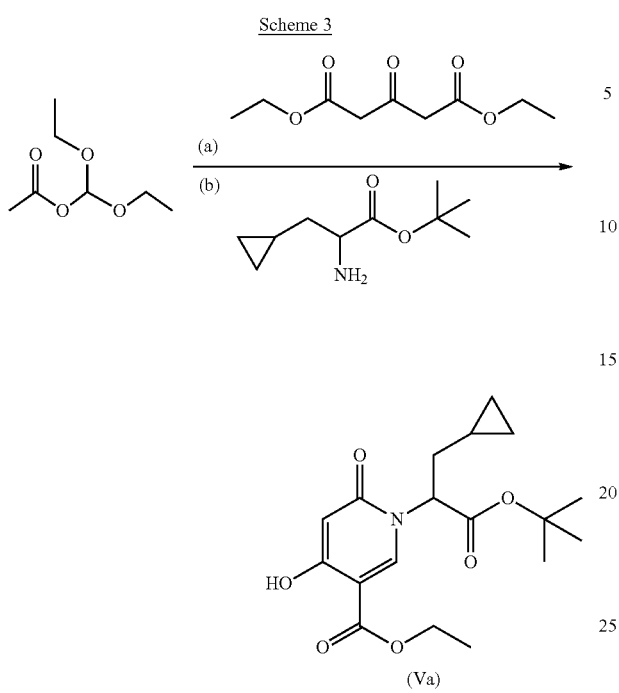

(Va)

Accordingly, diethoxymethyl acetate, a known compound or compound prepared by known methods is reacted sequentially with (a) diethyl 3-oxopentanedioate, a known compound or compound prepared by known methods; neat; at a suitable temperature, preferably at a temperature in the range of from about 50° C. to about 130° C., for example at about 100° C.; and then (b) with t-butyl 2-amino-3-cyclopropylpropanoate, a known compound or compound prepared as in for example, Intermediate Example 5, Step 1; in the presence of a suitably selected base such as NaOEt, NaOMe, NaH, LiHMDS, and the like; in a suitably selected solvent such as EtOH, DMF, THF, and the like; at a suitable temperature such as about room temperature; to yield the compound of formula (Va), also known as ethyl 1-(1-(tert-butoxy)-3-cyclopropyl-1-oxopropan-2-yl)-4-hydroxy-6-oxo-1,6-dihydropyridine-3-carboxylate, corresponding to a compound of formula (V), wherein $A^1$ is ethyl, $R^2$ is hydrogen and $R^3$ is cyclopropyl-methyl-.

Compounds of formula (V) wherein $R^2$ and $R^3$ are taken together with the carbon atoms to which they are bound to form

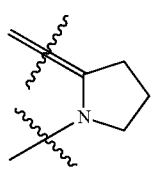 [SMILES: *N1CCCC1=*]

may be prepared for example, as described in Scheme 4, below.

Scheme 4

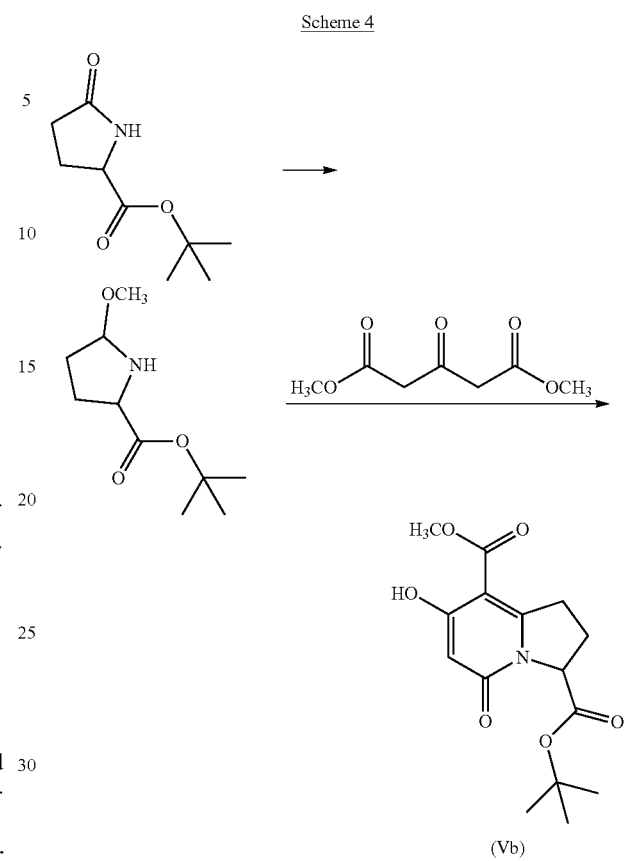

(Vb)

Accordingly, tert-butyl 5-oxopyrrolidine-2-carboxylate, a known compound or compound prepared by known methods is reacted with $Me_3OBF_4$ (trimethyloxonium tetrafluoroborate), a known compound, in a suitably selected solvent such as DCM, $Et_2O$, and the like; at a suitable temperature such as about room temperature; to yield tert-butyl 5-methoxypyrrolidine-2-carboxylate.

The tert-butyl 5-methoxypyrrolidine-2-carboxylate is reacted with dimethyl 3-oxopentanedioate, a known compound or compound prepared by known methods; in the presence of a suitably selected organic amine base such as TEA, DIEA, N-methylmorpholine, and the like; neat or in a suitably selected solvent such as DMF, DMSO, and the like; at a suitable temperature such as about room temperature; to yield the compound of formula (Vb), also known as 3-(tert-butyl) 8-methyl 7-hydroxy-5-oxo-1,2,3,5-tetrahydroindolizine-3,8-dicarboxylate, corresponding to a compound of formula (V), wherein $A^1$ is methyl and wherein $R^2$ and $R^3$ are taken together with the carbon atoms to which they are bound to form

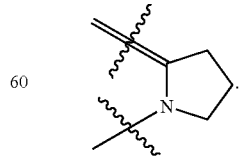

Compounds of formula (VII) wherein $R^7$, $R^8$ and $R^9$ are each hydrogen may be prepared for example, as described in Scheme 5, below.

Scheme 5

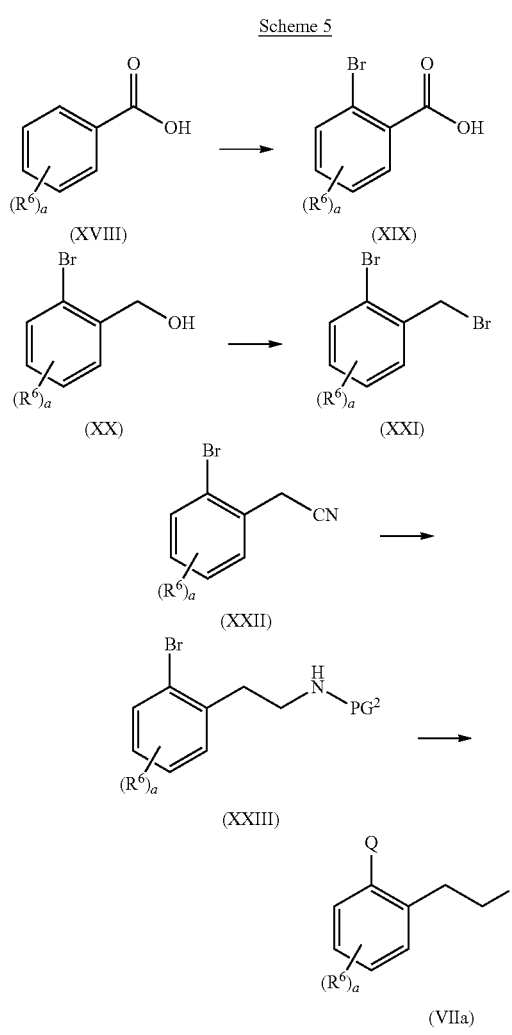

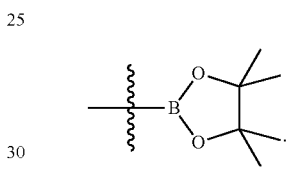

DMSO, DMF, EtOH, and the like; at a suitable temperature such as about room temperature; to yield the compound of formula (XXII).

The compound of formula (XXII) is reacted in the presence a suitably selected reducing agent such as NaBH$_4$/NiCl$_2$, LiAlH$_4$, BH$_3$-THF and the like; in a suitably selected solvent such as EtOH, MeOH, THF, and the like; with a suitably selected protecting agent such as di-tert-butyl dicarbonate, to yield the corresponding compound of formula (XXIII), wherein PG$^2$ is the corresponding nitrogen protecting group (for example wherein the protecting agent is di-tert-butyldicarbonate, then PG$^2$ is BOC).

The compound of formula (XXIII) is reacted according to known methods, to yield the corresponding compound of formula (VIIa). For example, the compound of formula (XXIII) may be reacted with 4,4,4',4',5,5,5',5'-octamethyl-2,2'-bi(1,3,2-dioxaborolane), in the presence of a suitably selected coupling agent such as Pd(dppf)Cl$_2$·CH$_2$Cl$_2$, Pd$_2$(dba)$_3$/DPEPhos, and the like; in the presence of a suitably selected base such as KOAc, NaOAc, and the like; in a suitably selected solvent such as 1,4-dioxane, and the like; to yield the corresponding compound of formula (VIIa) wherein Q is Compounds of formula (VII) wherein R$^7$ is hydrogen and wherein R$^8$ and R$^9$ are taken together with the carbon atom to which they are bound to form cyclopro-1,1-diyl, may be prepared for example, as described in Scheme 6, below.

Accordingly, a suitably substituted compound of formula (XVIII), a known compound or compound prepared by known methods, is reacted with a suitably selected brominating agent such as BrCCl$_2$CCl$_2$Br (DBTCE), Br$_2$, and the like; in the presence of a suitably selected organic amine base such as DIPEA, Et$_3$N, and the like; in a suitably selected solvent such as THF, Et$_2$O, and the like; at a suitable temperature, preferably at a temperature in the range of from about −78° C. to about 0° C., for example at about −70° C.; to yield the corresponding compound of formula (XIX).

The compound of formula (XIX) is reacted with a suitably selected agent such as BH$_3$, 4,4,5,5-tetramethyl-1,3,2-dioxaborolane, NaBH$_4$, BH$_3$Me$_2$S, LiAlH$_4$, and the like; in a suitably selected solvent such as THF, and the like; at a suitable temperature such as about room temperature; to yield the compound of formula (XX).

The compound of formula (XX) is reacted with a suitably selected brominating agent such as PBr$_3$, Br$_3$CCOCBr$_3$/PPh$_3$, Br$_2$, NBS, and the like; in a suitably selected solvent such as DCM, Et$_2$O, and the like; at a suitable temperature such as about room temperature; to yield the compound of formula (XXI).

The compound of formula (XXI) is reacted with a suitably selected agent such as TMSCN, TBAF, NaCN, KCN, and the like; in a suitable selected solvent such as MeCN, Scheme 6

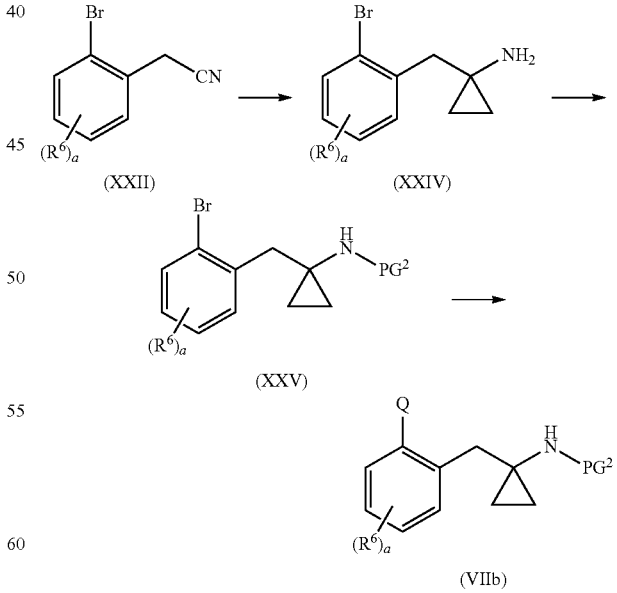

Accordingly, a suitably substituted compound of formula (XXII), a known compound or compound prepared for example, as described in Scheme 5 above, is reacted with EtMgBr, a known compound; in the presence of a suitably selected coupling agent such as Ti(Oi-Pr)$_4$, (i-PrO)$_3$TiMe, and the like; in the presence of a suitably selected agent such as BF$_3$·Et$_2$O, and the like; in a suitably selected solvent such as diethyl ether, THF, and the like; at a suitable temperature such as about room temperature; to yield the corresponding compound of formula (XXIV).

The compound of formula (XXIV) is protected according to known methods; to yield the corresponding compound of formula (XXV), wherein PG$^2$ is the corresponding nitrogen protecting group. For example, the compound of formula (XXIV) may be reacted with (Boc)$_2$O, a known compound, in the presence of a suitably selected organic amine base such as TEA, DIPEA, pyridine, and the like; in a suitably selected solvent such as DCM, THF, DMF, and the like; at a suitable temperature such as about room temperature; to yield the corresponding compound of formula (XXV) wherein PG$^2$ is Boc.

The compound of formula (XXV) is reacted according to known methods to yield the corresponding compound of formula (VIIb). For example, the compound of formula (XXV) may be reacted with B(OCH$_3$)$_3$; in the presence of a suitably selected lithium reagent such as n-BuLi, s-BuLi, and the like; optionally in the presence of a suitably selected lithium reagent such LiCH$_3$, NaH, KO-tBu, and the like; in a suitably selected solvent such as THF, and the like; at a suitable temperature in the range of from about −78 to about 0° C., for example at about −78° C.; to yield the corresponding compound of formula (VIIb), wherein Q is B(OH)$_2$.

Compounds of formula (VII) wherein R$^7$ is hydrogen and wherein R$^8$ and R$^9$ are taken together with the carbon atom to which they are bound to form cyclobut-1,1-diyl, cyclopent-1,1-diyl or cyclohex-1,1-yl may be prepared for example, as described in Scheme 7, below.

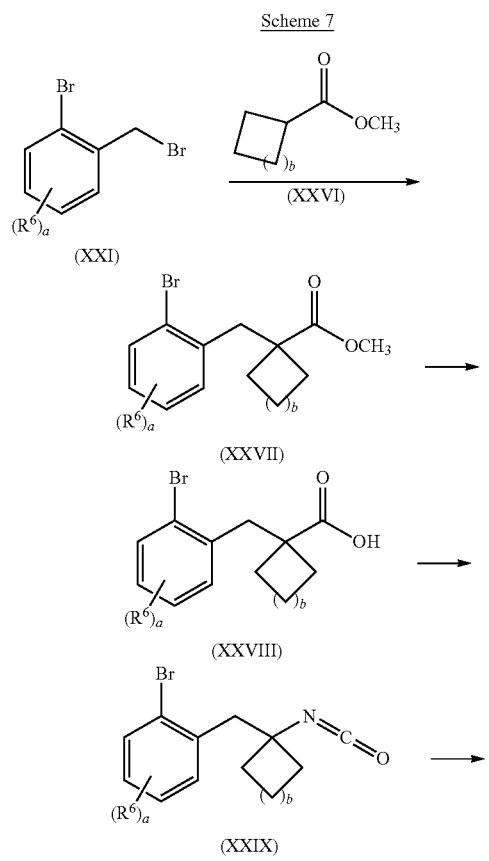

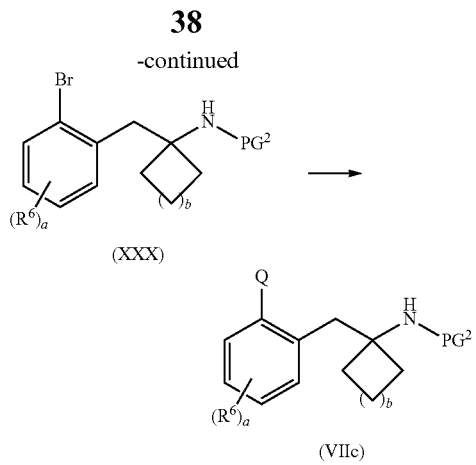

Accordingly, a suitably substituted compound of formula (XXI), a known compound or compound prepared for example as described in Scheme 5 above, is reacted with a suitably substituted compound of formula (XXVI) wherein b is an integer from 1 to 3 (such that the cycloalkyl ring is cyclobutyl, cyclopentyl or cyclohexyl), a known compound or compound prepared by known methods; in the presence of a suitably selected agent such n-BuLi, LiN(Pr-i)$_2$, LiHMDS, and the like; in the presence of a suitably selected organic amine base such as DIPEA, and the like; in a suitably selected solvent such as dry THF, PhMe, heptane, and the like; at a suitable temperature in the range of from about −78 to about 0° C., for example at about −78° C.; to yield the corresponding compound of formula (XXVII).

The compound of formula (XXVII) is reacted with a suitably selected base such as LiOH, KOH, NaOH, and the like; in the presence of a suitably selected alcohol such as EtOH, MeOH, CH$_3$CN, and the like; in a suitably selected solvent or mixture of solvents such as a mixture of THF/water, and the like; at a suitable temperature in the range of from about 0° C. to about 100° C., for example at about 50° C.; to yield the corresponding compound of formula (XXVIII).

The compound of formula (XXVIII) is reacted with a suitably selected agent such as diphenyl phosphorazidate, and the like; in the presence of a suitably selected organic amine base such as TEA, DIEA, and the like; in a suitably selected solvent such as toluene, and the like; at a suitable temperature such as about room temperature; to yield the corresponding compound of formula (XXIX).

The compound of formula (XXIX) is reacted with a suitably selected alcohol of the formula R'—OH such as 2-methyl-propan-2-ol, benzyl alcohol, and the like; to yield the corresponding compound of formula (XXX), wherein PG$^2$ is the corresponding —C(O)O—R' (For example, wherein the alcohol is 2-methyl-propan-2-ol, then PG$^2$ is BOC).

The compound of formula (XXX) is reacted according to known methods, to yield the corresponding compound of formula (VIIc). For example, the compound of formula (XXX) may be reacted with B(OCH$_3$)$_3$ or B(O-iPr)$_3$ in the presence of a suitably selected lithium reagent such as n-BuLi, Mg/I$_2$, and the like; optionally in the presence of a suitably selected lithium reagent such LiCH$_3$, NaH, KO-tBu, and the like; in a suitably selected solvent such as THF, and the like; at a suitable temperature in the range of from about −78 to about 0° C., for example at about −78° C.; to yield the corresponding compound of formula (VIIb), wherein Q is B(OH)$_2$.

Compounds of formula (VII) wherein $R^9$ is hydrogen and $R^7$ and $R^8$ are taken together with the carbon atoms to which they are bound to form phen-1,2-diyl or pyridin-3,4-diyl may be prepared for example, as described in Scheme 8, below.

Scheme 8

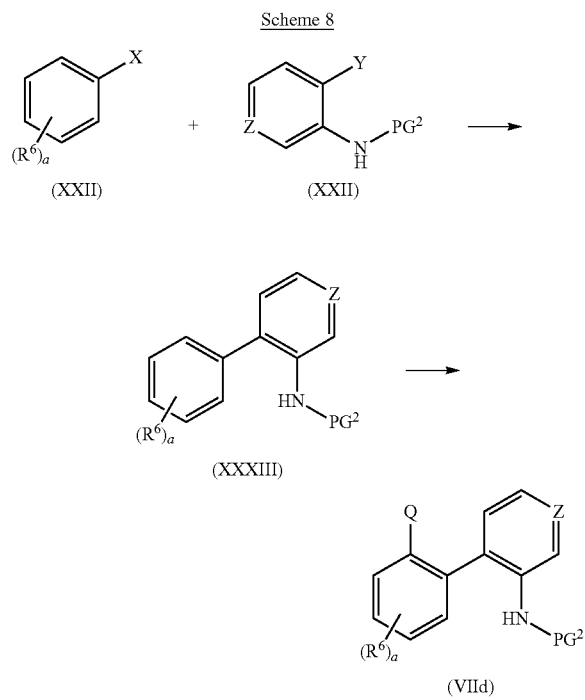

Accordingly, a suitably substituted compound of formula (XXXII), wherein X is $B(OH)_2$, $BF_4$ or

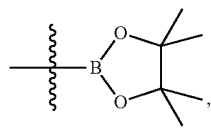 [SMILES: *B1OC(C)(C)C(C)(C)O1]

a known compound or compound prepared by known methods is reacted with a suitably substituted compound of formula (XXXII), wherein Y is a suitably selected leaving group such as Br, OTf, I, and the like, and wherein Z is selected from the group consisting of CH and N, known compound or compound prepared by known methods; in the presence of a suitably selected coupling agent such as $Pd(PPh_3)_4$, $PdCl_2dppf$, and the like; in the presence of a suitably selected base such as $K_2CO_3$, $Na_2CO_3$, $K_3PO_4$, and the like; in a suitably selected solvent or mixture of solvents such as a mixture of 1,4-dioxane/water, THF, DMF, and the like; at a suitably temperature such in the range of from about 50 to about 130° C., for example at about 90° C.; to yield the corresponding compound of formula (XXXIII).

Alternatively, a suitably substituted compound of formula (XXXI), wherein X is a suitably selected leaving group such as Br, OTf, I, and the like, a known compound or compound prepared by known methods, is reacted with a suitably substituted compound of formula (XXXII), wherein Y is $B(OH)_2$, $BF_4$ or

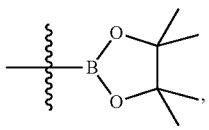

and wherein Z is selected from the group consisting of CH and N, a known compound or compound prepared by known methods; in the presence of a suitably selected coupling agent such as $Pd(PPh_3)_4$, $PdCl_2dppf$, $Pd_2(dba)_3$, and the like; in the presence of a suitably selected base such as $K_2CO_3$, $Na_2CO_3$, $K_3PO_4$, and the like; in a suitably selected solvent or mixture of solvents such as a mixture of 1,4-dioxane/water, DMF, THF, and the like; at a suitably temperature such in the range of from about 50° C. to about 130° C., for example at about 90° C.; to yield the corresponding compound of formula (XXXIII).

The compound of formula (XXXIII) is reacted according to known methods, to yield the corresponding compound of formula (VIId). For example, the compound of formula (XXXIII) may be reacted with $B(OCH_3)_3$; in the presence of a suitably selected lithium reagent such as n-BuLi, $Mg/I_2$, and the like; optionally in the presence of a suitably selected lithium reagent such $LiCH_3$, NaH, KOt-Bu, and the like; in a suitably selected solvent such as THF, and the like; at a suitable temperature in the range of from about –78° C. to about 0° C., for example at about –78° C.; to yield the corresponding compound of formula (VIId), wherein Q is $B(OH)_2$.

Compounds of formula (VII) wherein $R^7$ is hydrogen and wherein $R^8$ and $R^9$ are each independently selected from the group consisting of hydrogen, $C_{1-4}$ alkyl and $C_{1-4}$ alkoxy may be prepared for example, as described in Scheme 9, below.

Scheme 9

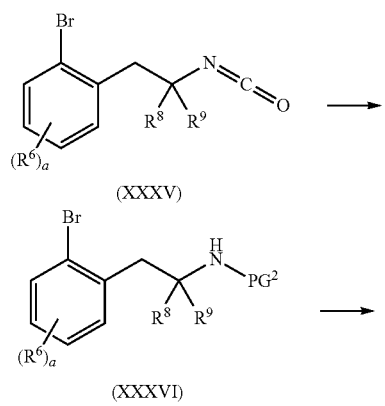

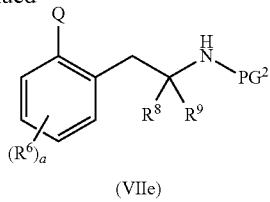

(VIIe)

Accordingly, a suitably substituted compound of formula (XXXIV), wherein $R^7$ is hydrogen and wherein $R^8$ and $R^9$ are each independently selected from the group consisting of hydrogen, $C_{1-4}$ alkyl and $C_{1-4}$ alkoxy, a known compound or compound prepared by known methods, is reacted with a suitably selected agent such as diphenylphodphoryl azide, $SOCl_2/NaN_3$, $TsCl/NaN_3$, and the like; in the presence of a suitably selected organic amine base such as TEA, $K_2CO_3$, and the like; in a suitably selected solvent such as toluene, MeCN, and the like; at a suitable temperature such as about room temperature; to yield the corresponding compound of formula (XXXV).

The compound of formula (XXXV) is reacted with a suitably selected alcohol of the formula (R')OH such as 2-methyl-propan-2-ol, benzyl alcohol, and the like; at a suitable temperature such as about room temperature; to yield the corresponding compound of formula (XXXVI), wherein $PG^2$ is the corresponding —C(O)O—R' (For example, wherein the alcohol is 2-methyl-propan-2-ol, then $PG^2$ is BOC).

The compound of formula (XXXVI) is reacted according to known methods, to yield the corresponding compound of formula (VIIe). For example, the compound of formula (XXXVI) may be reacted with $B(OCH_3)_3$ or $B(O\text{-}iPr)_3$; in the presence of a suitably selected lithium reagent such as n-BuLi, $Mg/I_2$, and the like; optionally in the presence of a suitably selected base such $LiCH_3$, NaH, and the like; in a suitably selected solvent such as THF, and the like; at a suitable temperature in the range of from about −78° C. to about 0° C., for example at about −78° C.; to yield the corresponding compound of formula (VIIe), wherein Q is $B(OH)_2$.

Compounds of formula (XI) may be prepared for example, as described in Scheme 10, below.

Scheme 10

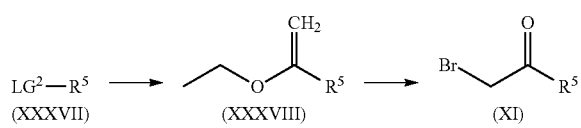

Accordingly, a suitably substituted compound of formula (XXXVII), wherein $LG^2$ is a suitably selected leaving group such as Br, I, and the like, a known compound or compound prepared by known methods, is reacted with tributyl(1-ethoxyvinyl)stannane, a known compound; in the presence of a suitably selected coupling agent such as $Pd(PPh_3)_4$, $PdCl_2dppf$, $PdCl_2(PPh_3)_2$, and the like; in a suitably selected solvent such as 1,4-dioxane, benzene, DMF, toluene, and the like; at a suitable temperature, preferably at a temperature in the range of from about room temperature to about 130° C., for example at about 100° C.; to yield the corresponding compound of formula (XXXVIII).

The compound of formula (XXXVIII) is reacted with a suitably selected brominating agent such as NBS, and the like; in a suitably selected solvent or mixture of solvents such as a mixture of THF/water, and the like; at a suitable temperature such as about room temperature; to yield the compound of formula (XI).

One skilled in the art will recognize that various substituent groups (for example, $R^5$, etc.) and/or functional groups on said substituent groups (for example —OH, —$NH_2$, etc.) may be protected prior to any reaction step described above, and then de-protected at a later step in the synthesis, as would be desirable or necessary, according to methods well known to those skilled in the art.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

One skilled in the art will recognize that wherein a reaction step of the present invention may be carried out in a variety of solvents or solvent systems, said reaction step may also be carried out in a mixture of the suitable solvents or solvent systems.

One skilled in the art will further recognize that the reaction or process step(s) as herein described are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly reduced amount of the desired product(s), as compared to the amounts of each present at the beginning of the reaction.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be measured in texts such as T. W. Greene & P. G. M. Wuts, Protective Groups in Organic Synthesis, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be measured in texts such as T. W. Greene & P. G. M. Wuts, Protective Groups in Organic Synthesis, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([a-obs]/[a-\max]) \times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

3. Pharmaceutical Compositions

The present invention further comprises pharmaceutical compositions containing a compound of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.05 mg/day to about 1000 mg/day, or any amount or range therein, about 0.1 mg/day to about 500 mg/day, or any amount or range therein, preferably from about 1 mg/day to about 300 mg/day, or any amount or range therein.

The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form yielding the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of the treatment and/or prophylaxis of thromboembolic disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein, preferably from about 0.05 mg to about 300 mg of the compound, or any amount or range therein, more preferably from about 0.1 mg to about 100 mg of the compound, or any amount or range therein, more preferably from about 0.1 mg to about 50 mg of the compound, or any amount or range therein; and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be measured in The Handbook of Pharmaceutical Excipients, published by the American Pharmaceutical Association and the Pharmaceutical Society of Great Britain. Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Compounds of the present invention may be administered in any of the foregoing compositions and according to dosage regimens established in the art whenever treatment or prophylaxis of thromboembolic disorders, inflammatory disorders or diseases or conditions in which plasma kallikrein activity is implicated is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug may be ordinarily supplied at a dosage level of from about 0.005 mg/kg to about 10 mg/kg of body weight per day, or any amount or range therein. Preferably, the range is from about 0.01 to about 5.0 mg/kg of body weight per day, or any amount or range therein, more preferably, from about 0.1 to about 1.0 mg/kg of body weight per day, or any amount or range therein, more preferably, from about 0.1 to about 0.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

4. Utility

The compounds of the present invention are useful for the treatment and/or prophylaxis of thromboembolic disorders, inflammatory disorders and diseases or conditions in which factor XIa and/or plasma kallikrein activity is implicated.

In some embodiments, the present invention is directed to methods for the treatment and/or prophylaxis of a thromboembolic disorder comprising administering to a patient in need of such treatment and/or prophylaxis a therapeutically effective amount of a least one of the compounds as described herein, or a stereoisomer, isotopologue, isotopomer or pharmaceutically acceptable salt or solvate thereof.

As used herein, the term "thromboembolic disorders" includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In some embodiments, the term "thromboembolic disorders" includes acute coronary syndrome, stroke, deep vein thrombosis, and pulmonary embolism. In some embodiments, the "thromboembolic disorders" include hereditary angioedema (HAE) and diabetic macular edema (DME).

In some embodiments, the present invention is directed to methods for the treatment and/or prophylaxis of an inflammatory disorder comprising: administering to a patient in need of such treatment and/or prophylaxis a therapeutically effective amount of at least one of the compounds of the present invention or a stereoisomer, isotopologue, isotopomer or pharmaceutically acceptable salt or solvate thereof. Examples of the inflammatory disorders include, but are not limited to, sepsis, acute respiratory distress syndrome, and systemic inflammatory response syndrome.

In some embodiments, the present invention is directed to methods for the treatment and/or prophylaxis of a disease or condition in which plasma kallikrein activity is implicated, comprising administering to a patient in need of such treatment and/or prophylaxis a therapeutically effective amount of at least one of the compounds of the present invention or a stereoisomer, isotopologue, isotopomer or pharmaceutically acceptable salt or solvate thereof. The diseases or conditions in which plasma kallikrein activity is implicated include, but are not limited to, impaired visual acuity, diabetic retinopathy, diabetic macular edema, hereditary angioedema, diabetes, pancreatitis, nephropathy, cardiomyopathy, neuropathy, inflammatory bowel disease, arthritis, inflammation, septic shock, hypotension, cancer, adult respiratory distress syndrome, disseminated intravascular coagulation, and cardiopulmonary bypass surgery.

In some embodiments, the present invention provides a method for treating the primary prophylaxis of a thromboembolic disorder. In some embodiments, the present invention provides a method for the primary prophylaxis of a thromboembolic disorder wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In some embodiments, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In some embodiments, the present invention provides a method for the secondary prophylaxis of a thromboembolic disorder. In some embodiments, the present invention provides a method for the secondary prophylaxis of a thromboembolic disorder. wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In some embodiments, the present invention provides a method for the secondary prophylaxis of a thromboembolic disorder, wherein the thromboembolic disorder is selected from acute coronary syndrome, stroke, atrial fibrillation and venous thrombosis.

One skilled in the art will recognize that wherein the present invention is directed to methods of prophylaxis, the subject in need thereof (i.e. a subject in need of prophylaxis) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prophylaxis or prophylactic treatment) as a consequence of the subject's medical history, including, but not limited to, family history, pre-disposition, co-existing (comorbid) disorders or conditions, genetic testing, and the like.

The compounds of the present invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, for example, may occur when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components. Possible favorable outcomes of treatment with a synergistic combination include, but are not limited to, (a) increased efficacy of the therapeutic effect, (b) ability to administer decreased dosage while increasing or maintaining efficacy (which in turn may also result in decreased toxicity and/or adverse side effects), (c) minimized or slowed development of drug resistance, (d) selective synergism against the biological target (or efficacy synergism) versus host (toxicity antagonism).

In some embodiments of the present invention, the compound of formula (I) may be administered in combination with one or more anticoagulant, anti-thrombin agent, anti-platelet agent, fibrinolytic, hypolipidemic agent, antihypertensive agent, and/or anti-ischemic agent. Suitable examples include, but are not limited to warfarin, heparin, aprotinin, a synthetic pentasaccharide, a boroarginine derivative, a boropeptide, heparin, hirudin, argatroban, a thromboxane-A2-receptor antagonist, a thromboxane-A2-synthetase inhibitor, a PDE-III inhibitor, a PDE V inhibitor, an ADP receptor antagonist, an antagonist of the purinergic receptor P2Y1, an antagonist of the purinergic receptor P2Y12, tissue plasminogen activator and modified forms thereof, anistreplase, urokinase, streptokinase, tenecteplase, lanoteplase, a PAI-1 inhibitor, an alpha-2-antiplasmin inhibitor, an anisoylated plasminogen streptokinase activator complex, a HMG-CoA reductase inhibitor, a squalene synthetase inhibitor, a fibrate, a bile acid sequestrant, an ACAT inhibitor, a MTP inhibitor, a lipooxygenase inhibitor, a cholesterol absorption inhibitor, a cholesterol ester transfer protein inhibitor, an alpha adrenergic blocker, a beta adrenergic blocker, a calcium channel blocker, a diuretic, a renin inhibitor, an angiotensin-converting enzyme inhibitor, an angiotensin-II-receptor antagonist, an ET receptor antagonist, a Dual ET/A11 antagonist, a neutral endopeptidase inhibitor, a vasopeptidase inhibitor, a Class I agent, a Class 11 agent, a Class III agent, a Class IV agent, an lAch inhibitor, an IKur inhibitor and a cardiac glycoside.

By "administered in combination" or "combination therapy" it is meant that the compound of the present invention and one or more additional therapeutic agents are administered concurrently or consecutively to the subject (preferably mammal, more preferably human) being treated. When administered in combination each component may be administered at the same time or sequentially in any order at different points in time. Thus, each component may be administered separately but sufficiently closely in time so as to provide the desired therapeutic effect. Chou, Theoretical Basis, Experimental Design, and Computerized Simulation of Synergism and Antagonism in Drug Combination Studies, Pharmacol Rev., 2006, vol. 58, 621-681.

5. Combination Therapy

One or more additional pharmacologically active agents may be administered in combination with the compounds of the invention. The additional active agent (or agents) is intended to mean a pharmaceutically active agent (or agents) that is active in the body, including pro-drugs that convert to pharmaceutically active form after administration, which is different from the compound of formula (I), and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of formula (I) in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin 11 receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885, 292) and pyrrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4 (S),5(S),7(S)—N-(2-carbamoyl-2-methylpropyl)-5-amino-4-hydroxy-2,7-diisopropyl-8-[4-methoxy-3-(3-methoxypropoxy)-phenyl]octanamide hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone prodrug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible. Compounds which can be alternatively or additionally administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Anticoagulant agents (or coagulation inhibitory agents) that may be used in combination with the compounds of this invention include warfarin, heparin (either unfractionated heparin or any commercially available low molecular weight heparin, for example enoxaparin and dalteparin), aprotinin, synthetic pentasaccharide inhibitors of Factor Xa such as fondaparinux and idraparinux, direct Factor Xa inhibitors such as rivaroxaban, apixaban, betrixaban, edoxaban, otamixaban, direct acting thrombin inhibitors including hirudin, dabigatran, argatroban, ximelagatran, melagatran, lepirudin, desirudin, and bivalirudin, as well as other factor VIIa inhibitors, VIIIa inhibitors, DCa inhibitors, Xa inhibitors, XIa inhibitors, fibrinogen receptor antagonists (including abciximab, eptifibatide and tirofiban), TAFI inibitors, and others known in the art. Factor DCa inhibitors include synthetic active-site blocked competitive inhibitors, oral inhibitors and RNA aptamers. These are described in Howard, E L, Becker K C, Rusconi, C P, Becker R C. Factor IXa Inhibitors as Novel Anticoagulents. Arterioscler Thromb Vasc Biol, 2007; 27: 722-727.

The term "anti-platelet agents" or "platelet inhibitory agents", as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term "anti-platelet agents" or "platelet inhibitory agents", as used herein, is also intended to include ADP (adenosine diphosphate) receptor antagonists, preferable antagonists of the purinergic receptors P2Y1 and P2Y12 with P2Y12 being even more preferred. Preferred P2Y12 receptor antagonists include ticlopidine, prasugrel, clopidogrel, elinogrel, ticagrelor and cangrelor, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term "thrombin inhibitors" or "anti-thrombin agents", as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, dabigatran and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term "hirudin", as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role. Thrombin receptor antagonist peptides have been identified based on structure-activity studies involving substitutions of amino acids on thrombin receptors. In Bernatowicz et al, J Med. Chem., vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH2 and N-trans-cinnamoyl-p-fluoroPhe-p-guanidinoPhe-Leu-Arg-Arg-NH2. Peptide thrombin receptor antagonists are also disclosed in WO 94/03479. Substituted tricyclic thrombin receptor antagonists are disclosed in U.S. Pat. Nos. 6,063,847, 6,326,380 and WO 01/96330. Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes. The term urokinase, as used herein, is intended to denote both dual and single chain urokinase, the latter also being referred to herein as prourokinase. Examples of suitable anti-arrhythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); 1Ach inhibitors, and IKur inhibitors (e.g., compounds such as those disclosed in WO01/40231).

6. Definitions

As used herein, unless otherwise noted, "halogen" shall mean chloro, bromo, fluoro and iodo, preferably bromo, fluoro or chloro, more preferably fluoro or chloro.

As used herein, unless otherwise noted, the term "oxo" shall mean a functional group of the structure =O (i.e. a substituent oxygen atom connected to another atom by a double bond).

As used herein, unless otherwise noted, the term "$C_{X-Y}$alkyl" wherein X and Y are integers, whether used alone or as part of a substituent group, include straight and branched chains containing between X and Y carbon atoms. For example, $C_{1-4}$ alkyl radicals include straight and branched chains of between 1 and 4 carbon atoms, including methyl, ethyl, propyl, isopropyl, butyl, isobutyl, sec-butyl and t-butyl.

As used herein, unless otherwise noted, the terms "—($C_{X-Y}$alkylene)- and —$C_{X-Y}$alkylene-" wherein X and Y are integers, shall denote any $C_{X-Y}$alkyl carbon chain as herein defined, wherein said $C_{X-Y}$alkyl chain is divalent and is further bound through two points of attachment, preferably through two terminal carbon atoms.

As used herein, unless otherwise noted, the term "hydroxy substituted $C_{1-4}$alkyl" shall mean any $C_{1-4}$alkyl group as defined above substituted with at least one hydroxy (—OH) groups, preferably one to three, more preferably one to two hydroxy groups. Suitable examples include but are not limited to —$CH_2OH$, —$CH_2CH_2OH$, —$CH(OH)CH_3$, —$CH(OH)CH_2OH$, —$CH_2CH_2CH_2OH$, —$C(CH_2OH)_3$, and the like.

As used herein, unless otherwise noted, "$C_{X-Y}$alkoxy" wherein X and Y are integers, shall mean an oxygen ether radical of the above described straight or branched chain $C_{X-Y}$alkyl groups containing between X and Y carbon atoms.

For example, $C_{1-4}$alkoxy shall include methoxy, ethoxy, n-propoxy, isopropoxy, n-butyloxy, iso-butyloxy, sec-butyloxy and tert-butyloxy.

As used herein, unless otherwise noted, the term "$C_{X-Y}$cycloalkyl", wherein X and Y are integers, shall mean any stable X- to Y-membered monocyclic, bicyclic, polycyclic, bridged or spiro-cyclic saturated ring system, preferably a monocyclic, bicyclic, bridged or spiro-cyclic saturated ring system. For example, the term "$C_{3-8}$ cycloalkyl" includes, but is not limited to cyclopropyl, cyclobutyl, cyclopentyl, cyclohexyl, cycloheptyl, bicyclo[2.2.1]hept-2-yl, cyclooctyl, bicyclo[2.2.2]octan-2-yl, and the like.

As used herein, unless otherwise noted, the term "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or nine or ten membered bicyclic aromatic ring structure containing at least one heteroatom selected from the group consisting of O, N and S, optionally containing one to four additional heteroatoms independently selected from the group consisting of O, N and S. The heteroaryl may be bound through any ring atom which results in a stable structure.

Suitable examples include, but are not limited to, furanyl, thienyl, furazanyl, oxazolyl, imidazolyl, pyrrolyl, pyrazolyl, thiazolyl, isoxazolyl, isothiazolyl, triazolyl, thiadiazolyl, oxadiazolyl, pyrazyl, pyridyl, pyridazinyl, pyrimidinyl, pyrazinyl, triazinyl, indolyl, indolizinyl, isoindolinyl, indazolyl, benzofuranyl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, imidazo[1,2-a]pyridin-7-yl, [1,2,4]triazolo[4,3-a]pyridin-7-yl, and the like.

As used herein, unless otherwise noted, the term "nitrogen containing heteroaryl" shall denote any five or six membered monocyclic aromatic ring structure containing at least one N heteroatom, optionally containing one to three additional heteroatoms independently selected from the group consisting of O, N and S; or nine or ten membered bicyclic aromatic ring structure containing at least one N heteroatom, optionally containing one to four additional heteroatoms independently selected from the group consisting of O, N and S. The nitrogen containing heteroaryl may be bound through any ring atom which results in a stable structure. Suitably examples include, but are not limited to furazanyl, oxazolyl, imidazolyl, pyrrolyl, pyrazolyl, thiazolyl, isoxazolyl, isothiazolyl, triazolyl, thiadiazolyl, oxadiazolyl, pyrazyl, pyridyl, pyridazinyl, pyrimidinyl, pyrazinyl, triazinyl, indolyl, indolizinyl, isoindolinyl, indazolyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, imidazo[1,2-a]pyridin-7-yl, [1,2,4]triazolo[4,3-a]pyridin-7-yl, and the like.

When a particular group is "substituted" (e.g. $C_{X-Y}$alkyl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the terms "combination" and "pharmaceutical combination" refer to either: 1) a fixed dose combination in one dosage unit form; or 2) a non-fixed dose combination, optionally packaged together for combined administration.

As used herein, the term "composition" is intended to encompass a product comprising the specified ingredients in the specified amounts, as well as any product which results, directly or indirectly, from combinations of the specified ingredients in the specified amounts.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, a-oxo-glutaric acid, glycolic acid, hippuric acid, hydrobromic acid, hydrochloric acid, (+)-L-lactic acid, (±)-DL-lactic acid, lactobionic acid, maleic acid, (±)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

As used herein, unless otherwise noted, the terms "treating", "treatment" and the like, shall include the management and care of a subject or patient, preferably a mammal, more preferably a human, for the purpose of combating a disease, condition, or disorder and includes the administration of a compound of the present invention to prevent the onset of the symptoms or complications, alleviate the symptoms or complications, slow the progression of the disease or disorder, or eliminate the disease, condition, or disorder. The terms "treating" or "treatment" further include: (a) inhibiting the disease-state, i.e., arresting its development; and/or (b) relieving the disease-state, i.e., causing regression of the disease state.

As used herein, "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a stereoisomer, isotopologue, isotopomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "risk reduction" covers therapies that lower the incidence of development of a clinical disease state. As such, primary and secondary prevention therapies are examples of risk reduction.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

EXAMPLES

Abbreviations used in the specification, particularly the Schemes and Examples, are as listed in the Table A, below:

TABLE A

| | Abbreviations |
|---|---|
| Ac = | Acetyl (i.e. —C(O)CH$_3$) |
| AcOH = | Acetic Acid |
| ACN or MeCN = | Acetonitrile |
| aq. = | Aqueous |
| BF$_3$•Et$_2$O = | Boron trifluoride diethyl etherate |
| BH$_3$•Me$_2$S = | Borane Dimethyl Sulfide |
| Boc or BOC = | tert-Butoxyloxycarbonyl (i.e. —C(O)—O—C(CH$_3$)$_3$) |
| Boc$_2$O = | Di-tert-butyl dicarbonate |
| B(O—iPr)$_3$ = | Tri(isopropyl) Borate |
| BSA = | Bovine Serum Albumin |
| Bu$_4$NF = | Tetra-n-butylammonium Fluoride |
| CHAPS | 3-[(3-Cholamidopropyl)dimethylammonio]-1-propanesulfonate |
| dba = | dibenzylideneacetone |
| DBTCE = | 1,2-dibromortetrachloroethane |
| DCM = | Dichloromethane |
| DEA = | Diethanolamine |
| DIEA or DIPEA = | Diisopropylethyl Amine |
| DME = | Diabetic Macular Edema |
| DMF = | N,N-Dimethylformamide |
| DMSO = | Dimethylsulfoxide |
| DPEPhos = | Bis[(2-diphenylphosphino)phenyl] ether |
| dppf = | 1,1'-Bis(diphenylphosphino)ferrocene |
| EA or EtOAc = | Ethyl Acetate |
| ee = | Enantiomeric Excess |
| ER = | End Point Read (assay) |
| equiv. = | Equivalents |
| ES or ESI = | Electrospray ionization |
| Et = | Ethyl |
| EtMgBr = | Ethyl Magnesium Bromide |
| EtOH = | Ethanol |
| Et$_2$O = | Diethyl Ether |
| FXIa = | Factor XIa |
| HAE = | Hereditary Angioedema |
| Hex = | Hexanes |
| HOAc = | Acetic Acid |
| HPLC = | High Performance Liquid Chromatography |
| KIN = | Kinetic Read (assay) |
| KOAc = | Potassium Acetate |
| LC-MS or LC/MS = | Liquid chromatography-mass spectrometry |
| LiHMDS = | Lithium bis(trimethylsilyl)amide |
| LiN(Pr-i)$_2$ or LiN(i-Pr)$_2$) | Lithium Diisopropylamide |
| Me = | Methyl |
| MeOH = | Methanol |
| Me$_3$OBF$_4$ = | Trimethyloxonium tetrafluoroborate |
| MOM = | Methoxy methyl |
| Ms or mesyl = | Methylsulfonyl (i.e. —SO$_2$—CH$_3$) |
| MTBE or MtBE = | Methyl tert-Butyl Ether |
| NaOAc = | Sodium Acetate |
| NaOEt = | Sodium Ethoxide |
| NaOMe = | Sodium Methoxide |
| NBS = | N-Bromosuccinimide |
| n-BuLi = | n-Butyl Lithium |
| NFSI = | N-Fluorobenzenesulfonimide |
| NH$_4$OAc = | Ammonium Acetate |
| NMR = | Nuclear Magnetic Resonance |
| OMs or mesylate = | Methanesulfonate (i.e. —O—SO$_2$—CH$_3$) |
| OTf or tritiate = | Trifluoromethanesulfonyl (i.e. —O—SO=—CF$_3$) |
| OTs or tosylate = | p-Toluenesulfonate (i.e. —O—SO$_2$-(p-methylphenyl)) |
| Pd(dppf)Cl$_2$ or PdCl$_2$(dppf) | [1,1'-Bis(diphenylphosphino)ferrocene] Palladium (II) Dichloride |
| PdCl$_2$(PPh$_3$)$_2$ or Pd(PPh$_3$)$_2$Cl$_2$ | Bis(triphenylphosphine)palladium (II) Dichloride |
| Pd$_2$(dba)$_3$ = | Tris(dibenzylideneacetone)dipalladium(0) |
| Pd(PPh$_3$)$_4$ = | Tetrakis(triphenylphosphine)palladium(0) |
| PE = | Petroleum ether |
| Ph = | Phenyl |
| PhMe = | Toluene |
| PK = | Plasma Kallikrein |
| PPh$_3$ = | Triphenylphosphine |
| RFU = | Relative Fluorescence Unit |
| sat. = | Saturated |
| s-BuLi = | sec-Butyl Lithium |
| SFC (purification) = | Supercritical Fluid Chromatography (purification) |
| TBAF = | Tetra-n-butylammonium fluoride |
| t-BuOK or KOt-Bu | Potassium tert-Butoxide |

TABLE A-continued

Abbreviations

| | |
|---|---|
| TEA ot Et₃N = | Triethylamine |
| Tf or triflyl = | Trifluoromethylsulfonyl (i.e. —SO₂—CF₃) |
| TFA = | Trifluoroacetic acid |
| THF = | Tetrahydrofuran |
| THP = | Tetrahydropyranyl |
| Ti(Oi-Pr)₄ = | Titanium(IV) Isopropoxide |
| (i-Pr)₃TiMe or Ti(i-Pr)₃Me | Methyl Triisopropoxy Titanium |
| TLC = | Thin Layer Chromatography |
| TMS = | Trimethysilyl |
| TMSCN = | Trimethylsilyl Cyanide |
| Tris (buffer) = | 2-Amino-2-(hydroxymethyl)-1,3-propanediol |
| Ts or tosyl = | —SO₂-(p-methylphenyl) |
| TsCl = | Tosyl Chloride |

The following Examples are set forth to aid in the understanding of the invention and are not intended and should not be construed to limit in any way the invention set forth in the claims which follow thereafter.

Unless otherwise indicated in the examples, all temperature is expressed in Centigrade (° C.). All reactions were conducted under an inert atmosphere at ambient temperature unless otherwise noted. Unless otherwise specified, reaction solutions were stirred at room temperature under a $N_{2(g)}$ or $Ar_{(g)}$ atmosphere. Reagents employed without synthetic details are commercially available or made according to known methods, for example according to literature procedures. When solutions were "concentrated to dryness", they were concentrated using a rotary evaporator under reduced pressure, when solutions were dried, they were typically dried over a drying agent such as $MgSO_4$ or $Na_2SO_4$. Where a synthesis product is listed as having been isolated as a residue, it will be understood by those skilled in the art that the term "residue" does not limit the physical state in which the product was isolated and may include, for example, a solid, an oil, a foam, a gum, a syrup, and the like.

In obtaining the compounds described in the examples below and the corresponding analytical data, the following experimental and analytical protocols were followed unless otherwise indicated.

LC-MS: Unless otherwise indicated, the analytical LC-MS system used consisted of a Shimadzu LCMS-2020 with electrospray ionization (ESI) in positive ion detection mode with 20ADXR pump, SIL-20ACXR autosampler, CTO-20AC column oven, M20A PDA Detector and LCMS 2020 MS detector. The column was a HALO a C18 30*5.0 mm, 2.7 µm. The mobile phase A was water containing 0.05% TFA and mobile phase B was acetonitrile containing 0.05% TFA. The gradient was from 5% mobile phase B to 100% (95%) in 2.0 min, hold 0.7 min, then revert to 5% mobile phase B over 0.05 min and maintain for 0.25 min. The Column Oven (CTO-20AC) was operated at a 40.0° C. The flow rate was 1.5 mL/min, and the injection volume was 1 µl. PDA (SPD-M20A) detection was in the range 190-400 nm. The MS detector, which was configured with electrospray ionization as ionizable source; Acquisition mode: Scan; Nebulizing Gas Flow: 1.5 L/min; Drying Gas Flow: 15 L/min; Detector Voltage: Tuning Voltage±0.2 kv; DL Temperature: 250° C.; Heat Block Temperature: 250° C.; Scan Range: 90.00-900.00 m/z. ELSD (Alltech 3300) detector Parameters: Drift Tube Temperature: 60±5° C.; N2 Flow-Rate: 1.8±0.2 L/min. Mobile phase gradients were optimized for the individual compounds. Calculated mass corresponds to the exact mass.

Preparative HPLC: Unless otherwise noted, preparative HPLC purifications were performed with Waters Auto purification system (2545-2767) with a 2489 UV detector. The column was selected from one of the following: Waters C18, 19×150 mm, 5 µm; XBridge Prep OBD C18 Column, 30×150 mm 5 µm; XSelect CSH Prep C18 OBD Column, 5 µm, 19150 mm; XBridge Shield RP18 OBD Column, 30×150 mm, 5 µm; Xselect CSH Fluoro Phenyl, 30×150 mm, 5 µm; or YMC-Actus Triart C18, 30×150 mm, 5 µm. The mobile phases consisted of mixtures of acetonitrile (5-95%) in water containing 0.1% FA or 10 mmol/L $NH_4HCO_3$. Flow rates were maintained at 25 mL/min, the injection volume was 1200 µL, and the UV detector used two channels 254 nm and 220 nm. Mobile phase gradients were optimized for the individual compounds.

Chiral chromatography: Chiral analytical chromatography was performed on one of Chiralpak AS, AD, Chiralcel OD, OJ Chiralpak IA, IB, IC, ID, IE, IF, IG, IH columns (Daicel Chemical Industries, Ltd.) (R,R)-Whelk-01, (S,S)-Whelk-01 columns (Regis technologies, Inc.) CHIRAL Cellulose-SB, SC, SA columns (YMC Co., Ltd.) as noted, at different column size (50×4.6 mm, 100×4.6 mm, 150×4.6 mm, 250×4.6 mm, 50×3.0 mm, 100×3.0 mm), with percentage of either ethanol in hexane (% Et/Hex) or isopropanol in hexane (% IPA/Hex) as isocratic solvent systems, or using supercritical fluid (SFC) conditions.

Normal phase flash chromatography: Unless otherwise noted, normal phase flash column chromatography (FCC) was performed on silica gel with pre-packaged silica gel columns (such as RediSep®), using ethyl acetate (EtOAc)/hexanes, ethyl acetate (EtOAc)/Petroleum ether (b.p. 60-90° C.), $CH_2Cl_2$/MeOH, or $CH_2Cl_2$/10% 2N $NH_3$ in MeOH, as eluent.

¹H NMR: Unless otherwise noted, ¹H NMR spectra were acquired using 400 MHz spectrometers (or 300 MHz spectrometers) in DMSO-d₆ solutions. The nuclear magnetic resonance (NMR) spectral characteristics refer to chemical shifts (δ) are expressed in parts per million (ppm). Tetramethylsilane (TMS) was used as internal reference in DMSO-d₆ solutions, and residual $CH_3OH$ peak or TMS was used as internal reference in $CD_3OD$ solutions. Coupling constants (J) are reported in hertz (Hz). The nature of the shifts as to multiplicity is reported as s (singlet), d (doublet), t (triplet), q (quartet), dd (double doublet), dt (double triplet), m (multiplet), br (broad).

SYNTHESIS EXAMPLES: INTERMEDIATES

Intermediate 1: 3-(Tert-butyl) 8-methyl 5-oxo-7-(((trifluoromethyl)sulfonyl)oxy)-1,2,3,5-tetrahydroindolizine-3,8-dicarboxylate

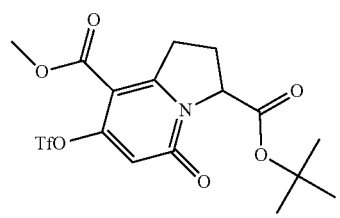

Step 1: Tert-butyl (S)-5-methoxy-3,4-dihydro-2H-pyrrole-2-carboxylate

To a solution of tert-butyl (S)-5-oxopyrrolidine-2-carboxylate (5.0 g, 27.00 mmol, 1.0 equiv.) in DCM (50 mL)

was added trimethyloxonium tetrafluoroborate (4.8 g, 32.39 mmol, 1.2 equiv.). The mixture was stirred at room temperature for 3 hours, then poured into a saturated aqueous solution of sodium hydrogen carbonate (200 mL) followed by extraction with dichloromethane. The combined organic layers were dried over $Na_2SO_4$ and concentrated under vacuum. The residue was purified by silica gel chromatography with MeOH/DCM (0→10%) to yield tert-butyl (S)-5-methoxy-3,4-dihydro-2H-pyrrole-2-carboxylate as colorless oil. LC/MS: mass calculated for $C_{10}H_{17}NO_3$: 199.12, measured: 200.10 $[M+H]^+$.

Step 2: 3-(Tert-butyl) 8-methyl 7-hydroxy-5-oxo-1,2,3,5-tetrahydroindolizine-3,8-dicarboxylate Tert-butyl (S)-5-methoxy-3,4-dihydro-2H-pyrrole-2-carboxylate (1.8 g, 9.03 mmol, 1.0 equiv.) was combined with dimethyl 3-oxopentanedioate (3.1 g, 18.06 mmol, 2.0 equiv.) and triethylamine (0.1 mL) and the mixture was stirred at 120° C. for 3 hours, then cooled to room temperature and purified by reverse column chromatography with $CH_3CN$/water (5%→70%) to yield 3-(tert-butyl) 8-methyl 7-hydroxy-5-oxo-1,2,3,5-tetrahydroindolizine-3,8-dicarboxylate as light yellow oil. LC/MS: mass calculated for $C_{15}H_{19}NO_6$: 309.12, measured: 310.10 $[M+H]^+$.

Step 3: 3-(Tert-butyl) 8-methyl 5-oxo-7-(((trifluoromethyl)sulfonyl)oxy)-1,2,3,5-tetrahydroindolizine-3,8-dicarboxylate To a solution of 3-(tert-butyl) 8-methyl 7-hydroxy-5-oxo-1,2,3,5-tetrahydroindolizine-3,8-dicarboxylate (0.7 g, 2.26 mmol, 1.0 equiv.) in DCM (20 mL) was added trifluoro-N-phenyl-N-(trifluoromethylsulfonyl) methanesulfonamide (0.97 g, 2.71 mmol, 1.2 equiv.), followed by the addition of triethylamine (0.69 g, 6.80 mmol, 3.0 equiv.) at 0° C. under $N_2$. The reaction mixture was stirred for 3 h at room temperature, then quenched with water, extracted with DCM, dried over $Na_2SO_4$, and concentrated under vacuum. The residue was purified by silica gel chromatography with EA/PE (0→50%) to yield 3-(tert-butyl) 8-methyl 5-oxo-7-(((trifluoromethyl)sulfonyl)oxy)-1,2,3,5-tetrahydroindolizine-3,8-dicarboxylate as colorless oil. LC/MS: mass calculated for $C_{16}H_{18}F_3NO_8S$: 441.07, measured 386.00 $[M-56+H]^+$.

Intermediate 2: (6-((1-(((tert-butoxycarbonyl)amino) cyclopropyl)methyl)-3-chloro-2-fluorophenyl)boronic acid

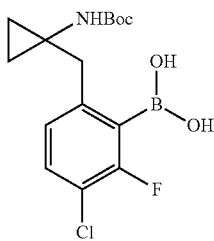 [SMILES: CC(C)(C)OC(=O)NC1(Cc2ccc(Cl)c(F)c2B(O)O)CC1]

Step 1: 2-Bromo-4-chloro-3-fluorobenzoic acid

To a cooled (−78° C.) solution of DIEA (8.9 g, 68.75 mmol, 0.3 equiv.) in THF was added dropwise n-BuLi (229.2 mL, 572.88 mmol, 2.5 equiv.). The mixture was stirred at −30° C. for 30 min, then cooled to −78° C., and a solution of 4-chloro-3-fluorobenzoic acid (40.0 g, 229.15 mmol, 1.0 equiv.) in THF was added over 1 h. The reaction was stirred at −78° C. for 6 h. A solution of 1,2-dibromo-1,1,2,2-tetrachloroethane (112.0 g, 343.73 mmol, 1.5 equiv.) in THF was then added and the reaction was stirred at −78° C. for further 2 h and then room temperature overnight. The reaction mixture was quenched with water, the layers were separated, and the aqueous layer washed with $Et_2O$. The aqueous layer was acidified with 1.5 M HCl and then extracted in EtOAc. The combined organic layers were dried over anhydrous sodium sulfate, filtered and concentrated to yield 2-bromo-4-chloro-3-fluorobenzoic acid as an off-white solid.

Step 2: (2-Bromo-4-chloro-3-fluorophenyl)methanol

To a solution of 2-bromo-4-chloro-3-fluorobenzoic acid (14.5 g, 57.21 mmol, 1.0 equiv.) in THF was added $BH_3$-THF (143.0 mL, 143.02 mmol, 2.5 equiv.) slowly over 30 min at 0° C. under $N_2$. The reaction mixture was stirred for 3 h at room temperature, then quenched with water, extracted with EA, washed with brine, dried over $Na_2SO_4$ and concentrated under vacuum to yield (2-bromo-4-chloro-3-fluorophenyl)methanol as a white solid.

Step 3: 2-Bromo-1-(bromomethyl)-4-chloro-3-fluorobenzene

To a solution of (2-bromo-4-chloro-3-fluorophenyl) methanol (11.5 g, 48.02 mmol, 1.0 equiv.) in DCM (150 mL) was added a solution of tribromophosphine in DCM (52.8 mL, 52.82 mmol, 1.1 equiv.) slowly at 0° C. under $N_2$. The mixture was stirred for 3 h at room temperature, then quenched with water, extracted with DCM, washed with $NaHCO_3$(aq.), dried over $Na_2SO_4$ and concentrated under vacuum. The residue was purified by silica gel chromatography with EA/PE (0→20%) to yield 2-bromo-1-(bromomethyl)-4-chloro-3-fluorobenzene as a white solid. $^1$H-NMR: (300 MHz, DMSO-$d_6$): δ 7.66 (dd, J=8.4, 7.3 Hz, 1H), 7.54 (dd, J=8.4, 1.6 Hz, 1H), 4.78 (s, 2H).

Step 4: 2-(2-Bromo-4-chloro-3-fluorophenyl)acetonitrile

To a solution of 2-bromo-1-(bromomethyl)-4-chloro-3-fluorobenzene (6.0 g, 19.84 mmol, 1.0 equiv.) in ACN (80 mL) was added trimethylsilanecarbonitrile (2.95 g, 29.76 mmol, 1.5 equiv.), then a solution of TBAF (29.8 mL, 29.77 mmol, 1 M in THF, 1.5 equiv.) was added under an atmosphere of nitrogen. The reaction mixture was stirred for 1 h at room temperature, then concentrated in vacuo. The residue was purified by silica gel chromatography with EA/PE (0→20%) to yield 2-(2-bromo-4-chloro-3-fluorophenyl) acetonitrile as a white solid. $^1$H-NMR: (300 MHz, DMSO-$d_6$): δ 7.72 (dd, J=8.4, 7.4 Hz, 1H), 7.45 (dd, J=8.5, 1.6 Hz, 1H), 4.17 (s, 2H).

Step 5: 1-(2-Bromo-4-chloro-3-fluorobenzyl)cyclopropan-1-amine

To a solution of 2-(2-bromo-4-chloro-3-fluorophenyl)acetonitrile (3.5 g, 14.08 mmol, 1.0 equiv.) and tetraisopropylorthotitanate (4.4 g, 15.49 mmol, 1.1 equiv.) in diethyl ether (60 mL) was slowly added ethylmagnesium bromide (2M in $Et_2O$, 14.1 mL, 28.17 mmol, 2.0 equiv.) at room temperature under N$_2$. After stirring for 2 h, boron trifluoride etherate (4.0 g, 28.17 mmol, 2.0 equiv.) was added and the reaction mixture was stirred for 1 h at room temperature The mixture was poured into a cold aqueous solution of NaOH (10%) and diluted with ethyl acetate and filtered. The filtrate was extracted with EA twice and the combined organic phases were dried over Na$_2$SO$_4$ and concentrated under vacuum. The residue was purified by reverse column chromatography with CH$_3$CN/0.05% TFA water (5%->50%) to yield 1-(2-bromo-4-chloro-3-fluorobenzyl)cyclopropanamine as a white solid (2.2 g, 56.0% yield). LC/MS: mass calculated for C$_{10}$H$_{10}$BrClFN: 276.97, measured: 279.90 [M+H+2]$^+$.

Step 6: Tert-butyl (1-(2-bromo-4-chloro-3-fluorobenzyl)cyclopropyl)carbamate

To a solution of 1-(2-bromo-4-chloro-3-fluorobenzyl)cyclopropanamine (3.0 g, 10.77 mmol, 1.0 equiv.) in DCM (50 mL) was added di-tert-butyl dicarbonate (3.5 g, 16.15 mmol, 1.5 equiv.), triethylamine (3.27 g, 32.31 mmol, 3.0 equiv.). The reaction mixture was stirred for 3 h at room temperature, then quenched with water, extracted with DCM, dried over Na$_2$SO$_4$, and concentrated under vacuum. The residue was purified by silica gel chromatography with EA/PE (0→20%) to yield tert-butyl 1-(2-bromo-4-chloro-3-fluorobenzyl)cyclopropylcarbamate as a white solid. LC/MS: mass calculated for C$_{15}$H$_{16}$BrClFNO$_2$: 377.02, measured: 321.9 [M−56+H]$^+$, 323.9 [M−56+2+H]$^+$.

Step 7: (6-((1-((Tert-butoxycarbonyl)amino)cyclopropyl)methyl)-3-chloro-2-fluorophenyl)boronic acid To a solution of tert-butyl 1-(2-bromo-4-chloro-3-fluorobenzyl)cyclopropylcarbamate (1.8 g, 4.75 mmol, 1.0 equiv.) in THF (40 mL) was added methyllithium (1.6 M in diethyl ether, 3.0 mL, 4.75 mmol, 1.0 equiv.) under N$_2$ at −78° C., the reaction mixture was stirred for 30 min, n-BuLi (2.5 M in hexane, 1.9 mL, 4.75 mmol, 1.0 equiv.) was added, the mixture was stirred for 30 min, and finally trimethyl borate (0.74 g, 7.13 mmol, 1.5 equiv.) was added. The reaction mixture was warmed to room temperature and stirred for 1 h at room temperature, then quenched with NH$_4$Cl (aq.), extracted with EA, washed brine, dried over Na$_2$SO$_4$, and concentrated under vacuum to yield 6-((1-(tert-butoxycarbonylamino)cyclopropyl)methyl)-3-chloro-2-fluorophenylboronic acid as a light yellow solid. LC/MS: mass calculated for C$_{15}$H$_{20}$BClFNO$_4$: 343.12, measured: 366.00 [M+Na]$^+$.

Intermediate 3: 7-chloro-1,10-dioxo-1,4,10,12,13,14-hexahydro-2H-spiro[benzo[5,6]azocino[4,3-g]indolizine-3,1'-cyclopropane]-12-carboxylic acid

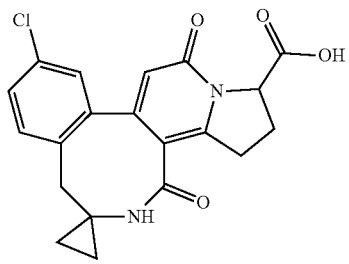 [SMILES: O=C1NC2(CC2)Cc2ccc(Cl)cc2-c2cc(=O)n3c(c21)CCC3C(=O)O]

Step 1:
1-(2-Bromo-4-chlorobenzyl)cyclopropan-1-amine

To a solution of 2-bromo-4-chlorophenylacetonitrile (28.0 g, 0.12 mol, 1.0 equiv.) and titanium tetraisopropanolate (39.5 g, 0.13 mol, 1.10 equiv.) in diethyl ether (300 mL), ethylmagnesium bromide (121.5 mL, 0.24 mol, 2.0 equiv., 2 M in Me-THF) was added at room temperature. The exothermic mixture was stirred for 1 h at room temperature. Boron trifluoride etherate (30.0 g, 0.24 mmol, 2.0 equiv.) was then added and the mixture was stirred for 1 h. The mixture was poured into a cold aqueous solution of NaOH (10%) and diluted with ethyl acetate. The mixture was filtered, and the organic layer was washed with water and brine, dried over anhydrous sodium sulfate, filtered, and the solvent evaporated under reduced pressure. The residue was purified by reverse phase chromatography on C18 (330 g, MeCN/H$_2$O (0.05% CF$_3$COOH): 0→30%) to yield 1-(2-bromo-4-chlorobenzyl)cyclopropan-1-amine as a light yellow oil. LC/MS: mass calculated for C$_{10}$H$_{11}$BrClN: 258.98, measured: 261.95 [M+H+2]$^+$.

Step 2: Tert-butyl (1-(2-bromo-4-chlorobenzyl)cyclopropyl)carbamate

To a mixture of 1-(2-bromo-4-chlorobenzyl)cyclopropan-1-amine (14.0 g, 25.11 mmol, 1.0 equiv.) in methanol (140 mL) was added triethylamine (9.0 mL, 64.48 mmol, 1.2 equiv.) and di-tert-butyl dicarbonate (17.6 g, 80.60 mmol, 1.5 equiv.) was stirred for 2 h at room temperature. The reaction was added water and extracted with EA twice. The combined organic layers were washed with brine, dried over Na$_2$SO$_4$, and concentrated under vacuum. The reaction mixture was purified by silica gel chromatography (0→20% EA/PE) to yield tert-butyl (1-(2-bromo-4-chlorobenzyl)cyclopropyl)carbamate as a white solid. LC/MS: mass calculated for C$_{15}$H$_{19}$BrClNO$_2$: 359.03, measured: 305.90 [M−t−Bu+H+2]$^+$.

Step 3: (2-((1-((Tert-butoxycarbonyl)amino)cyclopropyl)methyl)-5-chlorophenyl)boronic acid To a solution of tert-butyl (1-(2-bromo-4-chlorobenzyl)cyclopropyl)carbamate (10.0 g, 27.73 mmol, 1.0 equiv.) in dry tetrahydrofuran (160 mL) under nitrogen was added methyllithium (17.3 mL, 27.72 mmol, 1.60 M in Et$_2$O, 1.0 equiv.) at −78° C. and the solution was stirred for 1 h at this temperature. To the solution above was added n-butyllithium 11.1 mL, 27.73 mmol, 1.0 equiv., 2.0 M in THF) dropwise at −78° C. and the solution was allowed stirred for 1 h. To the solution above was added trimethyl borate (2.9 g, 27.73 mmol, 1.0 equiv.) and allowed to warm to room temperature for 1 h. The solution was quenched with sat. NH$_4$Cl (aq.) and extracted with ethyl acetate twice. The combined organic layer was washed with brine, dried over Na$_2$SO$_4$ and concentrated. The residue was purified by reverse phase chromatography on C18 (80 g, MeCN/H$_2$O (0.05% CF$_3$COOH): 0→50%) to yield (2-((1-((tert-butoxycarbonyl)amino)cyclopropyl)methyl)-5-chlorophenyl)boronic acid as a white solid. LC/MS: mass calculated for C$_{15}$H$_{21}$BClNO$_4$: 325.13, measured: 348.05 [M+Na]$^+$.

Step 4: 3-(Tert-butyl) 8-methyl 7-(2-((1-((tert-butoxycarbonyl)amino)cyclopropyl)methyl)-5-chlorophenyl)-5-oxo-1,2,3,5-tetrahydroindolizine-3,8-dicarboxylate To a mixture of 3-(tert-butyl) 8-methyl 5-oxo-7-(((perfluorobutyl)sulfonyl)oxy)-1,2,3,5-tetrahydroindolizine-3,8-dicarboxylate (1.7 g, 2.88 mmol, 1.0 equiv.), (2-((1-((tert-butoxycarbonyl)amino)cyclopropyl)methyl)-5-chlorophenyl)boronic acid (1.2 g, 3.73 mmol, 1.3 equiv.) and cesium fluoride (1.3 g, 8.624 mmol, 3.0 equiv.) in 1,4-dioxane (30 mL) was added Pd(PPh$_3$)$_4$ (332 mg, 0.29 mmol, 0.1 equiv.) and the mixture was stirred at 65° C. for 2 h. After the reaction mixture was cooled to room temperature, the resulting solution was diluted with water and extracted with ethyl acetate twice. The combined organic layer was washed with brine, dried over Na$_2$SO$_4$ and concentrated. The residue was purified by silica gel chromatography (0→80% EtOAc/petroleum ether) to yield 3-(tert-butyl) 8-methyl 7-(2-((1-((tert-butoxycarbonyl)amino)cyclopropyl)methyl)-5-chlorophenyl)-5-oxo-1,2,3,5-tetrahydroindolizine-3,8-dicarboxylate as a light yellow solid. LC/MS: mass calculated for C$_{30}$H$_{37}$ClN$_2$O$_7$: 572.23, measured: 573.15 [M+H]$^+$.

Step 5: 7-(2-((1-Aminocyclopropyl)methyl)-5-chlorophenyl)-8-(methoxycarbonyl)-5-oxo-1,2,3,5-tetrahydroindolizine-3-carboxylic acid To a solution of 3-(tert-butyl) 8-methyl 7-(2-((1-((tert-butoxycarbonyl)amino)cyclopropyl)methyl)-5-chlorophenyl)-5-oxo-1,2,3,5-tetrahydroindolizine-3,8-dicarboxylate (1.5 g, 2.62 mmol, 1.0 equiv.) in dichloromethane (15 mL) was added 2,2,2-trifluoroacetic acid (5 mL). The reaction mixture was stirred at room temperature overnight. The solution was concentrated under vacuum and purified by reverse phase chromatography on C18 (330 g, ACN/H$_2$O (0.05% CF$_3$COOH): 0→30%) to yield 7-(2-((1-aminocyclopropyl)methyl)-5-chlorophenyl)-8-(methoxycarbonyl)-5-oxo-1,2,3,5-tetrahydroindolizine-3-carboxylic acid as yellow solid. LC/MS: mass calculated for C$_{21}$H$_{21}$ClN$_2$O$_5$: 416.11, measured: 417.05 [M+H]$^+$.

Step 6: 7-Chloro-1,10-dioxo-1,4,10,12,13,14-hexahydro-2H-spiro[benzo[5,6]azocino[4,3-g]indolizine-3,1'-cyclopropane]-12-carboxylic acid To a solution of 7-(2-((1-aminocyclopropyl)methyl)-5-chlorophenyl)-8-(methoxycarbonyl)-5-oxo-1,2,3,5-tetrahydroindolizine-3-carboxylic acid (1.0 g, 2.40 mmol, 1.0 equiv.) and dry molecular sieve (1.0 g) in dry tetrahydrofuran (10 mL) was added sodium ethoxide (18.8 mL, 47.97 mmol, 20.0 equiv., 20% in ethanol). The mixture was stirred for 12 h at room temperature. After filtration, the filtrate was diluted with water and extracted with ethyl acetate twice. The combined organic layers were washed with brine, dried over anhydrous sodium sulfate, and concentrated. The residue was purified by reverse phase chromatography on C18 (330 g, ACN/H$_2$O: 0→28%) to yield 7-chloro-1,10-dioxo-1,4,10,12,13,14-hexahydro-2H-spiro[benzo[5,6]azocino[4,3-g]indolizine-3,1'-cyclopropane]-12-carboxylic acid as yellow solid. LC/MS: mass calculated for C$_{20}$H$_{17}$ClN$_2$O$_4$: 384.09, measured: 385.00 [M+H]$^+$.

Intermediate 4: 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid

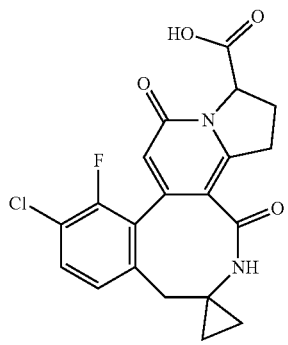 [SMILES: O=C1NC2(CC2)Cc2ccc(Cl)c(F)c2-c2cc(=O)n3c(c21)CCC3C(=O)O]

Step 1: 3-(Tert-butyl) 8-methyl 7-(6-((1-((tert-butoxycarbonyl)amino)cyclopropyl)methyl)-3-chloro-2-fluorophenyl)-5-oxo-1,2,3,5-tetrahydroindolizine-3,8-dicarboxylate To a solution of 3-(tert-butyl) 8-methyl 7-hydroxy-5-oxo-1,2,3,5-tetrahydroindolizine-3,8-dicarboxylate (0.65 g, 1.47 mmol, 1.0 equiv.) and 6-((1-(tert-butoxycarbonylamino)cyclopropyl)methyl)-3-chloro-2-fluorophenylboronic acid (0.56 g, 1.62 g, 1.1 equiv.) in 1,4-dioxane (20 mL) and water (4 mL) was added cesium fluoride (0.67 g, 4.41 mmol, 3.0 equiv.), potassium bromide (35 mg, 0.30 mmol, 0.2 equiv.) and Pd(PPh$_3$)$_4$ (0.17 g, 0.15 mmol, 0.1 equiv.) under N$_2$. The reaction mixture was stirred overnight at 100° C., then cooled to room temperature and quenched with water, extracted with EA, washed with brine, dried over Na$_2$SO$_4$, and concentrated under vacuum. The residue was purified by silica gel chromatography with EA/PE (0→80%) to yield 3-(tert-butyl) 8-methyl 7-(6-((1-((tert-butoxycarbonyl)amino)cyclopropyl)methyl)-3-chloro-2-fluorophenyl)-5-oxo-1,2,3,5-tetrahydroindolizine-3,8-dicarboxylate as light yellow oil. LC/MS: mass calculated for C$_{30}$H$_{36}$ClFN$_2$O$_7$: 590.22, measured: 591.25 [M+H]$^+$.

Step 2: 7-(6-((1-Aminocyclopropyl)methyl)-3-chloro-2-fluorophenyl)-8-(methoxycarbonyl)-5-oxo-1,2,3,5-tetrahydroindolizine-3-carboxylic acid To a solution of 3-(tert-butyl) 8-methyl 7-(6-((1-((tert-butoxycarbonyl)amino)cyclopropyl)methyl)-3-chloro-2-fluorophenyl)-5-oxo-1,2,3,5-tetrahydroindolizine-3,8-dicarboxylate (0.22 g, 0.37 mmol, 1.0 equiv.) in DCM (10 mL) was added TFA (2 mL). The reaction was stirred for 1 h at room temperature, then concentrated under vacuum. The residue was purified by reverse column chromatography with CH$_3$CN/water (5%→50%) to yield 7-(6-((1-aminocyclopropyl)methyl)-3-chloro-2-fluorophenyl)-8-(methoxycarbonyl)-5-oxo-1,2,3,5-tetrahydroindolizine-3-carboxylic acid as off-white solid. LC/MS: mass calculated for C$_{21}$H$_{20}$ClFN$_2$O$_5$: 434.10, measured: 435.10 [M+H]$^+$.

Step 3: 7-Chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid A solution of 7-(6-((1-aminocyclopropyl)methyl)-3-chloro-2-fluorophenyl)-8-(methoxycarbonyl)-5-oxo-1,2,3, 5-tetrahydroindolizine-3-carboxylic acid (0.12 g, 0.27 mmol, 1.0 equiv.) in THF (6 mL) was added under $N_2$ to activated 3 Å molecular sieve (dried at 300° C. in a drying cabinet overnight) and stirred at room temperature for 2 h. Subsequently, the reaction mixture was admixed under $N_2$ at room temperature with sodium ethoxide ethanol solution (1.79 g, 5.52 mmol, 20.0 equiv.; 21% in ethanol, dried beforehand over activated 3 Å molecular sieve for 2 h) and stirred overnight at 30° C. After dilution with EA, the reaction mixture was admixed with saturated aqueous $NH_4Cl$ solution and brought to pH 3 with 1M HCl solution and extracted with EA. The combined organic phases were washed with brine, dried over $Na_2SO_4$, and concentrated under vacuum to yield 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid a light brown solid. LC/MS (ES, m/z): mass calculated for $C_{20}H_{16}ClFN_2O_4$: 402.08, measured: 403.13 $[M+H]^+$.

Intermediate 5: ethyl 1-(1-(tert-butoxy)-3-cyclopropyl-1-oxopropan-2-yl)-6-oxo-4-(((trifluoromethyl)sulfonyl)oxy)-1,6-dihydropyridine-3-carboxylate

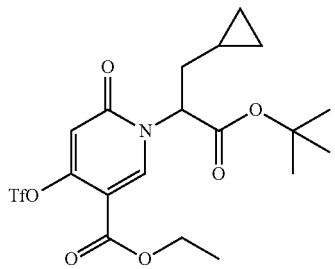 [SMILES: CCOC(=O)c1cn(C(CC2CC2)C(=O)OC(C)(C)C)c(=O)cc1OS(=O)(=O)C(F)(F)F]

Step 1: Tert-butyl (S)-2-amino-3-cyclopropylpropanoate (L)-2-amino-3-cyclopropylpropanoic acid (5.0 g, 38.71 mmol, 1.0 equiv.) was added to a mixture of 1,4-dioxane (100 mL) and sulfuric acid (10 mL) (prepared by cautious addition of the acid dropwise to 1,4-dioxane at 5° C.) at room temperature The solution was transferred into a sealed tube into which isobutylene (60 mL) was condensed at −78° C. The reaction mixture was then stirred overnight at room temperature. After the sealed tube was opened (while cooling), the reaction mixture was cautiously introduced into a stirred mixture of triethylamine (50 mL) and water (100 mL) cooled to 0° C. After removal of excess isobutylene, the product was extracted with EA (2×100 mL), dried over $Na_2SO_4$ and concentrated under vacuum to yield tert-butyl (S)-2-amino-3-cyclopropylpropanoate as yellow oil used in the next step without further purification. $^1$H-NMR: (400 MHz, DMSO-$d_6$): δ 3.23 (t, J=6.4 Hz, 1H), 1.84 (s, 2H), 1.33-1.47 (m, 11H), 0.69-0.80 (m, 1H), 0.34-0.44 (m, 2H), −0.02-0.10 (m, 2H).

Step 2: Ethyl 1-(1-(tert-butoxy)-3-cyclopropyl-1-oxopropan-2-yl)-4-hydroxy-6-oxo-1,6-dihydropyridine-3-carboxylate Diethyl 3-oxopentanedioate (5.75 g, 28.43 mmol, 1.0 equiv.) and diethoxymethyl acetate (6.46 g, 39.81 mmol, 1.4 equiv.) was stirred for 2 h at 100° C., and the mixture was cooled to room temperature, then co-evaporated three times with toluene and dried under vacuum. The residue was taken up in ethanol (60 mL), then a solution of (S)-tert-butyl 2-amino-3-cyclopropylpropanoate (5.53 g, 29.86 mmol, 1.05 equiv.) in ethanol (20 mL) was added at 0° C. and the reaction mixture was stirred for 2 h at room temperature. Subsequently, sodium ethoxide ethanol solution (21%) (9.2 g, 28.43 mmol, 1.0 equiv.) was added and the mixture was stirred for 1 h at room temperature The reaction mixture was quenched with $NH_4Cl$ (aq.), extracted with EA, washed with brine, dried over $Na_2SO_4$, and concentrated under vacuum. The residue was purified by silica gel chromatography with EA/PE (0→70%) to yield (S)-ethyl 1-(1-tert-butoxy-3-cyclopropyl-1-oxopropan-2-yl)-4-hydroxy-6-oxo-1,6-dihydropyridine-3-carboxylate as light yellow oil. LC/MS (ES, m/z): mass calculated for $C_{18}H_{25}NO_6$: 351.17, measured: 352.10 $[M+H]^+$.

Step 3: Ethyl 1-(1-(tert-butoxy)-3-cyclopropyl-1-oxopropan-2-yl)-6-oxo-4-(((trifluoromethyl)sulfonyl)oxy)-1,6-dihydropyridine-3-carboxylate To a solution of (S)-ethyl 1-(1-tert-butoxy-3-cyclopropyl-1-oxopropan-2-yl)-4-hydroxy-6-oxo-1,6-dihydropyridine-3-carboxylate (7.4 g, 21.05 mmol, 1.0 equiv.) in DCM (100 mL) was added trifluoro-N-phenyl-N-(trifluoromethylsulfonyl)methane sulfonamide (9.8 g, 27.38 mmol, 1.3 equiv.) followed by the addition of triethylamine (6.4 g, 63.18 mmol, 3.0 equiv.) at 0° C. under $N_2$. The reaction mixture was stirred for 3 h at room temperature, then quenched with water, extracted with DCM, dried over $Na_2SO_4$, and concentrated under vacuum. The residue was purified by silica gel chromatography with EA/PE (0→30%) to yield (S)-ethyl 1-(1-tert-butoxy-3-cyclopropyl-1-oxopropan-2-yl)-6-oxo-4-(trifluoromethylsulfonyloxy)-1,6-dihydropyridine-3-carboxylate as light yellow oil. LC/MS (ES, m/z): mass calculated for $C_{19}H_{24}F_3NO_8S$: 483.12, measured: 428.05 $[M-56+H]^+$.

Intermediate 6: 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoic acid

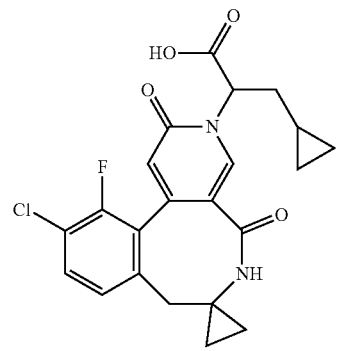 [SMILES: O=C1NC2(CC2)Cc2ccc(Cl)c(F)c2-c2cc(=O)n(C(CC3CC3)C(=O)O)cc21]

Step 1: Ethyl 1-(1-(tert-butoxy)-3-cyclopropyl-1-oxopropan-2-yl)-4-(6-((1-((tert-butoxycarbonyl)amino)cyclopropyl)methyl)-3-chloro-2-fluorophenyl)-6-oxo-1,6-dihydropyridine-3-carboxylate To a solution of ethyl 1-(1-tert-butoxy-3-cyclopropyl-1-oxopropan-2-yl)-6-oxo-4-(trifluoromethylsulfonyloxy)-1,6- dihydropyridine-3-carboxylate (2.25 g, 4.65 mmol, 1.0 equiv.) and 6-((1-(tert-butoxycarbonylamino)cyclopropyl)methyl)-3-chloro-2-fluorophenylboronic acid (1.6 g, 4.65 g, 1.0 equiv.) in 1,4-dioxane (30 mL) was added potassium carbonate (1.93 g, 13.97 mmol, 3.0 equiv.) and Pd(PPh$_3$)$_4$ (0.54 g, 0.47 mmol, 0.1 equiv.) under N$_2$. The reaction mixture was stirred overnight at 80° C., then cooled to room temperature and quenched with water, extracted with EA, washed with brine, dried over Na$_2$SO$_4$, and concentrated under vacuum. The residue was purified by silica gel chromatography with EA/PE (0→30%) to yield ethyl 1-(1-tert-butoxy-3-cyclopropyl-1-oxopropan-2-yl)-4-(6-((1-(tert-butoxycarbonylamino)cyclopropyl)methyl)-3-chloro-2-fluorophenyl)-6-oxo-1,6-dihydropyridine-3-carboxylate as light yellow oil. LC/MS (ES, m/z): mass calculated for C$_{33}$H$_{42}$ClFN$_2$O$_7$: 632.27, measured: 633.15 [M+H]$^+$.

Step 2: 2-(4-(6-((1-Aminocyclopropyl)methyl)-3-chloro-2-fluorophenyl)-5-(ethoxycarbonyl)-2-oxopyridin-1(2H)-yl)-3-cyclopropylpropanoic acid To a solution of ethyl 1-(1-tert-butoxy-3-cyclopropyl-1-oxopropan-2-yl)-4-(64(1-(tert-butoxycarbonylamino)cyclopropyl)methyl)-3-chloro-2-fluorophenyl)-6-oxo-1,6-dihydropyridine-3-carboxylate (1.15 g, 1.81 mmol, 1.0 equiv.) in DCM (25 mL) was added TFA (5 mL). The reaction was stirred overnight at room temperature, then concentrated under vacuum. The residue was purified by reverse column chromatography with CH$_3$CN/water (5%→50%) to yield 2-(4-(6-((1-aminocyclopropyl)methyl)-3-chloro-2-fluorophenyl)-5-(ethoxycarbonyl)-2-oxopyridin-1(2H)-yl)-3-cyclopropylpropanoic acid as an off-white solid. LC/MS (ES, m/z): mass calculated for C$_{24}$H$_{26}$ClFN$_2$O$_5$: 476.15, measured: 477.05 [M+H]$^+$.

Step 3: 2-(11-Chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoic acid A solution of 2-(4-(6-((1-aminocyclopropyl)methyl)-3-chloro-2-fluorophenyl)-5-(ethoxycarbonyl)-2-oxopyridin-1(2H)-yl)-3-cyclopropylpropanoic acid (0.6 g, 1.26 mmol, 1.0 equiv.) in THF (30 mL) was added under N$_2$ to activated 3 Å molecular sieve (dried at 300° C. in a drying cabinet overnight) and stirred at room temperature for 2 h. Subsequently, the reaction mixture was admixed under N$_2$ at room temperature with sodium ethoxide ethanol solution (8.15 g, 25.16 mmol, 20.0 equiv.; 21% in ethanol, dried beforehand over activated 3 Å molecular sieve for 2 h) and stirred at room temperature for 2 h. After dilution with EA, the reaction mixture was admixed with saturated aqueous NH$_4$Cl solution and brought to pH 3 with 1M HCl solution and extracted with EA. The combined organic phases were washed with brine, dried over Na$_2$SO$_4$, and concentrated under vacuum to yield 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoic acid methane as a light brown solid. LC/MS (ES, m/z): mass calculated for C$_{22}$H$_{20}$ClFN$_2$O$_4$: 430.11, measured: 431.00 [M+H]$^+$.

Intermediate 7: 7-chloro-8-fluoro-1,10-dioxo-1,2,3,4,10,12,13,14-octahydrobenzo[5,6]azocino[4,3-g]indolizine-12-carboxylic acid

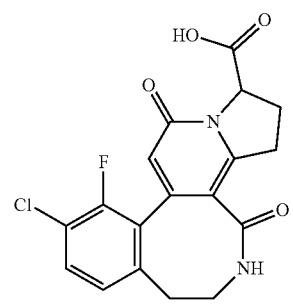 [SMILES: O=C1NCCc2ccc(Cl)c(F)c2-c2cc(=O)n3c(c21)CCC3C(=O)O]

Step 1: Tert-butyl (2-bromo-4-chloro-3-fluorophenethyl)carbamate

To a solution of 2-(2-bromo-4-chloro-3-fluorophenyl)acetonitrile (2.0 g, 8.05 mmol, 1.0 equiv.) in EtOH (30 mL) was added di-tert-butyl dicarbonate (2.1 g, 9.66 mmol, 1.2 equiv.), cobalt chloride hexahydrate (1.9 g, 8.04 mmol, 1.0 equiv.) followed by the addition of NaBH$_4$ (0.61 g, 16.10 mmol, 2.0 equiv.) at −30° C. The reaction mixture was stirred at −10° C. for 2 h, then quenched with NH$_4$Cl (aq.), extracted with EA, dried over Na$_2$SO$_4$, and concentrated under vacuum. The residue was purified by silica gel chromatography with EA/PE (0→20%) to yield tert-butyl (2-bromo-4-chloro-3-fluorophenethyl) carbamate as a white solid. LC/MS (ES, m/z): mass calculated for C$_{13}$H$_{16}$BrClFNO$_2$: 351.00, measured: 298.00 [M+2−56+H]$^+$.

Step 2: Tert-butyl (4-chloro-3-fluoro-2-(4,4,5,5-tetramethyl-1,3,2-dioxaborolan-2-yl)phenethyl)carbamate To a solution of tert-butyl (2-bromo-4-chloro-3-fluorophenethyl)carbamate (1.0 g, 2.83 mmol, 1.0 equiv.) in 1,4-dioxane (20 mL) was added 4,4,4',4',5,5,5',5'-octamethyl-2,2'-bi(1,3,2-dioxaborolane) (2.9 g, 11.34 mmol, 4.0 equiv.), potassium acetate (0.84 g, 8.51 mmol, 3.0 equiv.) and Pd(dppf)Cl$_2$CH$_2$Cl$_2$ (0.23 g, 0.28 mmol, 0.1 equiv.) under N$_2$. The reaction mixture was stirred for 5 h at 90° C., then quenched with water, extracted with EA, washed with brine, dried over Na$_2$SO$_4$, and concentrated under vacuum. The residue was purified by silica gel chromatography with EA/PE (0→30%) to yield tert-butyl (4-chloro-3-fluoro-2-(4,4,5,5-tetramethyl-1,3,2-dioxaborolan-2-yl)phenethyl)carbamate as light yellow oil. LC/MS (ES, m/z): mass calculated for C$_{19}$H$_{28}$BClFNO$_4$: 399.18, measured: 422.20 [M+Na]$^+$.

Step 3: 3-(Tert-butyl) 8-methyl 7-(6-(2-((tert-butoxycarbonyl)amino)ethyl)-3-chloro-2-fluorophenyl)-5-oxo-1,2,3,5-tetrahydroindolizine-3,8-dicarboxylate To a solution of 3-(tert-butyl) 8-methyl 5-oxo-7-(((trifluoromethyl)sulfonyl)oxy)-1,2,3,5-tetrahydroindolizine-3,8-dicarboxylate (0.35 g, 0.03 mmol, 1.0 equiv.) and tert-butyl (4-chloro-3-fluoro-2-(4,4,5,5-tetramethyl-1,3,2-dioxaborolan-2-yl)phenethyl)carbamate (0.79 g, 1.98 g, 2.5 equiv.) in 1,4-dioxane (10 mL) was added potassium carbonate (0.33 g, 2.38 mmol, 3.0 equiv.) and Pd(PPh$_3$)$_4$ (0.09 g, 0.08 mmol, 0.1 equiv.) under N$_2$. The reaction mixture was stirred for 2 h at 90° C., then quenched with water, extracted with EA, dried over Na$_2$SO$_4$, and concentrated under vacuum. The residue was purified by silica gel chromatography with EA/PE (0→50%) to yield 3-(tert-butyl) 8-methyl 7-(6-(2-((tert-butoxycarbonyl)amino)ethyl)-3-chloro-2-fluorophenyl)-5-oxo-1,2,3,5-tetrahydroindolizine-3,8-dicarboxylate as light yellow oil. LC/MS (ES, m/z): mass calculated for C$_{28}$H$_{34}$ClFN$_2$O$_7$: 564.20, measured: 587.25 [M+Na]$^+$.

Step 4: 7-(6-(2-Aminoethyl)-3-chloro-2-fluorophenyl)-8-(methoxycarbonyl)-5-oxo-1,2,3,5-tetrahydroindolizine-3-carboxylic acid To a solution of 3-(tert-butyl) 8-methyl 7-(6-(2-((tert-butoxycarbonyl)amino)ethyl)-3-chloro-2-fluorophenyl)-5-oxo-1,2,3,5-tetrahydroindolizine-3,8-dicarboxylate (0.4 g, 0.71 mmol, 1.0 equiv.) in DCM (20 mL) was added TFA (4 mL). The reaction was stirred for 3 h at room temperature, then concentrated under vacuum. The residue was purified by reverse column chromatography with CH$_3$CN/0.05% TFA water (5%→50%) to yield 7-(6-(2-aminoethyl)-3-chloro-2-fluorophenyl)-8-(methoxycarbonyl)-5-oxo-1,2,3,5-tetrahydroindolizine-3-carboxylic acid as light yellow oil. LC/MS (ES, m/z): mass calculated for C$_{19}$H$_{18}$ClFN$_2$O$_5$: 408.09, measured: 409.15 [M+H]$^+$.

Step 5: 7-chloro-8-fluoro-1,10-dioxo-1,2,3,4,10,12,13,14-octahydrobenzo[5,6]azocino[4,3-g]indolizine-12-carboxylic acid A solution of 7-(6-(2-aminoethyl)-3-chloro-2-fluorophenyl)-8-(methoxycarbonyl)-5-oxo-1,2,3,5-tetrahydroindolizine-3-carboxylic acid (0.2 g, 0.49 mmol, 1.0 equiv) in THF (15 mL) was added under N$_2$ to activated 3 Å molecular sieve (dried at 300° C. in a drying cabinet overnight) and stirred at room temperature for 2 h. Subsequently, the reaction mixture was admixed under N$_2$ at room temperature with sodium ethoxide ethanol solution (3.17 g, 9.78 mmol, 20.0 equiv.; 21% in ethanol, dried beforehand over activated 3 Å molecular sieve for 2 h) and stirred for 2 h at room temperature. After dilution with EA, the reaction mixture was admixed with saturated aqueous NH$_4$Cl solution and brought to pH 3 with 1M HCl solution and extracted with EA. The combined organic phases were washed with brine, dried over Na$_2$SO$_4$, and concentrated under vacuum to yield 7-chloro-8-fluoro-1,10-dioxo-1,2,3,4,10,12,13,14-octahydrobenzo[5,6]azocino[4,3-g]indolizine-12-carboxylic acid a light brown solid. LC/MS (ES, m/z): mass calculated for C$_{18}$H$_{14}$ClFN$_2$O$_4$: 376.06, measured: 377.00 [M+H]$^+$.

Intermediate 8: 7-chloro-8-fluoro-3,3-dimethyl-1,10-dioxo-1,2,3,4,10,12,13,14-octahydrobenzo[5,6]azocino[4,3-g]indolizine-12-carboxylic acid

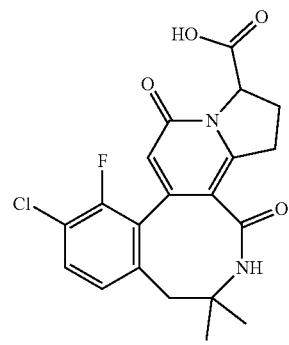 [SMILES: CC1(C)Cc2ccc(Cl)c(F)c2-c2cc(=O)n3c(c2C(=O)N1)CCC3C(=O)O]

Step 1: 2-Bromo-4-chloro-3-fluoro-1-(2-isocyanato-2-methylpropyl)benzene

To a solution of 3-(2-bromo-4-chloro-3-fluorophenyl)-2,2-dimethylpropanoic acid (1.5 g, 4.84 mmol, 1.0 equiv.) in toluene (15 mL) was added triethylamine (0.64 g, 6.30 mmol, 1.3 equiv.), diphenylphosphoryl azide (1.73 g, 6.30 mmol, 1.3 equiv.). The resulting mixture was maintained under nitrogen and stirred at room temperature for 1 h, and then the mixture was stirred at 100° C. for 3 h. After cooling down to room temperature, the reaction was quenched with water (50 mL). The resulting mixture was extracted with ethyl acetate (3×50 mL). The organic layers were combined, dried over anhydrous sodium sulfate, filtered and concentrated to yield 2-bromo-4-chloro-3-fluoro-1-(2-isocyanato-2-methylpropyl)benzene as a red-brown oil, which was used in the nest step without further purification. TLC: Rf=0.5 (EA/PE=1:5)

Step 2: Tert-butyl (1-(2-bromo-4-chloro-3-fluorophenyl)-2-methylpropan-2-yl) carbamate A solution of 2-bromo-4-chloro-3-fluoro-1-(2-isocyanato-2-methylpropyl)benzene (2.0 g, 6.52 mmol, 1.0 equiv.) in tert-butanol (20 mL) was stirred at 90° C. overnight. After cooling to room temperature, the mixture was concentrated. The residue was purified by silica gel chromatography (0→20% ethyl acetate/petroleum ether) to yield tert-butyl (1-(2-bromo-4-chloro-3-fluorophenyl)-2-methylpropan-2-yl)carbamate as a white solid. LC/MS (ES, m/z): mass calculated for C$_{15}$H$_{20}$BrClFNO$_2$: 379.03, measured: 365.05 [M−56+MeCN+H]$^+$, 367.05 [M−56+MeCN+H+2]$^+$.

Step 3: (6-(2-((Tert-butoxycarbonyl)amino)-2-methylpropyl)-3-chloro-2-fluorophenyl)boronic acid To a cooled (−78° C.) solution of tert-butyl (1-(2-bromo-4-chloro-3-fluorophenyl)-2-methylpropan-2-yl)carbamate (1.0 g, 2.62 mmol, 1.0 equiv.) in THF (10 mL) was added n-butyllithium (2.1 mL, 5.25 mmol, 2.5 M in hexane, 2.0 equiv.) under nitrogen. After stirring 1 h, a solution of trimethyl borate (2.7 g, 26.269 mmol, 10.0 equiv.) in THF (10 mL) was added. The resulting mixture was maintained under nitrogen and warmed to 0° C. slowly for 2 h. The reaction was quenched with HCl solution (2 M). The resulting mixture was extracted with ethyl acetate (3×50 mL). The organic layers were concentrated. The residue was purified by reverse-phase flash chromatography with the following conditions: Column, Cat No: SO230120-2, C18, 120 g, 20~35 μm, 100 Å, Lot: BT0010T1107; mobile phase, CH$_3$CN:H$_2$O (0.05% TFA)=30% increased to CH$_3$CN:H$_2$O (0.05% TFA)=60% in 30 min, hold CH$_3$CN:H$_2$O (0.05% TFA)=60% in 5 min, up to CH$_3$CN:H$_2$O (0.05% TFA)= 100% in 5 min, hold CH$_3$CN:H$_2$O (0.05% TFA)=100% in 5 min; Detector, UV 220 nm & 254 nm. The collected fractions were combined and lyophilized to yield (6-(2-((tert-butoxycarbonyl)amino)-2-methylpropyl)-3-chloro-2-fluorophenyl)boronic acid as a white solid. LC/MS (ES, m/z): mass calculated for C$_{15}$H$_{22}$BClFNO$_4$: 345.15, measured: 313.15 [M−56+Na]$^+$.

Step 4: 3-(Tert-butyl) 8-methyl 7-(6-(2-((tert-butoxycarbonyl)amino)-2-methylpropyl)-3-chloro-2-fluorophenyl)-5-oxo-1,2,3,5-tetrahydroindolizine-3,8-dicarboxylate To a solution of 3-(tert-butyl) 8-methyl 5-oxo-7-(((perfluorobutyl)sulfonyl)oxy)-1,2,3,5-tetrahydroindolizine-3,8-dicarboxylate (0.8 g, 1.35 mmol, 1.0 equiv.) and (6-(2-((tert-butoxycarbonyl)amino)-2-methylpropyl)-3-chloro-2-fluorophenyl)boronic acid (0.61 g, 1.76 mmol, 1.3 equiv.) in 1,4-dioxane (20 mL) was added potassium phosphate (0.43 g, 2.03 mmol, 1.5 equiv.) and Pd(PPh$_3$)$_4$ (0.16 g, 0.14 mmol, 0.1 equiv.) under N$_2$. The reaction mixture was stirred overnight at 90° C., then cooled to room temperature and quenched with water, extracted with EA, dried over Na$_2$SO$_4$, and concentrated under vacuum. The residue was purified by silica gel chromatography with EA/PE (0→60%) to yield 3-(tert-butyl) 8-methyl 7-(6-(2-((tert-butoxycarbonyl) amino)-2-methylpropyl)-3-chloro-2-fluorophenyl)-5-oxo-1, 2,3,5-tetrahydroindolizine-3,8-dicarboxylate as a white solid. LC/MS (ES, m/z): mass calculated for C$_{30}$H$_{38}$ClFN$_2$O$_7$: 592.24, measured: 593.35 [M+H]$^+$.

Step 5: 7-(6-(2-Amino-2-methylpropyl)-3-chloro-2-fluorophenyl)-8-(methoxycarbonyl)-5-oxo-1,2,3,5-tetrahydroindolizine-3-carboxylic acid To a solution of 3-(tert-butyl) 8-methyl 7-(6-(2-((tert-butoxycarbonyl)amino)-2-methylpropyl)-3-chloro-2-fluorophenyl)-5-oxo-1,2,3,5-tetrahydroindolizine-3,8-dicarboxylate (0.38 g, 0.64 mmol, 1.0 equiv.) in DCM (18 mL) was added TFA (6 mL) dropwise. The reaction was stirred for 3 h at room temperature, then concentrated under vacuum. The residue was purified by reverse column chromatography with CH$_3$CN/0.05% TFA water (5%→60%) to yield 7-(6-(2-amino-2-methylpropyl)-3-chloro-2-fluorophenyl)-8-(methoxycarbonyl)-5-oxo-1,2,3,5-tetrahydroindolizine-3-carboxylic acid as a white solid. LC/MS (ES, m/z): mass calculated for C$_{21}$H$_{22}$ClFN$_2$O$_5$: 436.12, measured: 437.10 [M+H]$^+$.

Step 6: 7-Chloro-8-fluoro-3,3-dimethyl-1,10-dioxo-1,2,3,4,10,12,13,14-octahydrobenzo[5,6]azocino[4, 3-g]indolizine-12-carboxylic acid To a solution of 7-(6-(2-amino-2-methylpropyl)-3-chloro-2-fluorophenyl)-8-(methoxycarbonyl)-5-oxo-1,2,3,5-tetrahydroindolizine-3-carboxylic acid (0.13 g, 0.29 mmol, 1.0 equiv.) in DCM (10 mL) was added trimethylaluminum (1.5 mL, 1.50 mmol, 1M in hexane, 5.0 equiv.) under N$_2$. The reaction was stirred for overnight at 30° C., then quenched with MeOH and concentrated under vacuum. The residue was purified by reverse column chromatography with CH$_3$CN/0.05% TFA water (5%→60%) to yield 7-chloro-8-fluoro-3,3-dimethyl-1,10-dioxo-1,2,3,4,10,12,13,14-octahydrobenzo[5,6]azocino[4,3-g]indolizine-12-carboxylic acid as a off-white solid. LC/MS (ES, m/z): mass calculated for C$_{20}$H$_{18}$ClFN$_2$O$_4$: 404.09, measured: 405.20 [M+H]$^+$.

Intermediate 9: 7-chloro-8-fluoro-1,10-dioxo-1,4,10, 12,13,14-hexahydro-2H-spiro[benzo[5,6]azocino[4, 3-g]indolizine-3,1'-cyclopentane]-12-carboxylic acid

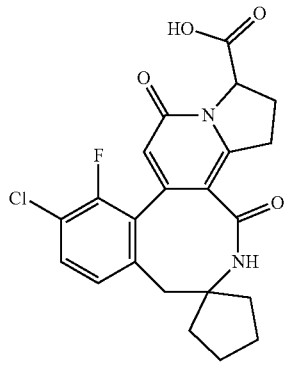 [SMILES: O=C1NC2(CCCC2)Cc2ccc(Cl)c(F)c2-c2cc(=O)n3c(c21)CCC3C(=O)O]

Step 1: Methyl 1-(2-bromo-4-chloro-3-fluorobenzyl)cyclopentane-1-carboxylate

Under nitrogen, diisopropylamine (2.0 g, 19.84 mmol, 1.5 equiv.) was dissolved in dry THF (15 mL), and the mixture was cooled to −20° C. n-BuLi solution (7.9 mL, 19.84 mmol, 1.5 equiv.; 2.5 M in hexane) was added dropwise, and the resulting mixture was stirred to −20° C. for 30 min, then cooled to −78° C. At this temperature, a solution of methyl cyclopentane carboxylate (2.54 g, 19.84 mmol, 1.5 equiv.) in THF (10 mL) was added dropwise. After 2 h of stirring at −78° C., a solution of 2-bromo-1-(bromomethyl)-4-chloro-3-fluorobenzene (4.0 g, 13.23 mmol, 1.0 equiv.) in THF (25 mL) was added. The reaction mixture was slowly warmed to room temperature for 2 h. The reaction was quenched with water (30 mL). The resulting mixture was extracted with ethyl acetate (3×50 mL). The organic layers were combined, dried over Na$_2$SO$_4$, filtered and concentrated. The residue was purified by silica gel chromatography (0→10% ethyl acetate/petroleum ether) to yield methyl 1-(2-bromo-4-chloro-3-fluorobenzyl)cyclopentane-1-carboxylate as a colorless oil. $^1$H NMR (400 MHz, Chloroform-d) δ (ppm): 7.20-7.26 (m, 1H), 6.86-6.91 (m, 1H), 3.65 (s, 3H), 3.16 (s, 2H), 1.93-2.28 (m, 2H), 1.54-1.76 (m, 6H).

Step 2: 1-(2-Bromo-4-chloro-3-fluorobenzyl)cyclopentane-1-carboxylic acid

To a solution of methyl 1-(2-bromo-4-chloro-3-fluorobenzyl)cyclopentane-1-carboxylate (2.2 g, 6.29 mmol, 1.0 equiv.) in the mixed solvent of THF (48 mL) and EtOH (12 mL) was added LiOH (753 mg, 157.31 mmol, 25.0 equiv.) in H$_2$O (12 mL). The resulting mixture was stirred at 50° C. overnight. The mixture was concentrated under vacuum and then diluted with H$_2$O (15 mL). The pH value of the solution was adjusted to 5-6 with 1 M HCl solution. The mixture was extracted with ethyl acetate (3×50 mL). The combined extracts were washed with water, saturated brine and dried over anhydrous Na$_2$SO$_4$, filtered and concentrated to yield 1-(2-bromo-4-chloro-3-fluorobenzyl)cyclopentane-1-carboxylic acid as a white solid. LC/MS (ES, m/z): mass calculated for C$_{13}$H$_{13}$BrClFO$_2$: 333.98, measured: 332.95, 334.95 [M–H, M–H+2]$^+$.

Step 3: 2-Bromo-4-chloro-3-fluoro-1-((1-isocyanatocyclopentyl)methyl)benzene

To a solution of 1-(2-bromo-4-chloro-3-fluorobenzyl)cyclopentane-1-carboxylic acid (2.0 g, 5.96 mmol, 1.0 equiv.) in toluene (20 mL) was added Et$_3$N (0.78 g, 7.74 mmol, 1.3 equiv.) and diphenyl phosphorazidate (2.1 g, 7.74 mmol, 1.3 equiv.) at room temperature The resulting mixture was stirred for 1 h at room temperature. The mixture was then stirred for 2 h at 100° C. The reaction was quenched with water (15 mL). The resulting mixture was extracted with ethyl acetate (3×50 mL). The organic layers were combined, dried over Na$_2$SO$_4$, filtered and concentrated to yield 2-bromo-4-chloro-3-fluoro-1-((1-isocyanatocyclopentyl)methyl)benzene as a yellow oil. TLC: Rf=0.60 (ethyl acetate/petroleum ether=1/5).

Step 4: Tert-butyl (1-(2-bromo-4-chloro-3-fluorobenzyl)cyclopentyl)carbamate

A mixture of 2-bromo-4-chloro-3-fluoro-1-((1-isocyanatocyclopentyl)methyl) benzene (1.8 g, 5.41 mmol, 1.0 equiv.) and 2-methylpropan-2-ol (20 mL) was stirred overnight at 90° C. The reaction was quenched with water (15 mL). The resulting mixture was extracted with ethyl acetate (3×40 mL). The organic layers were combined, dried over Na$_2$SO$_4$, filtered and concentrated. The residue was purified by silica gel chromatography (0→8% ethyl acetate/petroleum ether) to yield tert-butyl (1-(2-bromo-4-chloro-3-fluorobenzyl)cyclopentyl)carbamate as a white solid. TLC: Rf=0.65 (ethyl acetate/petroleum ether=1/20).

Step 5: (6-((1-((Tert-butoxycarbonyl)amino)cyclopentyl)methyl)-3-chloro-2-fluorophenyl)boronic acid To a solution of tert-butyl (1-(2-bromo-4-chloro-3-fluorobenzyl)cyclopentyl)carbamate (760 mg, 1.86 mmol, 1.0 equiv.) in THF (12 mL) was added n-BuLi (1.5 mL, 3.74 mmol, 2.0 equiv.) dropwise at –78° C. under nitrogen, and the reaction mixture was stirred at this temperature for 1 h. Trimethyl borate (1.94 g, 18.68 mmol, 10.0 equiv.) in THF (1 mL) was added at –78° C. under nitrogen and the reaction mixture was slowly warmed to room temperature overnight. The reaction was quenched with 2 M HCl (20 mL). The resulting mixture was extracted with ethyl acetate (3×50 mL). The organic layers were combined, dried over anhydrous sodium sulfate, and concentrated. The residue was purified by reverse column chromatography with CH$_3$CN/water (5%→70%) to yield (6-((1-((tert-butoxycarbonyl)amino)cyclopentyl)methyl)-3-chloro-2-fluorophenyl)boronic acid as a brown solid. LC/MS (ES, m/z): mass calculated for C$_{17}$H$_{24}$BClFNO$_4$: 371.15, measured: 394.20 [M+Na]$^+$.

Step 6: 3-(Tert-butyl) 8-methyl 7-(6-((1-((tert-butoxycarbonyl)amino)cyclopentyl) methyl)-3-chloro-2-fluorophenyl)-5-oxo-1,2,3,5-tetrahydroindolizine-3,8-dicarboxylate To a solution of (6-((1-((tert-butoxycarbonyl)amino)cyclopentyl) methyl)-3-chloro-2-fluorophenyl)boronic acid (383 mg, 1.03 mmol, 1.0 equiv.) in 1,4-dioxane (10 mL) was added 3-(tert-butyl) 8-methyl 5-oxo-7-(((perfluorobutyl)sulfonyl)oxy)-1,2,3,5-tetrahydroindolizine-3,8-dicarboxylate (610 mg, 0.54 mmol, 0.5 equiv.), K$_3$PO$_4$ (328 mg, 1.54 mmol, 1.5 equiv.), Pd(PPh$_3$)$_4$ (58 mg, 0.05 mmol, 0.05 equiv.) under nitrogen at room temperature. The resulting mixture was stirred overnight at 90° C. The reaction was quenched with water (10 mL). The resulting mixture was extracted with ethyl acetate (3×40 mL). The organic layers were combined, dried over Na$_2$SO$_4$, filtered and concentrated. The residue was purified by silica gel chromatography (0→30% ethyl acetate/petroleum ether) to yield 3-(tert-butyl) 8-methyl 7-(6-((1-((tert-butoxycarbonyl)amino)cyclopentyl)methyl)-3-chloro-2-fluorophenyl)-5-oxo-1,2,3,5-tetrahydroindolizine-3,8-dicarboxylate as a colorless oil. LC/MS (ES, m/z): mass calculated for C$_{32}$H$_{40}$ClFN$_2$O$_7$: 618.25, measured: 619.20 [M+H]$^+$.

Step 7: 7-(6((1-Aminocyclopentyl)methyl)-3-chloro-2-fluorophenyl)-8-(methoxycarbonyl)-5-oxo-1,2,3,5-tetrahydroindolizine-3-carboxylic acid To a solution of 3-(tert-butyl) 8-methyl 7-(6-((1-((tert-butoxycarbonyl)amino)cyclopentyl)methyl)-3-chloro-2-fluorophenyl)-5-oxo-1,2,3,5-tetrahydroindolizine-3,8-dicarboxylate (400 mg, 0.64 mmol, 1.0 equiv.) in DCM (15 mL) was added TFA (5 mL) at 0° C. The reaction was stirred at room temperature for 4 h. The mixture was concentrated under vacuum. The residue was purified by reverse column chromatography with CH$_3$CN/water (5%-40%) to yield 7-(6-((1-aminocyclopentyl)methyl)-3-chloro-2-fluorophenyl)-8-(methoxycarbonyl)-5-oxo-1,2,3,5-tetrahydroindolizine-3-carboxylic acid as a white solid. LC/MS (ES, m/z): mass calculated for C$_{23}$H$_{24}$ClFN$_2$O$_5$: 462.14, measured: 463.20 [M+H]$^+$.

Step 8: 7-Chloro-8-fluoro-1,10-dioxo-1,4,10,12,13,14-hexahydro-2H-spiro[benzo[5,6]azocino[4,3-g]indolizine-3,1'-cyclopentane]-12-carboxylic acid To a solution of 7-(6((1-aminocyclopentyl)methyl)-3-chloro-2-fluorophenyl)-8-(methoxycarbonyl)-5-oxo-1,2,3,5-tetrahydroindolizine-3-carboxylic acid (327 mg, 0.70 mmol, 1.0 equiv.) in DCM (30 mL) was added Al(CH$_3$)$_3$ (2.1 mL, 2.11 mmol, 3.0 equiv.) under nitrogen at 0° C. The resulting mixture was stirred overnight at room temperature. After dilution with DCM, the reaction mixture was quenched with water and adjusted to 4-5 with 2 M HCl solution. The mixture was extracted with DCM (3×30 mL). The organic layers were combined, dried over Na$_2$SO$_4$, filtered and concentrated. The residue was purified by reverse column chromatography with CH$_3$CN/water (5%-40%) to yield 7-chloro-8-fluoro-1,10-dioxo-1,4,10,12,13,14-hexahydro-2H-spiro[benzo[5,6]azocino[4,3-g]indolizine-3,1'-cyclopentane]-12-carboxylic acid as a white solid. LC/MS (ES, m/z): mass calculated for C$_{22}$H$_{20}$ClFN$_2$O$_4$: 430.11, measured: 431.20 [M+H]$^+$.

Intermediate 10: 7-chloro-8-fluoro-1,10-dioxo-1,4,10,12,13,14-hexahydro-2H-spiro[benzo[5,6]azocino[4,3-g]indolizine-3,1'-cyclobutane]-12-carboxylic acid

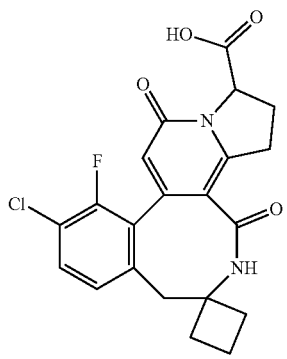 [SMILES: O=C1NC2(CCC2)Cc2ccc(Cl)c(F)c2-c2cc(=O)n3c(c21)CCC3C(=O)O]

Step 1: 3-(Tert-butyl) 8-methyl 7-(6-((1-((tert-butoxycarbonyl)amino)cyclobutyl)methyl)-3-chloro-2-fluorophenyl)-5-oxo-1,2,3,5-tetrahydroindolizine-3,8-dicarboxylate (6-((1-((Tert-butoxycarbonyl)amino)cyclobutyl)methyl)-3-chloro-2-fluorophenyl)boronic acid (500 mg, 1.39 mmol, 1.0 equiv.), 3-(tert-butyl) 8-methyl 5-oxo-7-(((trifluoromethyl) sulfonyl)oxy)-1,2,3,5-tetrahydroindolizine-3,8-dicarboxylate (679 mg, 1.54 mmol, 1.1 equiv.), $K_2CO_3$ (290 mg, 2.10 mmol, 1.5 equiv.) and $Pd(PPh_3)_4$ (162 mg, 0.14 mmol, 0.1 equiv.) were dissolved in 1,4-dioxane (5.0 mL). The flask was evacuated and flushed three times with nitrogen and the mixture was stirred 16 h at 80° C. under an atmosphere of nitrogen. The mixture was cooled to room temperature, EA (300 mL) was added and the resulting mixture washed by water (80 mL), then dried over anhydrous sodium sulphate, and concentrated under reduced pressure. The residue was purified by normal phase chromatography (mobile phase: PE/EA, 0→60%) to yield 3-(tert-butyl) 8-methyl 7-(6-((1-((tert-butoxycarbonyl)amino)cyclobutyl)methyl)-3-chloro-2-fluorophenyl)-5-oxo-1,2,3,5-tetrahydroindolizine-3,8-dicarboxylate as a yellow solid. LC/MS (ES, m/z): mass calculated for $C_{31}H_{38}ClFN_2O_7$: 604.24, measured: 605.30 $[M+H]^+$.

Step 2: 7-(6((1-Aminocyclobutyl)methyl)-3-chloro-2-fluorophenyl)-8-(methoxycarbonyl)-5-oxo-1,2,3,5-tetrahydroindolizine-3-carboxylic acid To a solution of 3-(tert-butyl) 8-methyl 7-(6-((1-((tert-butoxycarbonyl)amino)cyclobutyl) methyl)-3-chloro-2-fluorophenyl)-5-oxo-1,2,3,5-tetrahydroindolizine-3,8-dicarboxylate (233 mg, 0.38 mmol, 1.0 equiv.) in DCM (6 mL), was added TFA (1.2 mL) dropwise, and the resulting solution was stirred at room temperature for 1 h. The solvent was removed under vacuum to yield 7-(6((1-aminocyclobutyl)methyl)-3-chloro-2-fluorophenyl)-8-(methoxycarbonyl)-5-oxo-1,2,3,5-tetrahydroindolizine-3-carboxylic acid, which was used for the next step without further purification. LC/MS (ES, m/z): mass calculated for $C_{22}H_{22}ClFN_2O_5$: 448.12, measured: 449.20 $[M+H]^+$.

Step 3: 7-Chloro-8-fluoro-1,10-dioxo-1,4,10,12,13,14-hexahydro-2H-spiro[benzo[5,6]azocino[4,3-g]indolizine-3,1'-cyclobutane]-12-carboxylic acid A solution of trimethylaluminum (1.0 mL, 1.00 mmol, 1.0 equiv.) was added dropwise to a solution of 7-(6-((1-aminocyclobutyl)methyl)-3-chloro-2-fluorophenyl)-8-(methoxycarbonyl)-5-oxo-1,2,3,5-tetrahydroindolizine-3-carboxylic acid (150 mg, 0.33 mmol, 0.3 equiv.) in THF (3.0 mL) and the mixture stirred at room temperature overnight. EA (20 mL) was added and the resulting mixture washed by water (30 mL), then dried over anhydrous sodium sulphate, filtered, and concentrated under reduced pressure. The residue was purified by normal phase chromatography (mobile phase: DCM/MeOH, 0→20%) to yield 7-chloro-8-fluoro-1,10-dioxo-1,4,10,12,13,14-hexahydro-2H-spiro[benzo[5,6]azocino[4,3-g]indolizine-3,1'-cyclobutane]-12-carboxylic acid as a yellow solid. LC/MS (ES, m/z): mass calculated for $C_{21}H_{18}ClFN_2O_4$: 416.09, measured: 417.20 $[M+H]^+$.

Intermediate 11: 8-chloro-7-fluoro-5,16-dioxo-1,2,3,5,15,16-hexahydrobenzo[5,6]pyrido[4',3':7,8]azocino[4,3-g]indolizine-3-carboxylic acid

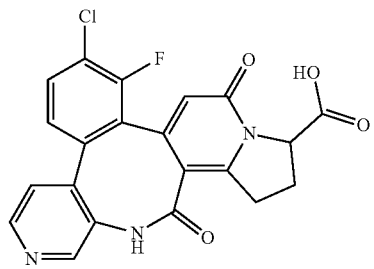 [SMILES: O=C1Nc2cnccc2-c2ccc(Cl)c(F)c2-c2cc(=O)n3c(c21)CCC3C(=O)O]

Step 1: Tert-butyl (4-(4-chloro-3-fluorophenyl)pyridin-3-yl)carbamate

To a solution of (4-chloro-3-fluorophenyl)boronic acid (2.0 g, 11.47 mmol, 1.0 equiv.) in 1,4-dioxane (40 mL) was added tert-butyl (4-bromopyridin-3-yl)carbamate (3.1 g, 11.47 mmol, 1.0 equiv.) and $Pd(PPh_3)_4$ (1.33 g, 1.15 mmol, 0.1 equiv.) under nitrogen at room temperature. $K_2CO_3$ (2.4 g, 17.21 mmol, 1.5 equiv.) in $H_2O$ (4 mL) was then added to the mixture. The resulting mixture was stirred for 4 h at 90° C. The reaction was quenched with $H_2O$ (15 mL). The resulting mixture was extracted with ethyl acetate (3×40 mL). The organic layers were combined, dried over $Na_2SO_4$, filtered and concentrated. The residue was purified by silica gel chromatography (0→70% ethyl acetate/petroleum ether) to yield tert-butyl (4-(4-chloro-3-fluorophenyl)pyridin-3-yl) carbamate as an off-white solid. LC/MS (ES, m/z): mass calculated for $C_{16}H_{16}ClFN_2O_2$: 322.09, measured: 323.05 $[M+H]^+$.

Step 2: (6-(3-((Tert-butoxycarbonyl)amino)pyridin-4-yl)-3-chloro-2-fluorophenyl)boronic acid Under nitrogen atmosphere, diisopropylamine (1.25 g, 12.39 mmol, 1.0 equiv.) was dissolved in dry THF (40 mL), and the mixture was cooled to −20° C. n-BuLi (5.0 mL, 12.40 mmol; 2.5 M in hexane) were added dropwise, and the resulting mixture was stirred to −20° C. for 1 h and then cooled to −78° C. At this temperature, a solution of tert-butyl (4-(4-chloro-3-fluorophenyl)pyridin-3-yl)carbamate (1.0 g, 3.10 mmol, 0.25 equiv.) in THF (10 mL) was added. After 2 h of stirring at −78° C., trimethyl borate (3.2 g, 30.98 mmol, 2.5 equiv.) was added dropwise. The reaction mixture was slowly warmed to room temperature overnight. The reaction was quenched with water. The pH value of the solution was adjusted to 4-5 with 1M HCl solution. The resulting mixture was extracted with ethyl acetate (3×80 mL). The organic layers were combined, dried over $Na_2SO_4$, filtered and concentrated. The residue was purified by reverse column chromatography with $CH_3CN$/0.05% TFA water (5%→60%) to yield (6-(3-((tert-butoxycarbonyl)amino)pyridin-4-yl)-3-chloro-2-fluorophenyl)boronic acid as a white solid. LC/MS (ES, m/z): mass calculated for $C_{16}H_{17}BClFN_2O_4$: 366.10, measured: 367.20 [M+H]$^+$.

Step 3: 3-(Tert-butyl) 8-methyl 7-(6-(3-aminopyridin-4-yl)-3-chloro-2-fluorophenyl)-5-oxo-1,2,3,5-tetrahydroindolizine-3,8-dicarboxylate To a solution of 3-(tert-butyl) 8-methyl 5-oxo-7-(((trifluoromethyl)sulfonyl)oxy)-1,2,3,5-tetrahydroindolizine-3,8-dicarboxylate (0.5 g, 1.13 mmol, 1.0 equiv.) and (6-(3-((tert-butoxycarbonyl)amino)pyridin-4-yl)-3-chloro-2-fluorophenyl)boronic acid (0.50 g, 1.36 mmol, 1.2 equiv.) in 1,4-dioxane (15 mL) was added potassium carbonate (0.47 g, 3.39 mmol, 3.0 equiv.) and Pd(PPh$_3$)$_4$ (0.13 g, 0.11 mmol, 0.1 equiv.) under N$_2$. The reaction mixture was stirred for 2 h at 90° C., then quenched with water, extracted with EA, dried over Na$_2$SO$_4$, and concentrated under vacuum. The residue was purified by silica gel chromatography with EA/PE (0→50%) to yield 3-(tert-butyl) 8-methyl 7-(6-(3-aminopyridin-4-yl)-3-chloro-2-fluorophenyl)-5-oxo-1,2,3,5-tetrahydroindolizine-3,8-dicarboxylate as light yellow oil. LC/MS (ES, m/z): mass calculated for $C_{26}H_{25}ClFN_3O_5$: 513.15, measured: 514.25 [M+H]$^+$.

Step 4: 7-(6-(3-Aminopyridin-4-yl)-3-chloro-2-fluorophenyl)-8-(methoxycarbonyl)-5-oxo-1,2,3,5-tetrahydroindolizine-3-carboxylic acid To a solution of 3-(tert-butyl) 8-methyl 7-(6-(3-aminopyridin-4-yl)-3-chloro-2-fluorophenyl)-5-oxo-1,2,3,5-tetrahydroindolizine-3,8-dicarboxylate (0.25 g, 0.41 mmol, 1.0 equiv.) in DCM (10 mL) was added TFA (2 mL). The reaction was stirred for 3 h at room temperature, then concentrated under vacuum. The residue was purified by reverse column chromatography with CH$_3$CN/0.05% TFA water (5%→60%) to yield 7-(6-(3-aminopyridin-4-yl)-3-chloro-2-fluorophenyl)-8-(methoxycarbonyl)-5-oxo-1,2,3,5-tetrahydroindolizine-3-carboxylic acid as a light yellow solid. LC/MS (ES, m/z): mass calculated for $C_{22}H_{17}ClFN_3O_5$: 457.08, measured: 458.05 [M+H]$^+$.

Step 5: 8-Chloro-7-fluoro-5,16-dioxo-1,2,3,5,15,16-hexahydrobenzo[5,6]pyrido[4',3':7,8]azocino[4,3-g]indolizine-3-carboxylic acid A solution of 7-(6-(3-aminopyridin-4-yl)-3-chloro-2-fluorophenyl)-8-(methoxycarbonyl)-5-oxo-1,2,3,5-tetrahydroindolizine-3-carboxylic acid (0.28 g, 0.51 mmol, 1.0 equiv.) in THF (15 mL) was added under N$_2$ to activated 3 Å molecular sieve (dried at 300° C. in a drying cabinet overnight) and stirred at room temperature for 2 h. Subsequently, the reaction mixture was admixed under N$_2$ at room temperature with sodium ethoxide ethanol solution (4.0 g, 12.23 mmol, 20.0 equiv.; 21% in ethanol, dried beforehand over activated 3 Å molecular sieve for 2 h) and stirred overnight for 3 h. The resulting solid was filtered out and washed with ethanol. The pH of filtrate was adjusted to be acidic. The resulting mixture was concentrated under vacuum. The residue was purified by reverse column chromatography with CH$_3$CN/0.05% TFA water (5%→60%) to yield 8-chloro-7-fluoro-5,16-dioxo-1,2,3,5,15,16-hexahydrobenzo[5,6]pyrido[4',3':7,8]azocino[4,3-g]indolizine-3-carboxylic acid as a light yellow solid. LC/MS (ES, m/z): mass calculated for $C_{21}H_{13}ClFN_3O_4$: 425.06, measured: 426.15 [M+H]$^+$.

Intermediate 12: 8-chloro-7-fluoro-5,16-dioxo-1,2,3,5,15,16-hexahydrodibenzo[5,6:7,8]azocino[4,3-g]indolizine-3-carboxylic acid

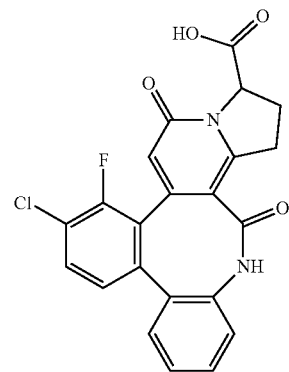 [SMILES: O=C1Nc2ccccc2-c2ccc(Cl)c(F)c2-c2cc(=O)n3c(c21)CCC3C(=O)O]

Step 1: Tert-butyl (4'-chloro-3'-fluoro-[1,1'-biphenyl]-2-yl)carbamate

4-Bromo-1-chloro-2-fluorobenzene (1.6 g, 7.64 mmol, 1.0 equiv.), tert-butyl (2-(4,4,5,5-tetramethyl-1,3,2-dioxaborolan-2-yl)phenyl)carbamate (3.0 g, 9.39 mmol, 1.2 equiv.), Pd(PPh$_3$)$_4$ (0.9 g, 0.78 mmol, 0.1 equiv.) and K$_2$CO$_3$ (1.6 g, 11.57 mmol, 1.5 equiv.) were dissolved in 1,4-dioxane (70.0 mL) and H$_2$O (7.0 mL). The flask was evacuated and flushed three times with nitrogen and the mixture was stirred 17 h at 80° C. under an atmosphere of nitrogen. The resulting solution was diluted with water (100 mL), then extracted with EA (3×20 mL). The organic layers were combined, washed with brine (50 mL×1), dried and concentrated under vacuum. The residue was applied onto a silica gel column with ethyl acetate/petroleum ether (1:1) to yield tert-butyl (4'-chloro-3'-fluoro-[1,1'-biphenyl]-2-yl)carbamate as an off-white solid. LC/MS (ES, m/z): mass calculated for $C_{17}H_{17}ClFNO_2$: 321.09, measured: 307.10 [M−56+H+MeCN]$^+$.

Step 2: (2'-((Tert-butoxycarbonyl)amino)-4-chloro-3-fluoro-[1,1'-biphenyl]-2-yl) boronic acid Diisopropylamine (1.25 g, 12.35 mmol, 4.0 equiv.) was dissolved in THF (10.0 mL). The flask was evacuated and flushed three times with nitrogen. Then the mixture was cooled to −78° C. n-BuLi (5.0 mL) was added and the mixture was stirred at this temperature for 1.5 h. tert-butyl (4'-chloro-3'-fluoro-[1,1'-biphenyl]-2-yl)carbamate (1.0 g, 3.11 mmol, 1.0 equiv.) was then added into the mixture and the mixture was stirred another 1 h. Trimethyl borate (1.6 g, 15.39 mmol, 5.0 equiv.) was added into the mixture and the mixture was slowly warmed to room temperature stirred for 17 h. Water (50 mL) was added and the resulting mixture was adjusted to pH-4 with NaHCO$_3$ saturated solution. The mixture was extracted with EA (20 mL×3). The organic layers were combined, washed with brine (50 mL×1), dried and concentrated under vacuum. The residue was purified by column chromatography on C18 (80 g, MeCN/H$_2$O (0.05% CF$_3$COOH): 0→60%) and obtained (2'-((tert-butoxycarbonyl)amino)-4-chloro-3-fluoro-[1,1'-biphenyl]-2-yl)boronic acid as an off-white solid. LC/MS (ES, m/z): mass calculated for C$_{17}$H$_{18}$BClFNO$_4$: 365.10, measured: 388.00 [M+Na]$^+$.

Step 3: 3-(Tert-butyl) 8-methyl 7-(2'-((tert-butoxycarbonyl)amino)-4-chloro-3-fluoro-[1,1'-biphenyl]-2-yl)-5-oxo-1,2,3,5-tetrahydroindolizine-3,8-dicarboxylate To a solution of 3-(tert-butyl) 8-methyl 5-oxo-7-(((trifluoromethyl)sulfonyl)oxy)-1,2,3,5-tetrahydroindolizine-3,8-dicarboxylate (0.3 g, 0.68 mmol, 1.0 equiv.) and (2'-((tert-butoxycarbonyl)amino)-4-chloro-3-fluoro-[1,1'-biphenyl]-2-yl)boronic acid (0.30 g, 0.82 mmol, 1.2 equiv.) in 1,4-dioxane (10 mL) was added potassium carbonate (0.28 g, 0.14 mmol, 3.0 equiv.) and Pd(PPh$_3$)$_4$ (0.08 g, 0.07 mmol, 0.1 equiv.) under N$_2$. The reaction mixture was stirred for 2 h at 90° C., then quenched with water, extracted with EA, dried over Na$_2$SO$_4$, and concentrated under vacuum. The residue was purified by silica gel chromatography with EA/PE (0→50%) to yield 3-(tert-butyl) 8-methyl 7-(2'-((tert-butoxycarbonyl)amino)-4-chloro-3-fluoro-[1,1'-biphenyl]-2-yl)-5-oxo-1,2,3,5-tetrahydroindolizine-3,8-dicarboxylate as light yellow oil. LC/MS (ES, m/z): mass calculated for C$_{32}$H$_{34}$ClFN$_2$O$_7$: 612.20, measured: 613.10 [M+H]$^+$.

Step 4: 7-(2'-Amino-4-chloro-3-fluoro-[1,1'-biphenyl]-2-yl)-8-(methoxycarbonyl)-5-oxo-1,2,3,5-tetrahydroindolizine-3-carboxylic acid To a solution of 3-(tert-butyl) 8-methyl 7-(2'-((tert-butoxycarbonyl)amino)-4-chloro-3-fluoro-[1,1'-biphenyl]-2-yl)-5-oxo-1,2,3,5-tetrahydroindolizine-3,8-dicarboxylate (0.25 g, 0.41 mmol, 1.0 equiv.) in DCM (10 mL) was added TFA (2 mL). The reaction was stirred for 3 h at room temperature, then concentrated under vacuum. The residue was purified by reverse column chromatography with CH$_3$CN/0.05% TFA water (5%→60%) to yield 7-(2'-amino-4-chloro-3-fluoro-[1,1'-biphenyl]-2-yl)-8-(methoxycarbonyl)-5-oxo-1,2,3,5-tetrahydroindolizine-3-carboxylic acid as a light yellow solid. LC/MS (ES, m/z): mass calculated for C$_{23}$H$_{18}$ClFN$_2$O$_5$: 456.09, measured: 457.05 [M+H]$^+$.

Step 5: 8-Chloro-7-fluoro-5,16-dioxo-1,2,3,5,15,16-hexahydrodibenzo[5,6:7,8]azocino[4,3-g]indolizine-3-carboxylic acid A solution of 7-(2'-amino-4-chloro-3-fluoro-[1,1'-biphenyl]-2-yl)-8-(methoxycarbonyl)-5-oxo-1,2,3,5-tetrahydroindolizine-3-carboxylic acid (0.13 g, 0.28 mmol, 1.0 equiv.) in THF (10 mL) was added under N$_2$ to activated 3 Å molecular sieve (dried at 300° C. in a drying cabinet overnight) and stirred at room temperature for 2 h. Subsequently, the reaction mixture was admixed under N$_2$ at room temperature with sodium ethoxide ethanol solution (1.84 g, 5.69 mmol, 20.0 equiv.; 21% in ethanol, dried beforehand over activated 3 Å molecular sieve for 2 h) and stirred overnight at room temperature. After dilution with EA, the reaction mixture was admixed with saturated aqueous NH$_4$Cl solution and brought to pH 3 with 1 M HCl solution and extracted with EA. The combined organic phases were washed with brine, dried over Na$_2$SO$_4$, and concentrated under vacuum to yield 8-chloro-7-fluoro-5,16-dioxo-1,2,3,5,15,16-hexahydrodibenzo[5,6:7,8]azocino[4,3-g]indolizine-3-carboxylic acid a light brown solid. LC/MS (ES, m/z): mass calculated for C$_{22}$H$_{14}$ClFN$_2$O$_4$: 424.06, measured: 425.20 [M+H]$^+$.

Intermediate 13: 7-chloro-8-fluoro-2-methyl-1,10-dioxo-1,4,10,12,13,14-hexahydro-2H-spiro[benzo[5,6]azocino[4,3-g]indolizine-3,1'-cyclopropane]-12-carboxylic acid

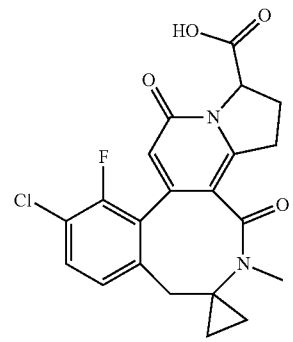 [SMILES: CN1C(=O)c2c(cc(=O)n3c2CCC3C(=O)O)-c2c(ccc(Cl)c2F)CC12CC2]

Step 1: tert-Butyl (1-(2-bromo-4-chloro-3-fluorobenzyl)cyclopropyl)(methyl) carbamate To a solution of tert-butyl (1-(2-bromo-4-chloro-3-fluorobenzyl)cyclopropyl)carbamate (2 g, 5.282 mmol) in DMF (20 mL) was added NaH (0.422 mg, 10.563 mmol) at 0° C. and room temperature. After 1 h, CH$_3$I (1.499 mg, 10.563 mmol) was added and the resulting mixture was maintained at room temperature for 2 h. The reaction was quenched with LiCl solution (20 mL). The resulting mixture was extracted with ethyl acetate (3×20 mL). The organic layers were combined, dried over anhydrous sodium sulfate, filtered, and concentrated. The residue was purified by silica gel chromatography (0-30% ethyl acetate/petroleum ether) to yield tert-butyl (1-(2-bromo-4-chloro-3-fluorobenzyl)cyclopropyl)(methyl)carbamate as a yellow oil. LC/MS: mass calculated for C$_{16}$H$_{20}$BrClFNO$_2$: 391.03, measured: 337.9 [M+H]$^+$.

Step 2: (6-((1-((tert-Butoxycarbonyl)(methyl)amino)cyclopropyl)methyl)-3-chloro-2-fluorophenyl)boronic acid To a solution of tert-butyl (1-(2-bromo-4-chloro-3-fluorobenzyl)cyclopropyl)(methyl)carbamate (1.9 g, 4.838 mmol) in THF (10 mL) was added n-BuLi (2.322 ml, 5.806 mmol) at −78° C. After 1 h, trimethyl borate (5.028 g, 30.558 mmol) in THF (3 mL) was added (−78° C.). The resulting mixture was maintained under nitrogen and stirred at room temperature for 2 h. The resulting residue was purified by reverse-phase flash with the following conditions: Column, Cat No: SO230120-2, C18, 120 g, 20~45 μm, 100 Å, Lot: BP0002P2503; mobile phase, CH$_3$CN:H$_2$O (0.05% TFA)= 20% increased to CH$_3$CN:H$_2$O (0.05% TFA)=70% in 40 min, hold CH$_3$CN:H$_2$O (0.05% TFA)=70% in 10 min, up to CH$_3$CN:H$_2$O (0.05% TFA)=95% in 2 min, hold CH$_3$CN:H$_2$O (0.05% TFA)=95% in 10 min; Detector, UV 220 nm & 254 nm. The collected fractions were combined and lyophilized to yield (6-((1-((tert-butoxycarbonyl)(methyl)amino)cyclopropyl)methyl)-3-chloro-2-fluorophenyl)boronic acid as a yellow solid. LC/MS: mass calculated for C$_{16}$H$_{22}$BClFNO$_4$: 357.14, measured: 303.0 [M+H-Bu].

Step 3: 3-(tert-Butyl) 8-methyl 7-(6-((1-((tert-butoxycarbonyl)(methyl)amino)cyclopropyl)methyl)-3-chloro-2-fluorophenyl)-5-oxo-1,2,3,5-tetrahydroindolizine-3,8-dicarboxylate To a solution of (6-((1-((tert-butoxycarbonyl)(methyl)amino)cyclopropyl)methyl)-3-chloro-2-fluorophenyl)boronic acid (250.000 mg, 0.699 mmol) in 1,4-dioxane (10 mL) was added 3-(tert-butyl) 8-methyl 5-oxo-7-(((trifluoromethyl)sulfonyl)oxy)-1,2,3,5-tetrahydroindolizine-3,8-dicarboxylate (617.114 mg, 1.398 mmol), K$_3$PO$_4$ (296.782 mg, 1.398 mmol) and Pd(PPh$_3$)$_4$ (80.785 mg, 0.070 mmol) at room temperature. The resulting mixture was maintained under nitrogen and stirred at 100° C. for 2 h. After cooling to room temperature, the reaction was quenched with water (5 mL). The resulting mixture was extracted with ethyl acetate. The organic layers were combined, dried over Na$_2$SO$_4$, filtered and concentrated. The residue was purified by silica gel chromatography (0-70% ethyl acetate/petroleum ether) to yield 3-(tert-butyl) 8-methyl 7-(6-((1-((tert-butoxycarbonyl)(methyl)amino)cyclopropyl)methyl)-3-chloro-2-fluorophenyl)-5-oxo-1,2,3,5-tetrahydroindolizine-3,8-dicarboxylate as a colorless oil. LC/MS: mass calculated for C$_{31}$H$_{38}$ClFN$_2$O$_7$: 604.24, measured: 605.4 [M+H]$^+$.

Step 4: 7-(3-Chloro-2-fluoro-6-((1-(methylamino)cyclopropyl)methyl)phenyl)-8-(methoxycarbonyl)-5-oxo-1,2,3,5-tetrahydroindolizine-3-carboxylic acid To a solution of 3-(tert-butyl) 8-methyl 7-(6-((1-((tert-butoxycarbonyl)(methyl)amino)cyclopropyl)methyl)-3-chloro-2-fluorophenyl)-5-oxo-1,2,3,5-tetrahydroindolizine-3,8-dicarboxylate (260 mg, 0.430 mmol) in DCM (9 mL) was added TFA (3 mL) at 0° C. The reaction was stirred at room temperature for 3 h. The mixture was concentrated to remove TFA under vacuum. The resulting residue was purified by reverse-phase flash chromatography with the following conditions: Column, Cat No: SO230120-2, C18, 80 g, 20~35 μm, 100 Å, Lot: BP002R1909; mobile phase, CH$_3$CN:H$_2$O (0.05% TFA)=5% increased to CH$_3$CN:H$_2$O (0.05% TFA)=30% in 20 min, hold CH$_3$CN:H$_2$O (0.05% TFA)=30% in 5 min, up to CH$_3$CN:H$_2$O (0.05% TFA)=95% in 2 min, hold CH$_3$CN:H$_2$O (0.05% TFA)=95% in 10 min; Detector, UV 220 nm & 254 nm. The collected fractions were concentrated to yield 7-(3-chloro-2-fluoro-6-((1-(methylamino)cyclopropyl)methyl)phenyl)-8-(methoxycarbonyl)-5-oxo-1,2,3,5-tetrahydroindolizine-3-carboxylic acid as a colorless oil. LC/MS: mass calculated for C$_{22}$H$_{22}$ClFN$_2$O$_5$: 448.12, measured: 449.3 [M+H]$^+$.

Step 5: 7-Chloro-8-fluoro-2-methyl-1,10-dioxo-1,4,10,12,13,14-hexahydro-2H-spiro[benzo[5,6]azocino[4,3-g]indolizine-3,1'-cyclopropane]-12-carboxylic acid To a solution of 7-(3-chloro-2-fluoro-6-((1-(methylamino)cyclopropyl)methyl)phenyl)-8-(methoxycarbonyl)-5-oxo-1,2,3,5-tetrahydroindolizine-3-carboxylic acid (180 mg, 0.401 mmol) in DCM (10 mL) was added Al(CH$_3$)$_3$ (1.203 mL, 1.203 mmol) under nitrogen at room temperature. The resulting mixture was stirred overnight at room temperature. The mixture was then diluted with EA, quenched with water and the pH was adjusted to 4-5 with 2M HCl solution. The mixture was extracted with ethyl acetate (3×50 mL). The organic layers were combined and washed with water (3×10 mL), dried over anhydrous Na$_2$SO$_4$, filtered and concentrated to yield 7-chloro-8-fluoro-2-methyl-1,10-dioxo-1,4,10,12,13,14-hexahydro-2H-spiro[benzo[5,6]azocino[4,3-g]indolizine-3,1'-cyclopropane]-12-carboxylic acid as a white solid. LC/MS: mass calculated for C$_{21}$H$_{18}$ClFN$_2$O$_4$: 416.09, measured: 417.0 [M+H]$^+$.

Intermediate 14: 7-chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylic acid

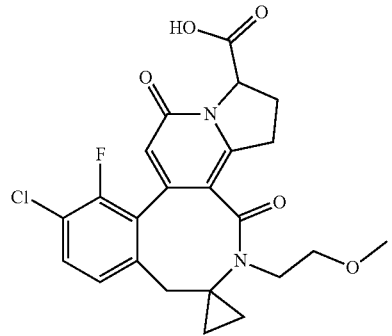 [SMILES: COCCN1C(=O)c2c(cc(=O)n3c2CCC3C(=O)O)-c2c(ccc(Cl)c2F)CC12CC2]

Step 1: Methyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate Thionyl chloride (354.426 mg, 2.979 mmol) was added to the solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (200.000 mg, 0.497 mmol) in MeOH (3.0 mL) and the reaction was stirred at room temperature for 5 hours. The solvent was removed under vacuum and the residue was purified by normal phase chromatography (mobile phase: DCM/MeOH, 0-20%) to yield methyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a yellow solid.

Step 2: 7-Chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylic acid To a solution of methyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (145.000 mg, 0.348 mmol) in DMF (4.5 mL) was added t-BuOK (117.105 mg, 1.044 mmol) at room temperature. After 30 min of stirring at room temperature, a solution of 1-iodo-2-methoxyethane (323.499 mg, 1.739 mmol) in DMF (0.5 mL) was added. The reaction mixture was stirred for 2 h at room temperature. The reaction was quenched with water (1 mL). The resulting residue was purified by reverse-phase flash chromatography with the following conditions: Column, Cat No: SO230120-2, C18, 80 g, 20~35 μm, 100 Å, Lot: BP002R1909; mobile phase, $CH_3CN:H_2O$ (0.05% TFA)= 5% increased to $CH_3CN:H_2O$ (0.05% TFA)=50% in 20 min, hold $CH_3CN:H_2O$ (0.05% TFA)=50% in 5 min, up to $CH_3CN:H_2O$ (0.05% TFA)=95% in 2 min, hold $CH_3CN:H_2O$ (0.05% TFA)=95% in 10 min; Detector, UV 220 nm & 254 nm. The collected fractions were combined and concentrated to yield 7-chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylic acid as a yellow solid. LC/MS: mass calculated for $C_{23}H_{22}ClFN_2O_5$: 460.12, measured: 461.2 $[M+H]^+$.

Intermediate 15: 1-(benzo[d][1,2,3]thiadiazol-5-yl)-2-bromoethan-1-one

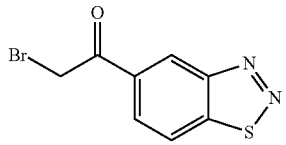 [SMILES: O=C(CBr)c1ccc2snnc2c1]

Step 1: 2-Amino-4-bromobenzenethiol

A solution of 5-bromobenzo[d]thiazol-2-amine (5.0 g, 21.83 mmol, 1.0 equiv.) in a mixture of aqueous 50% NaOH (25 mL) and ethylene glycol (25 mL) was heated under $N_2$ at 110° C. overnight. After cooling to room temperature, the mixture was poured into ice-water, acidified to pH=3 with 3N aqueous HCl and extracted with DCM. The combined organic layers were concentrated under vacuum. The residue was purified by silica gel chromatography with EA/PE (0→20%) to yield 2-amino-4-bromobenzenethiol as a yellow solid.

Step 2: 5-Bromobenzo[d][1,2,3]thiadiazole

To a mixture of 2-amino-4-bromobenzenethiol (3.4 g, 16.66 mmol, 1.0 equiv.) in water (20 mL) was added aqueous 12 N hydrochloric acid (4.2 mL, 49.98 mmol, 3.0 equiv.), slowly at room temperature. Sodium nitrite (1.7 g, 24.99 mmol, 1.5 equiv.) was then added slowly at room temperature. THF (10 mL) was added for solubility, and the reaction was stirred at room temperature for 30 min. The solution was neutralized with saturated aqueous potassium carbonate, then extracted with EA. The organic layer was purified by silica gel chromatography with EA/PE (0→20%) to yield 5-bromobenzo[d][1,2,3]thiadiazole as a yellow solid.

Step 3: 5-(1-Ethoxyvinyl)benzo[d][1,2,3]thiadiazole

To a solution of 5-bromobenzo[d][1,2,3]thiadiazole (1.0 g, 4.65 g, 1.0 equiv.) in 1,4-dioxane (20 mL) was added 1-ethoxyvinyl-tri-n-butyltin (1.8 g, 5.12 mmol, 1.1 equiv.) and $Pd(PPh_3)_4$ (0.54 g, 0.47 mmol, 0.1 equiv.) under $N_2$. The reaction mixture was stirred overnight at 100° C., then cooled to room temperature and quenched with water, extracted with EA, dried over $Na_2SO_4$, and concentrated under vacuum. The residue was purified by silica gel chromatography with EA/PE (0→20%) to yield 5-(1-ethoxyvinyl)benzo[d][1,2,3]thiadiazole as a light yellow solid. Step 4: 1-(Benzo[d][1,2,3]thiadiazol-5-yl)-2-bromoethan-1-one.

To a solution of n-(5-(1-ethoxyvinyl)-6-fluoropyridin-2-yl)acetamide (0.32 g, 1.55 mmol, 1.0 equiv.) in THF (6 mL) and water (2 mL) was added NBS (0.33 g, 1.86 mmol, 1.2 equiv.). The reaction mixture was stirred at room temperature for 2 h, then filtered. The filtrate was extracted with EA, washed with brine, dried over $Na_2SO_4$ and concentrated vacuum to yield 1-(benzo[d][1,2,3]thiadiazol-5-yl)-2-bromoethan-1-one as an off-white solid.

Intermediate 16: 2-bromo-1-(2-methylbenzo[d]thiazol-5-yl)ethan-1-one

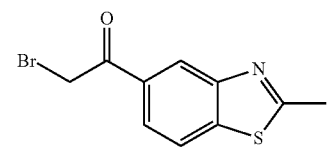

Step 1: 1-(2-Methylbenzo[d]thiazol-5-yl)ethan-1-one

To a solution of 5-bromo-2-methylbenzo[d]thiazole (1.0 g, 4.38 mmol, 1.0 equiv.) in 1,4-dioxane (20 mL) was added tributyl(1-ethoxyvinyl)tin (1.9 g, 5.26 mmol, 1.2 equiv.), and tetrakis(triphenylphosphine)palladium (0.51 g, 0.44 mmol, 0.1 equiv.). The resulting mixture was maintained under nitrogen and stirred at 100° C. for 4 h. After cooling to room temperature, the mixture was concentrated and diluted with water (100 mL) and EA (100 mL). The resulting mixture was extracted with ethyl acetate (3×50 mL) and washed with brine. The organic layers were combined, dried over anhydrous sodium sulfate, filtered, and concentrated. The residue was purified by silica gel chromatography (0→50% ethyl acetate/petroleum ether) to yield 1-(2-methylbenzo[d]thiazol-5-yl)ethan-1-one as a light yellow solid. LC/MS: mass calculated for $C_{16}H_{23}NO_2Si$: 191.04, measured (ES, m/z): 192.10 $[M+H]^+$.

Step 2: 2-Bromo-1-(2-methylbenzo[d]thiazol-5-yl)ethan-1-one

To a solution of 1-(2-methylbenzo[d]thiazol-5-yl)ethan-1-one (450 mg, 2.35 mmol, 1.0 equiv.), hydrobromic acid, acetic acid solution 33% (2.0 g, 4.71 mmol, 2.0 equiv.) in acetic acid glacial (20 mL) was added pyridinium tribromide 677 mg, 2.12 mmol, 0.9 equiv.) at 0° C. The resulting mixture was maintained under air and stirred at room temperature for 4 h. The resulting mixture was concentrated. The residue was purified by silica gel chromatography (0→33% ethyl acetate/petroleum ether) to yield 2-bromo-1-(2-methylbenzo[d]thiazol-5-yl)ethan-1-one as a yellow solid. LC/MS: mass calculated for $C_{10}H_8BrNOS$: 268.95, measured (ES, m/z): 270.10, 272.10 $[M+H, M+H+2]^+$.

Intermediate 17: 1-(benzo[d]thiazol-5-yl)-2-bromo-ethan-1-one

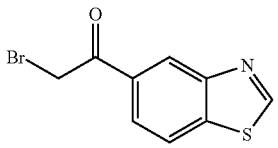 [SMILES: O=C(CBr)c1ccc2scnc2c1]

Step 1: 5-(1-Ethoxyvinyl)benzo[d]thiazole

5-Bromobenzo[d]thiazole (2.0 g, 9.30 mmol, 1.0 equiv.), tributyl(1-ethoxyvinyl)stannane (6.7 g, 18.60 mmol, 2.0 equiv.) and Pd(PPh$_3$)$_2$Cl$_2$ (656 mg, 0.93 mmol, 0.1 equiv.) were dissolved in 1,4-dioxane (100 mL). The flask was evacuated and flushed three times with nitrogen and the mixture was stirred 6 h at 100° C. under an atmosphere of nitrogen. The solvent was removed under reduced pressure to yield 1-(benzo[d]thiazol-5-yl)-2-bromoethan-1-one as a yellow solid. LC/MS: mass calculated for C$_{11}$H$_{11}$NOS: 205.06, measured (ES, m/z): 206.20 [M+H]$^+$.

Step 2: 1-(Benzo[d]thiazol-5-yl)-2-bromoethan-1-one 5-(1-Ethoxyvinyl)benzo[d]thiazole (1.0 g, 4.80 mmol, 1.0 equiv.) was dissolved in THF (20 mL) and H$_2$O (20 mL). NBS (1.7 g, 9.70 mmol, 2.0 equiv.) was added and the mixture was stirred at room temperature for 3 h. The resulting solution was diluted with water (20 mL), then extracted with EA (60 mL×3). The organic layers were combined, washed with brine (50 mL), dried and concentrated under vacuum. The residue was applied onto a silica gel column with MeOH/DCM (0→10%) to yield 1-(benzo[d]thiazol-5-yl)-2-bromoethan-1-one as a white solid. LC/MS: mass calculated for C$_9$H$_6$BrNOS: 254.94, measured (ES, m/z): 255.95, 257.95 [M+H, M+H+2]$^+$.

Intermediate 18: 2-bromo-1-(1-methyl-1H-imidazol-5-yl)ethan-1-one

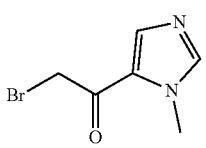

To a solution of 1-(1-methyl-1H-imidazol-5-yl)ethan-1-one (1.0 g, 8.05 mmol, 1.0 equiv.) in acetic acid (20 mL) was added hydrogen bromide solution in acetic acid (4.0 g, 16.11 mmol, 2.0 equiv.), followed by addition of pyridinium tribromide (2.6 g, 8.05 mmol, 1.0 equiv.) slowly. The reaction mixture was stirred at room temperature for 2 h, then concentrated under vacuum. The residue was co-evaporated twice with toluene to yield 2-bromo-1-(1-methyl-1H-imidazol-5-yl)ethan-1-one hydrobromide as a light yellow solid.

Intermediate 19: 4-(2-bromoacetyl)-1-methyl)pyridin-2(1H)-one

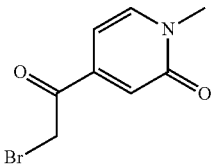

Step 1: 4-(1-Ethoxyvinyl)-1-methylpyridin-2(1H)-one

4-Bromo-1-methylpyridin-2(1H)-one (5.0 g, 26.59 mmol, 1.0 equiv.), tributyl(1-ethoxyvinyl)stannane (10 mL, 31.91 mmol. 1.2 equiv.), Pd(PPh$_3$)$_2$Cl$_2$ (1.8 g, 2.65 mmol. 0.1 equiv.) were placed in an oven dried Schlenk tube under nitrogen and 1,4-dioxane (100 mL) was added. The reaction mixture was stirred for overnight at 100° C. After cooling to room temperature, the reaction mixture was concentrated and purified by silica gel chromatography (0→15% methanol/dicholomethane) to yield 4-(1-ethoxyvinyl)-1-methylpyridin-2(1H)-one as a yellow solid.

Step 2: 4-(2-Bromoacetyl)-1-methylpyridin-2(1H)-one

To a solution of 4-(1-ethoxyvinyl)-1-methylpyridin-2(1H)-one (4.7 g, 26.22 mmol, 1.0 equiv.) in tetrahydrofuran/water (60 mL/20 mL) was added N-bromosuccinimide (4.6 g, 26.22 mmol, 1.0 equiv.) at room temperature. The reaction was then stirred at room temperature for 1 h. The reaction mixture was then concentrated and purified by silica gel chromatography (0→14% methanol/dicholomethane) to yield 4-(2-bromoacetyl)-1-methylpyridin-2(1H)-one as a yellow solid.

Intermediate 20: 5-(2-bromoacetyl)-1-methylpyridin-2(1H)-one

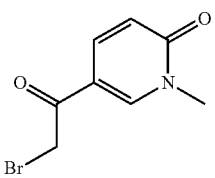

Step 1: 5-Acetyl-1-methylpyridin-2(1H)-one

To a solution of 5-bromo-1-methylpyridin-2(1H)-one (2.5 g, 13.30 mmol, 1.0 equiv.) and tributyl(1-ethoxyvinyl)stannane (5.3 g, 14.63 mmol, 1.1 equiv.) in 1,4-dioxane (20 mL) was added tetrakis(triphenylphosphine)palladium (0.77 g, 0.67 mmol, 0.05 equiv.) under an atmosphere of nitrogen. The reaction mixture was stirred overnight at 100° C. The mixture was quenched with water and extracted with ethyl acetate. The combined organic layers were dried over anhydrous sodium sulfate and concentrated under vacuum. The residue was applied onto a silica gel column (0-40% ethyl acetate/petroleum ether) to yield 5-acetyl-1-methylpyridin- 2(1H)-one as an off-white solid. LC/MS: mass calculated for $C_8H_9NO_2$: 151.06, measured (ES, m/z): 152.10 [M+H]$^+$.

Step 2:
5-(2-Bromoacetyl)-1-methylpyridin-2(1H)-one

To a solution of 1-(6-amino-2-methylpyridin-3-yl)ethan-1-one (1.2 g, 7.61 mmol, 1.0 equiv.) in acetic acid glacial (80 mL) was added hydrogen bromide (3.7 g, 15.22 mmol, 2.0 equiv.) and pyridinium tribromide (1.9 g, 6.09 mmol, 0.8 equiv.). The reaction mixture was stirred at room temperature for 2 h. The reaction mixture was concentrated under vacuum. The pH of the aqueous phase was adjusted to pH 10 using saturation sodium bicarbonate solution and then extracted with ethyl acetate. The combined organic layer was dried over anhydrous sodium sulfate and concentrated under vacuum. The residue was applied onto a silica gel column (0→40% ethyl acetate/petroleum ether) to yield 5-(2-bromoacetyl)-1-methylpyridin-2(1H)-one as an off-white solid. LC/MS: mass calculated for $C_8H_8BrNO_2$: 228.97, measured (ES, m/z): 229.95, 231.95 [M+H, M+H+2]$^+$.

Intermediate 21:
5-(2-bromoacetyl)-2-methylpyridazin-3(2H)-one

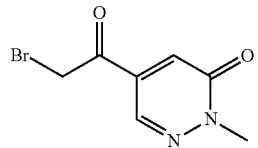

Step 1: 5-Iodo-2-methylpyridazin-3(2H)-one

To a stirring mixture of 5-iodopyridazin-3(2H)-one (10.0 g, 45.0 mmol, 1.0 equiv.) and potassium carbonate (12.4 g, 90.09 mmol, 2.0 equiv.) in acetonitrile (400 mL) was added iodomethane (6 mL, 96.40 mmol, 2.1 equiv.). The reaction mixture was heated at reflux for 18 h and then cooled to room temperature. The reaction mixture was filtered through a pad of silica gel and eluted with methanol. The filtrate was concentrated under reduced pressure and the residue was purified by column chromatography (1→5% methanol/dicholomethane) to yield 5-iodo-2-methylpyridazin-3(2H)-one as a brown solid.

Step 2:
5-(1-Ethoxyvinyl)-2-methylpyridazin-3(2H)-one

5-Iodo-2-methylpyridazin-3(2H)-one (3.0 g, 12.71 mmol, 1.0 equiv.), tributyl(1-ethoxyvinyl)stannane (5.1 mL, 15.25 mmol. 1.2 equiv.), Pd(PPh$_3$)$_4$ (1.5 g, 1.27 mmol. 0.1 equiv.) were placed in an oven dried Schlenk tube under nitrogen and 1,4-dioxane (40 mL) was added. The reaction mixture was stirred overnight at 100° C. After cooling to room temperature, the reaction mixture was concentrated and purified by silica gel chromatography (0→60% ethyl acetate/petroleum ether) to yield 5-(1-ethoxyvinyl)-2-methylpyridazin-3(2H)-one as a yellow solid.

Step 3:
5-(2-Bromoacetyl)-2-methylpyridazin-3(2H)-one

To a solution of 5-(1-ethoxyvinyl)-2-methylpyridazin-3(2H)-one (2.1 g, 11.65 mmol, 1.0 equiv.) in tetrahydrofuran/water (60 mL/20 mL) was added n-bromosuccinimide (2.1 g, 11.65 mmol, 1.0 equiv.) at room temperature The reaction mixture was then stirred at room temperature for 1 h. The reaction mixture was then concentrated and purified by silica gel chromatography (0→50% ethyl acetate/petroleum ether) to yield 5-(2-bromoacetyl)-2-methylpyridazin-3(2H)-one as a yellow solid.

Intermediate 22: 2-bromo-1-(1-methyl-1H-1,2,3-triazol-5-yl)ethan-1-one

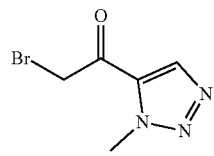

Step 1: 1-(1-Methyl-1H-1,2,3-triazol-5-yl)ethan-1-one

To a solution of 1-methyl-1H-1,2,3-triazole (7.2 g, 86.20 mmol, 1.0 equiv.) in THF (80 mL) was added dropwise n-BuLi (37.9 mL, 94.82 mmol, 1.05 equiv.) under N$_2$ at −78° C. The reaction mixture was stirred at −78° C. for 1 h, then a solution of n-methoxy-n-methylacetamide (16.0 g, 155.16 mmol, 1.8 equiv.) in THF (10 mL) was added dropwise. The reaction mixture was stirred 2 h at −78° C. and then warmed to room temperature and quenched with NH$_4$Cl (aq.). The resulting mixture was extracted with EA twice. The combined organic layers were washed with brine, dried over Na$_2$SO$_4$, and concentrated under vacuum. The residue was purified by silica gel chromatography with EA/PE (0→66%) to yield 1-(1-methyl-1H-1,2,3-triazol-5-yl)ethan-1-one as yellow oil. LC/MS: mass calculated for $C_5H_7N_3O$: 125.06, measured (ES, m/z): 126.00 [M+H]$^+$.

Step 2: 2-Bromo-1-(1-methyl-1H-1,2,3-triazol-5-yl)ethan-1-one

To a solution of 1-(4-bromopyridin-2-yl)ethan-1-one (8.0 g, 63.93 mmol, 1.0 equiv.) in HBr/AcOH (800 mL) was added pyridinium tribromide (20.1 g, 62.65 mmol, 1.0 equiv.). The reaction mixture was stirred at room temperature overnight. The mixture was extracted with EA twice. The combined organic layers were washed with NaHCO$_3$, dried and concentrated in vacuum to yield 2-bromo-1-(1-methyl-1H-1,2,3-triazol-5-yl)ethan-1-one as a black solid. LC/MS: mass calculated for $C_5H_6BrN_3O$: 202.97, measured (ES, m/z): 204.05 [M+H]$^+$.

Intermediate 23: 2-bromo-1-(imidazo[1,5-a]pyridin-6-yl)ethan-1-one

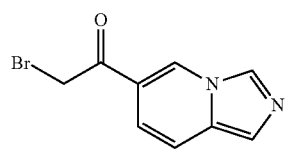 [SMILES: O=C(CBr)c1ccc2cncn2c1]

Step 1: 6-(1-Ethoxyvinyl)imidazo[1,5-a]pyridine

To a solution of 6-bromoimidazo[1,5-a]pyridine (1.0 g, 5.08 mmol, 1.0 equiv.) in 1,4-dioxane (50 mL) was added tributyl(1-ethoxyvinyl)stannane (2.2 g, 6.09 mmol, 1.2 equiv.) and tetrakis(triphenylphosphine)palladium (0.59 g, 0.51 mmol, 1.0 equiv.) under $N_2$. The reaction mixture stirred for 3 h at 100° C., then cooled to room temperature and extracted with EtOAc (300 mL). The organic layer was washed with water (50 mL), then dried over anhydrous sodium sulfate, filtered, and concentrated under reduced pressure. The residue was purified by normal phase chromatography (EA/PE, 0→60%) to yield 6-(1-ethoxyvinyl) imidazo[1,5-a]pyridine as a yellow solid.

Step 2: 1-(Imidazo[1,5-a]pyridin-6-yl)ethan-1-one

To a solution of 6-(1-ethoxyvinyl)imidazo[1,5-a]pyridine (1.0 g, 5.31 mmol, 1.0 equiv.) in THF (20 mL) was added 3 M HCl (10 mL). The mixture was stirred at room temperature for 2 h, then the pH was adjusted to pH 7-8 with $NaHCO_3$(aq.). The mixture was extracted with EA, dried over $Na_2SO_4$, and concentrated under vacuum. The residue was purified by silica gel chromatography with MeOH/DCM (0→10%) to yield 1-(imidazo[1,5-a]pyridin-6-yl) ethan-1-one as a yellow solid.

Step 3: 2-Bromo-1-(imidazo[1,5-a]pyridin-6-yl)ethan-1-one

To a solution of 1-(imidazo[1,5-a]pyridin-6-yl)ethan-1-one (0.30 g, 1.87 mmol, 1.0 equiv.) in acetic acid (15 mL) was added hydrogen bromide solution in acetic acid (0.92 g, 3.75 mmol, 2.0 equiv.) followed by the addition of pyridinium tribromide (0.60 g, 1.87 mmol, 1.0 equiv.) slowly. The reaction mixture was stirred at room temperature for 2 h, then concentrated under vacuum. The residue was admixed with water and extracted with EA. The organic layers were combined, washed with brine, dried over $Na_2SO_4$, filtered and concentrated. This resulted in 2-bromo-1-(imidazo[1,5-a]pyridin-6-yl)ethan-1-one as a brown solid.

Intermediate 24: 2-bromo-1-(3-bromoimidazo[1,2-a]pyridin-7-yl)ethan-1-one

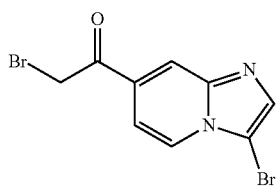 [SMILES: O=C(CBr)c1ccn2c(Br)cnc2c1]

Step 1: 7-(1-Ethoxyvinyl)imidazo[1,2-a]pyridine

To a solution of 7-bromoimidazo[1,2-a]pyridine (2.0 g, 10.15 mmol, 1.0 equiv.) in 1,4-dioxane (20 mL) was added to tributyl(1-ethoxyvinyl)stannane (4.4 g, 12.18 mmol, 1.2 equiv.) and tetrakis(triphenylphosphine) palladium (587 mg, 0.51 mmol, 0.05 equiv.). The resulting mixture was stirred at 90° C. for 4 h. After cooling to room temperature, the reaction was quenched with water (50 mL). The resulting mixture was extracted with ethyl acetate (3×50 mL). The organic layers were combined, dried over anhydrous sodium sulfate, filtered, and concentrated. The residue was purified by silica gel chromatography (0→20% ethyl acetate/petroleum ether) to yield 7-(1-ethoxyvinyl)imidazo[1,2-a]pyridine as a yellow solid.

Step 2: 1-(Imidazo[1,2-a]pyridin-7-yl)ethan-1-one

To a solution of 7-(1-ethoxyvinyl)imidazo[1,2-a]pyridine (2.7 g, 14.34 mmol) was added to hydrochloric acid (1 mL) and tetrahydrofuran (10 mL). The resulting mixture was stirred at room temperature for 2 h. The reaction was quenched with water (50 mL). The resulting mixture was extracted with ethyl acetate (3×50 mL). The organic layers were combined, dried over anhydrous sodium sulfate, filtered, and concentrated. The residue was purified by silica gel chromatography (0→80% ethyl acetate/petroleum ether) to yield 1-(imidazo[1,2-a]pyridin-7-yl)ethan-1-one.

Step 3: 2-Bromo-1-(3-bromoimidazo[1,2-a]pyridin-7-yl)ethan-1-one

To a solution of 1-(imidazo[1,2-a]pyridin-7-yl)ethan-1-one (590 mg, 3.68 mmol, 1.0 equiv.) in acetic acid (5 mL) was added pyridinium tribromide (2.4 g, 7.37 mmol, 2.0 equiv.) in acetic acid (3 mL) and hydrogen bromide (1.8 g, 7.37 mmol, 2.0 equiv.). The resulting mixture was stirred at room temperature for 3 h. The pH of the aqueous phase was adjusted to pH 8 by $NaHCO_3$ solution and then the resulting mixture was extracted with ethyl acetate (3×50 mL). The organic layers were combined, dried over anhydrous sodium sulfate, filtered, and concentrated. The residue was purified by silica gel chromatography (0→10% MeOH/DCM) to yield 2-bromo-1-(2-bromoimidazo[1,2-a]pyridin-7-yl)ethan-1-one.

Intermediate 25: 1-([1,2,4]triazolo[4,3-a]pyridin-7-yl)-2-bromoethan-1-one

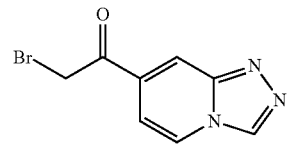 [SMILES: O=C(CBr)c1ccn2cnnc2c1]

Step 1: 7-(1-Ethoxyvinyl)-[1,2,4]triazolo[4,3-a]pyridine

To a solution of 7-bromo-[1,2,4]triazolo[4,3-a]pyridine (1.0 g, 5.05 mmol, 1.0 equiv.) in 1,4-dioxane (50 mL) was added tributyl(1-ethoxyvinyl)stannane (2.0 g, 5.56 mmol, 1.1 equiv.) and tetrakis(triphenylphosphine)palladium (584 mg, 0.51 mmol, 0.1 equiv.) under $N_2$. The reaction mixture stirred for 3 h at 100° C., cooled to room temperature and extracted with EtOAc (300 mL). The organic layer was washed with water (50 mL), then dried over anhydrous sodium sulfate, filtered, and concentrated under reduced pressure. The residue was purified by normal phase chromatography (EA/PE, 0→60%) to yield 7-(1-ethoxyvinyl)-[1,2,4]triazolo[4,3-a]pyridine as a yellow solid\.

Step 2: 1-([1,2,4]Triazolo[4,3-a]pyridin-7-yl)ethan-1-one

To a solution of 7-(1-ethoxyvinyl)-[1,2,4]triazolo[4,3-a] pyridine (500 mg, 2.64 mmol, 1.0 equiv.) in THF (10 mL)

was added HCl (1 mL). The mixture stirred at room temperature for 2 h. The reaction was quenched with water (10 mL). The resulting mixture was extracted with ethyl acetate (3×10 mL). The water layers were concentrated to yield 1-([1,2,4]triazolo[4,3-a]pyridin-7-yl)ethan-1-one as a gray solid.

Step 3: 1-([1,2,4]Triazolo[4,3-a]pyridin-7-yl)-2-bromoethan-1-one

To a solution of 1-([1,2,4]triazolo[4,3-a]pyridin-7-yl)ethan-1-one (150 mg, 0.93 mmol, 1.0 equiv.) in THF (5 mL) was added pyridinium tribromide (268 mg, 0.84 mmol, 0.9 equiv.) with THF (2 mL). The mixture was stirred at room temperature for 2 h. The resulting mixture was then dried to yield 1-([1,2,4]triazolo[4,3-a]pyridin-7-yl)-2-bromoethan-1-one as a yellow solid.

SYNTHESIS EXAMPLES: COMPOUNDS OF FORMULA (I)

In the synthesis examples which follow hereinafter, unless otherwise noted, where the example provides only analytical (physical) properties for the title compound, the skilled artisan will understand that the title compound was prepared according to the procedures as described in the Schemes and Examples herein, selecting and substituting suitable reagents and reactants, as would be readily recognized by those skilled in the art.

Example 1: 12-(5-(6-amino-2-fluoropyridin-3-yl)-4-fluoro-1H-imidazol-2-yl)-7-chloro-13,14-dihydro-2H-spiro[benzo[5,6]azocino[4,3-g]indolizine-3,1'-cyclopropane]-1,10(4H,12H)-dione

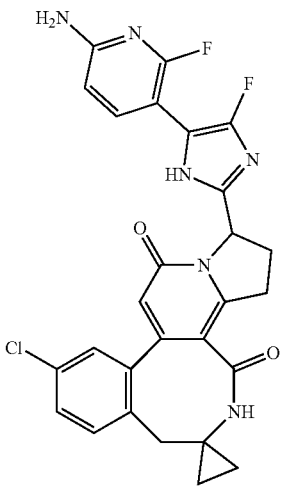 [SMILES: Nc1ccc(-c2[nH]c(C3CCc4c5c(cc(=O)n43)-c3cc(Cl)ccc3CC3(CC3)NC5=O)nc2F)c(F)n1]

Step 1: 2-(6-Acetamido-2-fluoropyridin-3-yl)-2-oxoethyl 7-chloro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-1,10-dioxo-1,4,10,12,13,14-hexahydro-2H-spiro[benzo[5,6]azocino[4,3-g]indolizine-3,1'-cyclopropane]-12-carboxylic acid (320 mg, 0.83 mmol, 1.0 equiv.) in N,N-dimethylformamide (5.0 mL) was added potassium carbonate (138 mg, 1.00 mmol, 1.2 equiv.). N-(5-(2-bromoacetyl)-6-fluoropyridin-2-yl)acetamide (298 mg, 1.08 mmol, 1.3 equiv.) was then added. The resulting solution was stirred at room temperature for 1.5 h. The mixture was added water and extracted with ethyl acetate twice. The combined organic layers were washed with brine, dried over $Na_2SO_4$, concentrated to yield 2-(6-acetamido-2-fluoropyridin-3-yl)-2-oxoethyl 7-chloro-1,10-dioxo-1,4,10,12,13,14-hexahydro-2H-spiro[benzo[5,6]azocino[4,3-g]indolizine-3,1'-cyclopropane]-12-carboxylate as a yellow solid. LC/MS: mass calculated for $C_{29}H_{24}ClFN_4O_6$: 578.14, measured (ES, m/z): 579.30 $[M+H]^+$ Step 2: N-(5-(2-(7-chloro-1,10-dioxo-1,4,10,12,13,14-hexahydro-2H-spiro[benzo[5,6]azocino[4,3-g]indolizine-3,1'-cyclopropan]-12-yl)-1H-imidazol-5-yl)-6-fluoropyridin-2-yl)acetamide To a mixture of 2-(6-acetamido-2-fluoropyridin-3-yl)-2-oxoethyl 7-chloro-1,10-dioxo-1,4,10,12,13,14-hexahydro-2H-spiro[benzo[5,6]azocino[4,3-g]indolizine-3,1'-cyclopropane]-12-carboxylate (430 mg, 0.74 mmol, 1.0 equiv.) in toluene (10 mL) and acetic acid (1.0 mL) was added ammonium acetate (573 mg, 7.43 mmol, 10.0 equiv.). The reaction mixture was stirred at 100° C. for 1 h. The resulting solution was concentrated under vacuum and purified by reverse phase chromatography on C18 (120 g, ACN/H₂O (0.05% $CF_3COOH$): 0-35%) to yield N-(5-(2-(7-chloro-1,10-dioxo-1,4,10,12,13,14-hexahydro-2H-spiro[benzo[5,6]azocino[4,3-g]indolizine-3,1'-cyclopropan]-12-yl)-1H-imidazol-5-yl)-6-fluoropyridin-2-yl)acetamide as yellow solid. LC/MS: mass calculated for $C_{29}H_{24}ClFN_6O_3$: 558.16, measured (ES, m/z): 559.15 $[M+H]^+$ Step 3: N-(5-(2-(7-chloro-1,10-dioxo-1,4,10,12,13,14-hexahydro-2H-spiro[benzo[5,6]azocino[4,3-g]indolizine-3,1'-cyclopropan]-12-yl)-4-fluoro-1H-imidazol-5-yl)-6-fluoropyridin-2-yl)acetamide To a solution of N-(5-(2-(7-chloro-1,10-dioxo-1,4,10,12,13,14-hexahydro-2H-spiro[benzo[5,6]azocino[4,3-g]indolizine-3,1'-cyclopropan]-12-yl)-1H-imidazol-5-yl)-6-fluoropyridin-2-yl)acetamide (150 mg, 0.27 mmol, 1.0 equiv.) in dichloromethane (3.0 mL) and acetone (3.0 mL) was added sodium bicarbonate (158 mg, 1.89 mmol, 7.0 equiv.) and NFSI (423 mg, 1.34 mmol, 5.0 equiv.). The solution was stirred at 50° C. for 5 h. The resulting mixture was then cooled to room temperature, to the reaction mixture was added water and the mixture was extracted with EA twice. The combined organic layers were washed with brine, dried over $Na_2SO_4$, and concentrated under vacuum. The residue was purified by reverse phase chromatography on C18 (120 g, ACN/H₂O (0.05% $CF_3COOH$): 0-40%) to yield N-(5-(2-(7-chloro-1,10-dioxo-1,4,10,12,13,14-hexahydro-2H-spiro[benzo[5,6]azocino[4,3-g]indolizine-3,1'-cyclopropan]-12-yl)-4-fluoro-1H-imidazol-5-yl)-6-fluoropyridin-2-yl)acetamide as a yellow solid. LC/MS: mass calculated for $C_{29}H_{23}ClF_2N_6O_3$: 576.15, measured (ES, m/z): 577.15 $[M+H]^+$.

Step 4: 12-(5-(6-amino-2-fluoropyridin-3-yl)-4-fluoro-1H-imidazol-2-yl)-7-chloro-13,14-dihydro-2H-spiro[benzo[5,6]azocino[4,3-g]indolizine-3,1'-cyclopropane]-1,10(4H,12H)-dione To a solution of N-(5-(2-(7-chloro-1,10-dioxo-1,4,10,12,13,14-hexahydro-2H-spiro[benzo[5,6]azocino[4,3-g]indolizine-3,1'-cyclopropan]-12-yl)-4-fluoro-1H-imidazol-5-yl)-6-fluoropyridin-2-yl)acetamide (70 mg, 0.12 mmol, 1.0 equiv.) in tetrahydrofuran (2 mL) was added hydrochloric acid (1.0 mL, 4 M). The solution was stirred at 50° C. for 2 h. The tetrahydrofuran was removed under vacuum. The residue was purified by reverse phase chromatography on C18 (80 g, ACN/H$_2$O (0.05% CF$_3$COOH): 0-30%) to yield 12-(5-(6-amino-2-fluoropyridin-3-yl)-4-fluoro-1H-imidazol-2-yl)-7-chloro-13,14-dihydro-2H-spiro[benzo[5,6]azocino[4,3-g]indolizine-3,1'-cyclopropane]-1,10(4H,12H)-dione as a white solid.

LC/MS: mass calculated for C$_{27}$H$_{21}$ClF$_2$N$_6$O$_2$:534.95, measured: 535.20 [M+H]$^+$. $^1$H NMR (300 MHz, DMSO-d$_6$) δ12.32-12.56 (m, 1H), 8.01-8.29 (m, 1H), 7.51-7.56 (m, 1H), 7.38-7.50 (m, 1H), 7.25-7.37 (m, 1H), 7.17-7.24 (m, 1H), 6.50-6.64 (m, 2H), 6.42 (dd, J=8.3, 2.0 Hz, 1H), 6.09 (s, 1H), 5.72 (d, J=8.5 Hz, 1H), 3.00-3.28 (m, 3H), 2.55-2.82 (m, 2H), 2.07-2.34 (m, 1H), 0.91-1.07 (m, 1H), 0.56-0.87 (m, 3H).

Example 2: 12-(5-(6-amino-2-fluoropyridin-3-yl)-1H-imidazol-2-yl)-7-chloro-13,14-dihydro-2H-spiro[benzo[5,6]azocino[4,3-g]indolizine-3,1'-cyclopropane]-1,10(4H,12H)-dione

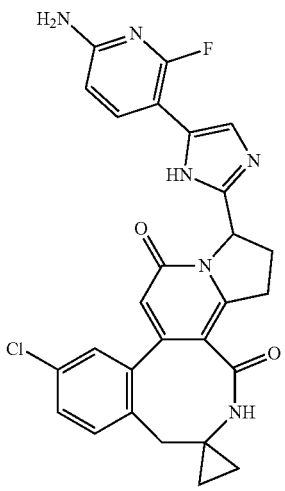 [SMILES: Nc1ccc(-c2cnc(C3CCc4c5c(cc(=O)n43)-c3cc(Cl)ccc3CC3(CC3)NC5=O)[nH]2)c(F)n1]

To a solution of N-(5-(2-(7-chloro-1,10-dioxo-1,4,10,12,13,14-hexahydro-2H-spiro[benzo[5,6]azocino[4,3-g]indolizine-3,1'-cyclopropan]-12-yl)-1H-imidazol-5-yl)-6-fluoropyridin-2-yl)acetamide (50 mg, 0.09 mmol, 1.0 equiv.) in tetrahydrofuran (1 mL) was added hydrochloric acid (0.5 mL, 2.0 mmol, 4 M). The solution was then stirred at 50° C. for 2 h. The tetrahydrofuran was removed under vacuum. The resulting residue was purified by reverse phase chromatography on C18 (80 g, ACN/H$_2$O (0.05% CF$_3$COOH): 0-30%) to yield 124546-amino-2-fluoropyridin-3-yl)-1H-imidazol-2-yl)-7-chloro-13,14-dihydro-2H-spiro[benzo[5,6]azocino[4,3-g]indolizine-3,1'-cyclopropane]-1,10(4H,12H)-dione as an off-white solid.

LC/MS: mass calculated for C$_{27}$H$_{22}$ClFN$_6$O$_2$:516.15, measured: 517.15 [M+H]$^+$. $^1$H NMR (300 MHz, DMSO-d$_6$) δ 7.80-7.96 (m, 1H), 7.40-7.68 (m, 2H), 7.28-7.36 (m, 1H), 7.15-7.25 (m, 1H), 6.38-6.52 (m, 1H), 6.06-6.20 (m, 1H), 5.78-5.97 (m, 1H), 3.34-3.49 (m, 1H), 3.12-3.34 (m, 1H), 2.92-3.12 (m, 1H), 2.61-2.91 (m, 2H), 2.30-2.40 (m, 1H), 0.89-1.07 (m, 1H), 0.56-0.87 (m, 3H). $^{19}$F NMR (282 MHz, DMSO-d$_6$) δ−69.32, −74.14.

Example 3: 7-chloro-8-fluoro-12-(5-(3-fluoro-2-(hydroxymethyl)pyridin-4-yl)-1H-imidazol-2-yl)-13,14-dihydro-2H-spiro[benzo[5,6]azocino[4,3-g]indolizine-3,1'-cyclopropane]-1,10(4H,12H)-dione

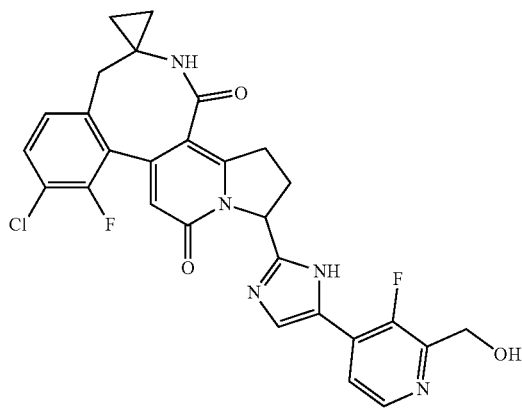 [SMILES: O=C1NC2(CC2)Cc2ccc(Cl)c(F)c2-c2cc(=O)n3c(c21)CCC3c1ncc(-c2ccnc(CO)c2F)[nH]1]

Step 1: 2-(2-(((Tert-butyldimethylsilyl)oxy)methyl)-3-fluoropyridin-4-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (60 mg, 0.15 mmol, 1.0 equiv.) in N,N-dimethylformamide (3.0 mL) was added potassium carbonate (31 mg, 0.22 mmol, 1.5 equiv.). After the reaction mixture was stirred at room temperature for 30 min, 2-bromo-1-(3-fluoro-2-(hydroxymethyl)pyridin-4-yl)ethan-1-one (110 mg, 0.45 mmol, 3.0 equiv.) was added. The reaction mixture was stirred 2 h at room temperature. The mixture was purified by reverse column chromatography with CH$_3$CN/0.05% TFA water (5%-80%) to yield of 2-(2-(((tert-butyldimethylsilyl)oxy)methyl)-3-fluoropyridin-4-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a brown solid. LC/MS: mass calculated for C$_{34}$H$_{36}$ClF$_2$N$_3$O$_6$Si: 683.20, measured (ES, m/z): 685.75 [M+H+2]$^+$.

Step 2: 7-Chloro-8-fluoro-12-(5-(3-fluoro-2-(hydroxymethyl)pyridin-4-yl)-1H-imidazol-2-yl)-13,14-dihydro-2H-spiro[benzo[5,6]azocino[4,3-g]indolizine-3,1'-cyclopropane]-1,10(4H,12H)-dione To a solution of 2-(2-(((tert-butyldimethylsilyl)oxy)methyl)-3-fluoropyridin-4-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (40 mg, 0.06 mmol, 1.0 equiv.) in toluene (2.5 mL) and acetic acid (0.125 mL) was added ammonium acetate (68 mg, 0.88 mmol, 15.0 equiv.). The reaction mixture was stirred at 100° C. for 1 h. The residue was purified by reverse column chromatography with CH$_3$CN/0.05% TFA water (5%-80%) to yield 7-chloro-8-fluoro-12-(5-(3-fluoro-2-(hydroxymethyl)pyridin-4-yl)-1H-imidazol-2-yl)-13,14-dihydro-2H-spiro[benzo[5,6]azocino[4,3-g]indolizine-3,1'-cyclopropane]-1,10(4H,12H)-dione as a white solid.

LC/MS: mass calculated for $C_{28}H_{22}ClF_2N_5O_3$: 549.14, measured: 550.10 [M+H]+. 1H NMR (300 MHz, Methanol-$d_4$) δ 8.20-8.35 (m, 1H), 7.90-8.10 (m, 1H), 7.68-7.75 (m, 1H), 7.45-7.58 (m, 1H), 7.02-7.15 (m, 1H), 6.35-6.43 (m, 1H), 5.90-6.02 (m, 1H), 4.70-4.85 (m, 2H), 3.46-3.84 (m, 2H), 3.01-3.23 (m, 1H), 2.45-2.98 (m, 3H), 0.63-1.02 (m, 4H). 19F NMR (282 MHz, Methanol-$d_4$) δ −117.83, −131.14.

Example 4: (S*)-7-chloro-8-fluoro-12-(5-(2-methylbenzo[d]thiazol-5-yl)-1H-imidazol-2-yl)-13,14-dihydro-2H-spiro[benzo[5,6]azocino[4,3-g]indolizine-3,1'-cyclopropane]-1,10(4H,12H)-dione

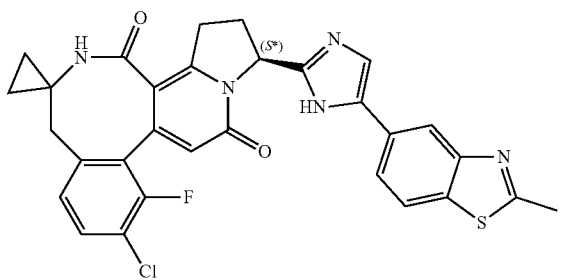 [SMILES: Cc1nc2cc(-c3cnc([C@@H]4CCc5c6c(cc(=O)n54)-c4c(ccc(Cl)c4F)CC4(CC4)NC6=O)[nH]3)ccc2s1]

The title compound was prepared following the procedure described in Example 5 above, selecting and substituting suitable reagents and reactants, as would be readily recognized by those skilled in the art.

LC/MS: mass calculated for $C_{30}H_{23}ClFN_5O_2S$: 571.12, measured (ES, m/z): 572.15 [M+H]+. 1H NMR (400 MHz, DMSO-$d_6$) δ 12.31 (s, 1H), 8.21 (d, J=1.7 Hz, 1H), 8.00-8.09 (m, 1H), 7.93 (d, J=8.3 Hz, 1H), 7.78 (dd, J=8.4, 1.6 Hz, 1H), 7.65-7.72 (m, 1H), 7.59 (t, J=7.9 Hz, 1H), 7.18 (d, J=8.3 Hz, 1H), 6.15-6.28 (m, 1H), 5.77 (d, J=8.8 Hz, 1H), 2.93-3.08 (m, 2H), 2.75-2.85 (m, 5H), 2.55-2.70 (m, 2H), 0.98-1.06 (m, 1H), 0.76-0.83 (m, 1H), 0.60-0.70 (m, 2H). 19F NMR (376 MHz, DMSO-$d_6$) δ −117.11.

Example 5: (R*)-7-chloro-8-fluoro-12-(5-(2-methylbenzo[d]thiazol-5-yl)-1H-imidazol-2-yl)-13,14-dihydro-2H-spiro[benzo[5,6]azocino[4,3-g]indolizine-3,1'-cyclopropane]-1,10(4H,12H)-dione

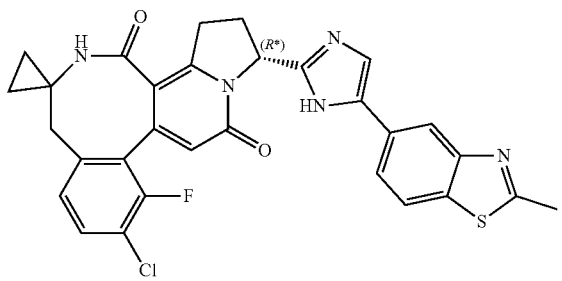 [SMILES: Cc1nc2cc(-c3cnc([C@H]4CCc5c6c(cc(=O)n54)-c4c(ccc(Cl)c4F)CC4(CC4)NC6=O)[nH]3)ccc2s1]

Step 1: 1-(2-Methylbenzo[d]thiazol-5-yl)ethan-1-one

To a solution of 5-bromo-2-methylbenzo[d]thiazole (250 mg, 1.10 mmol, 1.0 equiv.) in 1,4-dioxane (5 mL) was added tributyl(1-ethoxyvinyl)tin (475 mg, 1.32 mmol, 1.2 equiv.), tetrakis(triphenylphosphine)palladium (127 mg, 0.11 mmol, 0.1 equiv). The resulting mixture was maintained under nitrogen and stirred at 100° C. overnight. After cooling to room temperature, the mixture was concentrated. The resulting mixture was extracted with ethyl acetate (3×50 mL) and washed with brine. The organic layers were combined, dried over anhydrous sodium sulfate, filtered, and concentrated. The residue was purified by silica gel chromatography (0-65% ethyl acetate/petroleum ether) to yield 1-(2-methylbenzo[d]thiazol-5-yl)ethan-1-one as a little yellow solid. LC/MS: mass calculated for $C_{10}H_9NOS$: 191.04, measured: 192.10 [M+H]+.

Step 2: 2-Bromo-1-(2-methylbenzo[d]thiazol-5-yl)ethan-1-one

To a solution of 1-(2-methylbenzo[d]thiazol-5-yl)ethan-1-one (450 mg, 2.35 mmol, 1.0 equiv.), hydrobromic acid, acetic acid solution 33% (2.0 g, 4.71 mmol, 2.0 equiv.) in acetic acid glacial (20 mL) was added pyridinium tribromide (677 mg, 2.12 mmol, 0.9 equiv.) at 0° C. The resulting mixture was maintained under air and stirred at room temperature for 4 h. The resulting mixture was concentrated. The residue was purified by silica gel chromatography (0-33% ethyl acetate/petroleum ether) to yield 2-bromo-1-(2-methylbenzo[d]thiazol-5-yl)ethan-1-one as an yellow solid. LC/MS: mass calculated for $C_{10}H_8BrNOS$: 268.95, measured: 272.05 [M+H+2]+.

Step 3: 2-(2-Methylbenzo[d]thiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (110 mg, 0.27 mmol, 1.0 equiv.) in DMF (5 mL) was added $K_2CO_3$ (57 mg, 0.41 mmol, 1.5 equiv.). After stirring 0.5 h, 2-bromo-1-(2-methylbenzo[d]thiazol-5-yl)ethan-1-one (74 mg, 0.27 mmol, 1.0 equiv.) in DMF (0.5 mL) was added. The resulting mixture was stirred at room temperature for 2 h. The reaction was quenched with water. The resulting mixture was extracted with ethyl acetate. The organic layers were combined, dried over anhydrous sodium sulfate, filtered, and concentrated. The residue was purified by silica gel chromatography (0-10% MeOH/DCM) to yield 2-(2-methylbenzo[d]thiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a white solid. LC/MS: mass calculated for $C_{30}H_{23}ClFN_3O_5S$: 591.10, measured: 592.05 [M+H+2]+.

Step 4: (R*)-7-chloro-8-fluoro-12-(5-(2-methylbenzo[d]thiazol-5-yl)-1H-imidazol-2-yl)-13,14-dihydro-2H-spiro[benzo[5,6]azocino[4,3-g]indolizine-3,1'-cyclopropane]-1,10(4H,12H)-dione To a solution of 2-(2-methylbenzo[d]thiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (140 mg, 0.24 mmol, 1.0 equiv.) in toluene (14 mL) and AcOH (0.28 mL) was added $NH_4OAc$ (365 mg, 4.73 mmol, 20.0 equiv.). The resulting mixture was stirred at 100° C. for 1 h. After cooling to room temperature, the reaction was concentrated. The residue was purified by silica gel chromatography (0-10% MeOH/DCM)

to yield a residue which was further purified by Chiral-HPLC with MtBE (0.1% DEA):EtOH=50:50 to yield (R*)-7-chloro-8-fluoro-12-(5-(2-methylbenzo[d]thiazol-5-yl)-1H-imidazol-2-yl)-13,14-dihydro-2H-spiro[benzo[5,6]azocino[4,3-g]indolizine-3,1'-cyclopropane]-1,10(4H,12H)-dione as a white solid.

LC/MS: mass calculated for $C_{30}H_{23}ClFN_5O_2S$: 571.12, measured (ES, m/z): 572.10 [M+H]$^+$. $^1$H NMR (400 MHz, DMSO-d$_6$) δ 12.42 (s, 1H), 8.13-8.23 (m, 2H), 7.90 (d, J=8.4 Hz, 1H), 7.77 (dd, J=8.4, 1.6 Hz, 1H), 7.66 (d, J=2.0 Hz, 1H), 7.58 (t, J=7.9 Hz, 1H), 7.16 (d, J=8.3 Hz, 1H), 6.17-6.21 (m, 1H), 5.75-5.81 (m, 1H), 2.70-2.75 (m, 5H), 2.60-2.68 (m, 2H), 2.20-2.32 (m, 2H), 1.01-1.05 (m, 1H), 0.87-0.96 (m, 1H), 0.75-0.80 (m, 1H), 0.60-0.70 (m, 1H). $^{19}$F NMR (376 MHz, DMSO-d$_6$) δ−117.01.

Example 6: (R*)-12-(5-(1H-benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

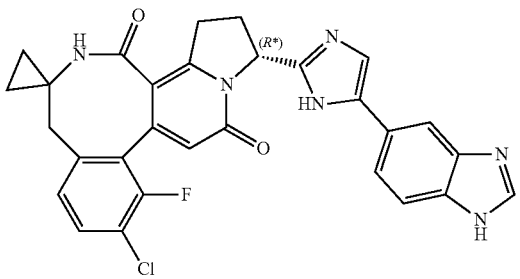 [SMILES: O=C1NC2(CC2)Cc2ccc(Cl)c(F)c2-c2cc(=O)n3c(c21)CC[C@@H]3c1ncc(-c2ccc3[nH]cnc3c2)[nH]1]

Step 1: 2-(1H-Benzo[d]imidazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate 7-Chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (809 mg, 2.00 mmol, 1.2 equiv.) and K$_2$CO$_3$ (254 mg, 1.80 mmol, 1.1 equiv.) were dissolved in DMF (2 mL). The mixture was stirred at 25° C. for 0.5 h. Then 1-(1H-benzo[d]imidazol-5-yl)-2-bromoethan-1-one (400 mg, 1.62 mmol, 1.0 equiv.) was added, and the mixture was stirred at 25° C. for 16 hrs. The reaction mixture was extracted with EA (50 mL), the organic layer was combined and concentrated under vacuum. The residue was applied onto a silica gel column (0→10% MeOH/DCM) to yield 2-(1H-benzo[d]imidazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a yellow solid. LC/MS: mass calculated for $C_{29}H_{22}ClFN_4O_5$: 560.13, measured (ES, m/z): 583.00 [M+Na]$^+$.

Step 2: (R*)-12-(5-(1H-Benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione To a solution of 2-(1H-benzo[d]imidazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (60 mg, 0.11 mmol, 1.0 equiv.) in acetic acid (0.2 mL) and toluene (10 mL) was added ammonium acetate (165 mg, 2.14 mmol, 20.0 equiv.). The resulting mixture was stirred at 100° C. for 1 h, then cooled to room temperature and concentrated under vacuum. The residue was purified by silica gel chromatography with MeOH/DCM (0→10%) and Chiral-HPLC with MtBE (0.1% DEA): MeOH=70:30 to yield (R*)-12-(5-(1H-benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as a white solid.

LC/MS: mass calculated for $C_{29}H_{22}ClFN_6O_2$: 540.15, measured: 541.10 [M+H]$^+$. $^1$H NMR (400 MHz, DMSO-d$_6$) δ 8.10-8.16 (m, 1H), 7.90-8.00 (m, 1H), 7.58-7.65 (m, 2H), 7.40-7.50 (m, 1H), 7.36 (s, 1H), 7.10-7.12 (m, 1H), 6.33 (s, 1H), 5.94-5.97 (m, 1H), 3.12-3.16 (m, 2H), 2.88-2.96 (m, 2H), 2.73-2.78 (m, 2H), 0.86-0.92 (m, 2H), 0.77-0.82 (m, 2H).

Example 7: (S*)-7-chloro-8-fluoro-12-(5-(imidazo[1,2-a]pyridin-7-yl)-1H-imidazol-2-yl)-13,14-dihydro-2H-spiro[benzo[5,6]azocino[4,3-g]indolizine-3,1'-cyclopropane]-1,10(4H,12H)-dione

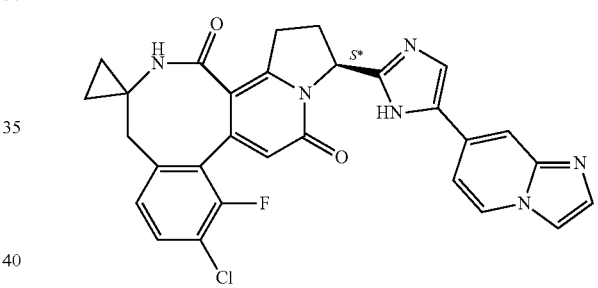

To a solution of 2-(imidazo[1,2-a]pyridin-7-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (80 mg, 0.14 mmol, 1.0 equiv.) in toluene (3 mL) was added ammonium acetate (220 mg, 2.85 mmol, 20.0 equiv.) followed by addition of acetic acid (0.06 mL). The resulting mixture was stirred at room temperature for 2 h and concentrated under vacuum. The residue was purified by silica gel chromatography with MeOH/DCM (0-10%) to yield a residue, which was purified by Chiral-HPLC with MtBE (0.1% DEA):MeOH=70:30 to yield (S*)-7-chloro-8-fluoro-12-(5-(imidazo[1,2-a]pyridin-7-yl)-1H-imidazol-2-yl)-13,14-dihydro-2H-spiro[benzo[5,6]azocino[4,3-g]indolizine-3,1'-cyclopropane]-1,10(4H,12H)-dione as a yellow solid.

LC/MS: mass calculated for $C_{29}H_{22}ClFN_6O_2$: 540.15, measured (ES, m/z): 541.05 [M+H]$^+$. $^1$H NMR (400 MHz, DMSO-d$_6$) δ12.39-12.64 (m, 1H), 8.70 (dd, J=22.3, 7.2 Hz, 1H), 8.19 (s, 1H), 7.95 (s, 1H), 7.77-7.91 (m, 2H), 7.55-7.64 (m, 2H), 7.29-7.40 (m, 1H), 7.19 (t, J=7.6 Hz, 1H), 6.16-6.27 (m, 1H), 5.73 (m, 1H), 3.12-3.23 (m, 1H), 2.95-3.10 (m, 1H), 2.77-2.81 (m, 3H), 2.21-2.35 (m, 1H), 0.79-1.11 (m, 4H). $^{19}$F NMR (376 MHz, DMSO-d$_6$) δ−73.41, −117.01.

Example 8: (R*)-7-chloro-8-fluoro-12-(5-(imidazo[1,2-a]pyridin-7-yl)-1H-imidazol-2-yl)-13,14-dihydro-2H-spiro[benzo[5,6]azocino[4,3-g]indolizine-3,1'-cyclopropane]-1,10(4H,12H)-dione

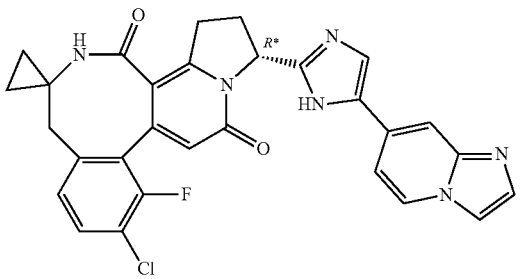 [SMILES: O=C1NC2(CC2)Cc2ccc(Cl)c(F)c2-c2cc(=O)n3c(c21)CC[C@@H]3c1ncc(-c2ccn3ccnc3c2)[nH]1]

Step 1: 2-(imidazo[1,2-a]pyridin-7-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (120 mg, 0.30 mmol, 1.0 equiv.) in N,N-dimethylformamide (5.0 mL) was added to 2-bromo-1-(imidazo[1,2-a]pyridin-7-yl)ethan-1-one (142 mg, 0.60 mmol, 2.0 equiv.) and potassium carbonate (62 mg, 0.45 mmol, 1.5 equiv.). The resulting mixture was stirred at room temperature for 3 h. The resulting mixture was extracted with ethyl acetate (3×50 mL). The organic layers were combined, dried over anhydrous sodium sulfate, filtered, and concentrated. The residue was purified by silica gel chromatography (0-10% MeOH/DCM) to yield 2-(imidazo[1,2-a]pyridin-7-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a yellow solid. LC/MS: mass calculated for $C_{29}H_{22}ClFN_4O_5$: 560.13, measured (ES, m/z): 561.00 [M+H]$^+$

Step 2: (R*)-7-chloro-8-fluoro-12-(5-(imidazo[1,2-a]pyridin-7-yl)-1H-imidazol-2-yl)-13,14-dihydro-2H-spiro[benzo[5,6]azocino[4,3-g]indolizine-3,1'-cyclopropane]-1,10(4H,12H)-dione To a solution of 2-(imidazo[1,2-a]pyridin-7-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (80 mg, 0.14 mmol, 1.0 equiv.) in toluene (3 mL) was added ammonium acetate (220 mg, 2.85 mmol, 20.0 equiv.) followed by addition of acetic acid (0.06 mL). The resulting mixture was stirred at room temperature for 2 h and concentrated under vacuum. The residue was purified by silica gel chromatography with MeOH/DCM (0-10%) to yield a residue, which was purified by Chiral-HPLC with MtBE (0.1% DEA):MeOH=70:30 to yield (R*)-7-chloro-8-fluoro-12-(5-(imidazo[1,2-a]pyridin-7-yl)-1H-imidazol-2-yl)-13,14-dihydro-2H-spiro[benzo[5,6]azocino[4,3-g]indolizine-3,1'-cyclopropane]-1,10(4H,12H)-dione as a yellow solid.
LC/MS: mass calculated for $C_{29}H_{22}ClFN_6O_2$: 540.15, measured (ES, m/z): 541.05 [M+H]$^+$. $^1$H NMR (400 MHz, DMSO-d$_6$) δ12.73 (s, 1H), 8.68-8.82 (m, 1H), 8.20 (s, 1H), 8.01-8.09 (m, 1H), 7.88-7.98 (m, 2H), 7.87 (s, 1H), 7.55-7.67 (m, 2H), 7.12-7.25 (m, 1H), 6.19-6.25 (m, 1H), 5.77-5.85 (m, 1H), 3.11-3.23 (m, 1H), 2.97-3.10 (m, 1H), 2.67-2.85 (m, 3H), 2.30-2.38 (m, 1H), 1.01-1.19 (m, 1H), 0.75-0.90 (m, 2H), 0.58-0.72 (m, 1H). $^{19}$F NMR (376 MHz, DMSO-d$_6$) δ−73.42, −116.98.

Example 9: (S*)-12-(5-(6-amino-2-fluoropyridin-3-yl)-1H-imidazol-2-yl)-7-chloro-8-fluoro-2-(2-hydroxyethyl)-13,14-dihydro-2H-spiro[benzo[5,6]azocino[4,3-g]indolizine-3,1'-cyclopropane]-1,10(4H,12H)-dione, R*,R* atropisomer

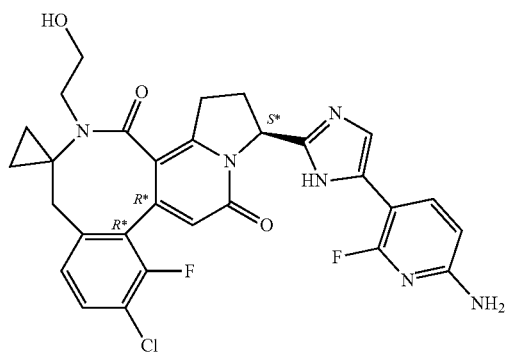 [SMILES: Nc1ccc(-c2cnc([C@@H]3CCc4c5c(cc(=O)n43)-c3c(ccc(Cl)c3F)CC3(CC3)N(CCO)C5=O)[nH]2)c(F)n1]

LC/MS: mass calculated for $C_{29}H_{25}ClF_2N_6O_3$: 578.16, measured (ES, m/z): 579.15 [M+H]$^+$. $^1$H NMR (300 MHz, DMSO-d$_6$) δ 12.30-12.40 (m, 1H), 7.90-8.04 (m, 1H), 7.58 (t, J=7.9 Hz, 1H), 7.08-7.22 (m, 2H), 6.12-6.35 (m, 3H), 5.73-5.82 (m, 1H), 4.67 (t, J=5.3 Hz, 1H), 3.43-3.58 (m, 2H), 3.15-3.32 (m, 4H), 2.95-3.05 (m, 1H), 2.50-2.65 (m, 2H), 2.12-2.28 (m, 1H), 1.30-1.38 (m, 1H), 1.01-1.11 (m, 1H), 0.60-0.88 (m, 2H). $^{19}$F NMR (282 MHz, DMSO-d$_6$) δ−70.55, −73.41, −116.56.

Example 10: (R*)-12-(5-(6-amino-2-fluoropyridin-3-yl)-1H-imidazol-2-yl)-7-chloro-8-fluoro-2-(2-hydroxyethyl)-13,14-dihydro-2H-spiro[benzo[5,6]azocino[4,3-g]indolizine-3,1'-cyclopropane]-1,10(4H,12H)-dione, R*,R* atropisomer

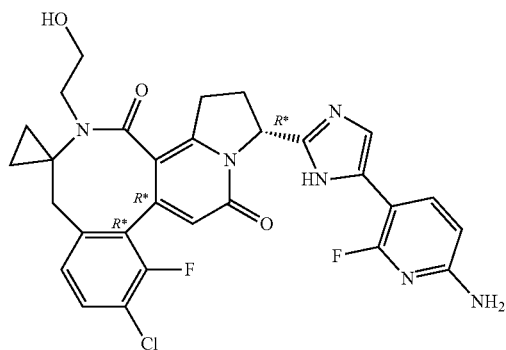 [SMILES: Nc1ccc(-c2cnc([C@H]3CCc4c5c(cc(=O)n43)-c3c(ccc(Cl)c3F)CC3(CC3)N(CCO)C5=O)[nH]2)c(F)n1]

LC/MS: mass calculated for $C_{29}H_{25}ClF_2N_6O_3$: 578.16, measured (ES, m/z): 579.15 [M+H]$^+$. $^1$H NMR (300 MHz, DMSO-d$_6$) δ 12.14-12.17 (m, 1H), 7.90-8.02 (m, 1H), 7.58 (t, J=7.9 Hz, 1H), 7.07-7.20 (m, 2H), 6.16-6.45 (m, 4H), 5.73-5.82 (m, 1H), 4.67 (s, 1H), 3.35-3.60 (m, 4H), 2.80-

3.08 (m, 2H), 2.55-2.75 (m, 4H), 0.80-0.90 (m, 2H), 0.55-0.78 (m, 2H). $^{19}$F NMR (282 MHz, DMSO-$d_6$) δ −70.75, −73.44, −116.13.

Example 11: (S*)-12-(5-(6-amino-2-fluoropyridin-3-yl)-1H-imidazol-2-yl)-7-chloro-8-fluoro-2-(2-hydroxyethyl)-13,14-dihydro-2H-spiro[benzo[5,6]azocino[4,3-g]indolizine-3,1'-cyclopropane]-1,10(4H,12H)-dione, S*,S* atropisomer

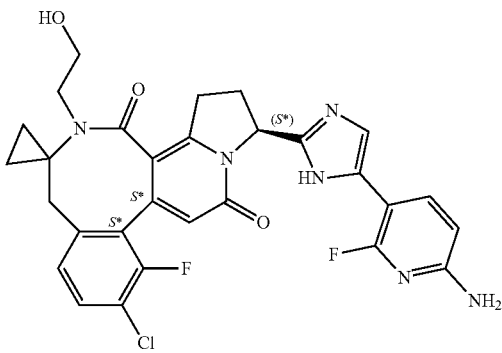 [SMILES: Nc1ccc(-c2cnc([C@@H]3CCc4c5c(cc(=O)n43)-c3c(ccc(Cl)c3F)CC3(CC3)N(CCO)C5=O)[nH]2)c(F)n1]

LC/MS: mass calculated for $C_{29}H_{25}ClF_2N_6O_3$: 578.16, measured (ES, m/z): 579.15 [M+H]$^+$. $^1$H NMR (300 MHz, DMSO-$d_6$) δ 7.80-7.92 (m, 1H), 7.58 (t, J=7.9 Hz, 1H), 7.03-7.19 (m, 2H), 6.25-6.60 (m, 3H), 6.22 (s, 1H), 5.81 (d, J=8.4 Hz, 1H), 4.45-4.80 (m, 1H), 3.40-3.57 (m, 3H), 3.01-3.15 (m, 2H), 2.75-2.90 (m, 2H), 2.50-2.63 (m, 3H), 1.27-1.38 (m, 1H), 0.70-0.88 (m, 1H), 0.50-0.72 (m, 2H). $^{19}$F NMR (282 MHz, DMSO-$d_6$) δ −73.53, −116.10.

Example 12: (R*)-12-(5-(6-amino-2-fluoropyridin-3-yl)-1H-imidazol-2-yl)-7-chloro-8-fluoro-2-(2-hydroxyethyl)-13,14-dihydro-2H-spiro[benzo[5,6]azocino[4,3-g]indolizine-3,1'-cyclopropane]-1,10(4H,12H)-dione, S*,S* atropisomer

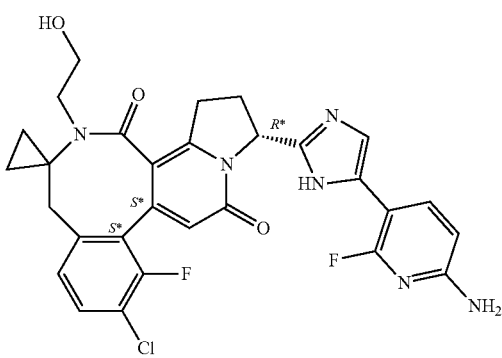 [SMILES: Nc1ccc(-c2cnc([C@H]3CCc4c5c(cc(=O)n43)-c3c(ccc(Cl)c3F)CC3(CC3)N(CCO)C5=O)[nH]2)c(F)n1]

Step 1: Methyl 2-(2-((tert-butyldimethylsilyl)oxy)ethyl)-7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of methyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (100 mg, 0.24 mmol, 1 equiv.) in DMF (5 mL) was added potassium tert-butoxide (40 mg, 0.36 mmol, 1.5 equiv.). After the mixture was stirred for 15 min, tert-butyl (2-iodoethoxy)dimethylsilane (103 mg, 0.36 mmol, 1.5 equiv.) was added. The reaction mixture was stirred for 2 h at room temperature, then purified by reverse column chromatography with CH$_3$CN/0.05% TFA water (5%-80%) to yield methyl 2-(2-((tert-butyldimethylsilyl)oxy)ethyl)-7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a light yellow solid. LC/MS: mass calculated for $C_{29}H_{36}ClFN_2O_5Si$: 574.21, measured (ES, m/z): 575.05 [M+H]$^+$ Step 2: 7-Chloro-8-fluoro-2-(2-hydroxyethyl)-1,10-dioxo-1,4,10,12,13,14-hexahydro-2H-spiro[benzo[5,6]azocino[4,3-g]indolizine-3,1'-cyclopropane]-12-carboxylic acid To a solution of methyl 2-(2-((tert-butyldimethylsilyl)oxy)ethyl)-7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (100 mg, 0.17 mmol, 1 equiv.) in THF (3 mL), MeOH (1 mL) and water (1 mL) was added lithium hydroxide (12 mg, 0.52 mmol, 3 equiv.). The reaction mixture was stirred for 2 h at room temperature. The pH was adjusted to 4-5 with 2M HCl, then the mixture was concentrated under vacuum. The residue was purified by reverse column chromatography with CH$_3$CN/0.05% TFA water (5%-60%) to yield 7-chloro-8-fluoro-2-(2-hydroxyethyl)-1,10-dioxo-1,4,10,12,13,14-hexahydro-2H-spiro[benzo[5,6]azocino[4,3-g]indolizine-3,1'-cyclopropane]-12-carboxylic acid as a light yellow solid. LC/MS: mass calculated for $C_{22}H_{20}ClFN_2O_5$: 446.10, measured (ES, m/z): 447.0 [M+H]$^+$ Step 3: 2-(6-Amino-2-fluoropyridin-3-yl)-2-oxoethyl 7-chloro-8-fluoro-2-(2-hydroxyethyl)-1,10-dioxo-1,4,10,12,13,14-hexahydro-2H-spiro[benzo[5,6]azocino[4,3-g]indolizine-3,1'-cyclopropane]-12-carboxylate 7-Chloro-8-fluoro-2-(2-hydroxyethyl)-1,10-dioxo-1,4,10,12,13,14-hexahydro-2H-spiro[benzo[5,6]azocino[4,3-g]indolizine-3,1'-cyclopropane]-12-carboxylic acid (45 mg, 0.10 mmol, 1 equiv.) were dissolved in DMF (2.5 mL) and stirred at room temperature for 0.5 h. Following this, a solution of 1-(6-amino-2-fluoropyridin-3-yl)-2-bromoethan-1-one (23 mg, 0.10 mmol, 1 equiv.) in DMF (2.5 mL) was added, the reaction mixture was stirred for another 2 h at room temperature. Following this, the mixture was diluted with EA (100 mL) and water (50 mL), the organic extracts were washed with water (2×50 mL) and then dried over anhydrous sodium sulfate, filtered, and concentrated under reduced pressure. The residue was purified by normal phase chromatography (mobile phase: DCM/MeOH, 0-20%) to yield 2-(6-amino-2-fluoropyridin-3-yl)-2-oxoethyl 7-chloro-8-fluoro-2-(2-hydroxyethyl)-1,10-dioxo-1,4,10,12,13,14-hexahydro-2H-spiro[benzo[5,6]azocino[4,3-g]indolizine-3,1'-cyclopropane]-12-carboxylate as a yellow solid. LC/MS: mass calculated for $C_{29}H_{25}ClF_2N_4O_6$: 598.14, measured (ES, m/z): 599.10 [M+H]$^+$ Step 4: (R*)-12-(5-(6-amino-2-fluoropyridin-3-yl)-1H-imidazol-2-yl)-7-chloro-8-fluoro-2-(2-hydroxyethyl)-13,14-dihydro-2H-spiro[benzo[5,6]azocino[4,3-g]indolizine-3,1'-cyclopropane]-1,10(4H,12H)-dione To a solution of 2-(6-amino-2-fluoropyridin-3-yl)-2-oxoethyl 7-chloro-8-fluoro-2-(2-hydroxyethyl)-1,10-dioxo-1,4,10,12,13,14-hexahydro-2H-spiro[benzo[5,6]azocino[4,3-g]indolizine-3,1'-cyclopropane]-12-carboxylate (40 mg, 0.07 mmol, 1.0 equiv.) in toluene (5 mL) was added ammonium acetate (103 mg, 1.33 mmol, 20 equiv.) followed by the addition of acetic acid (0.1 mL) under $N_2$. The reaction mixture was stirred for 3 h at 100° C., then cooled to room temperature and concentrated under vacuum. The residue was purified by silica gel chromatography with MeOH/DCM (0-10%) to yield racemic product, which was purified by chiral-HPLC with Hexane (0.1% DEA):EtOH=50:50 to yield (*R)-12-(5-(6-amino-2-fluoropyridin-3-yl)-1H-imidazol-2-yl)-7-chloro-8-fluoro-2-(2-hydroxyethyl)-13,14-dihydro-2H-spiro[benzo[5,6]azocino[4,3-g]indolizine-3,1'-cyclopropane]-1,10(4H,12H)-dione (0.02 TFA) as a white solid.

LC/MS: mass calculated for $C_{29}H_{25}ClF_2N_6O_3$: 578.16, measured (ES, m/z): 579.15 $[M+H]^+$ $^1H$ NMR (300 MHz, DMSO-$d_6$) δ12.32 (s, 1H), 7.91-8.03 (m, 1H), 7.58 (t, J=7.9 Hz, 1H), 7.08-7.21 (m, 2H), 6.16-6.35 (m, 4H), 5.77 (d, J=8.4 Hz, 1H), 4.67 (s, 1H), 3.42-3.58 (m, 2H), 3.18-3.22 (m, 4H), 2.97-3.04 (m, 1H), 2.50-2.68 (m, 2H), 2.10-2.25 (m, 1H), 1.35 (s, 1H), 0.97-1.12 (m, 1H), 0.65-0.92 (m, 2H). $^{19}F$ NMR (282 MHz, DMSO-$d_6$) δ−70.54, −73.44, −116.55.

Example 13: (S*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione, R*,R* atropisomer

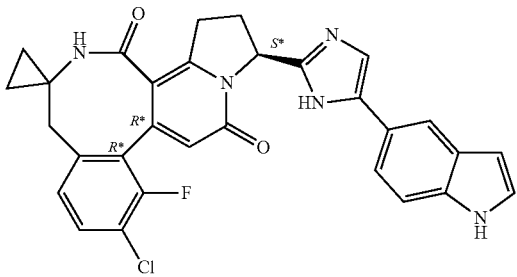 [SMILES: O=C1NC2(CC2)Cc2ccc(Cl)c(F)c2-c2cc(=O)n3c(c21)CC[C@H]3c1ncc(-c2ccc3[nH]ccc3c2)[nH]1]

Step 1: 1-(1-Tosyl-1H-indol-5-yl)ethan-1-one

To a solution of 1-(1H-indol-5-yl)ethan-1-one (500 mg, 3.14 mmol, 1.0 equiv.) in N,N-dimethylformamide (10 mL) was added sodium hydride (90 mg, 3.77 mmol, 1.2 equiv.). The resulting mixture was stirred at room temperature for 0.5 h. 4-Methylbenzenesulfonyl chloride (1.5 g, 7.85 mmol, 2.5 equiv.) was then added. The resulting mixture was stirred at room temperature for 2 h. The reaction was quenched with water (60 mL). The resulting mixture was extracted with ethyl acetate (3×60 mL). The organic layers were combined, dried over anhydrous sodium sulfate, filtered and concentrated to yield 1-(1-(((1E,3Z)-4-methylhexa-1,3,5-trien-1-yl)sulfonyl)-1H-indol-5-yl)ethan-1-one as a yellow solid. LC/MS: mass calculated for $C_{17}H_{15}NO_3S$: 313.08, measured (ES, m/z): 314.1 $[M+H]^+$ Step 2: 2-Bromo-1-(1-tosyl-1H-indol-5-yl)ethan-1-one To a solution of 1-(1-tosyl-1H-indol-5-yl)ethan-1-one (500 mg, 1.59 mmol, 1.0 equiv.) in acetic acid (10 mL) was added to pyridinium tribromide (306 mg, 0.96 mmol, 0.6 equiv.) and hydrogen bromide (782 mg, 3.19 mmol, 2.0 equiv.). The resulting mixture was stirred at room temperature for 3 h. The reaction was quenched with water (40 mL). The resulting mixture was extracted with ethyl acetate (3×40 mL). The organic layers were combined, dried over anhydrous sodium sulfate, filtered, and concentrated. The residue was purified by silica gel chromatography (0-20% ethyl acetate/petroleum ether) to yield 2-bromo-1-(1-tosyl-1H-indol-5-yl)ethan-1-one as an white solid. LC/MS: mass calculated for $C_{17}H_{14}BrNO_3S$: 390.99, measured (ES, m/z): 392.1 $[M+H]^+$ Step 3: 2-Oxo-2-(1-tosyl-1H-indol-5-yl)ethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate 7-Chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (100 mg, 0.25 mmol, 1.0 equiv.) and potassium carbonate (52 mg, 0.37 mmol, 1.5 equiv.) were dissolved in DMF (5 mL) and stirred at room temperature for 0.5 h. A solution of 2-bromo-1-(1-tosyl-1H-indol-5-yl)ethan-1-one (107 mg, 0.27 mmol, 1.1 equiv.) in DMF (5 mL) was then added, the reaction mixture was stirred for another 2 h at room temperature, diluted with EA (100 mL) and water (50 mL). The organic extracts were washed with water (2×50 mL) and then dried over anhydrous sodium sulfate, filtered, and concentrated under reduced pressure. The residue was purified by normal phase silica gel chromatography (mobile phase: DCM/MeOH, 0-20%) to yield 2-oxo-2-(1-tosyl-1H-indol-5-yl)ethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a yellow solid. LC/MS: mass calculated for $C_{37}H_{29}ClFN_3O_7S$: 713.14, measured (ES, m/z): 714.25 $[M+H]^+$ Step 4: 7-Chloro-8-fluoro-12-(5-(1-tosyl-1H-indol-5-yl)-1H-imidazol-2-yl)-13,14-dihydro-2H-spiro[benzo[5,6]azocino[4,3-g]indolizine-3,1'-cyclopropane]-1,10(4H,12H)-dione To a solution of 2-oxo-2-(1-tosyl-1H-indol-5-yl)ethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (160 mg, 0.22 mmol, 1.0 equiv.) in toluene (10 mL) was added ammonium acetate (345 mg, 4.48 mmol, 20 equiv.) followed by the addition of AcOH (0.25 mL) under $N_2$. The reaction mixture was stirred for 1.5 h at 100° C., then cooled to room temperature and concentrated under vacuum. The residue was purified by silica gel chromatography with MeOH/DCM (0-10%) to yield 7-chloro-8-fluoro-12-(5-(1-tosyl-1H-indol-5-yl)-1H-imidazol-2-yl)-13,14-dihydro-2H-spiro[benzo[5,6]azocino[4,3-g]indolizine-3,1'-cyclopropane]-1,10(4H,12H)-dione as a yellow solid. LC/MS: mass calculated for $C_{37}H_{29}ClFN_5O_4S$: 693.16, measured (ES, m/z): 694.3 $[M+H]^+$ Step 5: (S*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione To a solution of 7-chloro-8-fluoro-12-(5-(1-tosyl-1H-indol-5-yl)-1H-imidazol-2-yl)-13,14-dihydro-2H-spiro[benzo

[5,6]azocino[4,3-g]indolizine-3,1'-cyclopropane]-1,10(4H,12H)-dione (80 mg, 0.12 mmol) in MeOH (10 mL) was added NaOH (0.40 mL, 2N in water), the resulting solution was allowed to stirred at 60° C. 48 hours, then cooled to room temperature and concentrated under vacuum. The residue was purified by purified by reverse column with CH₃CN/H₂O (0-60%) to yield a residue, which was purified by Chiral-HPLC with (Hex:DCM=3:1)(0.1% DEA): EtOH=90:10 to yield (*S)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione (0.05 TFA salt) as a white solid.

LC/MS: mass calculated for $C_{30}H_{23}ClFN_5O_2$: 539.15, measured (ES, m/z): 540.15 [M+H]⁺. ¹H NMR (300 MHz, Methanol-$d_4$) δ 7.92-7.95 (m, 1H), 7.41-7.59 (m, 4H), 7.32 (d, J=3.2 Hz, 1H), 7.11-7.17 (m, 1H), 6.53 (d, J=3.1 Hz, 1H), 6.39 (s, 1H), 5.98-6.06 (m, 1H), 3.34-3.62 (m, 2H), 3.04 (s, 2H), 2.80-2.99 (m, 1H), 2.53-2.70 (m, 1H), 1.07-1.15 (m, 1H), 0.79-1.00 (m, 3H). ¹⁹F NMR (282 MHz, Methanol-$d_4$) δ-76.94, -118.50.

Example 14: (R*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione, R*,R* atropisomer

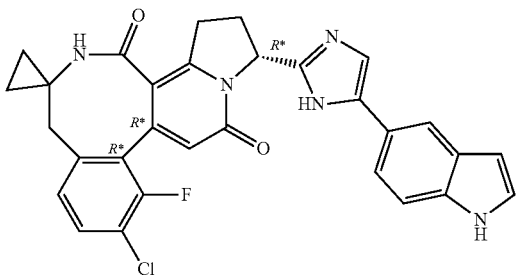 [SMILES: O=C1NC2(CC2)Cc2ccc(Cl)c(F)c2-c2cc(=O)n3c(c21)CC[C@@H]3c1ncc(-c2ccc3[nH]ccc3c2)[nH]1]

LC/MS: mass calculated for $C_{30}H_{23}ClFN_5O_2$: 539.15, measured (ES, m/z): 540.15 [M+H]⁺. ¹H NMR (300 MHz, DMSO-$d_6$) δ 11.07 (s, 1H), 8.08 (s, 1H), 7.89 (s, 1H), 7.61 (t, J=7.9 Hz, 1H), 7.25-7.53 (m, 4H), 6.44 (s, 1H), 6.22 (s, 1H), 5.80 (d, J=8.3 Hz, 1H), 3.45-3.62 (m, 1H), 2.92-3.12 (m, 2H), 2.56-2.88 (m, 2H), 2.25-2.47 (m, 1H), 0.96-1.06 (m, 1H), 0.74-0.89 (m, 1H), 0.58-0.71 (m, 2H). ¹⁹F NMR (282 MHz, DMSO-$d_6$) δ-116.95.

Example 15: (S*)-12-(5-([1,2,4]triazolo[4,3-a]pyridin-7-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

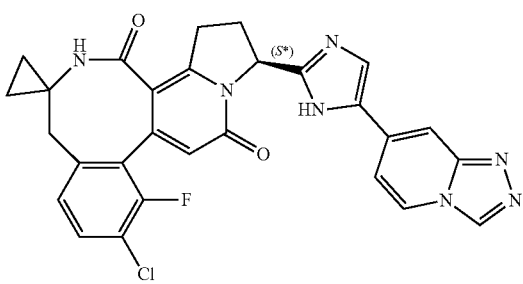 [SMILES: O=C1NC2(CC2)Cc2ccc(Cl)c(F)c2-c2cc(=O)n3c(c21)CC[C@H]3c1ncc(-c2ccn3cnnc3c2)[nH]1]

The title compound was prepared following the procedure described in Example 18 below, selecting and substituting suitable reagents and reactants, as would be readily recognized by those skilled in the art.

LC/MS: mass calculated for $C_{28}H_{21}ClFN_7O_2$:541.14, measured (ES, m/z): 542.10 [M+H]⁺. ¹H NMR (400 MHz, DMSO-$d_6$) δ 9.35 (s, 1H), 8.69 (d, J=7.2 Hz, 1H), 8.08 (d, J=9.0 Hz, 3H), 7.50-7.62 (m, 2H), 7.20 (d, J=8.3 Hz, 1H), 6.23 (s, 1H), 5.83 (dd, J=9.0, 2.7 Hz, 1H), 3.00-3.10 (m, 2H), 2.76-2.86 (m, 1H), 2.59-2.74 (m, 2H), 2.40-2.48 (m, 1H), 0.76-0.88 (m, 2H), 0.60-0.75 (m, 2H). ¹⁹F NMR (376 MHz, DMSO-$d_6$) δ-74.29, -116.96.

Example 16: (S*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione, S*,S* atropisomer

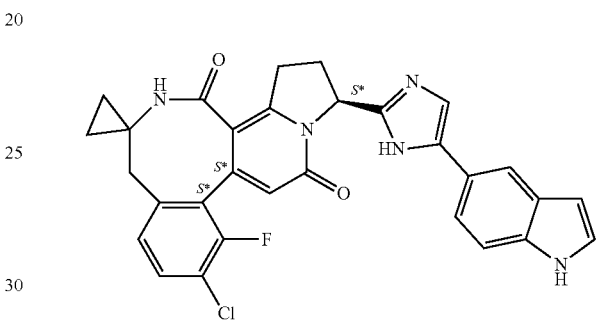

LC/MS: mass calculated for $C_{30}H_{23}ClFN_5O_2$: 539.15, measured (ES, m/z): 540.15 [M+H]⁺. ¹H NMR (300 MHz, Methanol-$d_4$) δ 7.91 (s, 1H), 7.39-7.56 (m, 4H), 7.29 (d, J=3.2 Hz, 1H), 7.15 (d, J=8.3 Hz, 1H), 6.51 (d, J=3.2 Hz, 1H), 6.41 (s, 1H), 6.03 (dd, J=9.0, 3.8 Hz, 1H), 3.61-3.79 (m, 1H), 3.08-3.22 (m, 2H), 2.78-2.99 (m, 2H), 2.56-2.69 (m, 1H), 0.85-0.96 (m, 2H), 0.74-0.85 (m, 2H). ¹⁹F NMR (282 MHz, Methanol-$d_4$) δ-76.94, -117.78.

Example 17: (R*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione, S*,S* atropisomer

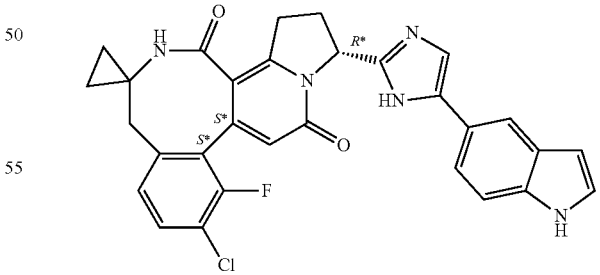

LC/MS: mass calculated for $C_{30}H_{23}ClFN_5O_2$: 539.15, measured (ES, m/z): 540.10 [M+H]⁺. ¹H NMR (300 MHz, DMSO-$d_6$) δ11.29 (s, 1H), 8.09 (s, 1H), 8.00 (s, 1H), 7.62 (t, J=7.8 Hz, 1H), 7.38-7.55 (m, 3H), 7.22 (d, J=8.2 Hz, 1H), 6.50 (s, 1H), 6.28 (s, 1H), 5.93 (s, 1H), 2.90-3.05 (m, 2H), 2.65-2.85 (m, 3H), 2.20-2.32 (m, 1H), 0.60-0.92 (m, 4H). ¹⁹F NMR (282 MHz, DMSO-$d_6$) δ-73.77, -117.25.

Example 18: (R*)-12-(5-([1,2,4]triazolo[4,3-a]pyridin-7-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

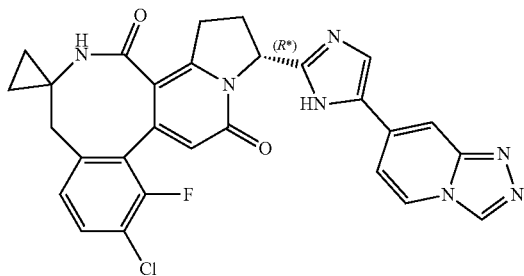 [SMILES: O=C1NC2(CC2)Cc2ccc(Cl)c(F)c2-c2cc(=O)n3c(c21)CC[C@@H]3c1ncc(-c2ccn3cnnc3c2)[nH]1]

Step 1: 7-(1-Ethoxyvinyl)-[1,2,4]triazolo[4,3-a]pyridine

7-Bromo-[1,2,4]triazolo[4,3-a]pyridine (1 g, 5.05 mmol, 1.0 equiv.), tributyl(1-ethoxyvinyl)stannane (2.0 g, 5.56 mmol, 1.1 equiv.) and tetrakis(triphenylphosphine)palladium (584 mg, 0.51 equiv., 0.1 equiv.) were added to a 150 mL flask under $N_2$. Following this, 1,4-dioxane (50 mL) was added, and the reaction mixture stirred for 3 h at 100° C., then cooled to room temperature and extracted with EtOAc (300 mL). The organic layer was washed with water (50 mL), then dried over anhydrous sodium sulfate, filtered and concentrated under reduced pressure. The residue was purified by normal phase chromatography (mobile phase: PE/EA, 0>>60%) to yield 7-(1-ethoxyvinyl)-[1,2,4]triazolo[4,3-a]pyridine as a yellow solid. LC/MS: mass calculated for $C_{10}H_{11}N_3O$: 189.09, measured: 190.05 [M+H]$^+$.

Step 2: 1-([1,2,4]Triazolo[4,3-a]pyridin-7-yl)ethan-1-one

To a solution of 7-(1-ethoxyvinyl)-[1,2,4]triazolo[4,3-a]pyridine (500 mg, 2.64 mmol, 1.0 equiv.) in THF (10 mL) was added HCl (1 mL), The mixture was stirred at room temperature for 2 h. The reaction was quenched with water (10 mL). The resulting mixture was extracted with ethyl acetate (3×10 mL). The organic layers were combined and concentrated to yield 1-([1,2,4]triazolo[4,3-a]pyridin-7-yl)ethan-1-one as a gray solid. LC/MS: mass calculated for $C_8H_7N_3O$: 161.06, measured: 162.10 [M+H]$^+$.

Step 3: 1-([1,2,4]Triazolo[4,3-a]pyridin-7-yl)-2-bromoethan-1-one

To a solution of 1-([1,2,4]triazolo[4,3-a]pyridin-7-yl)ethan-1-one (150 mg, 0.93 mmol, 1.0 equiv.) in THF (5 mL) was added pyridinium tribromide (268 mg, 0.84 mmol, 0.9 equiv.) with THF (2 ml). The mixture was stirred at room temperature for 2 h. The resulting mixture was then dried to yield 1-([1,2,4]triazolo[4,3-a]pyridin-7-yl)-2-bromoethan-1-one as a yellow solid. LC/MS: mass calculated for $C_8H_6BrN_3O$: 238.97, measured: 241.90 [M+H+2]$^+$.

Step 4: 2-([1,2,4]Triazolo[4,3-a]pyridin-7-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (80 mg, 0.20 mmol, 1.0 equiv.) in DMF (5 mL) was added $K_2CO_3$ (55 mg, 0.40 mmol, 2.0 equiv.). After 0.5 h of stirring, 1-([1,2,4]triazolo[4,3-a]pyridin-7-yl)-2-bromoethan-1-one (95 mg, 0.40 mmol, 2.0 equiv.) was added. The mixture stirred at room temperature for 1 h. The residue was purified by C18 column with $CH_3CN$/0.05% TFA water (5%-40%) to yield 2-([1,2,4]triazolo[4,3-a]pyridin-7-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a orange solid. LC/MS: mass calculated for $C_{28}H_{21}ClFN_5O_5$: 561.12, measured: 562.10 [M+H]$^+$.

Step 5: (*R)-12-(5-([1,2,4]triazolo[4,3-a]pyridin-7-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione To a solution of 2-([1,2,4]triazolo[4,3-a]pyridin-7-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (70 mg, 0.13 mmol, 1.0 equiv.) in toluene (10 mL) and acetic acid glacial (0.2 mL) was added ammonium acetate (192 mg, 2.49 mmol, 20.0 equiv.). The mixture stirred at 100° C. for 1 h. The residue was purified by silica gel chromatography with $CH_3CN$/0.05% TFA water (5%-40%) to yield a residue, which was purified by chiral-HPLC with (Hexane:DCM=1:1)(0.1% DEA):EtOH=50:50 to yield (*R)-12-(5-([1,2,4]triazolo[4,3-a]pyridin-7-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as a light yellow solid.

LC/MS: mass calculated for $C_{28}H_{21}ClFN_7O_2$:541.14, measured (ES, m/z): 542.15 [M+H]$^+$. $^1$H NMR (400 MHz, DMSO-d$_6$) δ12.87 (s, 1H), 9.32 (s, 1H), 8.67 (d, J=7.2 Hz, 1H), 8.20 (s, 1H), 7.90-8.10 (m, 2H), 7.54-7.65 (m, 2H), 7.19 (d, J=8.4 Hz, 1H), 6.22 (s, 1H), 5.83 (dd, J=8.7, 1.7 Hz, 1H), 3.28-3.40 (m, 2H), 3.15-3.28 (m, 1H), 2.64-2.83 (m, 2H), 2.25-2.35 (m, 1H), 0.99-1.12 (m, 1H), 0.76-0.94 (m, 2H), 0.65-0.72 (m, 1H). $^{19}$F NMR (376 MHz, DMSO-d$_6$) δ−74.46, −117.01.

Example 19: (R*)-12-(5-(1H-indazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

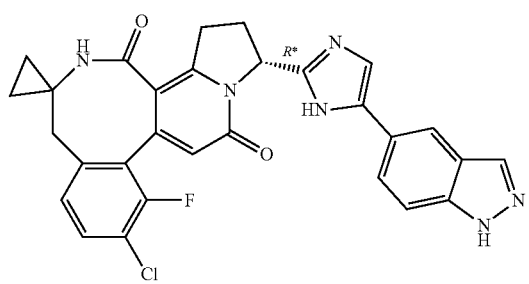 [SMILES: O=C1NC2(CC2)Cc2ccc(Cl)c(F)c2-c2cc(=O)n3c(c21)CC[C@@H]3c1ncc(-c2ccc3[nH]ncc3c2)[nH]1]

Step 1: 2-Bromo-1-(1H-indazol-5-yl)ethan-1-one

A mixture of 1-(1H-indazol-5-yl)ethan-1-one (200 mg, 1.25 mmol, 1.0 equiv.), pyridinium tribromide (399 mg, 1.25 mmol, 1.0 equiv.) in THF (5 mL) was stirred at room temperature for 2 h. After that, the pH was adjusted to pH 9 by NaHCO$_3$ and the resulting mixture extracted with EA (200 mL), then dried over anhydrous sodium sulfate, filtered and concentrated under reduced pressure to yield 2-bromo-1-(1H-indazol-5-yl)ethan-1-one as a residue, which was used for the next step without further purification. LC/MS: mass calculated for C$_9$H$_7$BrN$_2$O: 237.97, measured (ES, m/z): 241.05 [M+H+2]$^+$.

Step 2: 2-(1H-indazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate 7-Chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (200.0 mg, 0.50 mmol, 1.0 equiv.) and potassium carbonate (82 mg, 0.60 mmol, 1.2 equiv.) were dissolved in DMF (2.5 mL) and stirred at room temperature for 0.5 h. Following this, a solution of 2-bromo-1-(1H-indazol-5-yl)ethan-1-one (118.7 mg, 0.50 mmol, 1.0 equiv.) in DMF (2.5 mL) was added, and the reaction mixture was stirred for another 2 h at room temperature. The reaction mixture was then diluted with EA (100 mL) and water (50 mL), the organic extracts were washed with water (2×50 mL), then dried over anhydrous sodium sulfate, filtered, and concentrated under reduced pressure. The residue was purified by normal phase chromatography (mobile phase: DCM/MeOH, 0-20%) to yield 2-(1H-indazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a yellow solid. LC/MS: mass calculated for C$_{29}$H$_{22}$ClFN$_4$O$_5$: 560.13, measured (ES, m/z): 561.15 [M+H]$^+$ Step 3: (*R)-12-(5-(1H-indazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione To a solution of 2-(1H-indazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (70 mg, 0.13 mmol, 1.0 equiv.) in toluene (10 mL) was added ammonium acetate (192 mg, 2.50 mmol, 20 equiv.) followed by the addition of acetic acid (0.2 mL) under N$_2$. The reaction mixture was stirred for 2 h at 100° C., then cooled to room temperature and concentrated under vacuum. The residue was purified by silica gel chromatography with MeOH/DCM (0-10%) to yield a residue, which was purified by chiral-HPLC with MtBE (0.1% DEA): EtOH=75:25) to (*R)-12-(5-(1H-indazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as off-white solid.

LC/MS: mass calculated for C$_{29}$H$_{22}$ClFN$_6$O$_2$: 540.15, measured (ES, m/z): 541.15 [M+H]$^+$. $^1$H NMR (300 MHz, DMSO-d$_6$) δ12.96 (s, 1H), 12.28 (s, 1H), 8.15-8.24 (m, 1H), 8.05-8.14 (m, 1H), 7.95-8.05 (m, 1H), 7.75 (dd, J=8.7, 1.5 Hz, 1H), 7.40-7.71 (m, 3H), 7.14-7.26 (m, 1H), 6.21 (s, 1H), 5.75-5.85 (m, 1H), 3.40-3.42 (m, 1H), 3.12-3.27 (m, 2H), 2.56-2.79 (m, 2H), 2.21-2.33 (m, 1H), 0.93-1.18 (m, 2H), 0.60-0.88 (m, 2H). $^{19}$F NMR (282 MHz, DMSO-d$_6$) δ−73.39, −117.02.

Example 20: (S*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione, R*,R* atropisomer

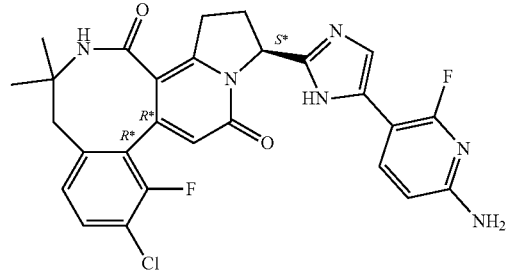 [SMILES: CC1(C)Cc2ccc(Cl)c(F)c2-c2cc(=O)n3c(c2C(=O)N1)CC[C@H]3c1ncc(-c2ccc(N)nc2F)[nH]1]

LC/MS: mass calculated for C$_{27}$H$_{23}$ClF$_2$N$_6$O$_2$: 536.15, measured (ES, m/z): 537.30 [M+H]$^+$. $^1$H NMR (400 MHz, Methanol-d$_4$): δ 7.90 (dd, J=10.1, 8.4 Hz, 1H), 7.66 (d, J=1.9 Hz, 1H), 7.56 (dd, J=8.2, 7.4 Hz, 1H), 7.19 (dd, J=8.2, 1.2 Hz, 1H), 6.57 (dd, J=8.4, 1.8 Hz, 1H), 6.34 (s, 1H), 6.12 (dd, J=9.2, 5.4 Hz, 1H), 3.58-3.69 (m, 1H), 3.21-3.29 (m, 1H), 2.89-3.05 (m, 2H), 2.79 (dd, J=14.1, 1.5 Hz, 1H), 2.46-2.57 (m, 1H), 1.42 (s, 3H), 1.36 (s, 3H). $^{19}$F NMR (376 MHz, Methanol-d$_4$): δ−71.28, −120.04.

Example 21: (R*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione, R*,R* atropisomer

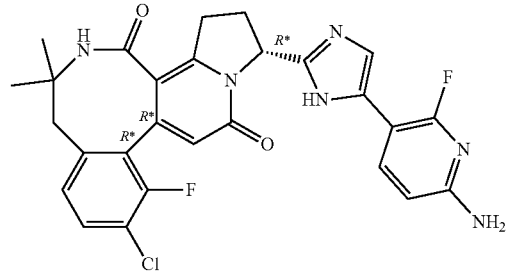 [SMILES: CC1(C)Cc2ccc(Cl)c(F)c2-c2cc(=O)n3c(c2C(=O)N1)CC[C@@H]3c1ncc(-c2ccc(N)nc2F)[nH]1]

Step 1: 2-(6-Amino-2-fluoropyridin-3-yl)-2-oxoethyl 7-chloro-8-fluoro-3,3-dimethyl-1,10-dioxo-1,2,3,4,10,12,13,14-octahydrobenzo[5,6]azocino[4,3-g]indolizine-12-carboxylate To a solution of 7-chloro-8-fluoro-3,3-dimethyl-1,10-dioxo-1,2,3,4,10,12,13,14-octahydrobenzo[5,6]azocino[4,3-g]indolizine-12-carboxylic acid (100 mg, 0.25 mmol, 1.0 equiv.) in DMF (5 mL) was added potassium carbonate (102 mg, 0.74 mmol, 3 equiv.). After the mixture was stirred for 10 min, 1-(6-amino-2-fluoropyridin-3-yl)-2-bromoethan-1-one (86 mg, 0.37 mmol, 1.5 equiv.) was added. The reaction mixture was stirred for 2 h at room temperature, then purified by reverse column chromatography with CH$_3$CN/ 0.05% TFA water (5%-60%) to yield 2-(6-amino-2-fluoropyridin-3-yl)-2-oxoethyl 7-chloro-8-fluoro-3,3-dimethyl-1,10-dioxo-1,2,3,4,10,12,13,14-octahydrobenzo[5,6]azocino

[4,3-g]indolizine-12-carboxylate as a light yellow solid. LC/MS: mass calculated for $C_{27}H_{23}ClF_2N_4O_5$: 556.13, measured: 557.25 [M+H]$^+$.

Step 2: (R*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione To a solution of 2-(6-amino-2-fluoropyridin-3-yl)-2-oxoethyl 7-chloro-8-fluoro-3,3-dimethyl-1,10-dioxo-1,2,3,4,10,12,13,14-octahydrobenzo[5,6]azocino[4,3-g]indolizine-12-carboxylate (110 mg, 0.20 mmol, 1.0 equiv.) in toluene (10 mL) was added ammonium acetate (304 mg, 3.95 mmol, 20 equiv.) followed by the addition of acetic acid (0.2 mL) under N$_2$. The reaction mixture was stirred for 3 h at 100° C., then cooled to room temperature and concentrated under vacuum. The residue was purified by silica gel chromatography with MeOH/DCM (0-10%) to yield a racemic product, which was purified by Chiral-HPLC with (Hexane:DCM=3:1)(0.1% DEA):EtOH=85:15 to yield (R*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione.

LC/MS: mass calculated for $C_{27}H_{23}ClF_2N_6O_2$: 536.15, measured (ES, m/z): 537.30 [M+H]$^+$. $^1$H NMR (400 MHz, Methanol-d$_4$): δ 7.99 (s, 1H), 7.52 (dd, J=8.2, 7.4 Hz, 1H), 7.08-7.26 (m, 2H), 6.36-6.50 (m, 1H), 6.27 (s, 1H), 5.91 (dd, J=8.5, 3.5 Hz, 1H), 3.40-3.52 (m, 2 H), 2.99-3.10 (m, 1H), 2.67-2.79 (m, 2H), 2.46-2.57 (m, 1H), 1.46 (s, 3H), 1.35 (s, 3H). $^{19}$F NMR (376 MHz, Methanol-d$_4$): δ −73.43, −76.95, −120.12.

Example 22: (R*)-7-chloro-8-fluoro-12-(5-(imidazo[1,5-a]pyridin-6-yl)-1H-imidazol-2-yl)-13,14-dihydro-2H-spiro[benzo[5,6]azocino[4,3-g]indolizine-3,1'-cyclopropane]-1,10(4H,12H)-dione

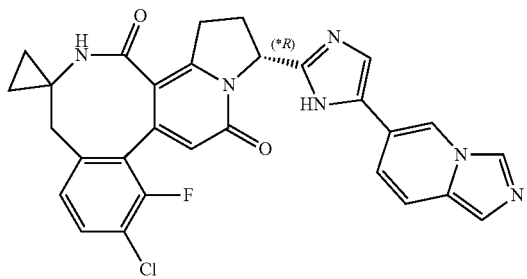 [SMILES: O=C1NC2(CC2)Cc2ccc(Cl)c(F)c2-c2cc(=O)n3c(c21)CC[C@@H]3c1ncc(-c2ccc3cncn3c2)[nH]1]

Step 1: 6-(1-Ethoxyvinyl)imidazo[1,5-a]pyridine

6-Bromoimidazo[1,5-a]pyridine (1.0 g, 5.07 mmol, 1.0 equiv.), tributyl(1-ethoxyvinyl)stannane (2.2 g, 6.09 mmol, 1.2 equiv.) and tetrakis(triphenylphosphine)palladium (586 mg, 0.51 mmol, 0.1 equiv.) were added to a 250 mL flask under N$_2$. Following this, 1,4-dioxane (50 mL) was added, and the reaction mixture stirred for 3 h at 100° C., then cooled to room temperature and extracted with EtOAc (300 mL). The organic layer was washed with water (50 mL), then dried over anhydrous sodium sulfate, filtered, and concentrated under reduced pressure. The residue was purified by normal phase chromatography (mobile phase: PE/EA, 0>>60%) to yield 6-(1-ethoxyvinyl)imidazo[1,5-a]pyridine as a yellow solid. LC/MS: mass calculated for $C_{11}H_{12}N_2O$: 188.09, measured: 189.20 [M+H]$^+$.

Step 2: 1-(Imidazo[1,5-a]pyridin-6-yl)ethan-1-one

To a solution of 6-(1-ethoxyvinyl)imidazo[1,5-a]pyridine (1.0 g, 5.31 mmol, 1.0 equiv.) in THF (20 mL) was added 3M HCl (10 mL). The mixture was stirred for 2 h at room temperature, then the pH was adjusted to pH 7-8 with NaHCO$_3$(aq.). The mixture was extracted with EA, dried over Na$_2$SO$_4$, and concentrated under vacuum. The residue was purified by silica gel chromatography with MeOH/DCM (0-10%) to yield 1-(imidazo[1,5-a]pyridin-6-yl)ethan-1-one as a yellow solid. LC/MS: mass calculated for $C_9H_8N_2O$: 160.06, measured: 161.05 [M+H]$^+$.

Step 3: 2-Bromo-1-(imidazo[1,5-a]pyridin-6-yl)ethan-1-one

To a solution of 1-(imidazo[1,5-a]pyridin-6-yl)ethan-1-one (0.3 g, 1.87 mmol, 1 equiv.) in acetic acid (15 mL) was added hydrogen bromide solution in acetic acid (0.9 g, 3.75 mmol, 2 equiv.) followed by the addition of pyridinium tribromide (0.6 g, 1.87 mmol, 1.0 equiv.) slowly. The reaction mixture was stirred for 2 h at room temperature, then concentrated under vacuum. The residue was mixed with water and extracted with EA. The organic layers were combined, washed with brine, dried over Na$_2$SO$_4$, filtered and concentrated to yield 2-bromo-1-(imidazo[1,5-a]pyridin-6-yl)ethan-1-one as a brown solid. LC/MS: mass calculated for $C_9H_7BrN_2O$: 237.97, measured: 238.90 [M+H]$^+$.

Step 4: 2-(Imidazo[1,5-a]pyridin-6-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-3,3-dimethyl-1,10-dioxo-1,2,3,4,10,12,13,14-octahydrobenzo[5,6]azocino[4,3-g]indolizine-12-carboxylic acid (100 mg, 0.25 mmol, 1.0 equiv.) in DMF (4 mL) was added potassium carbonate (137 mg, 0.99 mmol, 4 equiv.). After the mixture was stirred for 10 min, 2-bromo-1-(imidazo[1,5-a]pyridin-6-yl)ethan-1-one (178 mg, 0.75 mmol, 3 equiv.) was added. The reaction mixture was stirred for 2 h at room temperature, then purified by reverse column chromatography with CH$_3$CN/0.05% TFA water (5%-50%) to yield 2-(imidazo[1,5-a]pyridin-6-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a light brown solid. LC/MS: mass calculated for $C_{29}H_{22}ClFN_4O_5$: 560.13, measured: 561.10 [M+H]$^+$.

Step 5: (R*)-7-chloro-8-fluoro-12-(5-(imidazo[1,5-a]pyridin-6-yl)-1H-imidazol-2-yl)-13,14-dihydro-2H-spiro[benzo[5,6]azocino[4,3-g]indolizine-3,1'-cyclopropane]-1,10(4H,12H)-dione To a solution of 2-(benzo[d][1,2,3]thiadiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (110 mg, 0.19 mmol, 1.0 equiv.) in toluene (10 mL) was added ammonium acetate (293 mg, 3.80 mmol, 20 equiv.) followed by the addition of acetic acid (0.2 mL) under N$_2$. The reaction mixture was stirred for 3 h at 100° C., then cooled to room temperature and concentrated under vacuum. The residue was purified by silica gel chromatography with MeOH/DCM (0-10%) to yield a racemic product, which was purified by chiral-HPLC with MtBE (0.1% DEA):EtOH=50:50 to (*R)-12-(5-(benzo[d][1,2,3]thiadiazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as off-white solid.

LC/MS: mass calculated for $C_{29}H_{22}ClFN_6O_2$: 540.15, measured (ES, m/z): 541.05 [M+H]$^+$. $^1$H NMR (400 MHz, Methanol-d$_4$) δ 8.63 (s, 1H), 8.35 (s, 1H), 7.45-7.60 (m, 3H), 7.37 (s, 1H), 7.11-7.25 (m, 2H), 6.39 (s, 1H), 5.97 (dd, J=8.9, 2.7 Hz, 1H), 3.69-3.83 (m, 1H), 3.08-3.20 (m, 2H), 2.93 (d, J=15.3 Hz, 1H), 2.73-2.87 (m, 1H), 2.60-2.70 (m, 1H), 1.09-1.18 (m, 1H), 0.87-0.98 (m, 1H), 0.73-0.85 (m, 2H). $^{19}$F NMR (376 MHz, Methanol-d$_4$) δ−117.79.

Example 23: (S*)-7-chloro-8-fluoro-12-(5-(imidazo[1,5-a]pyridin-6-yl)-1H-imidazol-2-yl)-13,14-dihydro-2H-spiro[benzo[5,6]azocino[4,3-g]indolizine-3,1'-cyclopropane]-1,10(4H,12H)-dione

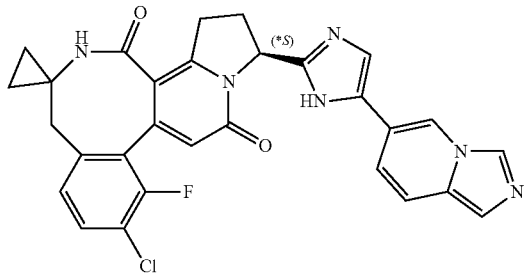 [SMILES: O=C1NC2(CC2)Cc2ccc(Cl)c(F)c2-c2cc(=O)n3c(c21)CC[C@H]3c1ncc(-c2ccc3cncn3c2)[nH]1]

The title compound was prepared following the procedure described in Example 22 above, selecting and substituting suitable reagents and reactants, as would be readily recognized by those skilled in the art.

LC/MS: mass calculated for $C_{29}H_{22}ClFN_6O_2$: 540.15, measured (ES, m/z): 541.05 [M+H]$^+$. $^1$H NMR (400 MHz, Methanol-d$_4$) δ 8.58 (s, 1H), 8.26 (s, 1H), 7.45-7.58 (m, 3H), 7.35 (s, 1H), 7.20 (d, J=9.5 Hz, 1H), 7.13 (d, J=8.3 Hz, 1H), 6.35 (s, 1H), 5.96 (dd, J=8.6, 2.1 Hz, 1H), 3.43-3.66 (m, 2H), 3.23 (d, J=15.5 Hz, 1H), 2.83-2.94 (m, 1H), 2.67-2.81 (m, 1H), 2.50-2.64 (m, 1H), 1.12-1.24 (m, 1H), 1.00-1.12 (m, 1H), 0.86-0.96 (m, 1H), 0.74-0.84 (m, 1H). $^{19}$F NMR (376 MHz, Methanol-d$_4$) δ−117.90.

Example 24: (R*)-12-(5-(6-amino-2-fluoropyridin-3-yl)-1H-imidazol-2-yl)-7-chloro-8-fluoro-2-(2-methoxyethyl)-13,14-dihydro-2H-spiro[benzo[5,6]azocino[4,3-g]indolizine-3,1'-cyclopropane]-1,10(4H,12H)-dione

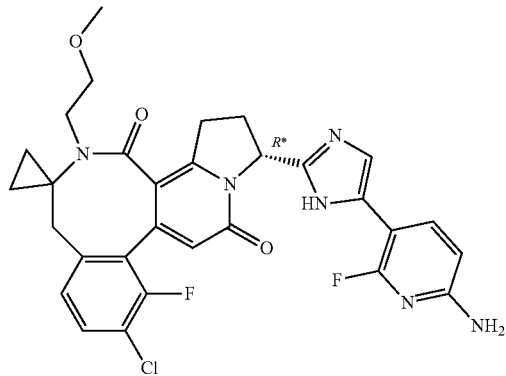 [SMILES: COCCN1C(=O)c2c(cc(=O)n3c2CC[C@@H]3c2ncc(-c3ccc(N)nc3F)[nH]2)-c2c(ccc(Cl)c2F)CC12CC2]

Step 1: 7-Chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylic acid To a solution of methyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (145 mg, 0.35 mmol, 1.0 equiv.) in DMF (4.5 mL) was added t-BuOK (117 mg, 1.04 mmol, 3.0 equiv.) at room temperature. After 30 min of stirring at room temperature, a solution of 1-iodo-2-methoxyethane (323 mg, 1.74 mmol, 5.0 equiv.) in DMF (0.5 mL) was added. The reaction mixture was stirred for 2 h at room temperature. The reaction was quenched with water (1 mL). The resulting residue was purified by reverse-phase flash with the following conditions: Column, Cat No: S0230120-2, C18, 80 g, 20~35 μm, 100 Å, Lot: BP002R1909; mobile phase, CH$_3$CN:H$_2$O (0.05% TFA)=5% increased to CH$_3$CN:H$_2$O (0.05% TFA)=50% in 20 min, hold CH$_3$CN:H$_2$O (0.05% TFA)=50% in 5 min, up to CH$_3$CN:H$_2$O (0.05% TFA)=95% in 2 min, hold CH$_3$CN:H$_2$O (0.05% TFA)=95% in 10 min; Detector, UV 220 nm & 254 nm, then concentrated to yield 7-chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylic acid as a yellow solid. LC/MS: mass calculated for $C_{23}H_{22}ClFN_2O_5$: 460.12, measured (ES, m/z): 461.20 [M+H]$^+$.

Step 2: 2-(6-Amino-2-fluoropyridin-3-yl)-2-oxoethyl 7-chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylic acid (50 mg, 0.11 mmol, 1.0 equiv.) in DMF (1.0 mL) was added K$_2$CO$_3$ (30 mg, 0.22 mmol, 2.0 equiv.). The mixture was stirred for 20 min at room temperature. 1-(6-Amino-2-fluoropyridin-3-yl)-2-bromoethan-1-one (38 mg, 0.16 mmol, 1.5 equiv.) was then added and the reaction mixture was stirred for 1 h at room temperature. The reaction was quenched with water (8 mL). The resulting mixture was extracted with ethyl acetate (3×30 mL). The organic layers were combined, dried over $Na_2SO_4$, filtered and concentrated. The residue was purified by silica gel chromatography (0-50% ethyl acetate/petroleum ether) to yield 2-(6-amino-2-fluoropyridin-3-yl)-2-oxoethyl 7-chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylate as a white solid. LC/MS: mass calculated for $C_{30}H_{27}ClF_2N_4O_6$: 612.16, measured (ES, m/z): 613.30 [M+H]$^+$.

Step 3: (R*)-12-(5-(6-amino-2-fluoropyridin-3-yl)-1H-imidazol-2-yl)-7-chloro-8-fluoro-2-(2-methoxyethyl)-13,14-dihydro-2H-spiro[benzo[5,6]azocino[4,3-g]indolizine-3,1'-cyclopropane]-1,10(4H,12H)-dione To a solution of 2-(6-amino-2-fluoropyridin-3-yl)-2-oxoethyl 7-chloro-8-fluoro-2-(2-methoxyethyl)-1,10-dioxo-1,4,10,12,13,14-hexahydro-2H-spiro[benzo[5,6]azocino[4,3-g]indolizine-3,1'-cyclopropane]-12-carboxylate (50.0 mg, 0.008 mmol, 1.0 equiv.) in toluene (1 mL) was added ammonium acetate (13 mg, 0.16 mmol, 20 equiv.) followed by the addition of acetic acid (0.025 mL) under $N_2$. The reaction mixture was stirred for 1.5 h at 100° C., then cooled to room temperature and concentrated under vacuum. The residue was purified by silica gel chromatography with MeOH/DCM (0-10%) to a residue, which was purified by chiral-HPLC with MTBE (0.1% DEA): EtOH=80:20 to yield (*S)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopentane]-1,10(4H,12H)-dione as a white solid.

LC/MS: mass calculated for $C_{30}H_{27}ClF_2N_6O_3$: 592.18, measured (ES, m/z): 593.30 [M+H]$^+$. $^1$H NMR (300 MHz, Methanol-$d_4$) δ 8.00-8.20 (m, 1H), 7.40-7.58 (m, 1H), 7.00-7.30 (m, 2H), 6.42 (d, J=8.4 Hz, 1H), 6.33 (s, 1H), 5.94 (d, J=8.6 Hz, 1H), 3.73-3.90 (m, 1H), 3.50-3.62 (m, 1H), 3.36-3.48 (m, 4H), 3.28-3.35 (m, 4H), 2.50-2.80 (m, 3H), 0.99-1.11 (m, 1H), 0.70-0.96 (m, 3H). $^{19}$F NMR (282 MHz, DMSO-$d_6$) δ −73.54, −96.32, −117.37.

Example 25: (S*)-12-(5-(6-amino-2-fluoropyridin-3-yl)-1H-imidazol-2-yl)-7-chloro-8-fluoro-2-(2-methoxyethyl)-13,14-dihydro-2H-spiro[benzo[5,6]azocino[4,3-g]indolizine-3,1'-cyclopropane]-1,10(4H,12H)-dione

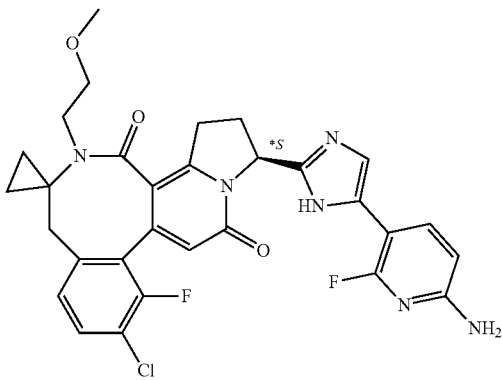 [SMILES: COCCN1C(=O)c2c(cc(=O)n3c2CC[C@H]3c2ncc(-c3ccc(N)nc3F)[nH]2)-c2c(ccc(Cl)c2F)CC12CC2]

The title compound was prepared following the procedure described in Example 24 above, selecting and substituting suitable reagents and reactants, as would be readily recognized by those skilled in the art.

LC/MS: mass calculated for $C_{30}H_{27}ClF_2N_6O_3$: 592.18, measured (ES, m/z): 593.30 [M+H]$^+$. $^1$H NMR (300 MHz, Methanol-$d_4$) δ 8.00-8.30 (m, 1H), 7.40-7.58 (m, 1H), 7.00-7.30 (m, 2H), 6.42 (d, J=8.3 Hz, 1H), 6.33 (s, 1H), 5.94 (d, J=8.7 Hz, 1H), 3.73-3.90 (m, 1H), 3.50-3.62 (m, 1H), 3.36-3.48 (m, 3H), 3.28-3.35 (m, 5H), 2.50-2.80 (m, 3H), 1.00-1.10 (m, 1H), 0.70-0.96 (m, 3H). $^{19}$F NMR (282 MHz, DMSO-$d_6$) δ −73.52, −76.95, −117.36.

Example 26: (R*)-12-(5-(benzo[d]thiazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

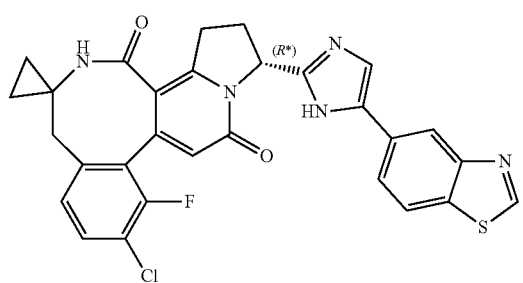 [SMILES: O=C1NC2(CC2)Cc2ccc(Cl)c(F)c2-c2cc(=O)n3c(c21)CC[C@@H]3c1ncc(-c2ccc3scnc3c2)[nH]1]

Step 1: 2-(Benzo[d]thiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate 7-Chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (151 mg, 0.38 mmol, 1.2 equiv.) and $K_2CO_3$ (47 mg, 0.34 mmol, 1.1 equiv.) was dissolved in DMF (5 mL). The mixture was cooled to 0° C. and stirred for 0.5 h. Then 1-(benzo[d]thiazol-5-yl)-2-bromoethan-1-one (80 mg, 0.31 mmol, 1.0 equiv.) was added into the mixture and stirred at 0° C. for 1.5 h. The resulting solution was diluted with water (30 mL), then extracted with EA (40 mL×3). The organic layers were combined, washed with brine (20 mL), dried and concentrated under vacuum. The resulting residue was applied onto a silica gel column with MeOH/DCM (0→5%) and obtained 2-(benzo[d]thiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a white solid. LC/MS: mass calculated for $C_{29}H_{21}ClFN_3O_5S$: 577.09, measured (ES, m/z): 578.20 [M+H]$^+$.

Step 2: (R*)-12-(5-(Benzo[d]thiazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione 2-(Benzo[d]thiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (130 mg, 0.23 mmol, 1.0 equiv.) was dissolved in toluene (8.0 mL) and AcOH (0.2 mL). NH$_4$OAc (37 mg, 0.45 mmol, 2.0 equiv.) was added to the mixture. The mixture was then heated to 100° C. for 2.0 h. The solvent was removed under reduced pressure. The reaction mixture was then purified by chromatography on C18 (80 g, MeCN/H$_2$O (0.05% CF$_3$COOH): 0→60%) and Prep-Chiral-HPLC to yield (*R)-12-(5-(1H-indazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as an off-white solid.

LC/MS: mass calculated for C$_{29}$H$_{21}$ClFN$_5$O$_2$S: 557.11, measured: 558.10 [M+H]$^+$. $^1$H NMR (400 MHz, DMSO-d$_6$) δ12.44 (s, 1H), 9.35 (s, 1H), 8.41 (d, J=1.6 Hz, 1H), 8.18-8.22 (m, 1H), 8.07 (d, J=8.4 Hz, 1H), 7.89 (dd, J=8.5, 1.6 Hz, 1H), 7.73 (d, J=1.9 Hz, 1H), 7.59-7.63 (m, 1H), 7.19 (d, J=8.3 Hz, 1H), 6.21 (s, 1H), 5.78-5.85 (m, 1H), 3.34-3.36 (m, 1H), 3.10-3.15 (m, 1H), 2.70-2.82 (m, 1H), 2.59-2.66 (m, 1H), 2.20-2.28 (m, 2H), 0.92-1.11 (m, 2H), 0.64-0.86 (m, 2H).

Example 27: (S*)-12-(5-(benzo[d]thiazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

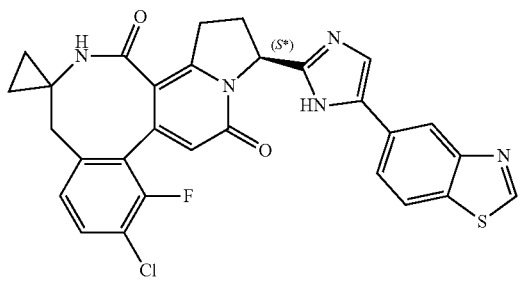 [SMILES: O=C1NC2(CC2)Cc2ccc(Cl)c(F)c2-c2cc(=O)n3c(c21)CC[C@H]3c1ncc(-c2ccc3scnc3c2)[nH]1]

The title compound was prepared following the procedure described in Example 26 above, selecting and substituting suitable reagents and reactants, as would be readily recognized by those skilled in the art.

LC/MS: mass calculated for C$_{29}$H$_{21}$ClFN$_5$O$_2$S: 557.11, measured: 558.10 [M+H]$^+$. $^1$H NMR (400 MHz, DMSO-d$_6$) δ12.35 (s, 1H), 9.37 (s, 1H), 8.38-8.41 (m, 1H), 8.02-8.10 (m, 2H), 7.79-8.01 (m, 1H), 7.74 (d, J=1.9 Hz, 1H), 7.59-7.65 (m, 1H), 7.21 (d, J=8.2 Hz, 1H), 6.20-6.25 (m, 1H), 5.76-5.86 (m, 1H), 3.48-3.66 (m, 1H), 2.94-3.12 (m, 2H), 2.80-2.83 (m, 1H), 2.56-2.72 (m, 2H), 0.98-1.07 (m, 1H), 0.76-0.88 (m, 1H), 0.61-0.73 (m, 2H).

Example 28: (R*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione, S*,S* atropisomer

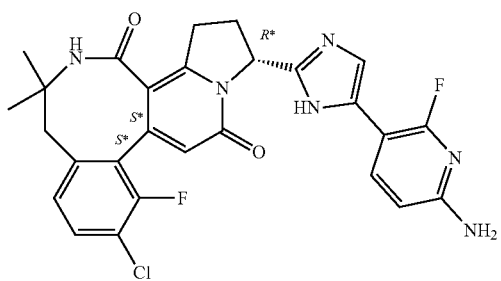 [SMILES: CC1(C)Cc2ccc(Cl)c(F)c2-c2cc(=O)n3c(c2C(=O)N1)CC[C@@H]3c1ncc(-c2ccc(N)nc2F)[nH]1]

The title compound was prepared following the procedure described in Example 29 below, selecting and substituting suitable reagents and reactants, as would be readily recognized by those skilled in the art.

LC/MS: mass calculated for C$_{27}$H$_{23}$ClF$_2$N$_6$O$_2$: 536.15, measured (ES, m/z): 537.30 [M+H]$^+$. $^1$H NMR (400 MHz, Methanol-d$_4$): δ 7.90 (dd, J=10.1, 8.4 Hz, 1H), 7.66 (d, J=1.8 Hz, 1H), 7.54-7.62 (m, 1H), 7.19 (dd, J=8.2, 1.2 Hz, 1H), 6.57 (dd, J=8.4, 1.8 Hz, 1H), 6.34 (s, 1H), 6.11 (dd, J=9.2, 5.4 Hz, 1H), 3.57-3.70 (m, 1H), 3.21-3.30 (m, 1H), 2.89-3.04 (m, 2H), 2.76-2.84 (m, 1H), 2.45-2.58 (m, 1H), 1.42 (s, 3H), 1.36 (s, 3H). $^{19}$F NMR (376 MHz, Methanol-d$_4$): δ−71.28, −120.04.

Example 29: (S*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione, S*,S* atropisomer 0.09 TFA

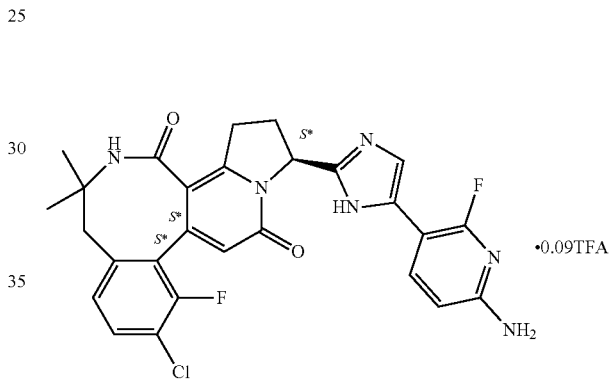

To a solution of 2-(6-amino-2-fluoropyridin-3-yl)-2-oxoethyl 7-chloro-8-fluoro-3,3-dimethyl-1,10-dioxo-1,2,3,4,10,12,13,14-octahydrobenzo[5,6]azocino[4,3-g]indolizine-12-carboxylate (0.11 g, 0.198 mmol, 1.0 equiv) in toluene (10 mL) was added ammonium acetate (0.304 g, 3.950 mmol, 20 equiv) followed by the addition of acetic acid (0.2 mL) under N$_2$. The reaction mixture was stirred for 3 h at 100° C., then cooled to room temperature and concentrated under vacuum. The residue was purified by silica gel chromatography with MeOH/DCM (0-10%) to yield racemic product, which was purified by chiral-HPLC with (Hex:DCM=3:1) (0.1% DEA):EtOH=85:15 to yield four isomers.

The second isomer, (S*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione was isolated as a white solid.

LC/MS: mass calculated for C$_{27}$H$_{23}$ClF$_2$N$_6$O$_2$: 536.15, measured (ES, m/z): 537.30 [M+H]$^+$. $^1$H NMR (400 MHz, Methanol-d$_4$): δ 7.95 (s, 1H), 7.45-7.58 (m, 1H), 7.11-7.24 (m, 2H), 6.42 (d, J=8.3 Hz, 1H), 6.27 (s, 1H), 5.91 (dd, J=8.6, 3.6 Hz, 1H), 3.38-3.53 (m, 2H), 3.04 (d, J=14.1 Hz, 1H), 2.67-2.80 (m, 2H), 2.47-2.57 (m, 1H), 1.45 (s, 3H), 1.35 (s, 3H). $^{19}$F NMR (376 MHz, Methanol-d$_4$): δ−73.37, −76.95, −117.78.

Example 30: (R*)-12-(5-(benzo[d][1,2,3]thiadiazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

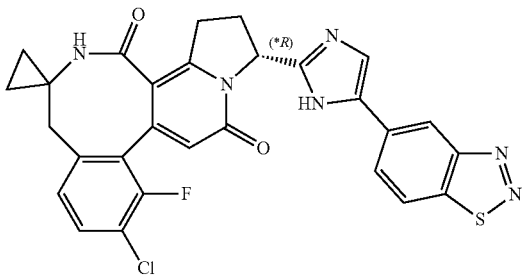 [SMILES: O=C1NC2(CC2)Cc2ccc(Cl)c(F)c2-c2cc(=O)n3c(c21)CC[C@@H]3c1ncc(-c2ccc3snnc3c2)[nH]1]

Step 1: 2-Amino-4-bromobenzenethiol

A solution of 5-bromobenzo[d]thiazol-2-amine (5 g, 21.825 mmol, 1 equiv.) in a mixture of aqueous 50% NaOH (25 mL) and ethylene glycol (25 mL) was heated at reflux under $N_2$ at 110° C. overnight. After cooling to room temperature, pour the mixture into ice-water, then acidified to pH=3 with 3 N aqueous HCl, and extracted with DCM. The combined organic layers were concentrated under vacuum. The residue was purified by silica gel chromatography with EA/PE (0-20%) to yield 2-amino-4-bromobenzenethiol as a yellow solid. LC/MS: mass calculated for $C_6H_6BrNS$: 202.94, measured: 406.95 $[2M+H]^+$.

Step 2: 5-Bromobenzo[d][1,2,3]thiadiazole

To a mixture of 2-amino-4-bromobenzenethiol (3.4 g, 16.6 mmol, 1 equiv.) in water (20 mL) was added aqueous 12 N hydrochloric acid (4.2 mL, 49.9 mmol, 3 equiv.) slowly at room temperature. Sodium nitrite (1.7 g, 24.9 mmol, 1.5 equiv.) was then added slowly at room temperature. THF (10 mL) was added for solubility, and the reaction was stirred at room temperature for 30 min. The solution was neutralized with saturated aqueous potassium carbonate, extracted with EA. The organic layer was concentrated and the residue was purified by silica gel chromatography with EA/PE (0-20%) to yield 5-bromobenzo[d][1,2,3]thiadiazole as a yellow solid. LC/MS: mass calculated for $C_6H_3BrN_2S$: 213.92, measured: 216.90 $[M+H+2]^+$.

Step 3: 5-(1-Ethoxyvinyl)benzo[d][1,2,3]thiadiazole

To a solution of 5-bromobenzo[d][1,2,3]thiadiazole (1.0 g, 4.6 mmol, 1 equiv.) in 1,4-dioxane (20 mL) was added 1-ethoxyvinyl-tri-n-butyltin (1.8 g, 5.1 mmol, 1.1 equiv.) and $Pd(PPh_3)_4$ (537 mg, 0.46 mmol, 0.1 equiv.) under $N_2$. The reaction mixture was stirred overnight at 100° C., then cooled to room temperature and quenched with water, extracted with EA, dried over $Na_2SO_4$, and concentrated under vacuum. The residue was purified by silica gel chromatography with EA/PE (0-20%) to yield 5-(1-ethoxyvinyl)benzo[d][1,2,3]thiadiazole as a light yellow solid. LC/MS: mass calculated for $C_{10}H_{10}N_2OS$: 206.05, measured: 207.00 $[M+H]^+$.

Step 4: 1-(Benzo[d][1,2,3]thiadiazol-5-yl)-2-bromoethan-1-one

To a solution of N-(5-(1-ethoxyvinyl)-6-fluoropyridin-2-yl)acetamide (320 mg, 1.55 mmol, 1 equiv.) in THF (6 mL) and water (2 mL) was added NBS (331 mg, 1.86 mmol, 1.2 equiv.). The reaction mixture was stirred for 2 h at room temperature, then filtered. The filtrate was extracted with EA, washed with brine, dried over $Na_2SO_4$ and concentrated vacuum to yield 1-(benzo[d][1,2,3]thiadiazol-5-yl)-2-bromoethan-1-one as off-white solid. LC/MS: mass calculated for $C_8H_5BrN_2OS$: 255.93, measured: 258.90 $[M+H+2]^+$.

Step 5: 2-(Benzo[d][1,2,3]thiadiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-3,3-dimethyl-1,10-dioxo-1,2,3,4,10,12,13,14-octahydrobenzo[5,6]azocino[4,3-g]indolizine-12-carboxylic acid (100 mg, 0.25 mmol, 1.0 equiv.) in DMF (4 mL) was added potassium carbonate (103 mg, 0.75 mmol, 3 equiv.). After the mixture was stirred for 10 min, 1-(benzo[d][1,2,3]thiadiazol-5-yl)-2-bromoethan-1-one (96 mg, 0.37 mmol, 1.5 equiv.) was added. The reaction mixture was stirred for 2 h at room temperature, then purified by reverse column chromatography with $CH_3CN$/0.05% TFA water (5%-50%) to yield 2-(benzo[d][1,2,3]thiadiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as off-white solid. LC/MS: mass calculated for $C_{28}H_2OClFN_4O_5S$: 578.08, measured: 579.20 $[M+H]^+$.

Step 6: (R*)-12-(5-(benzo[d][1,2,3]thiadiazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione To a solution of 2-(benzo[d][1,2,3]thiadiazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (110 mg, 0.19 mmol, 1.0 equiv.) in toluene (10 mL) was added ammonium acetate (293 mg, 3.80 mmol, 20 equiv.) followed by the addition of acetic acid (0.2 mL) under $N_2$. The reaction mixture was stirred for 3 h at 100° C., then cooled to room temperature and concentrated under vacuum. The residue was purified by silica gel chromatography with MeOH/DCM (0-10%) to yield racemic product, which was purified by chiral-HPLC with MtBE (0.1% DEA):EtOH=50:50 to (*R)-12-(5-(benzo[d][1,2,3]thiadiazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as off-white solid.

LC/MS: mass calculated for $C_{28}H_{20}ClFN_6O_2S$: 558.10, measured (ES, m/z): 559.25 $[M+H]^+$. $^1H$ NMR (400 MHz, Methanol-$d_4$): δ 9.14 (d, J=1.6 Hz, 1H), 8.46 (d, J=8.5 Hz, 1H), 8.19-8.26 (m, 2H), 7.49-7.58 (m, 1H), 7.15-7.24 (m, 1H), 6.41 (s, 1H), 6.11 (t, J=8.4 Hz, 1H), 3.37-3.61 (m, 2H), 3.20-3.28 (m, 1H), 2.98-3.10 (m, 1H), 2.89 (d, J=14.7 Hz, 1H), 2.65-2.77 (m, 1H), 1.07-1.15 (m, 1H), 0.90-1.03 (m, 3H). $^{19}F$ NMR (376 MHz, Methanol-$d_4$): δ −118.99.

Example 31: (S*)-12-(5-(benzo[d][1,2,3]thiadiazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

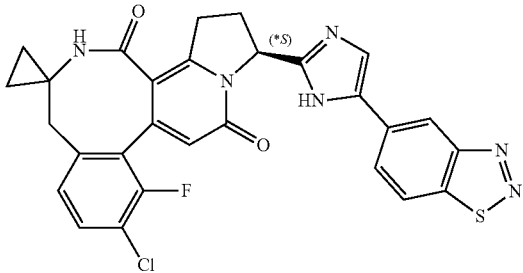 [SMILES: O=C1NC2(CC2)Cc2ccc(Cl)c(F)c2-c2cc(=O)n3c(c21)CC[C@H]3c1ncc(-c2ccc3snnc3c2)[nH]1]

The title compound was prepared following the procedure described in Example 30 above, selecting and substituting suitable reagents and reactants, as would be readily recognized by those skilled in the art.

LC/MS: mass calculated for $C_{28}H_{20}ClFN_6O_2S$: 558.10, measured (ES, m/z): 559.20 [M+H]$^+$. $^1$H NMR (400 MHz, Methanol-$d_4$): δ 9.08 (dd, J=1.7, 0.7 Hz, 1H), 8.46 (dd, J=8.6, 0.7 Hz, 1H), 8.21 (s, 1H), 8.17 (dd, J=8.5, 1.7 Hz, 1H), 7.50-7.57 (m, 1H), 7.16 (d, J=8.3 Hz, 1H), 6.42 (s, 1H), 6.18-6.24 (m, 1H), 3.60-3.71 (m, 1H), 3.22-3.29 (m, 1H), 3.00-3.19 (m, 2H), 2.92 (d, J=15.4 Hz, 1H), 2.53-2.65 (m, 1H), 1.07-1.17 (m, 1H), 0.87-0.96 (m, 1H), 0.76-0.86 (m, 2H). $^{19}$F NMR (376 MHz, Methanol-$d_4$): δ −118.09.

Example 32: (S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclobutane]-1,10(4H,12H)-dione

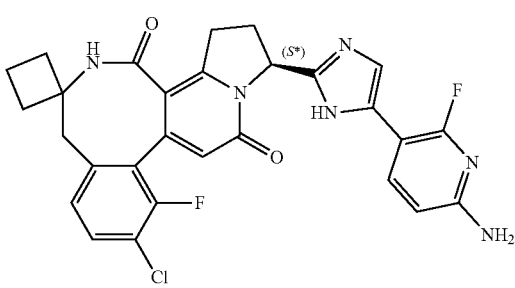 [SMILES: Nc1ccc(-c2cnc([C@@H]3CCc4c5c(cc(=O)n43)-c3c(ccc(Cl)c3F)CC3(CCC3)NC5=O)[nH]2)c(F)n1]

LC/MS: mass calculated for $C_{28}H_{23}ClF_2N_6O_2$: 548.15, measured (ES, m/z): 549.30 [M+H]$^+$. $^1$H NMR (300 MHz, Methanol-$d_4$) δ 8.03 (t, J=9.2 Hz, 1H), 7.45-7.60 (m, 1H), 7.08-7.31 (m, 2H), 6.38-6.56 (m, 1H), 6.30 (s, 1H), 5.85-5.99 (m, 1H), 3.39-3.53 (m, 2H), 3.06-3.29 (m, 2H), 2.62-2.84 (m, 1H), 2.47-2.62 (m, 1H), 2.15-2.47 (m, 4H), 1.90-2.10 (m, 2H). $^{19}$F NMR (282 MHz, DMSO-$d_6$) δ −73.43, −120.12.

Example 33: (R*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclobutane]-1,10(4H,12H)-dione

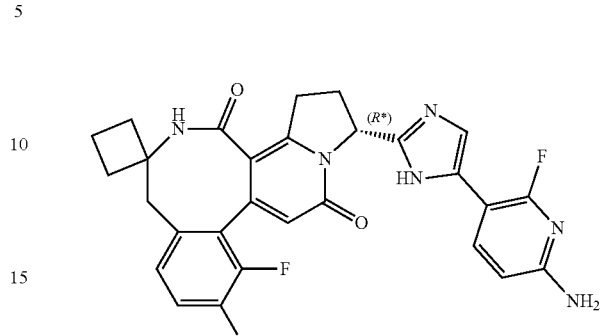

Step 1: 2-(6-Amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclobutane]-12-carboxylate 7-Chloro-8-fluoro-1,10-dioxo-1,4,10,12,13,14-hexahydro-2H-spiro[benzo[5,6]azocino[4,3-g]indolizine-3,1'-cyclobutane]-12-carboxylic acid (60 mg, 0.14 mmol, 1.0 equiv.) and potassium carbonate (59 mg, 0.42 mmol, 3.0 equiv.) were dissolved in DMF (1.5 mL) and stirred at room temperature for 0.5 h. Following this, a solution of 1-(6-amino-2-fluoropyridin-3-yl)-2-bromoethan-1-one (50 mg, 0.22 mmol, 1.5 equiv.) in DMF (1.5 mL) was added, and the reaction mixture stirred for another 2 h at room temperature. The mixture was then diluted with EA (100 mL) and water (50 mL), the organic extracts were washed with water (2×50 mL) and then dried over anhydrous sodium sulfate, filtered and concentrated under reduced pressure. The residue was purified by normal phase chromatography (mobile phase: DCM/MeOH, 0-20%) to yield 2-(6-amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclobutane]-12-carboxylate as a yellow solid. LC/MS: mass calculated for $C_{28}H_{23}ClF_2N_4O_5$: 568.13, measured: 569.00 [M+H]$^+$.

Step 2: (R*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclobutane]-1,10(4H,12H)-dione To a solution of 2-(6-amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclobutane]-12-carboxylate (50 mg, 0.088 mmol, 1.0 equiv.) in toluene (10 mL) was added ammonium acetate (135 mg, 1.76 mmol, 20 equiv.) followed by the addition of acetic acid (0.2 mL) under $N_2$. The reaction mixture was stirred for 2 h at 100° C., then cooled to room temperature and concentrated under vacuum. The residue was purified by silica gel chromatography with MeOH/DCM (0-10%) to yield a residue, which was purified by Chiral-HPLC with (Hex:DCM=3:1)(0.1% DEA):IPA=70:30) to (*R)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclobutane]-1,10(4H,12H)-dione as a light blue solid.

LC/MS: mass calculated for $C_{28}H_{23}ClF_2N_6O_2$: 548.15, measured (ES, m/z): 549.30 [M+H]$^+$. $^1$H NMR (300 MHz, Methanol-d$_4$) δ 8.04-8.24 (m, 1H), 7.46-7.59 (m, 1H), 7.14-7.28 (m, 2H), 6.48 (dd, J=8.3, 1.9 Hz, 1H), 6.33 (s, 1H), 5.94 (dd, J=8.9, 2.2 Hz, 1H), 3.60-3.80 (m, 1H), 3.29 (s, 1H), 2.99-3.19 (m, 2H), 2.51-2.88 (m, 2H), 2.50-2.11 (m, 4H), 1.91-2.02 (m, 2H). $^{19}$F NMR (282 MHz, DMSO-d$_6$) δ−73.30, −119.73.

Example 34: (R*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopentane]-1,10(4H,12H)-dione

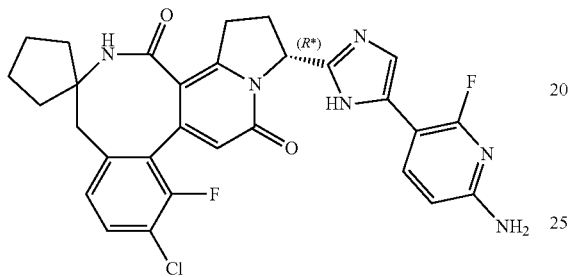

Step 1: 2-(6-Amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopentane]-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopentane]-12-carboxylic acid (165 mg, 0.38 mmol, 1.0 equiv.) in DMF (4 mL) was added K$_2$CO$_3$ (159 mg, 1.15 mmol, 3.0 equiv.). The mixture was stirred for 20 min at room temperature. Then 1-(6-amino-2-fluoropyridin-3-yl)-2-bromoethan-1-one (134 mg, 0.57 mmol, 1.5 equiv.) in DMF (1 mL) was added and the mixture stirred for 1 h at room temperature. The reaction was quenched with water (10 mL). The resulting mixture was extracted with ethyl acetate (3×40 mL). The organic layers were combined, dried over Na$_2$SO$_4$, filtered and concentrated. The residue was purified by reverse column chromatography with CH$_3$CN/water (5%-50%) to yield 2-(6-amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopentane]-12-carboxylate as a white solid. LC/MS: mass calculated for $C_{29}H_{25}ClF_2N_4O_5$: 582.15, measured (ES, m/z): 583.3 [M+H]$^+$ Step 2: (R*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopentane]-1,10(4H,12H)-dione To a solution of 2-(6-amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopentane]-12-carboxylate (135 mg, 0.23 mmol, 1.0 equiv.) in toluene (10 mL) was added ammonium acetate (357 mg, 4.63 mmol, 20 equiv.) followed by the addition of acetic acid (0.25 mL) under N$_2$. The reaction mixture was stirred for 1.5 h at 100° C., then cooled to room temperature and concentrated under vacuum. The residue was purified by silica gel chromatography with MeOH/DCM (0-10%) to yield a residue, which was purified by chiral-HPLC with MTBE (0.1% DEA): EtOH=80:20 to yield (*R)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopentane]-1,10(4H,12H)-dione as a white solid.

LC/MS: mass calculated for $C_{29}H_{25}ClF_2N_6O_2$: 562.17, measured (ES, m/z): 563.30 [M+H]$^+$. $^1$H NMR (400 MHz, DMSO-d$_6$) δ12.32 (s, 1H), 7.88 (dd, J=10.4, 8.2 Hz, 1H), 7.55-7.68 (m, 2H), 7.21 (d, J=8.2 Hz, 1H), 7.12 (d, J=3.7 Hz, 1H), 6.30 (dd, J=8.3, 2.2 Hz, 1H), 6.25 (s, 2H), 6.18 (s, 1H), 5.76-5.85 (m, 1H), 2.82-2.93 (m, 1H), 2.63-2.74 (m, 2H), 2.56-2.60 (m, 1H), 2.18-2.26 (m, 1H), 1.60-1.91 (m, 9H). $^{19}$F NMR (376 MHz, DMSO-d$_6$) δ−70.45, −119.39.

Example 35: (S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopentane]-1,10(4H,12H)-dione

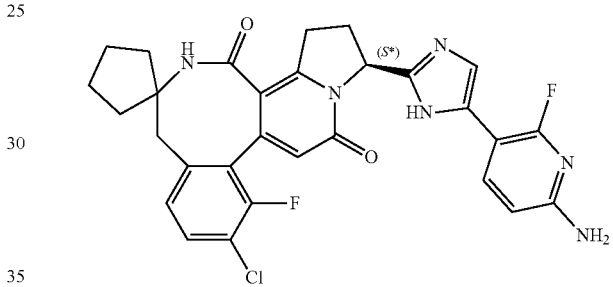

LC/MS: mass calculated for $C_{29}H_{25}ClF_2N_6O_2$: 562.17, measured (ES, m/z): 563.30 [M+H]$^+$. $^1$H NMR (400 MHz, DMSO-d$_6$) δ12.32 (s, 1H), 7.88 (dd, J=10.4, 8.2 Hz, 1H), 7.57-7.66 (m, 2H), 7.21 (d, J=8.2 Hz, 1H), 7.09-7.15 (m, 1H), 6.30 (dd, J=8.2, 2.1 Hz, 1H), 6.25 (s, 2H), 6.18 (s, 1H), 5.77-5.83 (m, 1H), 2.83-2.92 (m, 1H), 2.66-2.74 (m, 1H), 2.53-2.66 (m, 2H), 2.17-2.24 (m, 1H), 1.60-1.88 (m, 9H). $^{19}$F NMR (376 MHz, DMSO-d$_6$) δ−70.45, −119.39.

Example 36: (S*)-3-(5-(6-amino-2-fluoropyridin-3-yl)-1H-imidazol-2-yl)-8-chloro-7-fluoro-2,3-dihydrobenzo[5,6]pyrido[4',3':7,8]azocino[4,3-g]indolizine-5,16(1H,15H)-dione

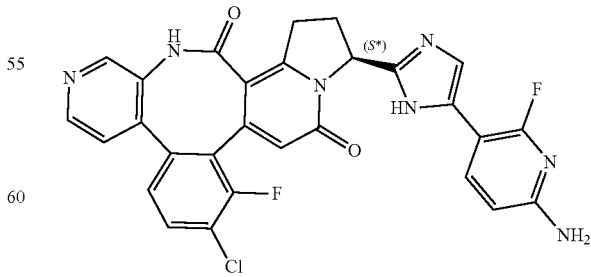

LC/MS: mass calculated for $C_{28}H_{18}ClF_2N_7O_2$: 557.12, measured (ES, m/z): 558.30 [M+H]$^+$. $^1$H NMR (400 MHz, Methanol-d$_4$): δ 8.56 (d, J=5.0 Hz, 1H), 8.52 (s, 1H), 7.96-8.09 (m, 1H), 7.77 (dd, J=8.3, 7.2 Hz, 1H), 7.45 (dd, J=5.0, 0.7 Hz, 1H), 7.25 (dd, J=8.3, 1.4 Hz, 1H), 7.20 (d, J=3.4 Hz, 1H), 6.47 (dd, J=8.3, 1.8 Hz, 1H), 6.20 (s, 1H), 5.78 (dd, J=9.1, 2.8 Hz, 1H), 3.71-3.84 (m, 1H), 3.13-3.25 (m, 1H), 2.59-2.74 (m, 1H), 2.47-2.59 (m, 1H). $^{19}$F NMR (376 MHz, Methanol-$d_4$): δ−73.37, −76.95, −117.78.

Example 37: (R*)-3-(5-(6-amino-2-fluoropyridin-3-yl)-1H-imidazol-2-yl)-8-chloro-7-fluoro-2,3-dihydrobenzo[5,6]pyrido[4',3':7,8]azocino[4,3-g]indolizine-5,16(1H,15H)-dione

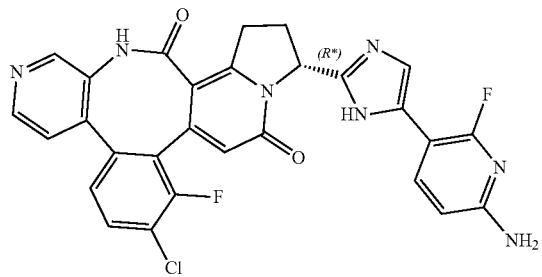 [SMILES: Nc1ccc(-c2cnc([C@H]3CCc4c5c(cc(=O)n43)-c3c(ccc(Cl)c3F)-c3ccncc3NC5=O)[nH]2)c(F)n1]

LC/MS: mass calculated for $C_{28}H_{18}ClF_2N_7O_2$: 557.12, measured (ES, m/z): 558.30 [M+H]$^+$. $^1$H NMR (400 MHz, Methanol-$d_4$): δ 8.51-8.61 (m, 2H), 7.72-7.83 (m, 2H), 7.44 (d, J=5.0 Hz, 1H), 7.24 (dd, J=8.3, 1.3 Hz, 1H), 7.14 (s, 1H), 6.48 (d, J=8.3 Hz, 1H), 6.18 (s, 1H), 5.81 (dd, J=8.7, 4.0 Hz, 1H), 3.40-3.63 (m, 2H), 2.63-2.78 (m, 1H), 2.44-2.56 (m, 1H). $^{19}$F NMR (376 MHz, Methanol-$d_4$): δ−73.56, −76.95, −118.13.

Example 38: (R*)-3-(5-(6-amino-2-fluoropyridin-3-yl)-1H-imidazol-2-yl)-8-chloro-7-fluoro-2,3-dihydrodibenzo[5,6:7,8]azocino[4,3-g]indolizine-5,16(1H,15H)-dione

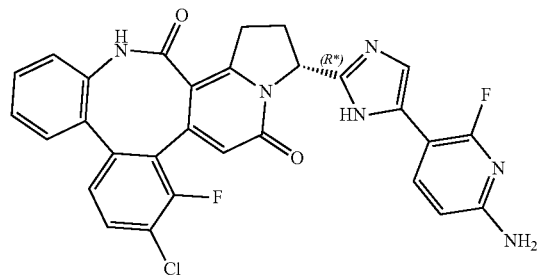 [SMILES: Nc1ccc(-c2cnc([C@H]3CCc4c5c(cc(=O)n43)-c3c(ccc(Cl)c3F)-c3ccccc3NC5=O)[nH]2)c(F)n1]

Step 1: 2-(6-Amino-2-fluoropyridin-3-yl)-2-oxoethyl 8-chloro-7-fluoro-5,16-dioxo-1,2,3,5,15,16-hexahydrodibenzo[5,6:7,8]azocino[4,3-g]indolizine-3-carboxylate To a solution of 8-chloro-7-fluoro-5,16-dioxo-1,2,3,5,15,16-hexahydrodibenzo[5,6:7,8]azocino[4,3-g]indolizine-3-carboxylic acid (100 mg, 0.24 mmol, 1.0 equiv.) in DMF (5 mL) was added potassium carbonate (98 mg, 0.71 mmol, 3 equiv.). After the mixture was stirred for 10 min, 1-(6-amino-2-fluoropyridin-3-yl)-2-bromoethan-1-one (82 mg, 0.35 mmol, 1.5 equiv.) was added. The reaction mixture was stirred for 2 h at room temperature, then purified by reverse column chromatography with $CH_3CN$/0.05% TFA water (5%-60%) to yield 2-(6-amino-2-fluoropyridin-3-yl)-2-oxoethyl 8-chloro-7-fluoro-5,16-dioxo-1,2,3,5,15,16-hexahydrodibenzo[5,6:7,8]azocino[4,3-g]indolizine-3-carboxylate as a light yellow solid. LC/MS: mass calculated for $C_{29}H_{19}ClF_2N_4O_5$: 576.10, measured: 577.10 [M+H]$^+$.

Step 2: (*R)-3-(5-(6-amino-2-fluoropyridin-3-yl)-1H-imidazol-2-yl)-8-chloro-7-fluoro-2,3-dihydrodibenzo[5,6:7,8]azocino[4,3-g]indolizine-5,16(1H,15H)-dione To a solution of 2-(6-amino-2-fluoropyridin-3-yl)-2-oxoethyl 8-chloro-7-fluoro-5,16-dioxo-1,2,3,5,15,16-hexahydrodibenzo[5,6:7,8]azocino[4,3-g]indolizine-3-carboxylate (70 mg, 0.12 mmol, 1.0 equiv.) in toluene (10 mL) was added ammonium acetate (187 mg, 2.43 mmol, 20 equiv.) followed by the addition of acetic acid (0.2 mL) under $N_2$. The reaction mixture was stirred for 2 h at 100° C., then cooled to room temperature and concentrated under vacuum. The residue was purified by silica gel chromatography with MeOH/DCM (0-10%) to yield a residue, which was purified by Chiral-HPLC with Hex (0.1% DEA):EtOH=50:50 to yield (*R)-3-(5-(6-amino-2-fluoropyridin-3-yl)-1H-imidazol-2-yl)-8-chloro-7-fluoro-2,3-dihydrodibenzo[5,6:7,8]azocino[4,3-g]indolizine-5,16(1H,15H)-dione as a white solid.

LC/MS: mass calculated for $C_{29}H_{19}ClF_2N_6O_2$: 556.12, measured (ES, m/z): 557.30 [M+H]$^+$. $^1$H NMR (400 MHz, Methanol-$d_4$): δ 7.75-7.80 (m, 1H), 7.70 (t, J=7.8 Hz, 1H), 7.45-7.54 (m, 1H), 7.38-7.45 (m, 1H), 7.29-7.37 (m, 2H), 7.24 (d, J=3.0 Hz, 1H), 7.17 (dd, J=8.3, 1.3 Hz, 1H), 6.47 (dd, J=8.3, 1.9 Hz, 1H), 6.19 (s, 1H), 5.84 (dd, J=8.6, 5.4 Hz, 1H), 3.49-3.62 (m, 1H), 3.36-3.44 (m, 1H), 2.70-2.83 (m, 1H), 2.42-2.55 (m, 1H). $^{19}$F NMR (376 MHz, Methanol-$d_4$): δ−72.82, −76.97, −118.80.

Example 39: (S*)-3-(5-(6-amino-2-fluoropyridin-3-yl)-1H-imidazol-2-yl)-8-chloro-7-fluoro-2,3-dihydrodibenzo[5,6:7,8]azocino[4,3-g]indolizine-5,16(1H,15H)-dione

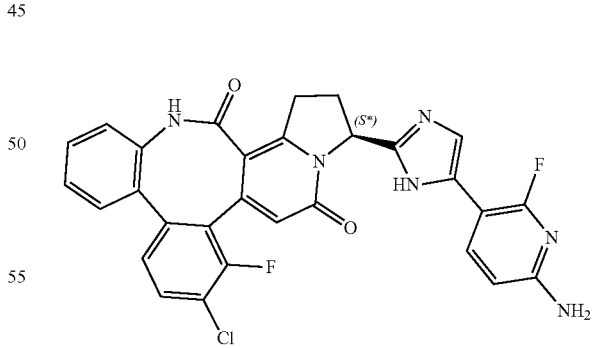

LC/MS: mass calculated for $C_{29}H_{19}ClF_2N_6O_2$: 556.12, measured (ES, m/z): 557.30 [M+H]$^+$. $^1$H NMR (400 MHz, Methanol-$d_4$): δ 8.01 (t, J=9.2 Hz, 1H), 7.66-7.73 (m, 1H), 7.38-7.50 (m, 2H), 7.23-7.36 (m, 3H), 7.14-7.20 (m, 1H), 6.48 (dd, J=8.3, 1.8 Hz, 1H), 6.19 (s, 1H), 5.79 (dd, J=9.1, 3.1 Hz, 1H), 3.68-3.81 (m, 1H), 3.10-3.20 (m, 1H), 2.46-2.72 (m, 2H). $^{19}$F NMR (376 MHz, Methanol-$d_4$): δ−73.14, −76.96, −118.64.

Example 40: (R*)-12-(5-(6-amino-2-fluoropyridin-3-yl)-1H-imidazol-2-yl)-7-chloro-8-fluoro-2-methyl-13,14-dihydro-2H-spiro[benzo[5,6]azocino[4,3-g]indolizine-3,1'-cyclopropane]-1,10(4H,12H)-dione

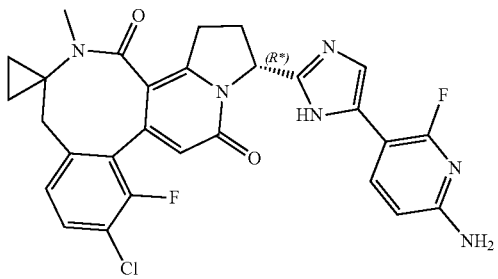 [SMILES: CN1C(=O)c2c(cc(=O)n3c2CC[C@@H]3c2ncc(-c3ccc(N)nc3F)[nH]2)-c2c(ccc(Cl)c2F)CC12CC2]

Step 1: (R*)-12-(5-(6-amino-2-fluoropyridin-3-yl)-1H-imidazol-2-yl)-7-chloro-8-fluoro-2-methyl-13,14-dihydro-2H-spiro[benzo[5,6]azocino[4,3-g]indolizine-3,1'-cyclopropane]-1,10(4H,12H)-dione To a solution of 7-chloro-8-fluoro-2-methyl-1,10-dioxo-1,4,10,12,13,14-hexahydro-2H-spiro[benzo[5,6]azocino[4,3-g]indolizine-3,1'-cyclopropane]-12-carboxylic acid (120 mg, 0.29 mmol, 1.0 equiv.) in DMF (5 mL) was added potassium carbonate (120 mg, 0.86 mmol, 3 equiv.). After the mixture was stirred for 10 min, 1-(6-amino-2-fluoropyridin-3-yl)-2-bromoethan-1-one (100 mg, 0.43 mmol, 1.5 equiv.) was added. The reaction mixture was stirred for 2 h at room temperature, then purified by reverse column chromatography with $CH_3CN$/0.05% TFA water (5%-60%) to yield 2-(6-amino-2-fluoropyridin-3-yl)-2-oxoethyl 7-chloro-8-fluoro-2-methyl-1,10-dioxo-1,4,10,12,13,14-hexahydro-2H-spiro[benzo[5,6]azocino[4,3-g]indolizine-3,1'-cyclopropane]-12-carboxylate as a light yellow solid. LC/MS: mass calculated for $C_{28}H_{23}ClF_2N_4O_5$: 568.13, measured (ES, m/z): 569.3 $[M+H]^+$.

Step 2: (R*)-12-(5-(6-amino-2-fluoropyridin-3-yl)-1H-imidazol-2-yl)-7-chloro-8-fluoro-2-methyl-13,14-dihydro-2H-spiro[benzo[5,6]azocino[4,3-g]indolizine-3,1'-cyclopropane]-1,10(4H,12H)-dione To a solution of 2-(6-amino-2-fluoropyridin-3-yl)-2-oxoethyl 7-chloro-8-fluoro-2-methyl-1,10-dioxo-1,4,10,12,13,14-hexahydro-2H-spiro[benzo[5,6]azocino[4,3-g]indolizine-3,1'-cyclopropane]-12-carboxylate (100 mg, 0.18 mmol, 1.0 equiv.) in toluene (10 mL) was added ammonium acetate (280 mg, 3.64 mmol, 20 equiv.) followed by the addition of acetic acid (0.2 mL) under $N_2$. The reaction mixture was stirred for 2 h at 100° C., then cooled to room temperature and concentrated under vacuum. The residue was purified by silica gel chromatography with MeOH/DCM (0-10%) to yield a residue, which was purified by Chiral-HPLC with Hex (0.1% DEA): EtOH=50:50 to yield (*R)-12-(5-(6-amino-2-fluoropyridin-3-yl)-1H-imidazol-2-yl)-7-chloro-8-fluoro-2-methyl-13,14-dihydro-2H-spiro[benzo[5,6]azocino[4,3-g]indolizine-3,1'-cyclopropane]-1,10(4H,12H)-dione as a white solid.
LC/MS: mass calculated for $C_{28}H_{23}ClF_2N_6O_2$: 548.15, measured (ES, m/z): 549.20 $[M+H]^+$. $^1$H NMR (400 MHz, Methanol-$d_4$) δ 8.07 (s, 1H), 7.50 (t, J=7.8 Hz, 1H), 7.06-7.28 (m, 2H), 6.48 (dd, J=8.3, 1.8 Hz, 1H), 6.39 (s, 1H), 5.96 (dd, J=8.9, 3.0 Hz, 1H), 3.61-3.77 (m, 1H), 3.57 (d, J=16.2 Hz, 1H), 2.99-3.11 (m, 1H), 2.84 (s, 3H), 2.69-2.78 (m, 2H), 2.58-2.69 (m, 1H), 1.23-1.34 (m, 1H), 0.89-0.98 (m, 1H), 0.73-0.88 (m, 2H). $^{19}$F NMR (376 MHz, Methanol-$d_4$) δ −73.42, −116.66.

Example 41: (S*)-12-(5-(6-amino-2-fluoropyridin-3-yl)-1H-imidazol-2-yl)-7-chloro-8-fluoro-2-methyl-13,14-dihydro-2H-spiro[benzo[5,6]azocino[4,3-g]indolizine-3,1'-cyclopropane]-1,10(4H,12H)-dione

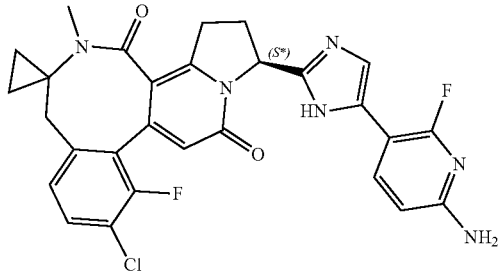 [SMILES: CN1C(=O)c2c(cc(=O)n3c2CC[C@H]3c2ncc(-c3ccc(N)nc3F)[nH]2)-c2c(ccc(Cl)c2F)CC12CC2]

The title compound was prepared following the procedure described in Example 40 above, selecting and substituting suitable reagents and reactants, as would be readily recognized by those skilled in the art.
LC/MS: mass calculated for $C_{28}H_{23}ClF_2N_6O_2$: 548.15, measured (ES, m/z): 549.20 $[M+H]^+$. $^1$H NMR (400 MHz, Methanol-$d_4$) δ 8.08 (s, 1H), 7.50 (t, J=7.8 Hz, 1H), 7.11-7.22 (m, 2H), 6.40 (d, J=34.0 Hz, 2H), 5.95 (d, J=8.5 Hz, 1H), 3.39-3.62 (m, 3H), 2.85 (s, 3H), 2.64-2.77 (m, 2H), 2.48-2.63 (m, 1H), 1.19-1.30 (m, 1H), 0.97-1.15 (m, 1H), 0.75-0.91 (m, 2H). $^{19}$F NMR (376 MHz, Methanol-$d_4$) δ −73.53, −117.16.

Example 42: (S*)-7-chloro-8-fluoro-12-(5-(1-methyl-1H-1,2,3-triazol-5-yl)-1H-imidazol-2-yl)-13,14-dihydro-2H-spiro[benzo[5,6]azocino[4,3-g]indolizine-3,1'-cyclopropane]-1,10(4H,12H)-dione

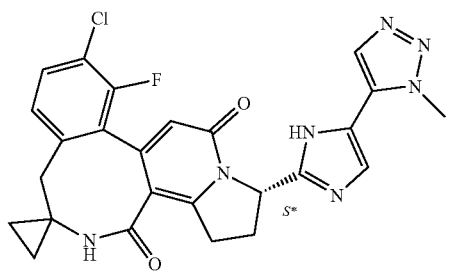 [SMILES: Cn1nncc1-c1cnc([C@@H]2CCc3c4c(cc(=O)n32)-c2c(ccc(Cl)c2F)CC2(CC2)NC4=O)[nH]1]

Step 1: 2-(1-methyl-1H-1,2,3-triazol-5-yl)-2-oxoethyl 7-chloro-8-fluoro-1,10-dioxo-1,2,3,4,10,12,13,14-octahydrobenzo[5,6]azocino[4,3-g]indolizine-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (100 mg, 0.25 mmol, 1 equiv.) in N,N-dimethylformamide (5 mL) was added potassium carbonate (103 mg, 0.75 mmol, 1.5 equiv.). After the reaction mixture was stirred at room temperature 30 min, 2-bromo-1-(1-methyl-1H-1,2,3-triazol-5-yl)ethan-1-one (1 mg, 0.75 mmol, 1.5 equiv.) was added. The reaction mixture was stirred 2 h at room temperature. The mixture was extracted with EA, dried over $Na_2SO_4$, and concentrated under vacuum. The residue was concentrated, and purified by silica gel chromatography (0-10% MeOH/DCM) to yield 2-(1-methyl-1H-1,2,3-triazol-5-yl)-2-oxoethyl 7-chloro-8-fluoro-1,10-dioxo-1,2,3,4,10,12,13,14-octahydrobenzo[5,6]azocino[4,3-g]indolizine-12-carboxylate as light yellow solid. LC/MS: mass calculated for $C_{30}H_{36}ClFN_2O_7$: 590.22, measured: 591.20 [M+H]$^+$.

Step 2: (*S)-7-chloro-8-fluoro-12-(5-(1-methyl-1H-1,2,3-triazol-5-yl)-1H-imidazol-2-yl)-13,14-dihydro-2H-spiro[benzo[5,6]azocino[4,3-g]indolizine-3,1'-cyclopropane]-1,10(4H,12H)-dione To a solution of 2-(1-methyl-1H-1,2,3-triazol-5-yl)-2-oxoethyl 7-chloro-8-fluoro-1,10-dioxo-1,2,3,4,10,12,13,14-octahydrobenzo[5,6]azocino[4,3-g]indolizine-12-carboxylate (50 mg, 0.10 mmol, 1.0 equiv.) in toluene (20 mL) was added ammonium acetate (110 mg, 1.43 mmol, 15.0 equiv.) and acetic acid glacial (57 mg, 0.95 mmol, 10.0 equiv.). The reaction mixture was stirred at 100° C. for 2 h. The residue was concentrated, and purified by silica gel chromatography (0-10% MeOH/DCM) to yield 7-chloro-8-fluoro-12-(5-(1-methyl-1H-1,2,3-triazol-5-yl)-1H-imidazol-2-yl)-13,14-dihydro-2H-spiro[benzo[5,6]azocino[4,3-g]indolizine-3,1'-cyclopropane]-1,10(4H,12H)-dione as light yellow solid. The racemic mixture was purified by Prep-Chiral-HPLC with MtBE (0.1% DEA):EtOH=50:50 to yield 10.6 mg (21.5%) of (*S)-7-chloro-8-fluoro-12-(5-(1-methyl-1H-1,2,3-triazol-5-yl)-1H-imidazol-2-yl)-13,14-dihydro-2H-spiro[benzo[5,6]azocino[4,3-g]indolizine-3,1'-cyclopropane]-1,10(4H,12H)-dione as an off-white solid.

LC/MS: mass calculated for $C_{25}H_{21}ClFN_7O_2$: 505.14, measured (ES, m/z): 506.15 [M+H]$^+$. $^1$H NMR (400 MHz, DMSO-d$_6$) δ12.78 (s, 1H), 8.19 (s, 1H), 7.78 (s, 1H), 7.55-7.66 (m, 2H), 7.18 (d, J=8.2 Hz, 1H), 6.21 (s, 1H), 5.81 (d, J=8.4 Hz, 1H), 4.16 (s, 3H), 3.30 (d, J=5.2 Hz, 2H), 3.17 (d, J=15.5 Hz, 1H), 2.73 (d, J=15.4 Hz, 1H), 2.61-2.67 (m, 1H), 2.23-2.31 (m, 1H), 0.96-1.06 (m, 1H), 0.78 (d, J=5.5 Hz, 2H), 0.57-0.63 (m, 1H). $^{19}$F NMR (376 MHz, DMSO-d$_6$) δ−117.00.

Example 43: (R*)-7-chloro-8-fluoro-12-(5-(1-methyl-1H-1,2,3-triazol-5-yl)-1H-imidazol-2-yl)-13,14-dihydro-2H-spiro[benzo[5,6]azocino[4,3-g]indolizine-3,1'-cyclopropane]-1,10(4H,12H)-dione

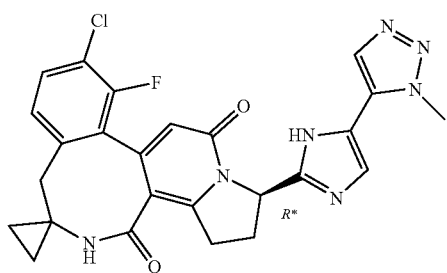 [SMILES: Cn1nncc1-c1cnc([C@H]2CCc3c4c(cc(=O)n32)-c2c(ccc(Cl)c2F)CC2(CC2)NC4=O)[nH]1]

The title compound was prepared following the procedure described in Example 42 above, selecting and substituting suitable reagents and reactants, as would be readily recognized by those skilled in the art.

LC/MS: mass calculated for $C_{25}H_{21}ClFN_7O_2$: 505.14, measured (ES, m/z): 506.15 [M+H]$^+$. $^1$H NMR (400 MHz, DMSO-d$_6$) δ12.64 (s, 1H), 8.09 (s, 1H), 7.84 (s, 1H), 7.57-7.65 (m, 2H), 7.20 (d, J=8.3 Hz, 1H), 6.23 (s, 1H), 5.79-5.86 (m, 1H), 4.16 (s, 3H), 3.47-3.52 (m, 1H), 2.94-3.11 (m, 2H), 2.80 (d, J=15.1 Hz, 1H), 2.60-2.67 (m, 1H), 2.40-2.46 (m, 1H), 1.24 (s, 1H), 0.98-1.04 (m, 1H), 0.61-0.72 (m, 2H). $^{19}$F NMR (376 MHz, DMSO-d$_6$) δ−117.18.

Example 44: (S*)-7-chloro-8-fluoro-12-(5-(1-methyl-1H-1,2,3-triazol-5-yl)-1H-imidazol-2-yl)-3,4,13,14-tetrahydrobenzo[5,6]azocino[4,3-g]indolizine-1,10(2H,12H)-dione

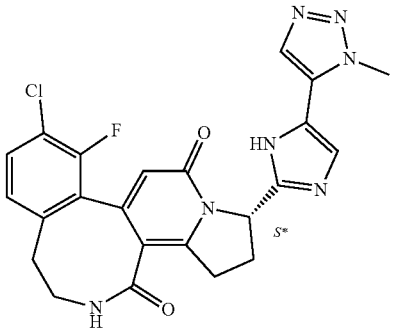 [SMILES: Cn1nncc1-c1cnc([C@@H]2CCc3c4c(cc(=O)n32)-c2c(ccc(Cl)c2F)CCNC4=O)[nH]1]

LC/MS: mass calculated for $C_{23}H_{19}ClFN_7O_2$: 479.13, measured (ES, m/z): 480.20 [M+H]$^+$. $^1$H NMR (300 MHz, DMSO-d$_6$): δ12.63 (s, 1H), 7.84 (s, 1H), 7.75 (t, J=6.1 Hz, 1H), 7.54-7.66 (m, 2H), 7.18 (d, J=8.3 Hz, 1H), 6.22 (s, 1H), 5.77 (dd, J=8.9, 2.1 Hz, 1H), 4.16 (s, 3H), 3.38-3.59 (m, 2H), 3.23-3.30 (m, 1H), 2.77-3.11 (m, 3H), 2.57-2.77 (m, 1H), 2.26-2.50 (m, 2H). $^{19}$F NMR (283 MHz, DMSO-d$_6$): δ−117.42.

Example 45: (R*)-7-chloro-8-fluoro-12-(5-(1-methyl-1H-1,2,3-triazol-5-yl)-1H-imidazol-2-yl)-3,4,13,14-tetrahydrobenzo[5,6]azocino[4,3-g]indolizine-1,10(2H,12H)-dione

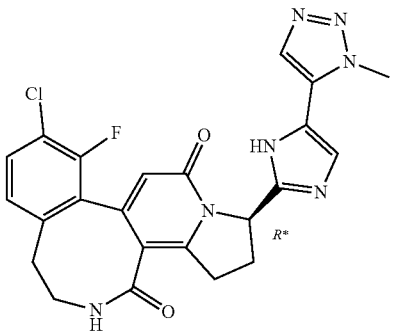 [SMILES: Cn1nncc1-c1cnc([C@H]2CCc3c4c(cc(=O)n32)-c2c(ccc(Cl)c2F)CCNC4=O)[nH]1]

LC/MS: mass calculated for $C_{23}H_{19}ClFN_7O_2$: 479.13, measured (ES, m/z): 480.20 [M+H]$^+$. $^1$H NMR (300 MHz, DMSO-d$_6$): δ 12.66 (s, 1H), 7.75-7.86 (m, 2H), 7.52-7.69 (m, 2H), 7.18 (d, J=8.3 Hz, 1H), 6.24 (s, 1H), 5.73-5.90 (m, 1H), 4.16 (s, 3H), 3.34-3.47 (m, 2H), 3.20-3.33 (m, 2H), 2.83-3.07 (m, 2H), 2.58-2.76 (m, 1H), 2.20-2.37 (m, 1H). $^{19}$F NMR (283 MHz, DMSO-d$_6$): δ−117.48.

Example 46: (S*)-12-(5-(6-amino-2-fluoropyridin-3-yl)-1H-imidazol-2-yl)-7-chloro-8-fluoro-3,4,13,14-tetrahydrobenzo[5,6]azocino[4,3-g]indolizine-1,10(2H,12H)-dione

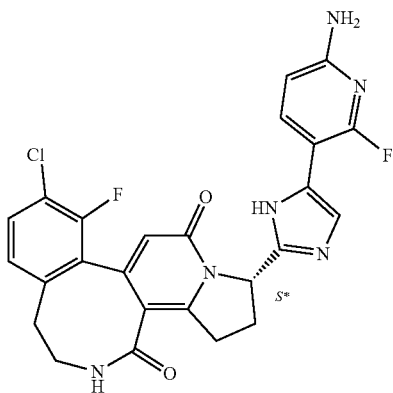 [SMILES: Nc1ccc(-c2cnc([C@@H]3CCc4c5c(cc(=O)n43)-c3c(ccc(Cl)c3F)CCNC5=O)[nH]2)c(F)n1]

The title compound was prepared following the procedure described in Example 47 below, selecting and substituting suitable reagents and reactants, as would be readily recognized by those skilled in the art.

LC/MS: mass calculated for C$_{25}$H$_{19}$ClF$_2$N$_6$O$_2$: 508.12, measured (ES, m/z): 509.20 [M+H]$^+$. $^1$H NMR (400 MHz, DMSO-d$_6$): δ 12.20 (s, 1H), 7.93-8.01 (m, 1H), 7.74 (t, J=6.1 Hz, 1H), 7.59 (t, J=7.9 Hz, 1H), 7.04-7.23 (m, 2H), 6.22-6.55 (m, 3H), 6.20 (s, 1H), 5.73 (d, J=8.8 Hz, 1H), 3.39-3.64 (m, 2H), 3.15-3.28 (m, 1H), 2.79-3.07 (m, 3H), 2.55-2.71 (m, 1H), 2.36-2.46 (m, 1H). $^{19}$F NMR (376 MHz, DMSO-d$_6$) δ−70.76, −73.41, −117.24.

Example 47: (R*)-12-(5-(6-amino-2-fluoropyridin-3-yl)-1H-imidazol-2-yl)-7-chloro-8-fluoro-3,4,13,14-tetrahydrobenzo[5,6]azocino[4,3-g]indolizine-1,10(2H,12H)-dione

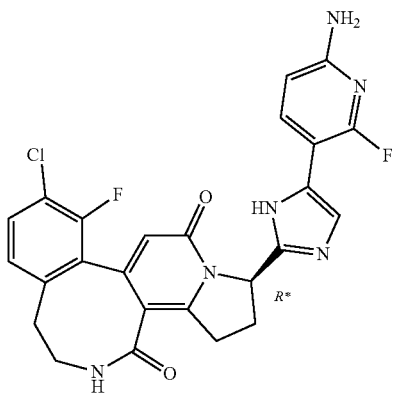 [SMILES: Nc1ccc(-c2cnc([C@H]3CCc4c5c(cc(=O)n43)-c3c(ccc(Cl)c3F)CCNC5=O)[nH]2)c(F)n1]

Step 1: 2-(6-amino-2-fluoropyridin-3-yl)-2-oxoethyl 7-chloro-8-fluoro-1,10-dioxo-1,2,3,4,10,12,13,14-octahydrobenzo[5,6]azocino[4,3-g]indolizine-12-carboxylate To a solution of 7-chloro-8-fluoro-1,10-dioxo-1,2,3,4,10,12,13,14-octahydrobenzo[5,6]azocino[4,3-g]indolizine-12-carboxylic acid (100 mg, 0.27 mmol, 1.0 equiv.) in DMF (5 mL) was added potassium carbonate (110 mg, 0.80 mmol, 3.0 equiv.). After the mixture was stirred for 30 min, 1-(6-amino-2-fluoropyridin-3-yl)-2-bromoethan-1-one (74 mg, 0.32 mmol, 1.2 equiv.) in DMF (1 mL) was added. The reaction mixture was stirred for 2 h at room temperature, then purified by reverse column chromatography with CH$_3$CN/0.05% TFA water (5%-80%) to yield 2-(6-amino-2-fluoropyridin-3-yl)-2-oxoethyl 7-chloro-8-fluoro-1,10-dioxo-1,2,3,4,10,12,13,14-octahydrobenzo[5,6]azocino[4,3-g]indolizine-12-carboxylate as a light yellow solid. LC/MS: mass calculated for C$_{25}$H$_{19}$ClF$_2$N$_4$O$_5$: 528.10, measured: 529.2 [M+H]$^+$.

Step 2: (*R)-12-(5-(6-amino-2-fluoropyridin-3-yl)-1H-imidazol-2-yl)-7-chloro-8-fluoro-3,4,13,14-tetrahydrobenzo[5,6]azocino[4,3-g]indolizine-1,10(2H,12H)-dione To a solution of 2-(6-amino-2-fluoropyridin-3-yl)-2-oxoethyl 7-chloro-8-fluoro-1,10-dioxo-1,2,3,4,10,12,13,14-octahydrobenzo[5,6]azocino[4,3-g]indolizine-12-carboxylate (80 mg, 0.15 mmol, 1.0 equiv.) in toluene (15 mL) was added ammonium acetate (175 mg, 13.43 mmol, 15.0 equiv.) followed by the addition of acetic acid (0.2 mL) under N$_2$. The reaction mixture was stirred for 2 h at 100° C., then cooled to room temperature and concentrated under vacuum. The residue was purified by silica gel chromatography with MeOH/DCM (0-10%) to yield a residue, which was purified by chiral-HPLC with MtBE (0.1% DEA):MeOH=70:30 to yield (*R)-12-(5-(6-amino-2-fluoropyridin-3-yl)-1H-imidazol-2-yl)-7-chloro-8-fluoro-3,4,13,14-tetrahydrobenzo[5,6]azocino[4,3-g]indolizine-1,10(2H,12H)-dione as a off-white solid.

LC/MS: mass calculated for C$_{25}$H$_{19}$ClF$_2$N$_6$O$_2$: 508.12, measured (ES, m/z): 509.20 [M+H]$^+$. $^1$H NMR (400 MHz, DMSO-d$_6$): δ12.16 (s, 1H), 7.94 (s, 1H), 7.81 (t, J=6.3 Hz, 1H), 7.60 (t, J=7.9 Hz, 1H), 7.08-7.23 (m, 2H), 6.16-6.48 (m, 4H), 5.79 (d, J=8.5 Hz, 1H), 3.35-3.54 (m, 2H), 3.18-3.31 (m, 2H), 2.85-3.08 (m, 2H), 2.58-2.72 (m, 1H), 2.27-2.42 (m, 1H). $^{19}$F NMR (376 MHz, DMSO-d$_6$) δ−70.68, −73.44, −117.40.

Example 48: (R*)-12-(5-(6-amino-2-chloropyridin-3-yl)-1H-imidazol-2-yl)-7-chloro-8-fluoro-3,4,13,14-tetrahydrobenzo[5,6]azocino[4,3-g]indolizine-1,10(2H,12H)-dione

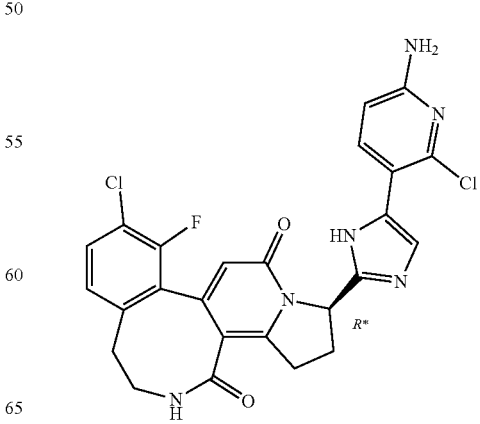

Step 1: 2-(6-amino-2-chloropyridin-3-yl)-2-oxoethyl 7-chloro-8-fluoro-1,10-dioxo-1,2,3,4,10,12,13,14-octahydrobenzo[5,6]azocino[4,3-g]indolizine-12-carboxylate To a solution of 7-chloro-8-fluoro-1,10-dioxo-1,2,3,4,10,12,13,14-octahydrobenzo[5,6]azocino[4,3-g]indolizine-12-carboxylic acid (100 mg, 0.27 mmol, 1.0 equiv.) in DMF (5 mL) was added potassium carbonate (110 mg, 0.08 mmol, 3.0 equiv.). After the mixture was stirred for 30 min, 1-(6-amino-2-chloropyridin-3-yl)-2-bromoethan-1-one (790 mg, 0.32 mmol, 1.2 equiv.) in DMF (1 mL) was added. The reaction mixture was stirred for 2 h at room temperature, then purified by reverse column chromatography with CH₃CN/0.05% TFA water (5%-80%) to yield 2-(6-amino-2-chloropyridin-3-yl)-2-oxoethyl 7-chloro-8-fluoro-1,10-dioxo-1,2,3,4,10,12,13,14-octahydrobenzo[5,6]azocino[4,3-g]indolizine-12-carboxylate as a light yellow solid. LC/MS: mass calculated for $C_{25}H_{19}Cl_2FN_4O_5$: 544.07, measured: 545.2 [M+H]⁺.

Step 2: (*R)-12-(5-(6-amino-2-chloropyridin-3-yl)-1H-imidazol-2-yl)-7-chloro-8-fluoro-3,4,13,14-tetrahydrobenzo[5,6]azocino[4,3-g]indolizine-1,10(2H,12H)-dione To a solution of 2-(6-amino-2-chloropyridin-3-yl)-2-oxoethyl 7-chloro-8-fluoro-1,10-dioxo-1,2,3,4,10,12,13,14-octahydrobenzo[5,6]azocino[4,3-g]indolizine-12-carboxylate (80 mg, 0.15 mmol, 1.0 equiv.) in toluene (15 mL) was added ammonium acetate (170 mg, 2.20 mmol, 15.0 equiv.) followed by the addition of acetic acid (0.2 mL) under N₂. The reaction mixture was stirred for 2 h at 100° C., then cooled to room temperature and concentrated under vacuum. The residue was purified by silica gel chromatography with MeOH/DCM (0-10%) to yield a residue, which was purified by Chiral-HPLC with MtBE (0.1% DEA):MeOH=70:30 to yield (*R)-12-(5-(6-amino-2-chloropyridin-3-yl)-1H-imidazol-2-yl)-7-chloro-8-fluoro-3,4,13,14-tetrahydrobenzo[5,6]azocino[4,3-g]indolizine-1,10(2H,12H)-dione as a off-white solid.

LC/MS: mass calculated for $C_{25}H_{19}Cl_2FN_6O_2$: 524.09, measured (ES, m/z): 525.20 [M+H]⁺. ¹H NMR (400 MHz, DMSO-d₆): δ12.21 (s, 1H), 7.91 (s, 1H), 7.81 (t, J=6.3 Hz, 1H), 7.60 (t, J=7.9 Hz, 1H), 7.45 (s, 1H), 7.18 (d, J=8.3 Hz, 1H), 6.28-6.58 (m, 3H), 6.24 (s, 1H), 5.80 (d, J=8.5 Hz, 1H), 3.37-3.52 (m, 2H), 3.21-3.31 (m, 2H), 2.87-3.04 (m, 2H), 2.59-2.70 (m, 1H), 2.30-2.41 (m, 1H). ¹⁹F NMR (376 MHz, DMSO-d₆) δ−77.75, −117.40.

Example 49: (S*)-12-(5-(6-amino-2-chloropyridin-3-yl)-1H-imidazol-2-yl)-7-chloro-8-fluoro-3,4,13,14-tetrahydrobenzo[5,6]azocino[4,3-g]indolizine-1,10(2H,12H)-dione

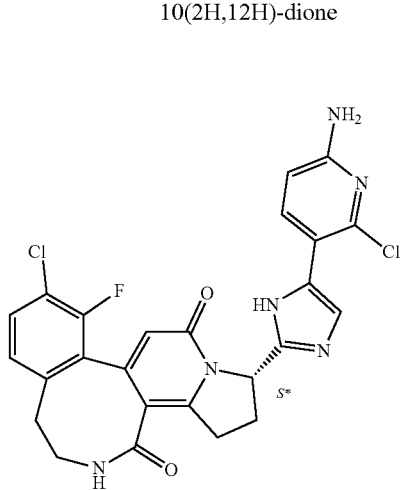

The title compound was prepared following the procedure described in Example 48 above, selecting and substituting suitable reagents and reactants, as would be readily recognized by those skilled in the art.

LC/MS: mass calculated for $C_{25}H_{19}Cl_2FN_6O_2$: 524.09, measured (ES, m/z): 525.10 [M+H]⁺. ¹H NMR (400 MHz, DMSO-d₆): δ12.16-12.36 (m, 1H), 7.99 (d, J=8.4 Hz, 1H), 7.74 (t, J=6.2 Hz, 1H), 7.59 (t, J=7.8 Hz, 1H), 7.44 (d, J=2.1 Hz, 1H), 7.18 (d, J=8.3 Hz, 1H), 6.41-6.55 (m, 1H), 6.32 (s, 2H), 6.20 (s, 1H), 5.73 (dd, J=9.0, 2.0 Hz, 1H), 3.39-3.62 (m, 2H), 3.15-3.28 (m, 1H), 2.92-3.05 (m, 2H), 2.80-2.92 (m, 1H), 2.56-2.72 (m, 1H), 2.37-2.47 (m, 1H). ¹⁹F NMR (376 MHz, DMSO-d₆) δ−73.40, −117.23.

Example 50: (S*)-7-chloro-8-fluoro-12-(3'-methyl-3H,3'H-[4,4'-biimidazol]-2-yl)-13,14-dihydro-2H-spiro[benzo[5,6]azocino[4,3-g]indolizine-3,1'-cyclopropane]-1,10(4H,12H)-dione

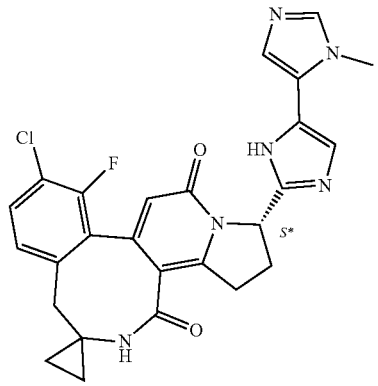 [SMILES: Cn1cncc1-c1cnc([C@@H]2CCc3c4c(cc(=O)n32)-c2c(ccc(Cl)c2F)CC2(CC2)NC4=O)[nH]1]

Step 1: 2-Bromo-1-(1-methyl-1H-imidazol-5-yl)ethan-1-one hydrobromide

To a solution of 1-(1-methyl-1H-imidazol-5-yl)ethan-1-one (1 g, 8.06 mmol, 1.0 equiv.) in acetic acid (20 mL) was added hydrogen bromide solution in acetic acid (4.0 g, 16.11 mmol, 2.0 equiv.) followed by the addition of pyridinium tribromide (2.6 g, 8.06 mmol, 1.0 equiv.) slowly. The reaction mixture was stirred for 2 h at room temperature, then concentrated under vacuum. The residue was co-evaporated twice with toluene to yield 2-bromo-1-(1-methyl-1H-imidazol-5-yl)ethan-1-one hydrobromide as a light yellow solid.

Step 2: 2-(1-methyl-1H-imidazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (100.0 mg, 0.25 mmol, 1 equiv.) in N,N-dimethylformamide (2 mL) was added potassium carbonate (68 mg, 0.50 mmol, 1.5 equiv.). After the reaction mixture was stirred at room temperature 30 min, 1-(6-amino-2-chloropyridin-3-yl)-2-bromoethan-1-one (93 mg, 0.37 mmol, 1.5 equiv.) was added. The reaction mixture was stirred 2 h at room temperature. The mixture was purified by reverse column chromatography with CH$_3$CN/0.05% TFA water (5%-80%) to yield 2-(1-methyl-1H-imidazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as an light yellow solid. LC/MS: mass calculated for C$_{26}$H$_{22}$ClFN$_4$O$_5$: 524.13, measured: 525.15 [M+H]$^+$.

Step 3: (S)-7-chloro-8-fluoro-12-(3'-methyl-3H,3'H-[4,4'-biimidazol]-2-yl)-13,14-dihydro-2H-spiro[benzo[5,6]azocino[4,3-g]indolizine-3,1'-cyclopropane]-1,10(4H,12H)-dione To a solution of 2-(1-methyl-1H-imidazol-4-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (80 mg, 0.15 mmol, 1.0 equiv.) in toluene (20 mL) was added ammonium acetate (176 mg, 2.29 mmol, 15.0 equiv.) and acetic acid glacial (92 mg, 1.52 mmol, 10.0 equiv.). The reaction mixture was stirred at 100° C. for 16 h. The residue was concentrated, and purified by silica gel chromatography (0-10% MeOH/DCM) to yield 7-chloro-8-fluoro-12-(3'-methyl-3H,3'H-[4,4'-biimidazol]-2-yl)-13,14-dihydro-2H-spiro[benzo[5,6]azocino[4,3-g]indolizine-3,1'-cyclopropane]-1,10(4H,12H)-dione as light yellow solid. The racemic mixture was purified by Prep-Chiral-HPLC with MtBE (0.1% DEA):EtOH=70:30 to yield (S)7-chloro-8-fluoro-12-(3'-methyl-3H,3'H-[4,4'-biimidazol]-2-yl)-13,14-dihydro-2H-spiro[benzo[5,6]azocino[4,3-g]indolizine-3,1'-cyclopropane]-1,10(4H,12H)-dione as an light yellow solid.

LC/MS: mass calculated for C$_{26}$H$_{22}$ClFN$_6$O$_2$: 504.15, measured (ES, m/z): 505.15 [M+H]$^+$ $^1$H NMR (400 MHz, DMSO-d$_6$) δ12.44 (s, 1H), 8.17 (s, 1H), 7.60 (t, J=7.9 Hz, 1H), 7.54 (s, 1H), 7.31 (d, J=2.0 Hz, 1H), 7.12-7.22 (m, 1H), 6.98 (d, J=1.2 Hz, 1H), 6.21 (s, 1H), 5.78 (d, J=8.5 Hz, 1H), 3.71 (d, J=13.9 Hz, 3H), 3.26-3.32 (m, 1H), 3.16 (d, J=15.5 Hz, 1H), 2.73 (d, J=15.5 Hz, 1H), 2.56-2.67 (m, 2H), 2.22-2.30 (m, 1H), 0.97-1.04 (m, 1H), 0.77 (d, J=5.6 Hz, 2H), 0.56-0.63 (m, 1H). $^{19}$F NMR (376 MHz, DMSO-d$_6$) δ−117.03

Example 51: (R*)-7-chloro-8-fluoro-12-(3'-methyl-3H,3'H-[4,4'-biimidazol]-2-yl)-13,14-dihydro-2H-spiro[benzo[5,6]azocino[4,3-g]indolizine-3,1'-cyclopropane]-1,10(4H,12H)-dione

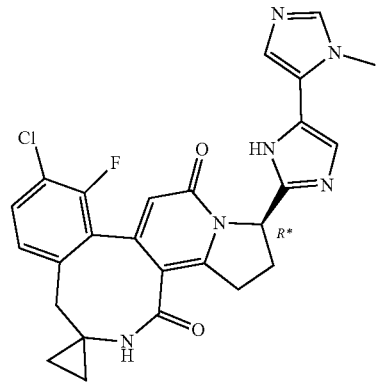 [SMILES: Cn1cncc1-c1cnc([C@H]2CCc3c4c(cc(=O)n32)-c2c(ccc(Cl)c2F)CC2(CC2)NC4=O)[nH]1]

LC/MS: mass calculated for C$_{26}$H$_{22}$ClFN$_6$O$_2$: 504.15, measured (ES, m/z): 505.15 [M+H]$^+$ $^1$H NMR (400 MHz, DMSO-d$_6$) δ12.40 (s, 1H), 8.07 (s, 1H), 7.79 (s, 1H), 7.61 (t, J=7.9 Hz, 1H), 7.36 (s, 1H), 7.20 (d, J=8.4 Hz, 1H), 7.13 (s, 1H), 6.22 (s, 1H), 5.79 (d, J=8.6 Hz, 1H), 3.74 (s, 3H), 3.44-3.54 (m, 1H), 3.07 (d, J=15.2 Hz, 1H), 2.91-3.02 (m, 2H), 2.80 (d, J=15.1 Hz, 1H), 2.57-2.67 (m, 1H), 0.76-0.88 (m, 2H), 0.61-0.69 (m, 2H). $^{19}$F NMR (376 MHz, DMSO-d$_6$) δ−117.21.

Example 52: (S)-12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

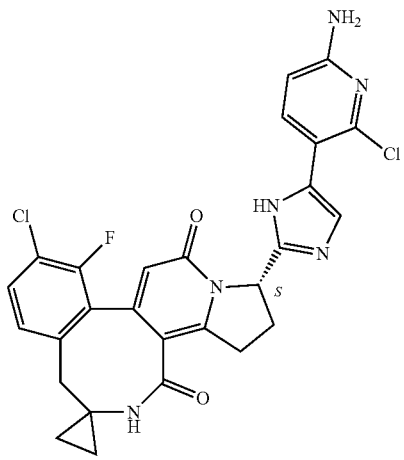

Step 1: 2-(6-amino-2-chloropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (100 mg, 0.25 mmol, 1.0 equiv.) in N,N-dimethylformamide (5 mL) was added potassium carbonate (69 mg, 0.50 mmol, 1.5 equiv.). After the reaction mixture was stirred at room temperature 30 min, 1-(6-amino-2-chloropyridin-3-yl)-2-bromoethan-1-one (93 mg, 0.37 mmol, 1.5 equiv.) was added. The reaction mixture was stirred 2 h at room temperature. The mixture was purified by reverse column chromatography with $CH_3CN$/0.05% TFA water (5%-80%) to yield 2-(6-amino-2-chloropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as an light green solid. LC/MS: mass calculated for $C_{27}H_{21}Cl_2FN_4O_5$: 570.09, measured: 571.15 $[M+H]^+$.

Step 2: (S)-12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione To a solution of 2-(6-amino-2-chloropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (60 mg, 0.11 mmol, 1.0 equiv.) in toluene (20 mL) was added ammonium acetate (121 mg, 1.58 mmol, 15.0 equiv.) and acetic acid glacial (63 mg, 1.05 mmol, 10 equiv.). The reaction mixture was stirred at 100° C. for 2 h. The residue was concentrated, and purified by silica gel chromatography (0-10% MeOH/DCM) to yield 12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as a light yellow solid. The racemic mixture was purified by Prep-Chiral-HPLC with MtBE (0.1% DEA): EtOH=70:30 to yield (S)-12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as an off-white solid.

LC/MS: mass calculated for $C_{27}H_{21}Cl_2FN_6O_2$: 550.11, measured (ES, m/z): 551.20 $[M+H]^+$. $^1H$ NMR (400 MHz, DMSO-$d_6$) δ12.34 (s, 1H), 8.18 (s, 1H), 8.00 (d, J=8.4 Hz, 1H), 7.60 (t, J=7.9 Hz, 1H), 7.45 (d, J=2.0 Hz, 1H), 7.18 (d, J=8.4 Hz, 1H), 6.41 (d, J=8.5 Hz, 1H), 6.30 (s, 2H), 6.20 (s, 1H), 5.79 (d, J=8.6 Hz, 1H), 3.28-3.31 (m, 1H), 3.17 (d, J=15.6 Hz, 1H), 2.74 (d, J=15.5 Hz, 1H), 2.52-2.67 (m, 1H), 2.20-2.29 (m, 1H), 1.76 (s, 1H), 1.02 (s, 1H), 0.80-0.89 (m, 1H), 0.74-0.78 (m, 1H), 0.58-0.62 (m, 1H). $^{19}F$ NMR (376 MHz, DMSO-$d_6$) δ 116.96.

Example 53: (R*)-12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

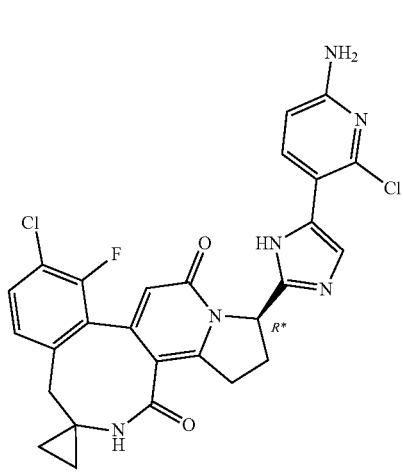 [SMILES: Nc1ccc(-c2cnc([C@H]3CCc4c5c(cc(=O)n43)-c3c(ccc(Cl)c3F)CC3(CC3)NC5=O)[nH]2)c(Cl)n1]

The title compound was prepared following the procedure described in Example 52 above, selecting and substituting suitable reagents and reactants, as would be readily recognized by those skilled in the art.

LC/MS: mass calculated for $C_{27}H_{21}Cl_2FN_6O_2$: 550.11, measured (ES, m/z): 551.20 $[M+H]^+$. $^1H$ NMR (400 MHz, DMSO-$d_6$) δ12.23 (s, 1H), 8.08 (s, 1H), 7.99 (d, J=8.4 Hz, 1H), 7.61 (t, J=7.9 Hz, 1H), 7.44 (s, 1H), 7.20 (d, J=8.3 Hz, 1H), 6.47 (d, J=8.5 Hz, 1H), 6.32 (s, 2H), 6.22 (s, 1H), 5.78 (d, J=8.8 Hz, 1H), 3.46-3.60 (m, 1H), 2.91-3.10 (m, 2H), 2.80 (d, J=15.2 Hz, 1H), 2.52-2.67 (m, 1H), 2.40-2.46 (m, 1H), 1.24 (s, 1H), 0.97-1.05 (m, 1H), 0.60-0.73 (m, 2H). $^{19}F$ NMR (376 MHz, DMSO-$d_6$) δ116.98.

Example 54: (R*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

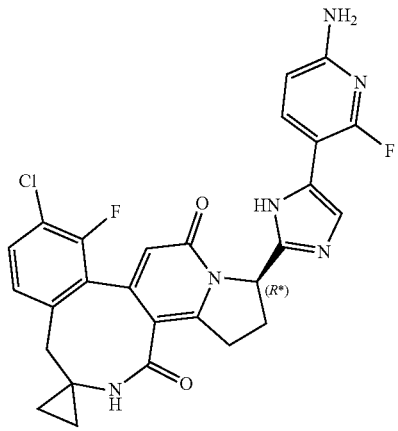 [SMILES: Nc1ccc(-c2cnc([C@H]3CCc4c5c(cc(=O)n43)-c3c(ccc(Cl)c3F)CC3(CC3)NC5=O)[nH]2)c(F)n1]

The title compound was prepared following the procedure described in Example 55 below, selecting and substituting suitable reagents and reactants, as would be readily recognized by those skilled in the art.

LC/MS: mass calculated for $C_{27}H_{21}ClF_2N_6O_2$: 534.95, measured (ES, m/z): 535.20 [M+H]$^+$. $^1$H NMR (400 MHz, DMSO-$d_6$) δ12.21 (s, 1H), 8.08 (s, 1H), 7.98 (s, 1H), 7.61-7.63 (m, 1H), 7.20 (d, J=8.3 Hz, 1H), 7.13 (s, 1H), 6.38 (d, J=8.2 Hz, 1H), 6.27 (s, 1H), 6.22 (s, 1H), 5.78 (d, J=8.7 Hz, 1H), 3.53 (s, 1H), 3.03-3.10 (m, 1H), 2.98 (dd, J=17.3, 8.5 Hz, 1H), 2.80 (d, J=15.0 Hz, 1H), 2.52-2.67 (m, 1H), 2.44 (s, 1H), 1.02-1.04 (m, 1H), 0.81 (s, 1H), 0.67-0.69 (m, 2H).

Example 55: (S)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

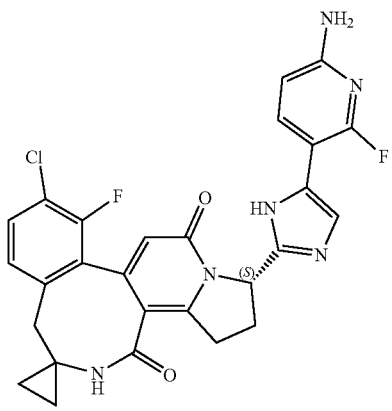

Step 1: 2-(6-amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate To a solution of 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylic acid (100.0 mg, 0.25 mmol, 1 equiv) in N,N-dimethylformamide (2 mL) was added potassium carbonate (68 mg, 0.50 mmol, 1.5 equiv). After the reaction mixture was stirred at room temperature 30 min, 1-(6-amino-2-chloropyridin-3-yl)-2-bromoethan-1-one (93.0 mg, 0.37 mmol, 1.5 equiv) was added. The reaction mixture was stirred 2 h at room temperature. The mixture was diluted with water, extracted with EA, the combined organic layers were washed with brine, dried over Na$_2$SO$_4$, filtered and evaporated to yield 2-(6-amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate as a light yellow solid, which was used in the next step without further purification.

Step 2: (S*)-12-(5-(6-Amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione To a solution of 2-(6-amino-2-fluoropyridin-3-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (100 mg, 0.18 mmol, 1.0 equiv.) in toluene (20 mL) was added ammonium acetate (208 mg, 2.70 mmol, 15.0 equiv.) and acetic acid glacial (108 mg, 1.80 mmol, 10.0 equiv.). The reaction mixture was stirred at 100° C. for 2 h. The residue was concentrated, and purified by silica gel chromatography (0→10% MeOH/DCM) to yield 12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as a light yellow solid. The racemic mixture was purified by Prep-Chiral-HPLC with MtBE (0.1% DEA):EtOH=80:20 to yield (S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as an off-white solid.

LC/MS: mass calculated for $C_{27}H_{21}ClF_2N_6O_2$: 534.95, measured (ES, m/z): 535.20 [M+H]$^+$. $^1$H NMR (400 MHz, DMSO-$d_6$) δ12.31 (s, 1H), 8.18 (s, 1H), 7.98 (dd, J=10.4, 8.2 Hz, 1H), 7.60-7.63 (m, 1H), 7.18 (d, J=8.3 Hz, 1H), 7.13 (dd, J=4.0, 2.0 Hz, 1H), 6.31 (dd, J=8.2, 2.1 Hz, 1H), 6.24 (s, 2H), 6.20 (s, 1H), 5.78 (d, J=8.5 Hz, 1H), 3.35 (s, 1H), 3.01-3.23 (m, 2H), 2.74 (d, J=15.5 Hz, 1H), 2.52-2.67 (m, 1H), 2.19-2.29 (m, 1H), 0.99-1.07 (m, 1H), 0.88-0.91 (m, 1H), 0.73-0.83 (m, 1H), 0.58-0.67 (m, 1H).

Example 56: (S*)-4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)pyridine 1-oxide

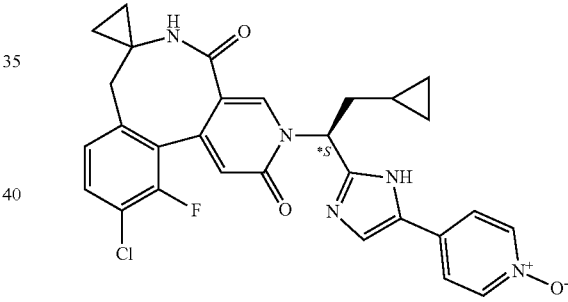

To a solution of 4-(2-((2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoyl)oxy)acetyl)pyridine 1-oxide (100 mg, 0.177 mmol, 1 equiv) in toluene (5 mL) was added ammonium acetate (136.194 mg, 1.767 mmol, 10 equiv.) and acetic acid glacial (31.831 mg, 0.530 mmol, 3 equiv.). The reaction mixture was stirred at 100° C. for 2 h. The mixture was quenched with water and extracted with ethyl acetate. The combined organic layer was dried over anhydrous sodium sulfate and concentrated under vacuum. The residue was purified by reverse column chromatography with CH$_3$CN/0.05% TFA water (5%-80%) to yield (S*)-4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)pyridine 1-oxide as an off-white solid; and (R*)-4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)pyridine 1-oxide as an off-white solid.

LC/MS: mass calculated for $C_{29}H_{25}ClFN_5O_3$: 545.16, measured: 546.20 [M+H]$^+$. $^1$H NMR (400 MHz, DMSO-$d_6$)

δ 8.36-8.30 (m, 2H), 8.10 (s, 1H), 8.00 (s, 1H), 7.89-7.78 (m, 3H), 7.62 (t, J=7.9 Hz, 1H), 7.25-7.16 (m, 1H), 6.47 (s, 1H), 6.22 (t, J=7.6 Hz, 1H), 3.15 (d, J=15.6 Hz, 1H), 2.71 (d, J=15.6 Hz, 1H), 2.25 (dt, J=13.5, 6.6 Hz, 1H), 2.07 (dt, J=14.5, 8.0 Hz, 1H), 0.95 (ddd, J=11.3, 6.9, 4.9 Hz, 1H), 0.75-0.65 (m, 2H), 0.57 (dt, J=9.6, 6.1 Hz, 1H), 0.53-0.45 (m, 1H), 0.41 (dt, J=7.4, 3.2 Hz, 2H), 0.15-0.04 (m, 2H) $^{19}$F NMR (400 MHz, DMSO-d$_6$) δ–74.43, –116.87.

Example 57: (R*)-4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropyl-ethyl)-1H-imidazol-5-yl)pyridine 1-oxide

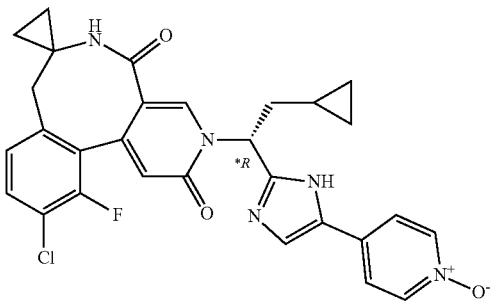 [SMILES: O=C1NC2(CC2)Cc2ccc(Cl)c(F)c2-c2cc(=O)n([C@H](CC3CC3)c3ncc(-c4cc[n+]([O-])cc4)[nH]3)cc21]

The title compound corresponds to the (R) isomer which was isolated as described in Example 56, above.

LC/MS: mass calculated for C$_{29}$H$_{25}$ClFN$_5$O$_3$: 545.16, measured: 546.20 [M+H]$^+$. $^1$H NMR (400 MHz, DMSO-d$_6$) δ 8.45-8.37 (m, 2H), 8.05 (d, J=13.9 Hz, 2H), 7.99-7.84 (m, 3H), 7.62 (t, J=7.9 Hz, 1H), 7.26-7.17 (m, 1H), 6.49 (s, 1H), 6.37-6.29 (m, 1H), 3.10 (dd, J=15.4, 1.6 Hz, 1H), 2.78 (d, J=15.3 Hz, 1H), 2.35-2.25 (m, 1H), 2.03 (dt, J=13.9, 8.0 Hz, 1H), 1.00 (td, J=10.0, 5.4 Hz, 1H), 0.79 (td, J=7.7, 3.8 Hz, 2H), 0.73-0.62 (m, 2H), 0.40 (dt, J=7.3, 3.2 Hz, 2H), 0.12 (q, J=3.7 Hz, 2H) $^{19}$F NMR (400 MHz, DMSO-d$_6$) δ–74.69, –117.11.

Example 58: (R*)-11-chloro-3-(2-cyclopropyl-1-(5-(1-methyl-6-oxo-1,6-dihydropyridazin-4-yl)-1H-imidazol-2-yl)ethyl)-12-fluoro-3H-spiro[benzo[e]pyrido[3,4-c]azocine-7,1'-cyclopropane]-2,5(6H,8H)-dione

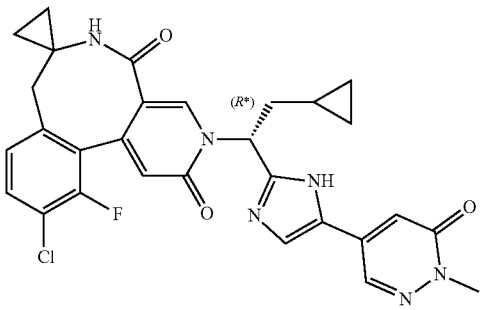 [SMILES: Cn1ncc(-c2cnc([C@@H](CC3CC3)n3cc4c(cc3=O)-c3c(ccc(Cl)c3F)CC3(CC3)NC4=O)[nH]2)cc1=O]

The title compound was prepared following the procedure described in Example 59 below, selecting and substituting suitable reagents and reactants, as would be readily recognized by those skilled in the art.

LC/MS: mass calculated for C$_{29}$H$_{26}$ClFN$_6$O$_3$:560.17, measured (ES, m/z): 561.1[M+H]$^+$. $^1$H NMR (400 MHz, DMSO-d$_6$): δ 8.35 (d, J=2.2 Hz, 1H), 8.07 (s, 1H), 8.02 (s, 1H), 7.97 (s, 1H), 7.62-7.65 (m, 1H), 7.20 (d, J=8.3 Hz, 1H), 7.11 (d, J=2.1 Hz, 1H), 6.48 (s, 1H), 6.33-6.35 (m, 1H), 3.64 (s, 3H), 3.09 (d, J=15.2 Hz, 1H), 2.78 (d, J=15.3 Hz, 1H), 2.21-2.32 (m, 1H), 2.00-2.12 (m, 1H), 0.96-1.06 (m, 1H), 0.74-0.86 (m, 2H), 0.60-0.71 (m, 2H), 0.33-0.43 (m, 2H), 0.08-0.17 (m, 2H). $^{19}$F NMR (376 MHz, DMSO-d$_6$): δ–74.63, –117.15.

Example 59: (S*)-11-chloro-3-(2-cyclopropyl-1-(5-(1-methyl-6-oxo-1,6-dihydropyridazin-4-yl)-1H-imidazol-2-yl)ethyl)-12-fluoro-3H-spiro[benzo[e]pyrido[3,4-c]azocine-7,1'-cyclopropane]-2,5(6H,8H)-dione

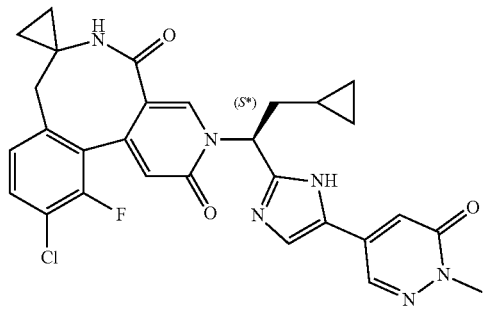 [SMILES: Cn1ncc(-c2cnc([C@H](CC3CC3)n3cc4c(cc3=O)-c3c(ccc(Cl)c3F)CC3(CC3)NC4=O)[nH]2)cc1=O]

Step 1: 2-(1-Methyl-6-oxo-1,6-dihydropyridazin-4-yl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate To a solution of 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoic acid (0.12 g, 0.28 mmol, 1.0 equiv.) in DMF (8 mL) was added cesium carbonate (0.054 g, 0.17 mmol, 0.6 equiv.). After the mixture was stirred for 1 h, 5-(2-bromoacetyl)-2-methylpyridazin-3(2H)-one (0.13 g, 0.56 mmol, 2.0 equiv.) was added. The reaction mixture was stirred at room temperature for 1 h, quenched with water, extracted withe EA, washed with brine, dried over Na$_2$SO$_4$, and concentrated under vacuum to yield 2-(1-methyl-6-oxo-1,6-dihydropyridazin-4-yl)-2-oxoethyl 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoate as a light yellow solid. LC/MS: mass calculated for C$_{29}$H$_{26}$ClFN$_4$O$_6$: 580.15, measured (ES, m/z): 581.10 [M+H]$^+$.

Step 2: (S*)-11-Chloro-3-(2-cyclopropyl-1-(5-(1-methyl-6-oxo-1,6-dihydropyridazin-4-yl)-1H-imidazol-2-yl)ethyl)-12-fluoro-3H-spiro[benzo[e]pyrido[3,4-c]azocine-7,1'-cyclopropane]-2,5(6H,8H)-dione To a solution of 2-(1-methyl-6-oxo-1,6-dihydropyridazin-4-yl)-2-oxoethyl 2-{4'-chloro-3'-fluoro-11',15'-dioxo-10', 14'-diazaspiro[cyclopropane-1,9'-tricyclo[10.4.0.0$^{2,7}$]hexadecane]-1'(16'), 2'(7),3',5',12'-pentaen-14'-yl}-3-cyclopropylpropanoate (0.16 g, 0.28 mmol, 1.0 equiv.) was added ammonium acetate (0.21 g, 2.75 mmol, 10.0 equiv.) followed by the addition of acetic acid (0.5 mL) under N$_2$. The reaction mixture was stirred for 2 h at 100° C., then cooled to room temperature and concentrated under vacuum. The residue was purified by reverse column chromatography with CH$_3$CN/0.05% TFA water (5→80%) to yield (*S)-11-chloro-3-(2-cyclopropyl-1-(5-(1-methyl-6-oxo-1,6-dihydropyridazin-4-yl)-1H-imidazol-2-yl)ethyl)-12-fluoro-3H-spiro[benzo[e]pyrido[3,4-c]azocine-7,1'-cyclopropane]-2,5 (6H,8H)-dione as an off-white solid.

LC/MS: mass calculated for C$_{29}$H$_{26}$ClFN$_6$O$_3$:560.17, measured (ES, m/z): 561.1[M+H]$^+$. $^1$H NMR (400 MHz, DMSO-d$_6$): δ 8.32 (d, J=2.1 Hz, 1H), 8.11 (s, 1H), 8.05 (s, 1H), 7.90 (s, 1H), 7.62-7.65 (m, 1H), 7.19 (d, J=8.3 Hz, 1H), 7.06 (d, J=2.1 Hz, 1H), 6.46 (s, 1H), 6.25-6.28 (m, 1H), 3.63 (s, 3H), 3.17 (d, J=15.6 Hz, 1H), 2.71 (d, J=15.6 Hz, 1H), 2.15-2.26 (m, 1H), 2.03-2.15 (m, 1H), 0.91-1.01 (m, 1H), 0.70-0.79 (m, 1H), 0.63-0.70 (m, 1H), 0.53-0.62 (m, 2H), 0.36-0.44 (m, 2H), 0.05-0.13 (m, 2H). $^{19}$F NMR (376 MHz, DMSO-d$_6$): δ−74.68, −116.87 Example 60: (R*)-11-chloro-3-(2-cyclopropyl-1-(5-(1-methyl-6-oxo-1,6-dihydropyridin-3-yl)-1H-imidazol-2-yl)ethyl)-12-fluoro-3H-spiro[benzo[e]pyrido[3,4-c]azocine-7,1'-cyclopropane]-2,5(6H,8H)-dione

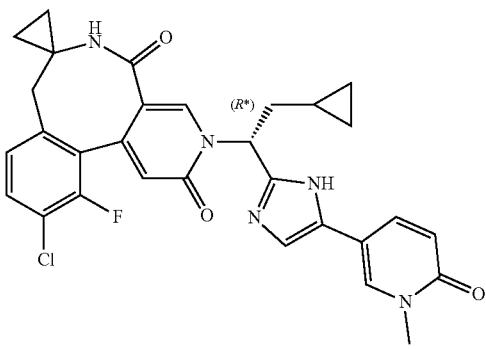 [SMILES: Cn1cc(-c2cnc([C@@H](CC3CC3)n3cc4c(cc3=O)-c3c(ccc(Cl)c3F)CC3(CC3)NC4=O)[nH]2)ccc1=O]

LC/MS: mass calculated for C$_{30}$H$_{27}$ClFN$_5$O$_3$:559.18, measured (ES, m/z): 560.1 [M+H]$^+$. $^1$H NMR (300 MHz, DMSO-d$_6$): δ 7.99-8.10 (m, 2H), 7.89 (s, 1H), 7.75-7.86 (m, 1H), 7.61-7.63 (m, 1H), 7.43-7.51 (m, 1H), 7.16-7.26 (m, 1H), 6.39-6.51 (m, 2H), 6.30-6.33 (m, 1H), 3.42-3.53 (m, 3H), 3.10 (d, J=15.5 Hz, 1H), 2.79 (d, J=15.3 Hz, 1H), 2.22-2.38 (m, 1H), 1.84-2.03 (m, 1H), 0.93-1.06 (m, 1H), 0.58-0.86 (m, 4H), 0.31-0.45 (m, 2H), 0.06-0.16 (m, 2H). $^{19}$F NMR (282 MHz, DMSO-d$_6$): δ−73.41, −117.16.

Example 61: Methyl (S)-(4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)phenyl) carbamate

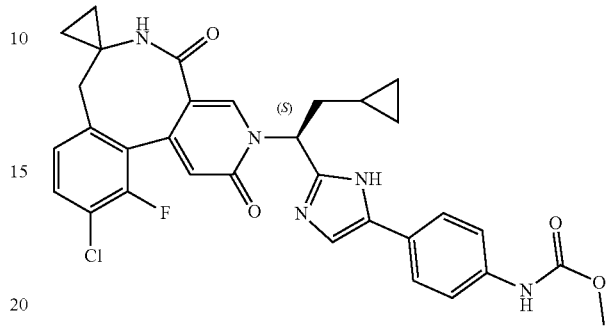

Step 1: 2-(4-((Methoxycarbonyl)amino)phenyl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate To a solution of 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoic acid (120 mg, 0.28 mmol, 1.0 equiv.) in DMF (10 mL) was added potassium carbonate (120 gm, 0.84 mmol, 3.0 equiv.). After the mixture was stirred for 30 min, methyl 4-(2-chloroacetyl)phenylcarbamate (95 mg, 0.42 mmol, 1.5 equiv.) was added. The reaction mixture was stirred at room temperature for 4 h, quenched with water, extracted withe EA, washed with brine, dried over Na$_2$SO$_4$, and concentrated under vacuum to yield 2-{4-[(methoxycarbonyl)amino]phenyl}-2-oxoethyl 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoate as a light brown solid. LC/MS: mass calculated for C$_{32}$H$_{29}$ClFN$_3$O$_7$: 621.17, measured (ES, m/z): 622.20 [M+H]$^+$.

Step 2: Methyl (S)-(4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)phenyl)carbamate To a solution of 2-{4-[(methoxycarbonyl)amino]phenyl}-2-oxoethyl 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'), 3',5',12'-pentaen-14'-yl}-3-cyclopropylpropanoate (0.17 g, 0.27 mmol, 1.0 equiv.) was added ammonium acetate (0.21 g, 2.73 mmol, 10.0 equiv.) followed by the addition of acetic acid (0.5 mL) under N$_2$. The reaction mixture was stirred for 2 h at 100° C., then cooled to room temperature and concentrated under vacuum. The residue was purified by reverse column chromatography with CH$_3$CN/0.05% TFA water (5→80%) to yield methyl (S)-(4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)phenyl)carbamate as a white solid.

LC/MS: mass calculated for $C_{32}H_{29}ClFN_5O_4$:601.19, measured (ES, m/z): 602.1 [M+H]⁺. ¹H NMR (300 MHz, DMSO-$d_6$): δ 9.55-9.78 (m, 1H), 8.02-8.13 (m, 1H), 7.82-7.94 (m, 1H), 7.56-7.71 (m, 3H), 7.27-7.56 (m, 3H), 7.18 (d, J=8.3 Hz, 1H), 6.46 (s, 1H), 6.21-6.35 (m, 1H), 3.67 (s, 3H), 3.15 (d, J=15.7 Hz, 1H), 2.71 (d, J=15.7 Hz, 1H), 2.16-2.31 (m, 1H), 1.85-2.09 (m, 1H), 0.83-0.98 (m, 1H), 0.63-0.77 (m, 2H), 0.45-0.62 (m, 2H), 0.29-0.45 (m, 2H), 0.03-0.16 (m, 2H). ¹⁹F NMR (282 MHz, DMSO-$d_6$): δ−116.90.

Example 62: Methyl (R*)-(4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)phenyl)carbamate

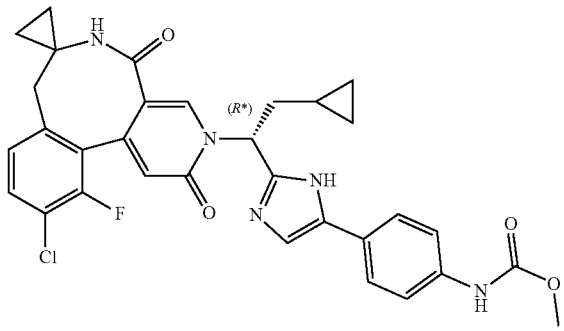

Step 1: 2-(4-((methoxycarbonyl)amino)phenyl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate To a solution of 2-{4'-chloro-3'-fluoro-11',15'-dioxo-10',14'-diazaspiro[cyclopropane-1,9'-tricyclo[10.4.0.0²,⁷]hexadecane]-1'(16'),2'(7'),3',5',12'-pentaen-14'-yl}-3-cyclopropylpropanoic acid (0.12 g, 0.28 mmol, 1.0 equiv) in DMF (10 mL) was added potassium carbonate (0.115 g, 0.84 mmol, 3 equiv). After the mixture was stirred for 30 min, methyl 4-(2-chloroacetyl)phenylcarbamate (0.095 g, 0.42 mmol, 1.5 equiv) was added. The reaction mixture was stirred for 4 h at room temperature, quenched with water, extracted withe EA, washed with brine, dried over $Na_2SO_4$, and concentrated under vacuum to yield 2-{4-[(methoxycarbonyl)amino]phenyl}-2-oxoethyl 2-{4'-chloro-3'-fluoro-11',15'-dioxo-10',14'-diazaspiro[cyclopropane-1,9'-tricyclo[10.4.0.0²,⁷]hexadecane]-1'(16'),2'(7'),3',5',12'-pentaen-14'-yl}-3-cyclopropylpropanoate as a light brown solid.

Step 2: methyl N-(4-{2-[(1*R)-1-{4'-chloro-3'-fluoro-11',15'-dioxo-10',14'-diazaspiro[cyclopropane-1,9'-tricyclo[10.4.0.0²,⁷]hexadecane]-1'(16'),2'(7'),3',5',12'-pentaen-14'-yl}-2-cyclopropylethyl]-1H-imidazol-5-yl}phenyl)carbamate To a solution of 2-{4-[(methoxycarbonyl)amino]phenyl}-2-oxoethyl 2-{4'-chloro-3'-fluoro-11',15'-dioxo-10',14'-diazaspiro[cyclopropane-1,9'-tricyclo[10.4.0.0²,⁷]hexadecane]-1'(16'),2'(7'), 3',5',12'-pentaen-14'-yl}-3-cyclopropylpropanoate (170 mg, 0.27 mmol, 1.0 equiv.) was added ammonium acetate (211 mg, 2.73 mmol, 10.0 equiv.) followed by the addition of acetic acid (0.5 mL) under $N_2$. The reaction mixture was stirred for 2 h at 100° C., then cooled to room temperature and concentrated under vacuum. The residue was purified by reverse column chromatography with $CH_3CN$/0.05% TFA water (5%-80%) to yield methyl N-(4-{2-[(1*R)-1-{4'-chloro-3'-fluoro-11',15'-dioxo-10',14'-diazaspiro[cyclopropane-1,9'-tricyclo[10.4.0.0²,⁷]hexadecane]-1'(16'),2'(7'),3',5',12'-pentaen-14'-yl}-2-cyclopropylethyl]-1H-imidazol-5-yl}phenyl)carbamate as a white solid.

LC/MS: mass calculated for $C_{32}H_{29}ClFN_5O_4$:601.19, measured (ES, m/z): 602.1 [M+H]⁺. ¹H NMR (300 MHz, DMSO-$d_6$): δ 12.31-12.52 (m, 1H), 9.58-9.75 (m, 1H), 7.95-8.05 (m, 2H), 7.54-7.73 (m, 4H), 7.31-7.53 (m, 2H), 7.20 (d, J=8.4 Hz, 1H), 6.47 (s, 1H), 6.25-6.39 (m, 1H), 3.62-3.72 (m, 3H), 3.10 (d, J=15.2 Hz, 1H), 2.79 (d, J=15.2 Hz, 1H), 2.24-2.37 (m, 1H), 1.84-2.03 (m, 1H), 0.96-1.06 (m, 1H), 0.60-0.86 (m, 4H), 0.34-0.44 (m, 2H), 0.07-0.19 (m, 2H). ¹⁹F NMR (282 MHz, DMSO-$d_6$): δ−117.13.

Example 63: (S*)-11-chloro-3-(2-cyclopropyl-1-(5-(1-methyl-6-oxo-1,6-dihydropyridin-3-yl)-1H-imidazol-2-yl)ethyl)-12-fluoro-3H-spiro[benzo[e]pyrido[3,4-c]azocine-7,1'-cyclopropan]-2,5(6H,8H)-dione

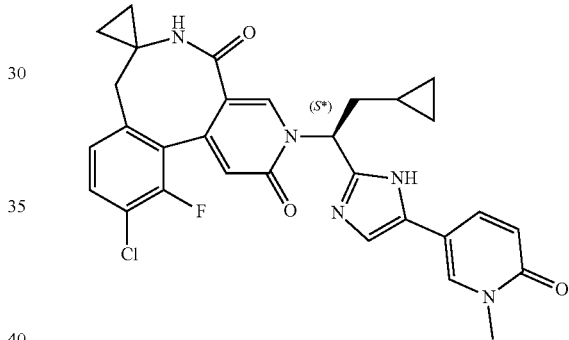

Step 1: 2-(1-Methyl-6-oxo-1,6-dihydropyridin-3-yl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate To a solution of 2-{4'-chloro-3'-fluoro-11',15'-dioxo-10',14'-diazaspiro[cyclopropane-1,9'-tricyclo[10.4.0.0²,⁷]hexadecane]-1'(16'),2'(7'),3',5',12'-pentaen-14'-yl}-3-cyclopropylpropanoic acid (0.12 g, 0.28 mmol, 1.0 equiv.) in DMF (10 mL) was added potassium carbonate (0.12 g, 0.84 mmol, 3.0 equiv.). After the mixture was stirred for 30 min, 5-(2-bromoacetyl)-1-methylpyridin-2(1H)-one (0.077 g, 0.33 mmol, 1.2 equiv.) was added. The reaction mixture was stirred at room temperature for 2 h, quenched with water, extracted withe EA, washed with brine, dried over $Na_2SO_4$, and concentrated under vacuum to yield 2-(1-methyl-6-oxo-1,6-dihydropyridin-3-yl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate as a light yellow solid. LC/MS: mass calculated for $C_{30}H_{27}ClFN_3O_6$: 579.16, measured (ES, m/z): 580.05 [M+H]⁺.

Step 2: (S*)-11-Chloro-3-(2-cyclopropyl-1-(5-(1-methyl-6-oxo-1,6-dihydropyridin-3-yl)-1H-imidazol-2-yl)ethyl)-12-fluoro-3H-spiro[benzo[e]pyrido[3,4-c]azocine-7,1'-cyclopropane]-2,5(6H,8H)-dione To a solution of 2-(1-methyl-6-oxo-1,6-dihydropyridin-3-yl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate (0.16 g, 0.29 mmol, 1.0 equiv.) was added ammonium acetate (0.22 g, 2.86 mmol, 10.0 equiv.) followed by the addition of acetic acid (0.5 mL) under $N_2$. The reaction mixture was stirred for 2 h at 100° C., then cooled to room temperature and concentrated under vacuum. The residue was purified by reverse column chromatography with $CH_3CN$/0.05% TFA water (5→80%) to yield (S*)-11-chloro-3-(2-cyclopropyl-1-(5-(1-methyl-6-oxo-1,6-dihydropyridin-3-yl)-1H-imidazol-2-yl)ethyl)-12-fluoro-3H-spiro[benzo[e]pyrido[3,4-c]azocine-7,1'-cyclopropane]-2,5(6H,8H)-dione as a white solid.

LC/MS: mass calculated for $C_{30}H_{27}ClFN_5O_3$:559.18, measured (ES, m/z): 560.1 [M+H]$^+$. $^1$H NMR (300 MHz, DMSO-$d_6$): δ 7.96-8.12 (m, 2H), 7.80 (d, J=12.3 Hz, 2H), 7.61 (t, J=7.9 Hz, 1H), 7.46 (s, 1H), 7.19 (d, J=8.3 Hz, 1H), 6.37-6.49 (m, 2H), 6.22 (t, J=7.8 Hz, 1H), 3.47 (s, 3H), 3.17 (d, J=15.6 Hz, 1H), 2.70 (d, J=15.7 Hz, 1H), 2.17-2.32 (m, 1H), 1.89-2.06 (m, 1H), 0.87-1.02 (m, 1H), 0.45-0.80 (m, 4H), 0.33-0.45 (m, 2H), 0.04-0.15 (m, 2H). $^{19}$F NMR (282 MHz, DMSO-$d_6$): δ−73.41, −116.87.

Example 64: (R*)-11-chloro-3-(2-cyclopropyl-1-(5-(4-fluorophenyl)-1H-imidazol-2-yl)ethyl)-12-fluoro-3H-spiro[benzo[e]pyrido[3,4-c]azocine-7,1'-cyclopropane]-2,5(6H,8H)-dione

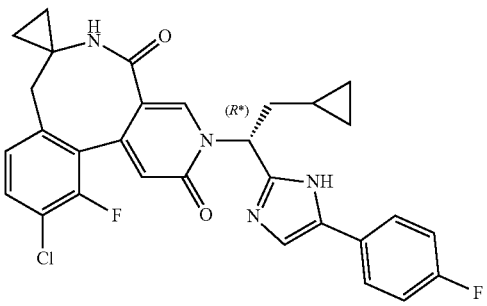

The title compound was prepared following the procedure described in Example 65 below, selecting and substituting suitable reagents and reactants, as would be readily recognized by those skilled in the art.

LC-MS: (ES, m/z): 547.0 [M+H]$^+$1H NMR: (300 MHz, DMSO-$d_6$): δ 7.96-8.03 (m, 2H), 7.70-7.87 (m, 2H), 7.57-7.68 (m, 2H), 7.13-7.31 (m, 3H), 6.47 (s, 1H), 6.28-6.39 (m, 1H), 3.10 (d, J=15.3 Hz, 1H), 2.79 (d, J=15.4 Hz, 1H), 2.22-2.38 (m, 1H), 1.87-2.06 (m, 1H), 0.94-1.07 (m, 1H), 0.61-0.85 (m, 4H), 0.31-0.47 (m, 2H), 0.06-0.17 (m, 2H). F NMR: (282 MHz, DMSO-$d_6$): δ−116.56, −116.91.

Example 65: (S*)-11-chloro-3-(2-cyclopropyl-1-(5-(4-fluorophenyl)-1H-imidazol-2-yl)ethyl)-12-fluoro-3H-spiro[benzo[e]pyrido[3,4-c]azocine-7,1'-cyclopropane]-2,5(6H,8H)-dione

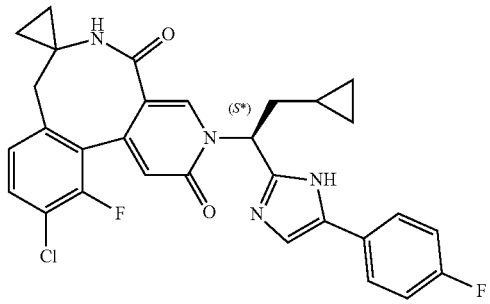

Step 1: 2-(4-Fluorophenyl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate To a solution of 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoic acid (120 mg, 0.28 mmol, 1.0 equiv.) in DMF (10 mL) was added potassium carbonate (120 mg, 0.84 mmol, 3.0 equiv.). After the mixture was stirred for 30 min, 2-bromo-1-(4-fluorophenyl)ethanone (73 mg, 0.33 mmol, 1.2 equiv.) was added. The reaction mixture was stirred at room temperature for 2 h, quenched with water, extracted withe EA, washed with brine, dried over $Na_2SO_4$ and concentrated under vacuum to yield 2-(4-fluorophenyl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate as a light yellow solid. LC/MS: mass calculated for $C_{30}H_{25}ClF_2N_2O_5$: 566.14, measured (ES, m/z): 567.10 [M+H]$^+$.

Step 2: (S*)-11-Chloro-3-(2-cyclopropyl-1-(5-(4-fluorophenyl)-1H-imidazol-2-yl)ethyl)-12-fluoro-3H-spiro[benzo[e]pyrido[3,4-c]azocine-7,1'-cyclopropane]-2,5(6H,8H)-dione To a solution of 2-(4-fluorophenyl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate (160 mg, 0.29 mmol, 1.0 equiv.) was added ammonium acetate (230 mg, 2.93 mmol, 10.0 equiv.) followed by the addition of acetic acid (0.5 mL) under $N_2$. The reaction mixture was stirred for 2 h at 100° C., then cooled to room temperature and concentrated under vacuum. The residue was purified by reverse column chromatography with $CH_3CN$/0.05% TFA water (5→80%) to yield (S*)-11-chloro-3-(2-cyclopropyl-1-(5-(4-fluorophenyl)-1H-imidazol-2-yl)ethyl)-12-fluoro-3H-spiro[benzo[e]pyrido[3,4-c]azocine-7,1'-cyclopropane]-2,5(6H,8H)-dione as a white solid.

LC/MS: mass calculated for $C_{30}H_{25}ClF_2N_4O_2$:546.16, measured (ES, m/z): 547.1 [M+H]$^+$. $^1$H NMR (300 MHz, DMSO-$d_6$): δ 8.00-8.13 (m, 1H), 7.89 (s, 1H), 7.68-7.86 (m, 2H), 7.57-7.68 (m, 2H), 7.12-7.40 (m, 3H), 6.46 (s, 1H), 6.19-6.36 (m, 1H), 3.15 (d, J=15.6 Hz, 1H), 2.70 (d, J=15.9

Hz, 1H), 2.16-2.33 (m, 1H), 1.86-2.07 (m, 1H), 0.84-1.00 (m, 1H), 0.63-0.78 (m, 2H), 0.28-0.62 (m, 4H), 0.09 (s, 2H). $^{19}$F NMR (282 MHz, DMSO-d$_6$): δ–116.65, –116.91.

Example 66: (R*)-11-chloro-3-(2-cyclopropyl-1-(5-(pyridin-4-yl)-1H-imidazol-2-yl)ethyl)-12-fluoro-3H-spiro[benzo[e]pyrido[3,4-c]azocine-7,1'-cyclopropane]-2,5(6H,8H)-dione

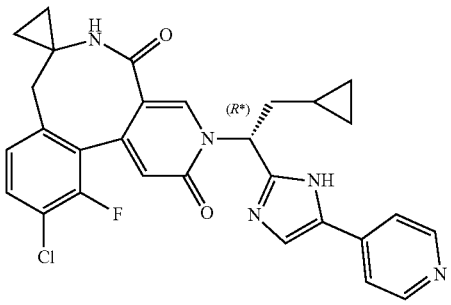

The title compound was prepared following the procedure described in Example 67 below, selecting and substituting suitable reagents and reactants, as would be readily recognized by those skilled in the art.

LC/MS: mass calculated for $C_{29}H_{25}ClFN_5O_2$: 529.17, measured (ES, m/z): 530.1 [M+H]$^+$. $^1$H NMR (300 MHz, DMSO-d$_6$): δ13.24 (s, 1H), 8.77 (d, J=6.4 Hz, 2H), 8.42 (s, 1H), 8.22 (d, J=6.3 Hz, 2H), 8.04 (s, 1H), 7.92 (s, 1H), 7.62-7.65 (m, 1H), 7.21 (d, J=8.3 Hz, 1H), 6.50 (s, 1H), 6.32-6.42 (m, 1H), 3.11 (d, J=15.1 Hz, 1H), 2.79 (d, J=15.3 Hz, 1H), 2.24-2.38 (m, 1H), 2.01-2.16 (m, 1H), 0.92-1.08 (m, 1H), 0.75-0.88 (m, 2H), 0.61-0.75 (m, 2H), 0.36-0.47 (m, 2H), 0.05-0.21 (m, 2H). $^{19}$F NMR (282 MHz, DMSO-d$_6$): δ–73.90, –117.16.

Example 67: (S*)-11-chloro-3-(2-cyclopropyl-1-(5-(pyridin-4-yl)-1H-imidazol-2-yl)ethyl)-12-fluoro-3H-spiro[benzo[e]pyrido[3,4-c]azocine-7,1'-cyclopropane]-2,5(6H,8H)-dione

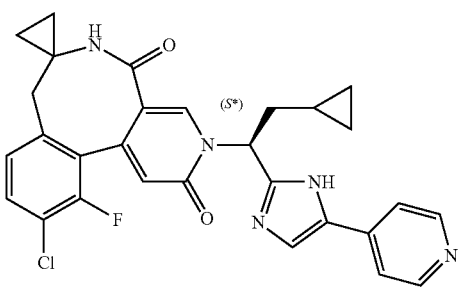 [SMILES: O=C1NC2(CC2)Cc2ccc(Cl)c(F)c2-c2cc(=O)n([C@@H](CC3CC3)c3ncc(-c4ccncc4)[nH]3)cc21]

Step 1: 2-Oxo-2-(pyridin-4-yl)ethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate To a solution of 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoic acid (330 mg, 0.77 mmol, 1.0 equiv.) in DMF (10 mL) was added potassium carbonate (423 mg, 3.06 mmol, 4 equiv.). After the mixture was stirred for 30 min, 2-bromo-1-(pyridin-4-yl)ethanone hydrobromide (430 mg, 1.53 mmol, 2 equiv.) was added. The reaction mixture was stirred for 3 h at room temperature, then quenched with water, extracted with EA, washed with brine, dried over Na$_2$SO$_4$, and concentrated under vacuum to yield 2-oxo-2-(pyridin-4-yl)ethyl 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoate as brown oil. LC/MS: mass calculated for $C_{29}H_{25}ClFN_3O_5$: 549.15, measured (ES, m/z): 550.10 [M+H]$^+$.

Step 2: (S)-11-chloro-3-(2-cyclopropyl-1-(5-(pyridin-4-yl)-1H-imidazol-2-yl)ethyl)-12-fluoro-3H-spiro[benzo[e]pyrido[3,4-c]azocine-7,1'-cyclopropane]-2,5(6H,8H)-dione To a solution of 2-oxo-2-(pyridin-4-yl)ethyl 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoate (380 mg, 0.69 mmol, 1.0 equiv.) in toluene (20 mL) was added ammonium acetate (533 mg, 6.91 mmol, 10 equiv.) followed by the addition of acetic acid (0.5 mL) under N$_2$. The reaction mixture was stirred for 1 h at 100° C., then cooled to room temperature and concentrated under vacuum. The residue was purified by reverse column chromatography with CH$_3$CN/0.05% TFA water (5%-80%) to yield (S)-11-chloro-3-(2-cyclopropyl-1-(5-(pyridin-4-yl)-1H-imidazol-2-yl)ethyl)-12-fluoro-3H-spiro[benzo[e]pyrido[3,4-c]azocine-7,1'-cyclopropane]-2,5(6H,8H)-dione as white solid.

LC/MS: mass calculated for $C_{29}H_{25}ClFN_5O_2$: 529.17, measured (ES, m/z): 530.1 [M+H]$^+$. $^1$H NMR (300 MHz, DMSO-d$_6$): δ13.16 (s, 1H), 8.75 (s, 2H), 8.39 (s, 1H), 8.19 (d, J=5.7 Hz, 2H), 8.11 (s, 1H), 7.87 (s, 1H), 7.63-7.65 (m, 1H), 7.20 (d, J=8.4 Hz, 1H), 6.48 (s, 1H), 6.15-6.28 (m, 1H), 3.16 (d, J=16.0 Hz, 1H), 2.67-2.78 (m, 1H), 2.20-2.33 (m, 1H), 2.05-2.20 (m, 1H), 1.46 (s, 1H), 0.90-1.01 (m, 1H), 0.65-0.79 (m, 2H), 0.46-0.64 (m, 2H), 0.33-0.46 (m, 2H), 0.05-0.16 (m, 2H). $^{19}$F NMR (282 MHz, DMSO-d$_6$): δ–73.8, –116.90.

Example 68: (R*)-11-chloro-3-(2-cyclopropyl-1-(5-(1-methyl-2-oxo-1,2-dihydropyridin-4-yl)-1H-imidazol-2-yl)ethyl)-12-fluoro-3H-spiro[benzo[e]pyrido[3,4-c]azocine-7,1'-cyclopropane]-2,5(6H,8H)-dione

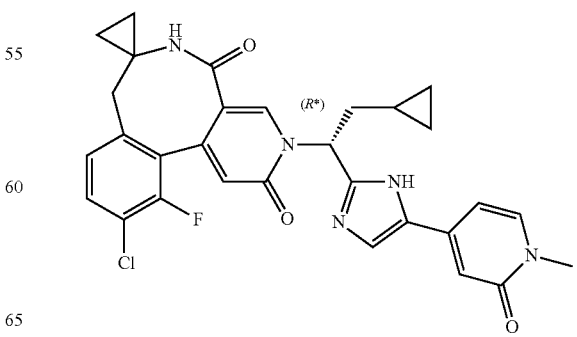

The title compound was prepared following the procedure described in Example 69 below, selecting and substituting suitable reagents and reactants, as would be readily recognized by those skilled in the art.

LC/MS: mass calculated for $C_{30}H_{27}ClFN_5O_3$:559.18, measured: 560.1 [M+H]$^+$. $^1$H NMR (300 MHz, DMSO-d$_6$): δ 7.90-8.07 (m, 3H), 7.70 (d, J=7.0 Hz, 1H), 7.62-7.65 (m, 1H), 7.20 (d, J=8.1 Hz, 1H), 6.79 (d, J=1.8 Hz, 1H), 6.64 (dd, J=7.0, 1.9 Hz, 1H), 6.48 (s, 1H), 6.31 (dd, J=8.4, 6.7 Hz, 1H), 3.41 (s, 3H), 3.10-3.13 (m, 1H), 2.78 (d, J=15.3 Hz, 1H), 2.21-2.36 (m, 1H), 1.97-2.13 (m, 1H), 0.94-1.07 (m, 1H), 0.75-0.85 (m, 2H), 0.58-0.74 (m, 2H), 0.33-0.45 (m, 2H), 0.07-0.16 (m, 2H). $^{19}$F NMR: (282 MHz, DMSO-d$_6$): δ −74.65, −117.09.

Example 69: (S*)-11-chloro-3-(2-cyclopropyl-1-(5-(1-methyl-2-oxo-1,2-dihydropyridin-4-yl)-1H-imidazol-2-yl)ethyl)-12-fluoro-3H-spiro[benzo[e]pyrido[3,4-c]azocine-7,1'-cyclopropane]-2,5(6H,8H)-dione

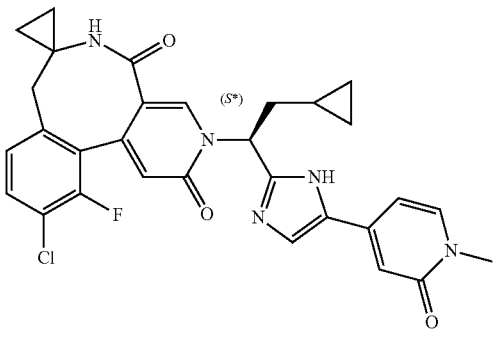 [SMILES: Cn1ccc(-c2cnc([C@H](CC3CC3)n3cc4c(cc3=O)-c3c(ccc(Cl)c3F)CC3(CC3)NC4=O)[nH]2)cc1=O]

Step 1: 2-(1-Methyl-2-oxo-1,2-dihydropyridin-4-yl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate To a solution of 2-{4'-chloro-3'-fluoro-11',15'-dioxo-10',14'-diazaspiro[cyclopropane-1,9'-tricyclo[10.4.0.0$^{2,7}$]hexadecane]-1'(16'),2'(7'),3',5',12'-pentaen-14'-yl}-3-cyclopropylpropanoic acid (0.12 g, 0.28 mmol, 1.0 equiv.) in DMF (10 mL) was added cesium carbonate (0.1 g, 0.31 mmol, 1.1 equiv.). After the mixture was stirred for 30 min, 4-(2-bromoacetyl)-1-methylpyridin-2(1H)-one (0.13 g, 0.56 mmol, 2.0 equiv.) was added. The reaction mixture was stirred overnight at room temperature. The reaction was quenched with water, extracted with EA, washed with brine, dried over Na$_2$SO$_4$, and concentrated under vacuum. The residue was purified by reverse column chromatography with CH$_3$CN/0.05% TFA water (5%-50%) to yield 2-(1-methyl-2-oxo-1,2-dihydropyridin-4-yl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate as an off-white solid. LC/MS: mass calculated for $C_{30}H_{27}ClFN_3O_6$: 579.16, measured (ES, m/z): 580.1 [M+H]$^+$ Step 2: (S*)-11-chloro-3-(2-cyclopropyl-1-(5-(1-methyl-2-oxo-1,2-dihydropyridin-4-yl)-1H-imidazol-2-yl)ethyl)-12-fluoro-3H-spiro[benzo[e]pyrido[3,4-c]azocine-7,1'-cyclopropan]-2,5(6H,8H)-dione To a solution of 2-(1-methyl-2-oxo-1,2-dihydropyridin-4-yl)-2-oxoethyl 2-(11-chloro-12-fluoro-2,5-dioxo-2,5,6,8-tetrahydro-3H-spiro[benzo[e]pyrido[3,4-c]azocine-7,1'-cyclopropan]-3-yl)-3-cyclopropylpropanoate (0.01 g, 0.017 mmol, 1.0 equiv.) in toluene (10 mL) was added ammonium acetate (0.12 g, 1.55 mmol, 10 equiv.) followed by the addition of acetic acid (0.1 mL) under N$_2$. The reaction mixture was stirred for 3 h at 100° C., then cooled to room temperature and concentrated under vacuum. The residue was purified by reverse column chromatography with CH$_3$CN/0.05% TFA water (5%-80%) to yield (S*)-11-chloro-3-(2-cyclopropyl-1-(5-(1-methyl-2-oxo-1,2-dihydropyridin-4-yl)-1H-imidazol-2-yl)ethyl)-12-fluoro-3H-spiro[benzo[e]pyrido[3,4-c]azocine-7,1'-cyclopropane]-2,5(6H,8H)-dione as a white solid LC/MS: mass calculated for $C_{30}H_{27}ClFN_5O_3$:559.18, measured: 560.1 [M+H]$^+$. $^1$H NMR (300 MHz, DMSO-d$_6$): δ 8.10 (s, 1H), 7.92 (s, 2H), 7.57-7.72 (m, 2H), 7.19 (d, J=8.3 Hz, 1H), 6.75 (d, J=1.8 Hz, 1H), 6.61 (dd, J=7.0, 1.9 Hz, 1H), 6.47 (s, 1H), 6.22-6.25 (m, 1H), 3.40 (s, 3H), 3.15 (d, J=15.6 Hz, 1H), 2.67-2.78 (m, 1H), 2.15-2.30 (m, 1H), 1.99-2.15 (m, 1H), 0.91-1.02 (m, 1H), 0.48-0.79 (m, 4H), 0.35-0.45 (m, 2H), 0.04-0.15 (m, 2H). $^{19}$F NMR (282 MHz, DMSO-d$_6$): δ −74.52, −116.92.

Example 70 (S*)-12-(5-(1H-benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

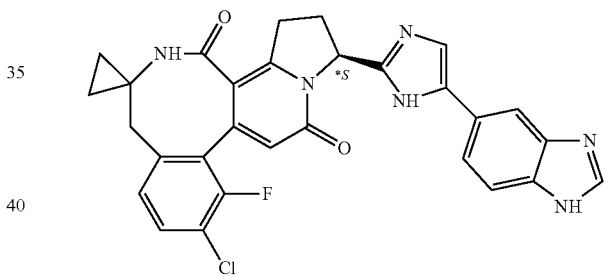

To a solution of 2-(1H-benzo[d]imidazol-5-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (60 mg, 0.107 mmol, 1.0 equiv) in acetic acid (0.2 mL) and toluene (10 mL) was added ammonium acetate (164.894 mg, 2.139 mmol, 20 equiv). The resulting mixture was stirred at 100° C. for 1 h, then cooled to room temperature and concentrated under vacuum. The residue was purified by silica gel chromatography with MeOH/DCM (0-10%) to yield a residue which was purified by Chiral-HPLC with MtBE (0.1% DEA): MeOH=70:30 to yield (S*)-12-(5-(1H-benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as a white solid.

LC/MS (ESI, m/z): 541.15 (MH$^+$). $^1$H NMR (400 MHz, Methanol-d$_4$) δ 8.15 (s, 1H), 7.94-8.03 (m, 1H), 7.63 (s, 2H), 7.48-7.52 (m, 1H), 7.42 (s, 1H), 7.12-7.14 (m, 1H), 6.37 (s, 1H), 5.95-5.98 (m, 1H), 3.10-3.17 (m, 2H), 2.91-2.95 (m, 2H), 2.60-2.84 (m, 2H), 0.88-0.95 (m, 2H), 0.78-0.83 (m, 2H). $^{19}$F NMR (400 MHz, Methanol-d$_4$) d −76.95, −117.73.

Example 71: (*S)-12-(5-(3-Bromoimidazo[1,2-a]pyridin-7-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

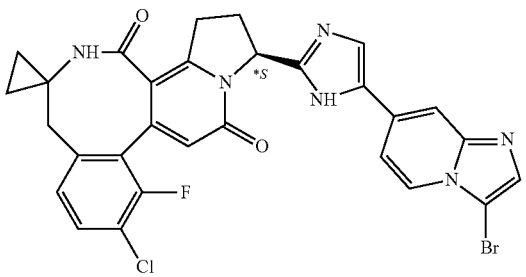 [SMILES: O=C1NC2(CC2)Cc2ccc(Cl)c(F)c2-c2cc(=O)n3c(c21)CC[C@H]3c1ncc(-c2ccn3c(Br)cnc3c2)[nH]1]

To a solution of 2-(3-bromoimidazo[1,2-a]pyridin-7-yl)-2-oxoethyl 7-chloro-8-fluoro-1,10-dioxo-1,4,10,12,13,14-hexahydro-2H-spiro[benzo[5,6]azocino[4,3-g]indolizine-3,1'-cyclopropane]-12-carboxylate (80.000 mg, 0.125 mmol) in toluene (3 ml) and acetic acid (0.06 ml) was added ammonium acetate (192.750 mg, 2.501 mmol). The resulting mixture was stirred at 100° C. for 2 h, then cooled to room temperature and concentrated under vacuum. The residue was purified by silica gel chromatography with MeOH/DCM (0-10%) to yield a residue, which was purified by Chiral-HPLC with MtBE (0.1% DEA):MeOH=50:50 to yield (*S)-12-(5-(3-bromoimidazo[1,2-a]pyridin-7-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione as a light yellow solid.

LC/MS (ESI, m/z): 620.95 (MH$^+$). $^1$H NMR (300 MHz, DMSO-d$_6$) δ 8.42 (d, J=7.3 Hz, 1H), 8.09 (s, 1H), 7.80-7.96 (m, 3H), 7.58-7.70 (m, 2H), 7.21 (d, J=8.2 Hz, 1H), 6.24 (s, 1H), 5.81 (dd, J=8.8, 2.2 Hz, 1H), 2.95-3.14 (m, 2H), 2.55-2.87 (m, 3H), 2.25-2.31 (m, 1H), 0.97-1.09 (m, 1H), 0.75-0.91 (m, 1H), 0.61-0.92 (m, 2H). $^{19}$F NMR (282 MHz, DMSO-d$_6$) δ−116.96.

Example 72: (*R)-12-(5-(3-Bromoimidazo[1,2-a]pyridin-7-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione

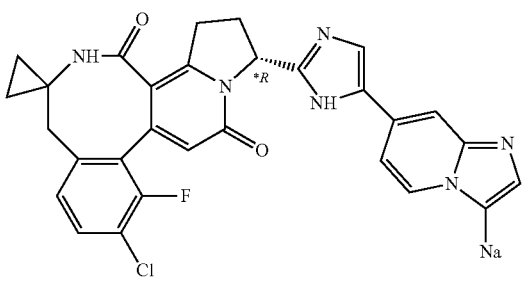

The title compound was prepared according to the procedure as described in Example 71 above, selecting and substituting suitable reagents and starting materials, as would be readily recognized by those skilled in the art.

$^1$H NMR (300 MHz, DMSO-d$_6$) δ 12.65 (s, 1H), 8.34 (d, J=7.3 Hz, 1H), 8.20 (s, 1H), 7.90 (s, 2H), 7.78 (s, 1H), 7.51-7.66 (m, 2H), 7.15-7.24 (m, 1H), 6.22 (s, 1H), 5.77-5.86 (m, 1H), 3.20 (d, J=15.0 Hz, 1H), 2.60-2.80 (m, 3H), 2.23-2.34 (m, 2H), 1.02-1.09 (m, 1H), 0.60-0.78 (m, 3H). $^{19}$F NMR (282 MHz, DMSO-d$_6$) δ−117.02.

BIOLOGICAL AND FORMULATION EXAMPLES

Biological Example 1: Factor XIa Inhibition Assay Utilizing a Fluorophore-Quencher Pair Peptide Substrate A fluorescence intensity (FLINT) based assay was used to monitor inhibition of Factor XIa. The peptide substrate, 5Fam-KLTRAETV-K5Tamra (purchased from New England Peptide) was chosen based on the FXI sequence. Conversion of zymogen FXI to its activated form, FXIa, occurs by proteolytic cleavage by FXIa at two sites, Arg146 and Arg180. The custom peptide used in this assay was based on the Arg146 cleavage site of FXI. The peptide substrate was designed with a fluorophore-quencher pair, where the fluorescence is quenched until FXIa cleaves the 8-mer peptide after the Arg residue. The substrate K$_M$ was fit to a substrate inhibition model whereby k$_{cat}$=0.86 s$^{-1}$, K$_M$=12.4 μM, K$_i$=61.6 μM with an enzymatic efficiency, and k$_{cat}$/K$_M$=69523 M$^{-1}$ s$^{-1}$.

The Factor XIa FLINT assay was used with the following 5Fam-KLTRAETV-K5Tamra assay buffer: 50 mM Tris, pH 7.5, 100 mM NaCl, 5 mM CaCl$_2$), 0.1 mg/mL BSA, 0.03% CHAPS. Assay buffer was prepared by mixing all ingredients fresh. 5Fam-KLTRAETV-K5Tamra peptide substrate was first prepared at 10 mM in 100% DMSO, then diluted to 3 mM in 100% DMSO. Assay buffer was then added directly to the 3 mM stock of substrate to prepare the 30 μM 2× working concentration (15 μM final concentration). The 2× Factor XIa stock solution was prepared by diluting 6.562 μM stock in 1× assay buffer for a 200 μM working stock solution (100 μM final concentration).

Test compound(s) were run in an 11-point, 3-fold serial dilution with a final top compound concentration of 100 nM. Final DMSO in assay was 2%. FXIa was preincubated with compound for 30-minutes and then substrate was added to initiate the reaction. The assay was run with kinetic (KIN) reads at 5 min intervals over 30 minutes. The time course was linear using 100 μM FXIa greater than 30 minutes. More specifically, the assay was run as follows:
- 100 nL of 0.01 mM test compound was dispensed into black 384-well non-binding Greiner BioOne 784900 plate for 0.1 μM final concentration;
- 5 μL of 1× assay buffer was dispensed to column 24 (low control) and 5 μL 2× Factor XIa solution was dispensed to columns 1-23 (column 23 high control);
- the plate was centrifuged with a "cover" plate at 500 rpm for 1 min
- the plate was pre-incubated for 30 minutes at room temperature with plate covered;
- 5 μL of 2×5Fam-KLTRAETV-K5Tamra peptide substrate was dispensed into the entire plate, columns 1-24;
- the plate was centrifuged with a "cover" plate at 500 rpm for 1 min;
- the plate was read monitoring fluorescence intensity on the BMG PHERAStar at room temperature, using fluorescence module 485 nm/520 nm.

Percent inhibition (IC$_{50}$) curves were generated per compound tested, and data was analyzed using a 4-parameter logistic fit using GeneData Screener. The relative fluorescence unit (RFU) values were normalized to percent inhibition using the following equation:

% inhibition=((HC−LC)−(compound−LC)/(HC−LC))
*100 where LC−low control=mean signal of no Factor XIa or 100% inhibition of Factor XIa; HC−high control=mean signal of Factor XIa+5Fam-KLTRAETV-K5Tamra peptide substrate with DMSO only.

An 11-point dose response curve for the test compound(s) was generated using GENDATA to determine $IC_{50}$ value based on the following equation:

Y=Bottom+(Top−Bottom)/(1+10^((log $IC_{50}$−X)*Hill-Slope))

where Y is the % inhibition in the presence of X inhibitor concentration, Top=high control=mean signal of Factor XIa+5Fam-KLTRAETV-K5Tamra peptide substrate with DMSO only; Bottom=low control−mean signal of no Factor XIa or 100% inhibition of Factor XIa; HillSlope−Hill coefficient; and IC50=concentration of compound with 50% inhibition in relation to top/high control.

Biological Example 2: Kallikrein Inhibition Assay Utilizing a Quenched AMC Peptide Substrate A fluorescence intensity (FLINT) based assay was used to monitor inhibition of human plasma kallikrein. The peptide substrate, Z-Gly-Pro-Arg-AMC (Purchased from Bachem; Catalog #1-1150) was chosen based on its relatively low KM for kallikrein which enables running the assay at lower substrate concentrations to control background fluorescence. The kinetic parameters for this substrate were determined by fitting titration data to the Michaelis-Menten equation yielding a $K_M$=40 μM, $k_{cat}$=0.76 s$^{-1}$, and $k_{cat}/K_M$=18932 M$^{-1}$ s$^{-1}$.

The Kallikrein FLINT assay was used with the following Z-Gly-Pro-Arg-AMC assay buffer: 50 mM Tris, pH 7.5, 100 mM NaCl, 5 mM CaCl$_2$), 0.1 mg/mL BSA, 0.03% CHAPS. Assay buffer was prepared by mixing all ingredients fresh. 2× Z-Gly-Pro-Arg-AMC peptide substrate was prepared by diluting 10 mM stock into 1× assay buffer for a 100 μM working concentration (50 μM final concentration). The 2× kallikrein stock solution was prepared by diluting 14.76 μM stock in 1× assay buffer for a 4 nM working stock solution (2 nM final concentration).

Test compound(s) were run in an 11-point, 3-fold serial dilution with a final top compound concentration of 1 μM. Final DMSO in assay was 2%. Plasma kallikrein was pre-incubated for 30-minute with compound and then 50 μM substrate was added to initiate the reaction. The assay was run with kinetic (KIN) reads at 5 min intervals over 30 minutes. The time course was linear using 2 nM kallikrein greater than 30 minutes. More specifically, the assay was run as follows:

100 nL of 0.1 mM test compound was dispensed into black 384-well non-binding Greiner BioOne 784900 plate for 1 μM final concentration;

5 μL of 1× assay buffer was dispensed to columns 24 (low control) and 5 μL 2× human kallikrein enzyme solution was dispensed to columns 1-23 (column 23 high control);

the plate was centrifuged with a "cover" plate at 500 rpm for 1 min the plate was pre-incubated for 30 minutes at room temperature with plate covered;

5 μL of 2× Z-Gly-Pro-Arg-AMC peptide substrate was dispensed into the entire plate, columns 1-24;

the plate was centrifuged with a "cover" plate at 500 rpm for 1 min; the plate was read monitoring fluorescence intensity on the BMG PHERAStar at room temperature, using fluorescence module 340 nm/440 nm.

Percent inhibition ($IC_{50}$) curves were generated per compound tested, and data was analyzed using a 4-parameter logistic fit using GeneData Screener. The relative fluorescence unit (RFU) values were normalized to percent inhibition using the following equation:

% inhibition=((HC−LC)−(compound−LC)/(HC−LC))
*100 where LC—low control=mean signal of human kallikrein enzyme or 100% inhibition of human kallikrein enzyme; HC—high control=mean signal of Factor XIa+Z-Gly-Pro-Arg-AMC peptide substrate with DMSO only.

An 11-point dose response curve for the test compound(s) was generated using GENDATA to determine $IC_{50}$ value based on the following equation:

Y=Bottom+(Top−Bottom)/(1+10^((log $IC_{50}$−X)*Hill-Slope))

where Y is the % inhibition in the presence of X inhibitor concentration, Top=high control=mean signal of human kallikrein enzyme+Z-Gly-Pro-Arg-AMC peptide substrate with DMSO only; Bottom=low control−mean signal of no human kallikrein enzyme or 100% inhibition of human kallikrein enzyme; HillSlope—Hill coefficient; and $IC_{50}$=concentration of compound with 50% inhibition in relation to top/high control.

Representative compounds of formula (I) of the present invention were tested according to the procedure described in Biological Example 1 and Biological Example 2 above, with results as listed in Table 3, below.

TABLE 3

Biological Activity, Representative Compounds of Formula (I)

| ID No. | FXIa $IC_{50}$ (nM) | FXIa Ki (nM) | Plasma Kallikrein $IC_{50}$ (μM) |
|---|---|---|---|
| 1 | 1.5 | 0.8 | 0.54 |
| 2 | 3.0 | 1.5 | 0.47 |
| 3 | 15.3 | 7.6 | 0.79 |
| 4 | 2.29 μM | 1.15 μM | >10 μM |
| 5 | 2.1 | 1.0 | 0.06 |
| 6 | 0.6 | 0.3 | 0.06 |
| 7 | 2.3 | 1.1 | 0.42 |
| 8 | 1.9 | 0.9 | 0.47 |
| 9 | 6.58 μM | 3.29 μM | >10 μM |
| 10 | 1.85 μM | 925.9 | >10 μM |
| 11 | 1.17 μM | 588.0 | >10 μM |
| 12 | 69.2 | 34.6 | >10 μM |
| 13 | 2.0 | 1.0 | 0.07 |
| 14 | 2.03 μM | 1.02 μM | >10 μM |
| 15 | 5.82 μM | 2.91 μM | >10 μM |
| 16 | 1.07 μM | 535.0 | >10 μM |
| 17 | 1.59 μM | 795.9 | >10 μM |
| 18 | 13.2 | 6.6 | 0.82 |
| 19 | 1.0 | 0.5 | 0.02 |
| 20 | 7.65 μM | 3.83 μM | >10 μM |
| 21 | 1.20 μM | 598.0 | >10 μM |
| 22 | 5.07 μM | 2.54 μM | >10 μM |
| 23 | 7.0 | 3.5 | 0.54 |
| 24 | >10 | >5 μM | >10 μM |
| 25 | 260.1 | 130.0 | >10 μM |
| 26 | 0.5 | 0.3 | 0.07 |
| 27 | 2.39 μM | 1.19 μM | >10 μM |
| 28 | ~783.4 | ~391.7 | >10 μM |
| 29 | 0.8 | 0.4 | 0.35 |
| 30 | 5.7 | 2.9 | 0.33 |
| 31 | 1.18 μM | 587.7 | >10 μM |
| 32 | 0.7 | 0.4 | 0.23 |

TABLE 3-continued

Biological Activity, Representative Compounds of Formula (I)

| ID No. | FXIa IC$_{50}$ (nM) | FXIa Ki (nM) | Plasma Kallikrein IC$_{50}$ (μM) |
|---|---|---|---|
| 33 | 236.9 | 118.4 | >10 μM |
| 34 | 33.7 | 16.9 | 6.21 |
| 35 | 0.4 | 0.2 | 0.09 |
| 36 | ~5.75 μM | ~2.87 μM | >10 μM |
| 37 | ~78 | ~39.14 | 3.95 |
| 38 | 37.2 | 18.6 | 1.62 |
| 39 | >10 μM | >5 μM | >10 μM |
| 40 | >10 μM | >5 μM | >10 μM |
| 41 | 8.6 | 4.3 | >10 μM |
| 42 | 928.5 | 464.3 | >10 μM |
| 43 | >10 μM | >5 μM | >10 μM |
| 44 | >10 μM | >5 μM | >10 μM |
| 45 | 5.15 μM | 2.58 μM | >10 μM |
| 46 | 9.15 μM | 4.57 μM | >10 μM |
| 47 | 5.0 | 2.5 | 0.40 |
| 48 | 2.3 | 1.2 | 0.21 |
| 49 | 2.59 μM | 1.29 μM | >10 μM |
| 50 | 300.8 | 150.4 | >20 μM |
| 51 | >10 μM | >5 μM | >10 μM |
| 52 | 0.2 | 0.1 | 0.07 |
| 53 | 95.9 | 47.9 | >10 μM |
| 54 | 224.1 | 112.1 | >10 μM |
| 55 | 0.3 | 0.1 | 0.09 |
| 56 | 881.5 | 440.7 | >10 μM |
| 57 | 9.69 μM | 4.84 μM | >10 μM |
| 58 | >10 μM | >5 μM | >10 μM |
| 59 | 4.39 μM | 2.19 μM | >10 μM |
| 60 | ~9.61 μM | ~4.81 μM | >10 μM |
| 61 | 1.0 | 0.5 | 0.12 |
| 62 | 48.6 | 24.3 | 5.37 |
| 63 | 1.16 μM | 577.9 | >10 μM |
| 64 | 1.13 μM | 563.7 | >10 μM |
| 65 | 101.7 | 50.8 | 5.72 |
| 66 | 183.4 | 91.7 | >10 μM |
| 67 | 12.9 | 6.4 | 1.39 |
| 68 | 2.24 μM | 1.12 μM | >10 μM |
| 69 | 108.2 | 54.1 | 8.08 |
| 70 | NT$^a$ | NT$^a$ | NT$^a$ |
| 71 | >10 μM | >5 μM | >10 μM |
| 72 | 26.7 | 13.3 | 3.54 |

$^a$NT indicates that the compound was not tested.

Formulation Example 1: Solid, Oral Dosage Form—Prophetic Example

As a specific embodiment of an oral composition, 100 mg of any of Compound ID No. 6, prepared as described in Example 6, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

What is claimed:

1. A compound of formula (I)

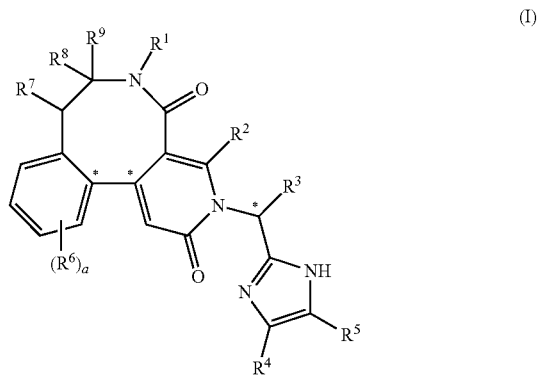

wherein

R$^1$ is selected from the group consisting of hydrogen, C$_{1-2}$alkyl, —(C$_{1-2}$alkylene)-OH and —(C$_{1-2}$alkylene)-O-(C$_{1-2}$alkyl);

R$^2$ is hydrogen and R$^3$ is cyclopropyl-methyl-;

alternatively, R$^2$ and R$^3$ are taken together with the carbon atoms to which they are bound to form

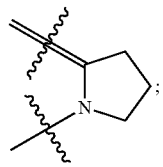 [SMILES: *N1CCCC1=*]

R$^4$ is selected from the group consisting of hydrogen and halogen;

R$^5$ is selected from the group consisting of phenyl, heteroaryl and pyridin-4-yl-1-oxide;

wherein the phenyl or heteroaryl is optionally substituted with one or more substituents independently selected from the group consisting of halogen, hydroxy, oxo, C1-4alkyl, hydroxy substituted C1-4alkyl, NR$^A$R$^B$ and —NH—C(O)-(C1-4alkyl); wherein R$^A$ and R$^B$ are each independently selected from the group consisting of hydrogen and C1-2alkyl;

a is an integer from 0 to 3;

each R$^6$ is independently selected from the group consisting of chloro, fluoro and methyl;

R$^7$ is hydrogen, and R$^8$ and R$^9$ are each independently selected from the group consisting of hydrogen, C$_{1-4}$alkyl, and C$_{1-4}$alkoxy;

alternatively, R$^7$ is hydrogen, and R$^8$ and R$^9$ are taken together with the carbon atom to which they are bound to form a ring structure selected from the group consisting of cycloprop-1,1-diyl, cyclobut-1,1-diyl, cyclopent-1,1-diyl, and cyclohex-1,1-yl;

alternatively, R$^9$ is hydrogen, and R$^7$ and R$^8$ are taken together with the carbon atoms to which they are bound to form a ring structure selected from the group consisting of phen-1,2-diyl and pyridin-3,4-diyl;

or a stereoisomer, isotopologue, isotopomer, or pharmaceutically acceptable salt or solvate thereof.

2. The compound of claim 1 having the formula (I-A)

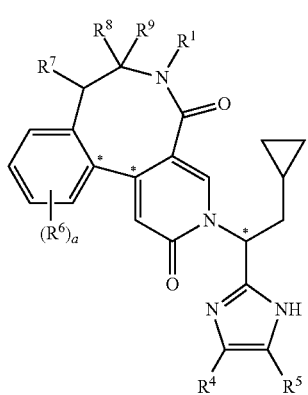

(I-A)

or a stereoisomer, isotopologue, isotopomer, or pharmaceutically acceptable salt or solvate thereof.

3. The compound of claim 1 having the formula (I-B)

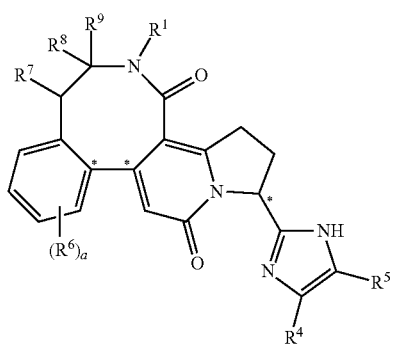

(I-B)

or a stereoisomer, isotopologue, isotopomer, or pharmaceutically acceptable salt or solvate thereof.

4. The compound of claim 1, wherein $R^1$ is selected from the group consisting of hydrogen, $C_{1-2}$alkyl, —($C_{1-2}$alkylene)-OH and —($C_{1-2}$alkylene)-O-($C_{1-2}$alkyl);

$R^2$ is hydrogen and $R^3$ is cyclopropyl-methyl-;

alternatively, $R^2$ and $R^3$ are taken together with the carbon atoms to which they are bound to form

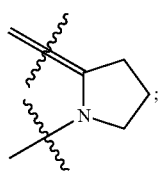

$R^4$ is selected from the group consisting of hydrogen, fluoro and chloro;

$R^5$ is selected from the group consisting of phenyl, nitrogen containing heteroaryl and pyridin-4-yl-1-oxide;

wherein the phenyl or heteroaryl is optionally substituted with one to two substituents independently selected from the group consisting of halogen, oxo, $C_{1-2}$alkyl, hydroxy substituted $C_{1-2}$alkyl, $NR^AR^B$ and —NH—C(O)-($C_{1-2}$alkyl); wherein $R^A$ and $R^B$ are each independently selected from the group consisting of hydrogen and C1-2alkyl;

a is an integer from 1 to 2;

each $R^6$ is independently selected from the group consisting of chloro and fluoro;

$R^7$ is hydrogen, and $R^8$ and $R^9$ are the same and selected from the group consisting of hydrogen, $C_{1-2}$alkyl, and $C_{1-2}$alkoxy;

alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl, and cyclopent-1,1-diyl;

alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;

or stereoisomer, isotopologue, isotopomer, or pharmaceutically acceptable salt or solvate thereof.

5. A compound of formula (I)

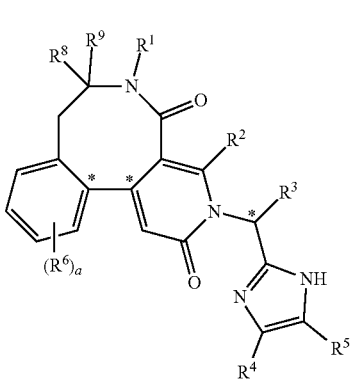

(I)

wherein $R^1$ is selected from the group consisting of hydrogen, methyl, 2-hydroxy-ethyl- and 2-methoxy-ethyl-;

$R^2$ is hydrogen and $R^3$ is cyclopropyl-methyl-;

alternatively, $R^2$ and $R^3$ are taken together with the carbon atoms to which they are bound to form;

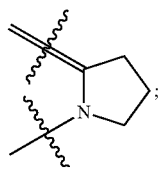 [SMILES: *N1CCCC1=*]

$R^4$ is selected from the group consisting of hydrogen and fluoro;

$R^5$ is selected from the group consisting of 4-fluoro-phenyl, 4-(methoxy-carbonyl-amino)-phenyl, 1-methyl-imidazol-5-yl, 1-methyl-1,2,3-triazol-5-yl, 1-methyl-pyrimidin-4-yl-6-one, 2-fluoro-6-amino-pyridin-3-yl, 2-chloro-6-amino-pyridin-3-yl, 1-methyl-pyridin-3-yl-6-one, pyridin-4-yl, 2-chloro-6-amino-pyridin-4-yl, 2-(hydroxy-methyl)-3-fluoro-pyridin-4-yl, 2-fluoro-6-amino-pyridin-4-yl, 1-methyl-pyridin-4-yl-6-one, pyridin-4-yl-1-oxide, 2-chloro-6-amino-pyridin-5-yl, indol-5-yl, indazol-5-yl, benzimidazol-5- yl, benzothiazol-5-yl, 2-methyl-benzothiazol-5-yl, benzo[1,2,3]thiadiazol-5-yl, imidazo[1,2-a]pyridin-7-yl, 3-bromo-imidazo[1,2-a]pyridin-7-yl and [1,2,4]triazolo[4,3-a]pyridin-7-yl;

a is an integer from 1 to 2;

each $R^6$ is independently selected from the group consisting of 11-chloro and 12-fluoro;

$R^7$ is hydrogen, and $R^8$ and $R^9$ are the same and selected from the group consisting of hydrogen, and methyl;

alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl and cyclopent-1,1-diyl;

alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;

or stereoisomer or pharmaceutically acceptable salt thereof.

6. The compound of claim 5, wherein $R^1$ is selected from the group consisting of hydrogen, methyl, and 2-hydroxy-ethyl-;

$R^2$ is hydrogen and $R^3$ is cyclopropyl-methyl-;

alternatively, $R^2$ and $R^3$ are taken together with the carbon atoms to which they are bound to form;

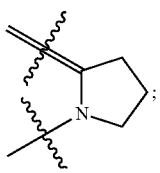

$R^4$ is selected from the group consisting of hydrogen and fluoro;

$R^5$ is selected from the group consisting of 4-fluoro-phenyl, 4-(methoxy-carbonyl-amino)-phenyl, 2-fluoro-6-amino-pyridin-3-yl, 2-chloro-6-amino-pyridin-3-yl, pyridin-4-yl, 2-chloro-6-amino-pyridin-4-yl, 2-(hydroxy-methyl)-3-fluoro-pyridin-4-yl, 2-fluoro-6-amino-pyridin-4-yl, 1-methyl-pyridin-4-yl-6-one, indol-5-yl, indazol-5-yl, benzimidazol-5-yl, benzothiazol-5-yl, 2-methyl-benzothiazol-5-yl, benzo[1,2,3]thiadiazol-5-yl, imidazo[1,2-a]pyridin-7-yl, 3-bromo-imidazo[1,2-a]pyridin-7-yl and [1,2,4]triazolo[4,3-a]pyridin-7-yl;

a is an integer from 1 to 2;

each $R^6$ is independently selected from the group consisting of 11-chloro and 12-fluoro;

$R^7$ is hydrogen, and $R^8$ and $R^9$ are the same and selected from the group consisting of hydrogen, and methyl;

alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl and cyclopent-1,1-diyl;

alternatively, $R^9$ is hydrogen, and $R^7$ and $R^8$ are taken together with the carbon atoms to which they are bound to form a ring structure selected from the group consisting of phen-1,2-diyl and pyridin-3,4-diyl;

or a pharmaceutically acceptable salt thereof.

7. The compound of claim 5, wherein $R^1$ is selected from the group consisting of hydrogen, and methyl;

$R^2$ is hydrogen and $R^3$ is cyclopropyl-methyl-;

alternatively, $R^2$ and $R^3$ are taken together with the carbon atoms to which they are bound to form;

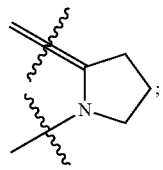 [SMILES: *N1CCCC1=*]

$R^4$ is selected from the group consisting of hydrogen and fluoro;

$R^5$ is selected from the group consisting of 4-(methoxy-carbonyl-amino)-phenyl, 2-fluoro-6-amino-pyridin-3-yl, 2-chloro-6-amino-pyridin-3-yl, 2-chloro-6-amino-pyridin-4-yl, 2-fluoro-6-amino-pyridin-4-yl, indol-5-yl, indazol-5-yl, benzimidazol-5-yl, benzothiazol-5-yl, 2-methyl-benzothiazol-5-yl, benzo[1,2,3]thiadiazol-5-yl, and imidazo[1,2-a]pyridin-7-yl;

a is an integer from 1 to 2;

each $R^6$ is independently selected from the group consisting of 11-chloro and 12-fluoro;

$R^7$ is hydrogen, and $R^8$ and $R^9$ are the same and selected from the group consisting of hydrogen, and methyl;

alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl and cyclopent-1,1-diyl;

or a pharmaceutically acceptable salt thereof.

8. The compound of claim 5, wherein $R^1$ is hydrogen;

$R^2$ is hydrogen and $R^3$ is cyclopropyl-methyl-;

alternatively, $R^2$ and $R^5$ are taken together with the carbon atoms to which they are bound to form;

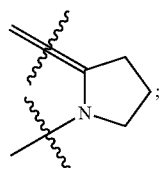 [SMILES: *N1CCCC1=*]

$R^4$ is hydrogen;

$R^5$ is selected from the group consisting of 4-(methoxy-carbonyl-amino)-phenyl, 2-fluoro-6-amino-pyridin-3-yl, 2-chloro-6-amino-pyridin-3-yl, 2-fluoro-6-amino-pyridin-4-yl, indazol-5-yl, benzimidazol-5-yl, and benzothiazol-5-yl;

a is 2;

one $R^6$ is 11-chloro and the other $R^6$ is 12-fluoro;

$R^7$ is hydrogen, and $R^8$ and $R^9$ are each methyl;

alternatively, $R^7$ is hydrogen, and $R^8$ and $R^9$ are taken together with the carbon atom to which they are bound to form a ring structure selected from the group consisting of cycloprop-1,1-diyl, cyclobut-1,1-diyl and cyclopent-1,1-diyl;

or a pharmaceutically acceptable salt thereof.

9. The compound of claim 1, selected from the group consisting of (R*)-12-(5-(1H-benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S*)-12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(R*)-12-(5-(6-amino-2-chloropyridin-3-yl)-1H-imidazol-2-yl)-7-chloro-8-fluoro-3,4,13,14-tetrahydrobenzo[5,6]azocino[4,3-g]indolizine-1,10(2H,12H)-dione;

(S*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione;

(S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclobutane]-1,10(4H,12H)-dione;

(S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopentane]-1,10(4H,12H)-dione;

(S*)-12-(5-(6-amino-2-fluoropyridin-3-yl)-1H-imidazol-2-yl)-7-chloro-8-fluoro-2-methyl-13,14-dihydro-2H-spiro[benzo[5,6]azocino[4,3-g]indolizine-3,1'-cyclopropane]-1,10(4H,12H)-dione;

and pharmaceutically acceptable salt thereof.

10. The compound of claim 5, selected from the group consisting of (R*)-12-(5-(1H-benzo[d]imidazol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione, (S*)-12-(5-(1H-indol-5-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(S*)-12-(5-(6-amino-2-chloropyridin-3-yl)-1H-imidazol-2-yl)-7-chloro-8-fluoro-13,14-dihydro-2H-spiro[benzo[5,6]azocino[4,3-g]indolizine-3,1'-cyclopropane]-1,10(4H,12H)-dione;

(R*)-12-(5-(6-amino-2-chloropyridin-3-yl)-1H-imidazol-2-yl)-7-chloro-8-fluoro-3,4,13,14-tetrahydrobenzo[5,6]azocino[4,3-g]indolizine-1,10(2H,12H)-dione;

(S*)-12-(5-(6-amino-2-fluoropyridin-3-yl)-1H-imidazol-2-yl)-7-chloro-8-fluoro-3,3-dimethyl-3,4,13,14-tetrahydrobenzo[5,6]azocino[4,3-g]indolizine-1,10(2H,12H)-dione;

(S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclobutane]-1,10(4H,12H)-dione;

(S*)-12-(5-(6-amino-2-fluoropyridin-3-yl)-1H-imidazol-2-yl)-7-chloro-8-fluoro-13,14-dihydro-2H-spiro[benzo[5,6]azocino[4,3-g]indolizine-3,1'-cyclopentane]-1,10(4H,12H)-dione;

(S*)-12-(5-(6-amino-2-fluoropyridin-3-yl)-1H-imidazol-2-yl)-7-chloro-8-fluoro-2-methyl-13,14-dihydro-2H-spiro[benzo[5,6]azocino[4,3-g]indolizine-3,1'-cyclopropane]-1,10(4H,12H)-dione;

methyl (S*)-(4-(2-(1-(11-chloro-12-fluoro-2,5-dioxo-2,5,6,8-tetrahydro-3H-spiro[benzo[e]pyrido[3,4-c]azocine-7,1'-cyclopropan]-3-yl)-2-cyclopropylethyl)-1H-imidazol-5-yl)phenyl)carbamate;

and pharmaceutically acceptable salt thereof.

11. A pharmaceutical composition comprising a pharmaceutically acceptable carrier and a compound of claim 1.

* * * * *